US012162925B2

(12) United States Patent
Weiner et al.

(10) Patent No.: US 12,162,925 B2
(45) Date of Patent: Dec. 10, 2024

(54) DNA-ENCODED MONOCLONAL ANTIBODIES TARGETING THE EBOLAVIRUS GLYCOPROTEIN

(71) Applicant: The Wistar Institute of Anatomy and Biology, Philadelphia, PA (US)

(72) Inventors: David Weiner, Merion, PA (US); Ami Patel, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 42 days.

(21) Appl. No.: 16/647,082

(22) PCT Filed: Sep. 17, 2018

(86) PCT No.: PCT/US2018/051290
§ 371 (c)(1),
(2) Date: Mar. 13, 2020

(87) PCT Pub. No.: WO2019/139648
PCT Pub. Date: Jul. 18, 2019

(65) Prior Publication Data
US 2020/0216519 A1    Jul. 9, 2020

Related U.S. Application Data

(60) Provisional application No. 62/559,422, filed on Sep. 15, 2017.

(51) Int. Cl.
C07K 16/10        (2006.01)
A61K 39/00        (2006.01)
A61P 31/14        (2006.01)

(52) U.S. Cl.
CPC ........ *C07K 16/10* (2013.01); *A61K 2039/505* (2013.01); *A61P 31/14* (2018.01);
(Continued)

(58) Field of Classification Search
CPC ...................................................... C07K 16/10
See application file for complete search history.

(56) References Cited

U.S. PATENT DOCUMENTS

2016/0215040 A1*   7/2016   Kyratsous .............. C07K 16/10
2016/0326234 A1   11/2016   Hiatt
2017/0266282 A1*   9/2017   Weiner ................... C07K 14/82

FOREIGN PATENT DOCUMENTS

| WO | 2015089492 | 6/2015 |
| WO | 2016054598 | 4/2016 |
| WO | 2016145385 | 9/2016 |

OTHER PUBLICATIONS

Fitch, W. M., May 2000, Homology: a personal view on some of the problems, TIG 16(5):227-231.*

(Continued)

*Primary Examiner* — Jeffrey S Parkin
(74) *Attorney, Agent, or Firm* — Riverside Law LLP

(57) ABSTRACT

Disclosed herein is a composition including a recombinant nucleic acid sequence that encodes an antibody to an Ebola viral antigen. Also disclosed herein is a method of generating a synthetic antibody in a subject by administering the composition to the subject. The disclosure also provides a method of preventing and/or treating an Ebola virus infection in a subject using said composition and method of generation.

13 Claims, 18 Drawing Sheets
(18 of 18 Drawing Sheet(s) Filed in Color)
Specification includes a Sequence Listing.

(52) U.S. Cl.
CPC ...... *C07K 2317/10* (2013.01); *C07K 2317/21* (2013.01); *C07K 2317/24* (2013.01); *C07K 2317/76* (2013.01); *C12N 2760/14111* (2013.01)

(56) References Cited

OTHER PUBLICATIONS

Theiben, G., Feb. 2002, Secret life of genes, Nature 415:741.*
Wec, A. Z., et al., May 2017, Antibodies from a huma survivor define sites of vulnerability for broad protection against Ebolaviruses, Cell 169:878-890.*
Tiller, K. E., and P. M. Tessier, 2015, Advances in antibody design, Annu. Rev. Biomed. Eng. 17:191-216.*
Yuan, W., and C. R. Parrish, 2000, Comparison of two single-chain antibodies that neutralize canine parvovirus: analysis of an antibody-combining site and mechanisms of neutralization, Virol. 269:471-480.*
Ami et al: "In Vivo Delivery of Synthetic Human DNA-Encoded Monoclonal Antibodies Protect against Ebolavirus Infection in a Mouse Model", Cell Reports, vol. 25, No. 7, 1982-1993.
Andrews et al: "In Vivo Production of Monoclonal Antibodies by Gene Transfer via Electroporation Protects against Lethal Influenza and Ebola Infections", Molecular Therapy—Methods & Clinical Develop, vol. 7: 74-82.
Audet et al, "Molecular Characterization of the Monoclonal Antibodies Composing ZMAb: A Protective Cocktail Against Ebola Virus" , Scientific Reports, vol. 4, No. 1.
Bogan and Thorn, 1998, "Anatomy of Hot Spots in Protein Interfaces," J. Mol. Biol, 280, 1-9.
Bornholdt et al, "Isolation of potent neutralizing antibodies from a survivor of the 2014 Ebola virus outbreak (Author Manuscript)" , Science, vol. 351, No. 6277, 1078-1083.
Chen et al., 2016, "The potential of plants as a system for the development and production of human biologics," F1000Research 5:912.
Davidson et al., "Mechanism of Binding to Ebola Virus Glycoprotein by the ZMapp, ZMAb, and MB-003 Cocktail Antibodies," J Virol., 2015, 89(21):10982-92.
Dunbar et al., 2016, "SAbPred: a structure-based antibody prediction server," NAR 44:W474-8.
Flingai et al: "Protection against dengue disease by synthetic nucleic acid antibody prophylaxis/immunotherapy", Scientific Reports, vol. 5, No. 1.
Flyak et al., 2016, "Cross-Reactive and Potent Neutralizing Antibody Responses in Human Survivors of Natural Ebolavirus Infection," Cell 164:392-405.
Janda et al., 2016, "Ig Constant Region Effects on Variable Region Structure and Function," Front Microbiol 7:22.
Kugelman et al., 2015, "Emergence of Ebola Virus Escape Variants in Infected Nonhuman Primates Treated with the MB-003 Antibody Cocktail," cell Rep 12:2111-20.
Lefranc, 2001, "IMGT, the international ImMunoGeneTics database," NAR 29:207-099.
Limberis et al., 2016, "Adeno-Associated Virus Serotype 9-Expressed ZMapp in Mice Confers Protection Against Systemic and Airway-Acquired Ebola Virus Infection," J Infect Dis 214:1975-9.
Lo Conte, et al., 1999, "The atomic structure of protein-protein recognition sites." J. Mol. Biol. 285, 2177-2198.
Miler et al., 2016, Initiating a watch list for Ebola virus antibody escape mutations, Peerj 4:e1674.
Muthumani et al., 2016, "Rapid and Long-Term Immunity Elicited by DNA-Encoded Antibody Prophylaxis and DNA Vaccination Against Chikungunya Virus," J Infect Dis 214:369-78.
Seeliger et al., 2015, "Boosting antibody developability through rational sequence optimization," Mabs-Austin 7:505-15.
Sharma et al., 2014, "In silico selection of therapeutic antibodies for development: viscosity, clearance, and chemical stability," PNAS 111:18601-6.
Tudor et al., 2012, "Isotype modulates epitope specificity, affinity, and antiviral activities of anti-HIV-1 human broadly neutralizing 2F5 antibody," PNAS 109:12680-5.
Wec et al., "Vulnerability for Broad Protection against Ebolaviruses", Cell, vol. 169, No. 5:878-890.
Yang et al., 2017, "IgG cooperativity—Is there allostery? Implications for antibody functions and therapeutic antibody development," Mabs-Austin 9:1231-52.
Zhao et al 2016, "Toremifene interacts with and destabilizes the Ebola virus glycoprotein," Nature, 535(7610):169-172.

* cited by examiner

| *In vitro* DMAb expression [μg/mL] | | | | | |
|---|---|---|---|---|---|
| | Technical Replicate # | | | | |
| GP-DMAb | 1 | 2 | 3 | Average | SD |
| DMAb-1 | 1.86 | 2.01 | 2.22 | 2.03 | 0.18 |
| DMAb-2 | 0.49 | 0.53 | 0.75 | 0.59 | 0.14 |
| DMAb-3 | 2.16 | 1.83 | 2.05 | 2.01 | 0.16 |
| DMAb-4 | 0.00 | 0.13 | 0.00 | 0.04 | 0.07 |
| DMAb-5 | 2.44 | 2.46 | 2.34 | 2.41 | 0.06 |
| DMAb-6 | 0.16 | 0.13 | 0.16 | 0.15 | 0.02 |
| DMAb-7 | 0.51 | 0.45 | 0.47 | 0.48 | 0.03 |
| DMAb-8 | 0.38 | 0.32 | 0.32 | 0.34 | 0.03 |
| DMAb-9 | 1.21 | 1.47 | 1.19 | 1.29 | 0.16 |
| DMAb-10 | 0.40 | 0.28 | 0.00 | 0.23 | 0.20 |
| DMAb-11 | 6.32 | 5.12 | 7.59 | 6.34 | 1.24 |
| DMAb-12 | 1.62 | 1.86 | 1.21 | 1.56 | 0.33 |
| DMAb-13 | 0.85 | 0.64 | 0.96 | 0.82 | 0.17 |
| DMAb-21 | 0.59 | 0.70 | 0.79 | 0.69 | 0.10 |
| DMAb-22 | 0.63 | 0.67 | 0.79 | 0.70 | 0.08 |
| DMAb-24 | 0.64 | 0.54 | 0.65 | 0.61 | 0.06 |
| DMAb-25 | 14.63 | 12.27 | 10.50 | 12.47 | 2.07 |
| DMAb-26 | 2.12 | 2.61 | 1.69 | 2.14 | 0.46 |
| DMAb-27 | 1.94 | 1.90 | 1.90 | 1.91 | 0.02 |
| DMAb-30 | 4.27 | 6.09 | 3.82 | 4.73 | 1.20 |
| DMAb-31 | 2.59 | 2.32 | 2.36 | 2.42 | 0.15 |
| DMAb-34 | 3.57 | 3.34 | 2.77 | 3.23 | 0.41 |
| DMAb-35 | 10.58 | 11.75 | 6.06 | 9.46 | 3.00 |
| DMAb-38 | 0.80 | 1.00 | 1.16 | 0.99 | 0.18 |
| DMAb-39 | 3.73 | 3.30 | 3.46 | 3.49 | 0.22 |
| DMAb-40 | 0.00 | 0.11 | 0.01 | 0.04 | 0.06 |
| DMAb-41 | 2.10 | 1.81 | 1.59 | 1.83 | 0.25 |
| pVax1 | 0.00 | 0.00 | 0.00 | 0.00 | 0.00 |

Figure 12

DNA-ENCODED MONOCLONAL ANTIBODIES TARGETING THE EBOLAVIRUS GLYCOPROTEIN

CROSS-REFERENCE TO RELATED APPLICATIONS

This application is a U.S. national phase application filed under 35 U.S.C. § 371 claiming priority to International Patent Application No. PCT/US2018/051290, filed Sep. 17, 2018, which is entitled to priority under 35 U.S.C. § 119 (e) to U.S. Provisional Application No. 62/559,422, filed Sep. 15, 2017, the contents of each of which are incorporated by reference herein in their entireties.

STATEMENT OF GOVERNMENT INTEREST

This invention was made with government support under W31P4Q-15-1-0003 awarded by Defense Advanced Research Projects Agency (DARPA). The government has certain rights in the invention.

TECHNICAL FIELD

The present invention relates to a composition comprising a recombinant nucleic acid sequence for generating one or more synthetic antibodies, and functional fragments thereof, in vivo, and a method of preventing and/or treating viral infection in a subject by administering said composition.

BACKGROUND

Monoclonal antibodies (mAbs) targeting the Ebola virus glycoprotein (GP) represent an important treatment approach against Ebola virus disease (EVD). It has been shown that individual mAbs and mAb cocktails can successfully protect small animals and non-human primates against lethal Ebola virus infection. MAb-based therapy against EVD is further supported by favorable recovery in confirmed human EVD cases that received the anti-GP mAb cocktail, ZMapp. However, the dramatic cost, slow development, and requirement for several high-dose administrations (mg/kg) represent a significant challenge for protein mAb delivery, especially during a possible outbreak.

Thus, there is need in the art for improved therapeutics that prevent and/or treat Ebola virus infection. The current invention satisfies this need.

SUMMARY

The present invention is directed to a nucleic acid molecule encoding one or more synthetic antibodies, wherein the nucleic acid molecule comprises at least one selected from the group consisting of a) a nucleotide sequence encoding an anti-Ebola virus glycoprotein (GP) synthetic antibody; and b) a nucleotide sequence encoding a fragment of an anti-Ebola virus glycoprotein (GP) synthetic antibody.

In one embodiment, the nucleic acid molecule comprises a nucleotide sequence encoding a cleavage domain.

In one embodiment, the nucleic acid molecule comprises a nucleotide sequence encoding one or more of a variable heavy chain region and a variable light chain region of an anti-Ebola virus GP antibody.

In one embodiment, the nucleic acid molecule encodes one or more synthetic bispecific antibodies. A bispecific antibody molecule according to the invention may have two binding sites of any desired specificity. In some embodiments one of the binding sites is capable of binding an Ebola virus antigen. In some embodiment, one of the binding sites is capable of binding a cell surface marker on an immune cell.

In one embodiment, the nucleic acid molecule comprises a nucleotide sequence encoding a variable heavy chain region and a variable light chain region of an anti-Ebola virus GP antibody.

In one embodiment, the nucleic acid molecule comprises one or more nucleotide sequences encoding one or more sequences as set forth in SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO: 125, SEQ ID NO: 127, SEQ ID NO:129, SEQ ID NO: 131 and SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO:151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, and SEQ ID NO: 169.

In one embodiment, the nucleic acid molecule comprises one or more nucleotide sequences comprising a sequence selected from the group comprising SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO:136, SEQ ID NO:138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO:156, SEQ ID NO:158, SEQ ID NO: 160, SEQ ID NO: 162, SEQ ID NO: 164, SEQ ID NO: 166, SEQ ID NO: 168, and SEQ ID NO: 170.

In one embodiment, the nucleic acid molecule comprises a nucleotide sequence encoding a polypeptide comprising a variable heavy chain region; an IRES element; and a variable light chain region. In one embodiment, the IRES element is one of a viral IRES or an eukaryotic IRES.

In one embodiment, the nucleic acid molecule comprises one or more nucleotide sequences having at least about 95% identity over an entire length of the nucleic acid sequence to a nucleic acid encoding an sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO: 103, SEQ ID NO: 105, SEQ ID NO: 107, SEQ ID NO: 109, SEQ ID NO:111, SEQ ID NO:113, SEQ ID NO:115, SEQ ID NO:117, SEQ ID NO:119, SEQ ID NO: 121, SEQ ID NO: 123, SEQ ID NO: 125, SEQ ID NO: 127, SEQ ID NO: 129, SEQ ID NO: 131 and SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, and SEQ ID NO:169.

In one embodiment, the nucleic acid molecule comprises one or more nucleotide sequences encoding a sequence selected from the group consisting of SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO: 111, SEQ ID NO:113, SEQ ID NO:115, SEQ ID NO:117, SEQ ID NO:119, SEQ ID NO:121, SEQ ID NO: 123, SEQ ID NO: 125, SEQ ID NO:127, SEQ ID NO: 129, SEQ ID NO: 131 and SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO:151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, and SEQ ID NO: 169.

In one embodiment, the nucleic acid molecule comprises one or more nucleotide sequences having at least about 95% identity over an entire length of the nucleic acid sequence to a nucleic acid sequence selected from the group consisting of SEQ ID NO:2, SEQ ID NO:4, SEQ ID NO:6, SEQ ID NO:8, SEQ ID NO: 10, SEQ ID NO: 12, SEQ ID NO:14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO: 134, SEQ ID NO: 136, SEQ ID NO: 138, SEQ ID NO: 140, SEQ ID NO:142, SEQ ID NO: 144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, and SEQ ID NO:170.

In one embodiment, the nucleic acid molecule comprises one or more nucleotide sequences selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO:104, SEQ ID NO: 106, SEQ ID NO: 108, SEQ ID NO: 110, SEQ ID NO: 112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO: 136, SEQ ID NO: 138, SEQ ID NO: 140, SEQ ID NO: 142, SEQ ID NO:144, SEQ ID NO:146, SEQ ID NO:148, SEQ ID NO:150, SEQ ID NO:152, SEQ ID NO:154, SEQ ID NO: 156, SEQ ID NO: 158, SEQ ID NO: 160, SEQ ID NO: 162, SEQ ID NO:164, SEQ ID NO: 166, SEQ ID NO: 168, and SEQ ID NO: 170.

In one embodiment, the nucleic acid molecule comprises a RNA sequence transcribed from a DNA sequence described herein. For example, in one embodiment, the nucleic acid molecule comprises a RNA sequence transcribed by the DNA sequence of one or more of SEQ ID NO: 1, SEQ ID NO:3, SEQ ID NO:5, SEQ ID NO:7, SEQ ID NO:9, SEQ ID NO: 11, SEQ ID NO:13, SEQ ID NO: 15, SEQ ID NO: 17, SEQ ID NO:19, SEQ ID NO:21, SEQ ID NO:23, SEQ ID NO:25, SEQ ID NO:27, SEQ ID NO:29, SEQ ID NO:31 and SEQ ID NO:33, or variants thereof or fragments thereof. In another embodiment, the nucleic acid molecule comprises an RNA sequence transcribed by a DNA sequence encoding the polypeptide sequence of one or more of SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32 and SEQ ID NO:34, or variants thereof or fragments thereof.

In one embodiment, the nucleotide sequence encodes a leader sequence. In one embodiment, the nucleic acid molecule comprises an expression vector.

The invention further provides a composition comprising any of the nucleic acid molecules described herein.

In one embodiment, the composition comprises a pharmaceutically acceptable excipient.

The invention further relates to a method of preventing or treating a disease in a subject, the method comprising administering to the subject a nucleic acid molecule or a composition as described herein.

In one embodiment, the disease is an Ebola virus infection.

In one embodiment, the method further comprises administering a therapeutic agent to the subject. In one embodiment, a therapeutic agent is administered less than 10 days after administration of the nucleic acid molecule or composition.

In one embodiment, the method further comprises administering a antibiotic agent to the subject. In one embodiment a therapeutic agent is administered less than 10 days after administration of the nucleic acid molecule or composition.

In one embodiment, the invention provides novel sequences for use for producing monoclonal antibodies in mammalian cells or for delivery in DNA or RNA vectors including bacterial, yeast, as well as viral vectors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1, comprising FIG. 1A depicts a schematic diagram of DMAb construct design and in vivo mAb delivery. DMAbs can be delivered as a single-plasmid construct encoding both HC and LC in a single transcript or as dual-plasmids with the HC an LC encoded on two separate DNA plasmids. DMAb plasmids are injected intramuscularly where the mAb transgene expresses, assembles, and secretes full-length human Ig into systemic circulation. FIG. 1B depicts anti-GP DMAb expression in mouse muscle. BALB/c mice were injected in the quadriceps muscle with an anti-GP DMAb (50 μg). The muscle was excised 48 hours later and frozen in O.T.C. compound before sectioning. Sections were stained with an unconjugated goat anti-human IgG-Fc antibody, followed by detection with a donkey anti-goat antibody conjugated to AF488 (green), and DAPI (blue) (Nikon 80i, magnification 40×). DMAb expression is also shown as a pseudocolour image (red=highest expression intensity, dark blue=lowest expression intensity) to demonstrate the contrast in expression between DMAb expressing muscle cells and the negative control group.

FIG. 2, comprising FIG. 2A through FIG. 2D depicts in vivo optimizations of anti-GP DMAbs.

FIG. 3, comprising FIG. 3A through FIG. 3F depicts the characterization of DMAb-11 and DMAb-34.

FIG. 4, comprising FIG. 4A depicts drop-out mutations identified for protein IgG 5.6.1A2 and DMAb-11. Monclonal antibody 5.6.1A2 and serum from BALB/c mice expressing DMAb-11 show reactivity with the fusion loop of EBOV GP2. FIG. 4B depicts drop-out mutations identified for protein IgG 15784 and DMAb-34. MAb 15784 and serum from BALB/c mice expressing DMAb-34 show reactivity with the base/fusion loop of EBOV GP2. Residues identified as critical for DMAb-11 and DMAb-34 binding are shown mapped in green spheres on the GP monomer (left) and trimer structures (center and right) from EBOV GP crystal structure (PDB id 5JQ3, Zhao et al, 2016). GP1 is shown as yellow, GP2 as red. The right-hand figure shows the entire space-filled GP surface model.

FIG. 5, comprising FIG. 5A depicts an overview of the injection regimen. DMAbs (50 μg/mouse or 100 μg/mouse) were administered on day −28 and serum was collected on day −14 before lethal challenge with 1000 LD50 of mouse-adapted EBOV (Mayinga). Animals were monitored for 21 days post-challenge for signs of disease and weight loss. FIG. 5B depicts survival and percentage weight change for positive control group receiving human 2G4 IgG1 (100 μg/mouse) and negative control group receiving DMAb empty vector pVax1. FIG. 5C depicts DMAb-11 expression at day −14 before challenge, survival, and weight change. FIG. 5D depicts DMab-34 expression at day −14 before challenge, survival, and weight change.

FIG. 6, comprising FIG. 6A depicts an overview of the challenge experiment. FIG. 6B depicts the combined expression of DMAb-11 and DMAb-34 at day −14. FIG. 6C depicts survival. FIG. 6D depicts percentage weight change.

FIG. 7, comprising FIG. 7A depicts an overview of the injection regimens. DMAbs were administered on day −14 or day −8 before lethal challenge with 1000 LD50 of mouse-adapted EBOV (Mayinga). Animals were monitored for 22 days post-challenge for signs of disease and weight loss. FIG. 7B depicts Survival in DMAb-11 groups receiving injection on day −14 or day −8 and the negative control. FIG. 7C depicts the percent weight change in DMAb-11 groups receiving injection on day −14 or day −8 and the negative control.

FIG. 9, comprising FIG. 9A depicts in vitro western blot of DMAb-11 and DMAb-34 showing Ig HC and LC. HEK 293 T cells were transfected with DMAb-11 or DMAb-34. Cell lysates were harvested 40 hours following transfection and run in duplicate on an SDS-PAGE gel before transferring to a PVDF membrane. Empty DMAb vector pVax1 and corresponding protein mAbs 5.6. 1A2 and 15784 were run in parallel. Western blots were probed with LI-COR anti-human IgG IRDye 800CW and anti-mouse beta-actin IRDye 680RD. Bands for the HC, beta-actin, and LC were visualized at approximately 50 kDa, 45 kDa, and 25 kDa, respectively. FIG. 9B, comprising FIG. 9B$i$ and FIG. 9B$ii$, depict the in vivo pharmacokinetic expression of DMAb-11 and DMAb-34. FIG. 9B$i$ depicts experimental results of BALB/c mice injected with the single-plasmid construct (n=9) or dual-plasmid constructs (n=8) of DMAb-11. Human IgG1 was monitored in mouse serum for >365 days. FIG. 9B$i$ depicts experimental results of BALB/c mice injected with dual-plasmid constructs (n=5) of DMAb-34. Human IgG1 was monitored in mouse serum for >168 days.

FIG. 10, comprising FIG. 10A depicts an overview of the single-plasmid injection design and regimen. DMAbs were administered on day −28 and serum was collected from animals on day −14 before lethal challenge with 1000 LD50 of mouse-adapted EBOV (Mayinga). Animals were monitored for 21 days post-challenge for signs of disease and weight loss. FIG. 10B depicts expression of increasing doses of DMAb-11 in mouse serum at day −14 before challenge. FIG. 10C depicts survival. FIG. 10D depicts percent weight change.

FIG. 11, comprising FIG. 11A depicts an overview of injection regimen. DMAbs were administered to BALB/c mice (n=10/group) −82 days before lethal challenge and serum was collected on day −56 before lethal challenge with 1000 LD50 of mouse-adapted EBOV (Mayinga). Animals were monitored for 21 days post-challenge administration. FIG. 11B depicts DMAb-11 expression in mouse serum. FIG. 11C depicts survival. FIG. 11D depicts percent weight change. Grey box represents shipment and acclimatization period.

FIG. 12 depicts experimental results of in vitro transfection of anti-GP DMAbs.

DETAILED DESCRIPTION

Figures 1A, 1B:
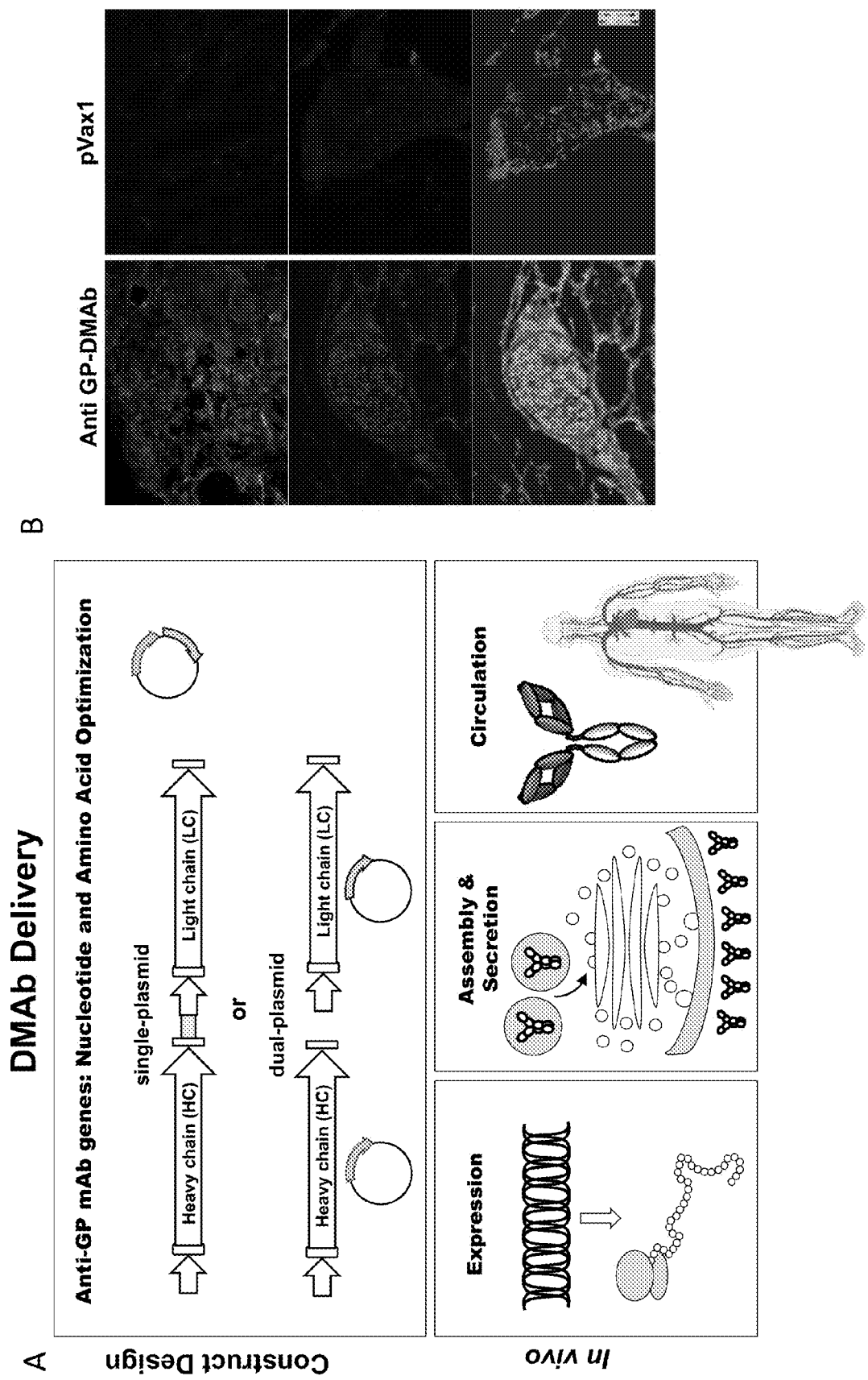
FIG. 1A through FIG. 1B, depicts an overview of DMAb expression and in vivo expression.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

A sequence listing provided herewith contains a list of sequences including the following:

SEQ ID NO:1 is the amino acid sequence of DMAb-2G4.
SEQ ID NO:2 is the nucleotide sequence of DMAb-2G4, pGX9226.
SEQ ID NO:3 is the amino acid sequence of DMAb-4G7.
SEQ ID NO:4 is the nucleotide sequence of DMAb-4G7, pGX9229.
SEQ ID NO:5 is the amino acid sequence of DMAb-4.
SEQ ID NO:6 is the nucleotide sequence of DMAb-4, pGX9230.
SEQ ID NO:7 is the amino acid sequence of DMAb-10.
SEQ ID NO:8 is the nucleotide sequence of DMAb-10, pGX9244.
SEQ ID NO:9 is the amino acid sequence of DMAb-11.
SEQ ID NO: 10 is the nucleotide sequence of DMAb-11, pGX9256.
SEQ ID NO:11 is the amino acid sequence of DMAb-12.
SEQ ID NO: 12 is the nucleotide sequence of DMAb-12, pGX9260.
SEQ ID NO:13 is the amino acid sequence of DMAb-13.
SEQ ID NO: 14 is the nucleotide sequence of DMAb-13, pGX9261.

SEQ ID NO: 15 is the amino acid sequence of DMAb-34 heavy chain.
SEQ ID NO: 16 is the nucleotide sequence of DMAb-34 heavy chain.
SEQ ID NO:17 is the amino acid sequence of DMAb-34 light chain.
SEQ ID NO: 18 is the nucleotide sequence of DMAb-34 light chain.
SEQ ID NO: 19 is the amino acid sequence of DMAb-4G7 heavy chain.
SEQ ID NO:20 is the nucleotide sequence of DMAb-4G7 heavy chain.
SEQ ID NO:21 is the amino acid sequence of DMAb-4G7 light chain.
SEQ ID NO:22 is the nucleotide sequence of DMAb-4G7 light chain.
SEQ ID NO:23 is the amino acid sequence of DMAb-4 heavy chain.
SEQ ID NO:24 is the nucleotide sequence of DMAb-4 heavy chain.
SEQ ID NO:25 is the amino acid sequence of DMAb-4 light chain.
SEQ ID NO:26 is the nucleotide sequence of DMAb-4 light chain.
SEQ ID NO:27 is the amino acid sequence of DMAb-11 heavy chain.
SEQ ID NO:28 is the nucleotide sequence of DMAb-11 heavy chain.
SEQ ID NO:28 is the amino acid sequence of DMAb-11 light chain.
SEQ ID NO:30 is the nucleotide sequence of DMAb-11 light chain.
SEQ ID NO:31 is the amino acid sequence of DMAb-30 heavy chain.
SEQ ID NO:32 is the nucleotide sequence of DMAb-30 heavy chain.
SEQ ID NO:33 is the amino acid sequence of DMAb-30 light chain.
SEQ ID NO:34 is the nucleotide sequence of DMAb-30 light chain.
SEQ ID NO:35 is the amino acid sequence of DMAb-1 heavy chain.
SEQ ID NO:36 is the nucleotide sequence of DMAb-1 heavy chain.
SEQ ID NO:37 is the amino acid sequence of DMAb-1 light chain.
SEQ ID NO:38 is the nucleotide sequence of DMAb-1 light chain.
SEQ ID NO:39 is the amino acid sequence of DMAb-2 heavy chain.
SEQ ID NO:40 is the nucleotide sequence of DMAb-2 heavy chain.
SEQ ID NO:41 is the amino acid sequence of DMAb-2 light chain.
SEQ ID NO:42 is the nucleotide sequence of DMAb-2 light chain.
SEQ ID NO:43 is the amino acid sequence of DMAb-3 heavy chain.
SEQ ID NO:44 is the nucleotide sequence of DMAb-3 heavy chain.
SEQ ID NO:45 is the amino acid sequence of DMAb-3 light chain.
SEQ ID NO:46 is the nucleotide sequence of DMAb-3 light chain.
SEQ ID NO:47 is the amino acid sequence of DMAb-10 heavy chain.
SEQ ID NO:48 is the nucleotide sequence of DMAb-10 heavy chain.
SEQ ID NO:49 is the amino acid sequence of DMAb-10 light chain.
SEQ ID NO:50 is the nucleotide sequence of DMAb-10 light chain.
SEQ ID NO:51 is the amino acid sequence of DMAb-5 heavy chain.
SEQ ID NO:52 is the nucleotide sequence of DMAb-5 heavy chain.
SEQ ID NO:53 is the amino acid sequence of DMAb-5 light chain.
SEQ ID NO:54 is the nucleotide sequence of DMAb-5 light chain.
SEQ ID NO:55 is the amino acid sequence of DMAb-6 heavy chain.
SEQ ID NO:56 is the nucleotide sequence of DMAb-6 heavy chain.
SEQ ID NO:57 is the amino acid sequence of DMAb-6 light chain.
SEQ ID NO:58 is the nucleotide sequence of DMAb-6 light chain.
SEQ ID NO:59 is the amino acid sequence of DMAb-7 heavy chain.
SEQ ID NO:60 is the nucleotide sequence of DMAb-7 heavy chain.
SEQ ID NO:61 is the amino acid sequence of DMAb-7 light chain.
SEQ ID NO:62 is the nucleotide sequence of DMAb-7 light chain.
SEQ ID NO:63 is the amino acid sequence of DMAb-8 heavy chain.
SEQ ID NO:64 is the nucleotide sequence of DMAb-8 heavy chain.
SEQ ID NO:65 is the amino acid sequence of DMAb-8 light chain.
SEQ ID NO:66 is the nucleotide sequence of DMAb-8 light chain.
SEQ ID NO:67 is the amino acid sequence of DMAb-9 heavy chain.
SEQ ID NO:68 is the nucleotide sequence of DMAb-9 heavy chain.
SEQ ID NO:69 is the amino acid sequence of DMAb-9 light chain.
SEQ ID NO:70 is the nucleotide sequence of DMAb-9 light chain.
SEQ ID NO:71 is the amino acid sequence of DMAb-12 heavy chain.
SEQ ID NO:72 is the nucleotide sequence of DMAb-12 heavy chain.
SEQ ID NO:73 is the amino acid sequence of DMAb-12 light chain.
SEQ ID NO:74 is the nucleotide sequence of DMAb-12 light chain.
SEQ ID NO:75 is the amino acid sequence of DMAb-13 heavy chain.
SEQ ID NO:76 is the nucleotide sequence of DMAb-13 heavy chain.
SEQ ID NO:77 is the amino acid sequence of DMAb-13 light chain.
SEQ ID NO:78 is the nucleotide sequence of DMAb-13 light chain.
SEQ ID NO:79 is the amino acid sequence of DMAb-14 heavy chain.
SEQ ID NO:80 is the nucleotide sequence of DMAb-14 heavy chain.

SEQ ID NO:81 is the amino acid sequence of DMAb-14 light chain.
SEQ ID NO:82 is the nucleotide sequence of DMAb-14 light chain.
SEQ ID NO:83 is the amino acid sequence of DMAb-15 heavy chain.
SEQ ID NO:84 is the nucleotide sequence of DMAb-15 heavy chain.
SEQ ID NO:85 is the amino acid sequence of DMAb-15 light chain.
SEQ ID NO:86 is the nucleotide sequence of DMAb-15 light chain.
SEQ ID NO:87 is the amino acid sequence of DMAb-16 heavy chain.
SEQ ID NO:88 is the nucleotide sequence of DMAb-16 heavy chain.
SEQ ID NO:89 is the amino acid sequence of DMAb-16 light chain.
SEQ ID NO:90 is the nucleotide sequence of DMAb-16 light chain.
SEQ ID NO:91 is the amino acid sequence of DMAb-17 heavy chain.
SEQ ID NO:92 is the nucleotide sequence of DMAb-17 heavy chain.
SEQ ID NO:93 is the amino acid sequence of DMAb-17 light chain.
SEQ ID NO:94 is the nucleotide sequence of DMAb-17 light chain.
SEQ ID NO:95 is the amino acid sequence of DMAb-20 heavy chain.
SEQ ID NO:96 is the nucleotide sequence of DMAb-20 heavy chain.
SEQ ID NO:97 is the amino acid sequence of DMAb-20 light chain.
SEQ ID NO:98 is the nucleotide sequence of DMAb-20 light chain.
SEQ ID NO:99 is the amino acid sequence of DMAb-21 heavy chain.
SEQ ID NO: 100 is the nucleotide sequence of DMAb-21 heavy chain.
SEQ ID NO: 101 is the amino acid sequence of DMAb-21 light chain.
SEQ ID NO: 102 is the nucleotide sequence of DMAb-21 light chain.
SEQ ID NO: 103 is the amino acid sequence of DMAb-22 heavy chain.
SEQ ID NO: 104 is the nucleotide sequence of DMAb-22 heavy chain.
SEQ ID NO: 105 is the amino acid sequence of DMAb-22 light chain.
SEQ ID NO: 106 is the nucleotide sequence of DMAb-22 light chain.
SEQ ID NO: 107 is the amino acid sequence of DMAb-24 heavy chain.
SEQ ID NO: 108 is the nucleotide sequence of DMAb-24 heavy chain.
SEQ ID NO: 109 is the amino acid sequence of DMAb-24 light chain.
SEQ ID NO: 110 is the nucleotide sequence of DMAb-24 light chain.
SEQ ID NO: 111 is the amino acid sequence of DMAb-25 heavy chain.
SEQ ID NO: 112 is the nucleotide sequence of DMAb-25 heavy chain.
SEQ ID NO: 113 is the amino acid sequence of DMAb-25 light chain.
SEQ ID NO: 114 is the nucleotide sequence of DMAb-25 light chain.
SEQ ID NO: 115 is the amino acid sequence of DMAb-26 heavy chain.
SEQ ID NO: 116 is the nucleotide sequence of DMAb-26 heavy chain.
SEQ ID NO: 117 is the amino acid sequence of DMAb-26 light chain.
SEQ ID NO: 118 is the nucleotide sequence of DMAb-26 light chain.
SEQ ID NO: 119 is the amino acid sequence of DMAb-27 heavy chain.
SEQ ID NO: 120 is the nucleotide sequence of DMAb-27 heavy chain.
SEQ ID NO: 121 is the amino acid sequence of DMAb-27 light chain.
SEQ ID NO: 122 is the nucleotide sequence of DMAb-27 light chain.
SEQ ID NO: 123 is the amino acid sequence of DMAb-28 heavy chain.
SEQ ID NO: 124 is the nucleotide sequence of DMAb-28 heavy chain.
SEQ ID NO: 125 is the amino acid sequence of DMAb-28 light chain.
SEQ ID NO: 126 is the nucleotide sequence of DMAb-28 light chain.
SEQ ID NO: 127 is the amino acid sequence of DMAb-29 heavy chain.
SEQ ID NO: 128 is the nucleotide sequence of DMAb-29 heavy chain.
SEQ ID NO: 129 is the amino acid sequence of DMAb-29 light chain.
SEQ ID NO: 130 is the nucleotide sequence of DMAb-29 light chain.
SEQ ID NO: 131 is the amino acid sequence of DMAb-31 heavy chain.
SEQ ID NO: 132 is the nucleotide sequence of DMAb-31 heavy chain.
SEQ ID NO: 133 is the amino acid sequence of DMAb-31 light chain.
SEQ ID NO: 134 is the nucleotide sequence of DMAb-31 light chain.
SEQ ID NO: 135 is the amino acid sequence of DMAb-32 heavy chain.
SEQ ID NO: 136 is the nucleotide sequence of DMAb-32 heavy chain.
SEQ ID NO: 137 is the amino acid sequence of DMAb-32 light chain.
SEQ ID NO: 138 is the nucleotide sequence of DMAb-32 light chain.
SEQ ID NO: 139 is the amino acid sequence of DMAb-33 heavy chain.
SEQ ID NO: 140 is the nucleotide sequence of DMAb-33 heavy chain.
SEQ ID NO: 141 is the amino acid sequence of DMAb-33 light chain.
SEQ ID NO: 142 is the nucleotide sequence of DMAb-33 light chain.
SEQ ID NO: 143 is the amino acid sequence of DMAb-35 heavy chain.
SEQ ID NO: 144 is the nucleotide sequence of DMAb-35 heavy chain.
SEQ ID NO: 145 is the amino acid sequence of DMAb-35 light chain.
SEQ ID NO: 146 is the nucleotide sequence of DMAb-35 light chain.

SEQ ID NO: 147 is the amino acid sequence of DMAb-36 heavy chain.
SEQ ID NO: 148 is the nucleotide sequence of DMAb-36 heavy chain.
SEQ ID NO: 149 is the amino acid sequence of DMAb-36 light chain.
SEQ ID NO: 150 is the nucleotide sequence of DMAb-36 light chain.
SEQ ID NO: 151 is the amino acid sequence of DMAb-37 heavy chain.
SEQ ID NO: 152 is the nucleotide sequence of DMAb-37 heavy chain.
SEQ ID NO: 153 is the amino acid sequence of DMAb-37 light chain.
SEQ ID NO: 154 is the nucleotide sequence of DMAb-37 light chain.
SEQ ID NO: 155 is the amino acid sequence of DMAb-38 heavy chain.
SEQ ID NO: 156 is the nucleotide sequence of DMAb-38 heavy chain.
SEQ ID NO: 157 is the amino acid sequence of DMAb-38 light chain.
SEQ ID NO: 158 is the nucleotide sequence of DMAb-38 light chain.
SEQ ID NO: 159 is the amino acid sequence of DMAb-39 heavy chain.
SEQ ID NO: 160 is the nucleotide sequence of DMAb-39 heavy chain.
SEQ ID NO: 161 is the amino acid sequence of DMAb-39 light chain.
SEQ ID NO: 162 is the nucleotide sequence of DMAb-39 light chain.
SEQ ID NO: 163 is the amino acid sequence of DMAb-40 heavy chain.
SEQ ID NO: 164 is the nucleotide sequence of DMAb-40 heavy chain.
SEQ ID NO: 165 is the amino acid sequence of DMAb-40 light chain.
SEQ ID NO: 166 is the nucleotide sequence of DMAb-40 light chain.
SEQ ID NO: 167 is the amino acid sequence of DMAb-41 heavy chain.
SEQ ID NO: 168 is the nucleotide sequence of DMAb-41 heavy chain.
SEQ ID NO: 169 is the amino acid sequence of DMAb-41 light chain.
SEQ ID NO: 170 is the nucleotide sequence of DMAb-41 light chain.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-Ebola Glycoprotein (anti-Ebola GP) antibody.

In one embodiment, the nucleotide sequence encoding an anti-Ebola GP antibody comprises one or more codon optimized nucleic acid sequences encoding an amino acid sequence at least 95% homologues to an amino acid sequence as set forth in one of SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO: 123, SEQ ID NO: 125, SEQ ID NO:

127, SEQ ID NO: 129, SEQ ID NO:131 and SEQ ID NO:133, SEQ ID NO:135, SEQ ID NO:137, SEQ ID NO:139, SEQ ID NO:141, SEQ ID NO: 143, SEQ ID NO: 145, SEQ ID NO: 147, SEQ ID NO: 149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, and SEQ ID NO:169, or a fragment thereof.

In one embodiment, the nucleotide sequence encoding an anti-Ebola GP antibody comprises one or more codon optimized nucleic acid sequences encoding an amino acid sequence as set forth in one of SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO: 103, SEQ ID NO: 105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO: 129, SEQ ID NO:131 and SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO: 149, SEQ ID NO:151, SEQ ID NO: 153, SEQ ID NO: 155, SEQ ID NO:157, SEQ ID NO:159, SEQ ID NO:161, SEQ ID NO:163, SEQ ID NO:165, SEQ ID NO:167, and SEQ ID NO:169, or a fragment thereof In one embodiment, the nucleotide sequence encoding an anti-Ebola GP antibody comprises one or more RNA sequence transcribed from one or more DNA sequences encoding an amino acid sequence at least 95% homologues to an amino acid sequence as set forth in one of SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO: 103, SEQ ID NO: 105, SEQ ID NO: 107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131 and SEQ ID NO:133, SEQ ID NO:135, SEQ ID NO:137, SEQ ID NO:139, SEQ ID NO:141, SEQ ID NO:143, SEQ ID NO: 145, SEQ ID NO: 147, SEQ ID NO:149, SEQ ID NO:151, SEQ ID NO: 153, SEQ ID NO: 155, SEQ ID NO: 157, SEQ ID NO:159, SEQ ID NO:161, SEQ ID NO:163, SEQ ID NO:165, SEQ ID NO:167, and SEQ ID NO:169, or a fragment thereof.

In one embodiment, the nucleotide sequence encoding an anti-Ebola GP antibody comprises one or more RNA sequence transcribed from one or more DNA sequences encoding an amino acid sequence as set forth in one of SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO: 123, SEQ ID NO: 125, SEQ ID NO: 127, SEQ ID NO:129, SEQ ID NO: 131 and SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO:151, SEQ ID NO: 153, SEQ ID NO: 155, SEQ ID NO: 157, SEQ ID NO:159, SEQ ID NO: 161, SEQ ID NO: 163, SEQ ID NO: 165, SEQ ID NO: 167, and SEQ ID NO: 169, or a fragment thereof.

In one embodiment, the nucleotide sequence encoding an anti-Ebola GP antibody comprises one or more codon optimized nucleic acid sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO:126, SEQ ID NO: 128, SEQ ID NO: 130, SEQ ID NO: 132, SEQ ID NO: 134, SEQ ID NO:136, SEQ ID NO:138, SEQ ID NO: 140, SEQ ID NO: 142, SEQ ID NO: 144, SEQ ID NO:146, SEQ ID NO: 148, SEQ ID NO: 150, SEQ ID NO: 152, SEQ ID NO: 154, SEQ ID NO:156, SEQ ID NO:158, SEQ ID NO:160, SEQ ID NO:162, SEQ ID NO:164, SEQ ID NO:166, SEQ ID NO: 168, and SEQ ID NO: 170, or a fragment thereof.

In one embodiment, the nucleotide sequence encoding an anti-Ebola GP antibody comprises one or more codon optimized nucleic acid sequences as set forth in SEQ ID NO:2, SEQ ID NO:4, SEQ ID NO:6, SEQ ID NO:8, SEQ ID NO:10, SEQ ID NO: 12, SEQ ID NO:14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO: 134, SEQ ID NO: 136, SEQ ID NO: 138, SEQ ID NO: 140, SEQ ID NO:142, SEQ ID NO: 144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, and SEQ ID NO:170, or a fragment thereof.

In one embodiment, the nucleotide sequence encoding an anti-Ebola GP antibody comprises one or more RNA sequence transcribed from one or more DNA sequences at least 95% homologous to one or more DNA sequences set forth in SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO: 126, SEQ ID NO:128, SEQ ID NO:130, SEQ ID NO:132, SEQ ID NO:134, SEQ ID NO: 136, SEQ ID NO: 138, SEQ ID NO: 140, SEQ ID NO: 142, SEQ ID NO:144, SEQ ID NO:146, SEQ ID NO:148, SEQ ID NO:150, SEQ ID NO:152, SEQ ID NO:154, SEQ ID NO: 156, SEQ ID NO: 158, SEQ ID NO: 160, SEQ ID NO: 162, SEQ ID NO:164, SEQ ID NO: 166, SEQ ID NO: 168, and SEQ ID NO: 170.

In one embodiment, the nucleotide sequence encoding an anti-Ebola GP antibody comprises one or more RNA sequence transcribed from one or more DNA sequences as set forth in SEQ ID NO:2, SEQ ID NO:4, SEQ ID NO:6, SEQ ID NO:8, SEQ ID NO: 10, SEQ ID NO:12, SEQ ID NO:14, SEQ ID NO: 16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO: 104, SEQ ID NO: 106, SEQ ID NO: 108, SEQ ID NO:110, SEQ ID NO:112, SEQ ID NO:114, SEQ ID NO:116, SEQ ID NO:118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO:138, SEQ ID NO: 140, SEQ ID NO: 142, SEQ ID NO:144, SEQ ID NO: 146, SEQ ID NO: 148, SEQ ID NO: 150, SEQ ID NO: 152, SEQ ID NO:154, SEQ ID NO: 156, SEQ ID NO:158, SEQ ID NO: 160, SEQ ID NO: 162, SEQ ID NO:164, SEQ ID NO: 166, SEQ ID NO: 168, and SEQ ID NO:170.

In one embodiment, the nucleic acid molecule comprises a nucleotide sequence encoding a variable heavy chain region and a nucleotide sequence encoding a variable light chain region of an anti-Ebola virus GP antibody. In one embodiment, the nucleotide sequence encoding a variable heavy chain region is a sequence encoding an amino acid sequence at least 95% identical to an amino acid sequence of SEQ ID NO: 15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO: 103, SEQ ID NO: 107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167. In one embodiment, the nucleotide sequence encoding a variable heavy chain region is a sequence encoding an amino acid sequence of SEQ ID NO: 15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO: 103, SEQ ID NO: 107, SEQ ID NO: 111, SEQ ID NO:115, SEQ ID NO:119, SEQ ID NO:123, SEQ ID NO: 127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO: 163, SEQ ID NO: 167.

In one embodiment, the nucleotide sequence encoding a variable light chain region is a sequence encoding an amino acid sequence at least 95% identical to an amino acid sequence of SEQ ID NO: 17, SEQ ID NO:21, SEQ ID NO:25, SEQ ID NO:29, SEQ ID NO:33, SEQ ID NO:37, SEQ ID NO:41, SEQ ID NO:45, SEQ ID NO:49, SEQ ID NO:53, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO:161, SEQ ID NO:165, SEQ ID NO:169. In one embodiment, the nucleotide sequence encoding a variable light chain region is a sequence encoding an amino acid sequence of SEQ ID NO: 17, SEQ ID NO:21, SEQ ID NO:25, SEQ ID NO:29, SEQ ID NO:33, SEQ ID NO:37, SEQ ID NO:41, SEQ ID NO:45, SEQ ID NO:49, SEQ ID NO:53, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO:161, SEQ ID NO:165, SEQ ID NO:169.

In one embodiment, the nucleotide sequence encoding a variable heavy chain region comprises a nucleic acid sequence at least 95% identical to one of SEQ ID NO: 16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO: 100, SEQ ID NO: 104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO: 160, SEQ ID NO:164, SEQ ID NO: 168. In one embodiment, the nucleotide sequence encoding a variable heavy chain region comprises a nucleic acid sequence of SEQ ID NO: 16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO: 100, SEQ ID NO: 104, SEQ ID NO: 108, SEQ ID NO: 112, SEQ ID NO: 116, SEQ ID NO:120, SEQ ID NO: 124, SEQ ID NO: 128, SEQ ID NO: 132, SEQ ID NO:136, SEQ ID NO: 140, SEQ ID NO:144, SEQ ID NO:148, SEQ ID NO:152, SEQ ID NO:156, SEQ ID NO:160, SEQ ID NO:164, and SEQ ID NO:168.

In one embodiment, the nucleotide sequence encoding a variable light chain region comprises a nucleic acid sequence at least 95% identical to one of SEQ ID NO: 18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, SEQ ID NO:62, SEQ ID NO:66, SEQ ID NO:70, SEQ ID NO:74, SEQ ID NO:78, SEQ ID NO:82, SEQ ID NO:86, SEQ ID NO:90, SEQ ID NO:94, SEQ ID NO:98, SEQ ID NO: 102, SEQ ID NO: 106, SEQ ID NO:110, SEQ ID NO:114, SEQ ID NO:118, SEQ ID NO:122, SEQ ID NO:126, SEQ ID NO:130, SEQ ID NO: 134, SEQ ID NO: 138, SEQ ID NO: 142, SEQ ID NO:146, SEQ ID NO:150, SEQ ID NO:154, SEQ ID NO:158, SEQ ID NO: 162, SEQ ID NO:166, SEQ ID NO: 170. In one embodiment, the nucleotide sequence encoding a variable light chain region comprises a nucleic acid sequence of SEQ ID NO: 18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, SEQ ID NO:62, SEQ ID NO:66, SEQ ID NO:70, SEQ ID NO:74, SEQ ID NO:78, SEQ ID NO:82, SEQ ID NO:86, SEQ ID NO:90, SEQ ID NO:94, SEQ ID NO:98, SEQ ID NO: 102, SEQ ID NO: 106, SEQ ID NO: 110, SEQ ID NO: 114, SEQ ID NO: 118, SEQ ID NO:122, SEQ ID NO: 126, SEQ ID NO: 130, SEQ ID NO: 134, SEQ ID NO:138, SEQ ID NO: 142, SEQ ID NO: 146, SEQ ID NO: 150, SEQ ID NO: 154, SEQ ID NO:158, SEQ ID NO:162, SEQ ID NO:166, SEQ ID NO:170.

In one embodiment, the nucleotide sequence encoding a variable heavy chain region comprises a nucleic acid sequence encoding an amino acid sequence at least 95% identical to SEQ ID NO: 15 and the nucleotide sequence encoding a variable light chain region comprises a nucleic acid sequence encoding an amino acid sequence at least 95% identical to SEQ ID NO: 17. In one embodiment, the nucleotide sequence encoding a variable heavy chain region comprises a nucleic acid sequence encoding an amino acid sequence of SEQ ID NO: 15 and the nucleotide sequence encoding a variable light chain region comprises a nucleic acid sequence encoding an amino acid sequence of SEQ ID NO: 17.

In one embodiment, the nucleotide sequence encoding a variable heavy chain region comprises a nucleic acid sequence at least 95% identical to SEQ ID NO: 16 and the nucleotide sequence encoding a variable light chain region comprises a nucleic acid sequence at least 95% identical to SEQ ID NO: 18. In one embodiment, the nucleotide sequence encoding a variable heavy chain region comprises a nucleic acid sequence of SEQ ID NO: 16 and the nucleotide sequence encoding a variable light chain region comprises a nucleic acid of SEQ ID NO: 18.

In one embodiment, the nucleotide sequence encoding a variable heavy chain region comprises a nucleic acid sequence encoding an amino acid sequence at least 95% identical to SEQ ID NO: 19 and the nucleotide sequence encoding a variable light chain region comprises a nucleic acid sequence encoding an amino acid sequence at least 95% identical to SEQ ID NO: 21. In one embodiment, the nucleotide sequence encoding a variable heavy chain region comprises a nucleic acid sequence encoding an amino acid sequence of SEQ ID NO: 19 and the nucleotide sequence encoding a variable light chain region comprises a nucleic acid sequence encoding an amino acid sequence of SEQ ID NO: 21.

In one embodiment, the nucleotide sequence encoding a variable heavy chain region comprises a nucleic acid sequence at least 95% identical to SEQ ID NO: 20 and the nucleotide sequence encoding a variable light chain region comprises a nucleic acid sequence at least 95% identical to SEQ ID NO: 22. In one embodiment, the nucleotide sequence encoding a variable heavy chain region comprises a nucleic acid sequence of SEQ ID NO: 20 and the nucleotide sequence encoding a variable light chain region comprises a nucleic acid of SEQ ID NO: 22.

In one embodiment, the nucleotide sequence encoding a variable heavy chain region comprises a nucleic acid sequence encoding an amino acid sequence at least 95% identical to SEQ ID NO: 23 and the nucleotide sequence encoding a variable light chain region comprises a nucleic acid sequence encoding an amino acid sequence at least 95% identical to SEQ ID NO: 25. In one embodiment, the nucleotide sequence encoding a variable heavy chain region comprises a nucleic acid sequence encoding an amino acid sequence of SEQ ID NO: 23 and the nucleotide sequence encoding a variable light chain region comprises a nucleic acid sequence encoding an amino acid sequence of SEQ ID NO: 25.

In one embodiment, the nucleotide sequence encoding a variable heavy chain region comprises a nucleic acid sequence at least 95% identical to SEQ ID NO: 24 and the nucleotide sequence encoding a variable light chain region comprises a nucleic acid sequence at least 95% identical to SEQ ID NO: 26. In one embodiment, the nucleotide sequence encoding a variable heavy chain region comprises a nucleic acid sequence of SEQ ID NO: 24 and the nucleotide sequence encoding a variable light chain region comprises a nucleic acid of SEQ ID NO: 26.

In one embodiment, the nucleotide sequence encoding a variable heavy chain region comprises a nucleic acid sequence encoding an amino acid sequence at least 95% identical to SEQ ID NO: 27 and the nucleotide sequence encoding a variable light chain region comprises a nucleic acid sequence encoding an amino acid sequence at least 95% identical to SEQ ID NO: 29. In one embodiment, the nucleotide sequence encoding a variable heavy chain region comprises a nucleic acid sequence encoding an amino acid sequence of SEQ ID NO: 27 and the nucleotide sequence encoding a variable light chain region comprises a nucleic acid sequence encoding an amino acid sequence of SEQ ID NO: 29.

In one embodiment, the nucleotide sequence encoding a variable heavy chain region comprises a nucleic acid sequence at least 95% identical to SEQ ID NO: 28 and the nucleotide sequence encoding a variable light chain region comprises a nucleic acid sequence at least 95% identical to SEQ ID NO: 30. In one embodiment, the nucleotide sequence encoding a variable heavy chain region comprises a nucleic acid sequence of SEQ ID NO: 28 and the nucleotide sequence encoding a variable light chain region comprises a nucleic acid of SEQ ID NO: 30.

In one embodiment, the nucleotide sequence encoding a variable heavy chain region comprises a nucleic acid sequence encoding an amino acid sequence at least 95% identical to SEQ ID NO: 31 and the nucleotide sequence encoding a variable light chain region comprises a nucleic acid sequence encoding an amino acid sequence at least 95% identical to SEQ ID NO: 33. In one embodiment, the nucleotide sequence encoding a variable heavy chain region comprises a nucleic acid sequence encoding an amino acid sequence of SEQ ID NO: 31 and the nucleotide sequence encoding a variable light chain region comprises a nucleic acid sequence encoding an amino acid sequence of SEQ ID NO: 33.

In one embodiment, the nucleotide sequence encoding a variable heavy chain region comprises a nucleic acid sequence at least 95% identical to SEQ ID NO: 32 and the nucleotide sequence encoding a variable light chain region comprises a nucleic acid sequence at least 95% identical to SEQ ID NO: 34. In one embodiment, the nucleotide sequence encoding a variable heavy chain region comprises a nucleic acid sequence of SEQ ID NO: 32 and the nucleotide sequence encoding a variable light chain region comprises a nucleic acid of SEQ ID NO: 34.

In one embodiment, the nucleotide sequence encoding a variable heavy chain region comprises a nucleic acid sequence encoding an amino acid sequence at least 95% identical to SEQ ID NO: 35 and the nucleotide sequence encoding a variable light chain region comprises a nucleic acid sequence encoding an amino acid sequence at least 95% identical to SEQ ID NO: 37. In one embodiment, the nucleotide sequence encoding a variable heavy chain region comprises a nucleic acid sequence encoding an amino acid sequence of SEQ ID NO: 35 and the nucleotide sequence encoding a variable light chain region comprises a nucleic acid sequence encoding an amino acid sequence of SEQ ID NO: 37.

In one embodiment, the nucleotide sequence encoding a variable heavy chain region comprises a nucleic acid sequence at least 95% identical to SEQ ID NO: 36 and the nucleotide sequence encoding a variable light chain region comprises a nucleic acid sequence at least 95% identical to SEQ ID NO: 38. In one embodiment, the nucleotide sequence encoding a variable heavy chain region comprises a nucleic acid sequence of SEQ ID NO: 36 and the nucleotide sequence encoding a variable light chain region comprises a nucleic acid of SEQ ID NO: 38.

In one embodiment, the nucleotide sequence encoding a variable heavy chain region comprises a nucleic acid sequence encoding an amino acid sequence at least 95% identical to SEQ ID NO: 39 and the nucleotide sequence encoding a variable light chain region comprises a nucleic acid sequence encoding an amino acid sequence at least 95% identical to SEQ ID NO: 41. In one embodiment, the nucleotide sequence encoding a variable heavy chain region comprises a nucleic acid sequence encoding an amino acid sequence of SEQ ID NO: 39 and the nucleotide sequence encoding a variable light chain region comprises a nucleic acid sequence encoding an amino acid sequence of SEQ ID NO: 41.

In one embodiment, the nucleotide sequence encoding a variable heavy chain region comprises a nucleic acid sequence at least 95% identical to SEQ ID NO: 40 and the nucleotide sequence encoding a variable light chain region comprises a nucleic acid sequence at least 95% identical to SEQ ID NO: 42. In one embodiment, the nucleotide sequence encoding a variable heavy chain region comprises a nucleic acid sequence of SEQ ID NO: 40 and the nucleotide sequence encoding a variable light chain region comprises a nucleic acid of SEQ ID NO: 42.

In one embodiment, the nucleotide sequence encoding a variable heavy chain region comprises a nucleic acid sequence encoding an amino acid sequence at least 95% identical to SEQ ID NO: 43 and the nucleotide sequence encoding a variable light chain region comprises a nucleic acid sequence encoding an amino acid sequence at least 95% identical to SEQ ID NO: 45. In one embodiment, the nucleotide sequence encoding a variable heavy chain region comprises a nucleic acid sequence encoding an amino acid sequence of SEQ ID NO: 43 and the nucleotide sequence encoding a variable light chain region comprises a nucleic acid sequence encoding an amino acid sequence of SEQ ID NO: 45.

In one embodiment, the nucleotide sequence encoding a variable heavy chain region comprises a nucleic acid sequence at least 95% identical to SEQ ID NO: 44 and the nucleotide sequence encoding a variable light chain region comprises a nucleic acid sequence at least 95% identical to SEQ ID NO: 46. In one embodiment, the nucleotide sequence encoding a variable heavy chain region comprises a nucleic acid sequence of SEQ ID NO: 44 and the nucleotide sequence encoding a variable light chain region comprises a nucleic acid of SEQ ID NO: 46.

In one embodiment, the nucleotide sequence encoding a variable heavy chain region comprises a nucleic acid sequence encoding an amino acid sequence at least 95% identical to SEQ ID NO: 47 and the nucleotide sequence encoding a variable light chain region comprises a nucleic acid sequence encoding an amino acid sequence at least 95% identical to SEQ ID NO: 49. In one embodiment, the nucleotide sequence encoding a variable heavy chain region comprises a nucleic acid sequence encoding an amino acid sequence of SEQ ID NO: 47 and the nucleotide sequence encoding a variable light chain region comprises a nucleic acid sequence encoding an amino acid sequence of SEQ ID NO: 49.

In one embodiment, the nucleotide sequence encoding a variable heavy chain region comprises a nucleic acid sequence at least 95% identical to SEQ ID NO: 48 and the nucleotide sequence encoding a variable light chain region comprises a nucleic acid sequence at least 95% identical to SEQ ID NO: 50. In one embodiment, the nucleotide sequence encoding a variable heavy chain region comprises a nucleic acid sequence of SEQ ID NO: 48 and the nucleotide sequence encoding a variable light chain region comprises a nucleic acid of SEQ ID NO: 50.

In one embodiment, the nucleotide sequence encoding a variable heavy chain region comprises a nucleic acid sequence encoding an amino acid sequence at least 95% identical to SEQ ID NO: 51 and the nucleotide sequence encoding a variable light chain region comprises a nucleic acid sequence encoding an amino acid sequence at least 95% identical to SEQ ID NO: 53. In one embodiment, the nucleotide sequence encoding a variable heavy chain region comprises a nucleic acid sequence encoding an amino acid sequence of SEQ ID NO: 51 and the nucleotide sequence encoding a variable light chain region comprises a nucleic acid sequence encoding an amino acid sequence of SEQ ID NO: 53.

In one embodiment, the nucleotide sequence encoding a variable heavy chain region comprises a nucleic acid sequence at least 95% identical to SEQ ID NO: 52 and the nucleotide sequence encoding a variable light chain region comprises a nucleic acid sequence at least 95% identical to SEQ ID NO: 54. In one embodiment, the nucleotide sequence encoding a variable heavy chain region comprises a nucleic acid sequence of SEQ ID NO: 52 and the nucleotide sequence encoding a variable light chain region comprises a nucleic acid of SEQ ID NO: 54.

In one embodiment, the nucleotide sequence encoding a variable heavy chain region comprises a nucleic acid sequence encoding an amino acid sequence at least 95% identical to SEQ ID NO: 55 and the nucleotide sequence encoding a variable light chain region comprises a nucleic acid sequence encoding an amino acid sequence at least 95% identical to SEQ ID NO: 57. In one embodiment, the nucleotide sequence encoding a variable heavy chain region comprises a nucleic acid sequence encoding an amino acid sequence of SEQ ID NO: 55 and the nucleotide sequence encoding a variable light chain region comprises a nucleic acid sequence encoding an amino acid sequence of SEQ ID NO: 57.

In one embodiment, the nucleotide sequence encoding a variable heavy chain region comprises a nucleic acid sequence at least 95% identical to SEQ ID NO: 56 and the nucleotide sequence encoding a variable light chain region comprises a nucleic acid sequence at least 95% identical to SEQ ID NO: 58. In one embodiment, the nucleotide sequence encoding a variable heavy chain region comprises a nucleic acid sequence of SEQ ID NO: 56 and the nucleotide sequence encoding a variable light chain region comprises a nucleic acid of SEQ ID NO: 58.

In one embodiment, the nucleotide sequence encoding a variable heavy chain region comprises a nucleic acid sequence encoding an amino acid sequence at least 95% identical to SEQ ID NO: 59 and the nucleotide sequence encoding a variable light chain region comprises a nucleic acid sequence encoding an amino acid sequence at least 95% identical to SEQ ID NO: 61. In one embodiment, the nucleotide sequence encoding a variable heavy chain region comprises a nucleic acid sequence encoding an amino acid sequence of SEQ ID NO: 59 and the nucleotide sequence encoding a variable light chain region comprises a nucleic acid sequence encoding an amino acid sequence of SEQ ID NO: 61.

In one embodiment, the nucleotide sequence encoding a variable heavy chain region comprises a nucleic acid sequence at least 95% identical to SEQ ID NO: 60 and the nucleotide sequence encoding a variable light chain region comprises a nucleic acid sequence at least 95% identical to SEQ ID NO: 62. In one embodiment, the nucleotide sequence encoding a variable heavy chain region comprises a nucleic acid sequence of SEQ ID NO: 60 and the nucleotide sequence encoding a variable light chain region comprises a nucleic acid of SEQ ID NO: 62.

In one embodiment, the nucleotide sequence encoding a variable heavy chain region comprises a nucleic acid sequence encoding an amino acid sequence at least 95% identical to SEQ ID NO: 63 and the nucleotide sequence encoding a variable light chain region comprises a nucleic acid sequence encoding an amino acid sequence at least 95% identical to SEQ ID NO: 65. In one embodiment, the nucleotide sequence encoding a variable heavy chain region comprises a nucleic acid sequence encoding an amino acid sequence of SEQ ID NO: 63 and the nucleotide sequence encoding a variable light chain region comprises a nucleic acid sequence encoding an amino acid sequence of SEQ ID NO: 65.

In one embodiment, the nucleotide sequence encoding a variable heavy chain region comprises a nucleic acid sequence at least 95% identical to SEQ ID NO: 64 and the nucleotide sequence encoding a variable light chain region comprises a nucleic acid sequence at least 95% identical to SEQ ID NO: 66. In one embodiment, the nucleotide sequence encoding a variable heavy chain region comprises a nucleic acid sequence of SEQ ID NO: 64 and the nucleotide sequence encoding a variable light chain region comprises a nucleic acid of SEQ ID NO: 66.

In one embodiment, the nucleotide sequence encoding a variable heavy chain region comprises a nucleic acid sequence encoding an amino acid sequence at least 95% identical to SEQ ID NO: 67 and the nucleotide sequence encoding a variable light chain region comprises a nucleic acid sequence encoding an amino acid sequence at least 95% identical to SEQ ID NO: 69. In one embodiment, the nucleotide sequence encoding a variable heavy chain region comprises a nucleic acid sequence encoding an amino acid sequence of SEQ ID NO: 67 and the nucleotide sequence encoding a variable light chain region comprises a nucleic acid sequence encoding an amino acid sequence of SEQ ID NO: 69.

In one embodiment, the nucleotide sequence encoding a variable heavy chain region comprises a nucleic acid sequence at least 95% identical to SEQ ID NO: 68 and the nucleotide sequence encoding a variable light chain region comprises a nucleic acid sequence at least 95% identical to SEQ ID NO: 70. In one embodiment, the nucleotide sequence encoding a variable heavy chain region comprises a nucleic acid sequence of SEQ ID NO: 68 and the nucleotide sequence encoding a variable light chain region comprises a nucleic acid of SEQ ID NO: 70.

In one embodiment, the nucleotide sequence encoding a variable heavy chain region comprises a nucleic acid sequence encoding an amino acid sequence at least 95% identical to SEQ ID NO: 71 and the nucleotide sequence encoding a variable light chain region comprises a nucleic acid sequence encoding an amino acid sequence at least 95% identical to SEQ ID NO: 73. In one embodiment, the nucleotide sequence encoding a variable heavy chain region comprises a nucleic acid sequence encoding an amino acid sequence of SEQ ID NO: 71 and the nucleotide sequence encoding a variable light chain region comprises a nucleic acid sequence encoding an amino acid sequence of SEQ ID NO: 73.

In one embodiment, the nucleotide sequence encoding a variable heavy chain region comprises a nucleic acid sequence at least 95% identical to SEQ ID NO: 72 and the nucleotide sequence encoding a variable light chain region comprises a nucleic acid sequence at least 95% identical to SEQ ID NO: 74. In one embodiment, the nucleotide sequence encoding a variable heavy chain region comprises a nucleic acid sequence of SEQ ID NO: 72 and the nucleotide sequence encoding a variable light chain region comprises a nucleic acid of SEQ ID NO: 74.

In one embodiment, the nucleotide sequence encoding a variable heavy chain region comprises a nucleic acid sequence encoding an amino acid sequence at least 95% identical to SEQ ID NO: 75 and the nucleotide sequence encoding a variable light chain region comprises a nucleic acid sequence encoding an amino acid sequence at least 95% identical to SEQ ID NO: 77. In one embodiment, the nucleotide sequence encoding a variable heavy chain region comprises a nucleic acid sequence encoding an amino acid sequence of SEQ ID NO: 75 and the nucleotide sequence encoding a variable light chain region comprises a nucleic acid sequence encoding an amino acid sequence of SEQ ID NO: 77.

In one embodiment, the nucleotide sequence encoding a variable heavy chain region comprises a nucleic acid sequence at least 95% identical to SEQ ID NO: 76 and the nucleotide sequence encoding a variable light chain region comprises a nucleic acid sequence at least 95% identical to SEQ ID NO: 78. In one embodiment, the nucleotide sequence encoding a variable heavy chain region comprises a nucleic acid sequence of SEQ ID NO: 76 and the nucleotide sequence encoding a variable light chain region comprises a nucleic acid of SEQ ID NO: 78.

In one embodiment, the nucleotide sequence encoding a variable heavy chain region comprises a nucleic acid sequence encoding an amino acid sequence at least 95% identical to SEQ ID NO: 79 and the nucleotide sequence encoding a variable light chain region comprises a nucleic acid sequence encoding an amino acid sequence at least 95% identical to SEQ ID NO: 81. In one embodiment, the nucleotide sequence encoding a variable heavy chain region comprises a nucleic acid sequence encoding an amino acid sequence of SEQ ID NO: 79 and the nucleotide sequence encoding a variable light chain region comprises a nucleic acid sequence encoding an amino acid sequence of SEQ ID NO: 81.

In one embodiment, the nucleotide sequence encoding a variable heavy chain region comprises a nucleic acid sequence at least 95% identical to SEQ ID NO: 80 and the nucleotide sequence encoding a variable light chain region comprises a nucleic acid sequence at least 95% identical to SEQ ID NO: 82. In one embodiment, the nucleotide sequence encoding a variable heavy chain region comprises a nucleic acid sequence of SEQ ID NO: 80 and the nucleotide sequence encoding a variable light chain region comprises a nucleic acid of SEQ ID NO: 82.

In one embodiment, the nucleotide sequence encoding a variable heavy chain region comprises a nucleic acid sequence encoding an amino acid sequence at least 95% identical to SEQ ID NO: 83 and the nucleotide sequence encoding a variable light chain region comprises a nucleic acid sequence encoding an amino acid sequence at least 95% identical to SEQ ID NO: 85. In one embodiment, the nucleotide sequence encoding a variable heavy chain region comprises a nucleic acid sequence encoding an amino acid sequence of SEQ ID NO: 83 and the nucleotide sequence encoding a variable light chain region comprises a nucleic acid sequence encoding an amino acid sequence of SEQ ID NO: 85.

In one embodiment, the nucleotide sequence encoding a variable heavy chain region comprises a nucleic acid sequence at least 95% identical to SEQ ID NO: 84 and the nucleotide sequence encoding a variable light chain region comprises a nucleic acid sequence at least 95% identical to SEQ ID NO: 86. In one embodiment, the nucleotide sequence encoding a variable heavy chain region comprises a nucleic acid sequence of SEQ ID NO: 84 and the nucleotide sequence encoding a variable light chain region comprises a nucleic acid of SEQ ID NO: 86.

In one embodiment, the nucleotide sequence encoding a variable heavy chain region comprises a nucleic acid sequence encoding an amino acid sequence at least 95% identical to SEQ ID NO: 87 and the nucleotide sequence encoding a variable light chain region comprises a nucleic acid sequence encoding an amino acid sequence at least 95% identical to SEQ ID NO: 89. In one embodiment, the nucleotide sequence encoding a variable heavy chain region comprises a nucleic acid sequence encoding an amino acid sequence of SEQ ID NO: 87 and the nucleotide sequence encoding a variable light chain region comprises a nucleic acid sequence encoding an amino acid sequence of SEQ ID NO: 89.

In one embodiment, the nucleotide sequence encoding a variable heavy chain region comprises a nucleic acid sequence at least 95% identical to SEQ ID NO: 88 and the nucleotide sequence encoding a variable light chain region comprises a nucleic acid sequence at least 95% identical to SEQ ID NO: 90. In one embodiment, the nucleotide sequence encoding a variable heavy chain region comprises a nucleic acid sequence of SEQ ID NO: 88 and the nucleotide sequence encoding a variable light chain region comprises a nucleic acid of SEQ ID NO: 90.

In one embodiment, the nucleotide sequence encoding a variable heavy chain region comprises a nucleic acid sequence encoding an amino acid sequence at least 95% identical to SEQ ID NO: 91 and the nucleotide sequence encoding a variable light chain region comprises a nucleic acid sequence encoding an amino acid sequence at least 95% identical to SEQ ID NO: 93. In one embodiment, the nucleotide sequence encoding a variable heavy chain region comprises a nucleic acid sequence encoding an amino acid sequence of SEQ ID NO: 91 and the nucleotide sequence encoding a variable light chain region comprises a nucleic acid sequence encoding an amino acid sequence of SEQ ID NO: 93.

In one embodiment, the nucleotide sequence encoding a variable heavy chain region comprises a nucleic acid sequence at least 95% identical to SEQ ID NO: 92 and the nucleotide sequence encoding a variable light chain region comprises a nucleic acid sequence at least 95% identical to SEQ ID NO: 94. In one embodiment, the nucleotide sequence encoding a variable heavy chain region comprises a nucleic acid sequence of SEQ ID NO: 92 and the nucleotide sequence encoding a variable light chain region comprises a nucleic acid of SEQ ID NO: 94.

In one embodiment, the nucleotide sequence encoding a variable heavy chain region comprises a nucleic acid sequence encoding an amino acid sequence at least 95% identical to SEQ ID NO: 95 and the nucleotide sequence encoding a variable light chain region comprises a nucleic acid sequence encoding an amino acid sequence at least 95% identical to SEQ ID NO: 97. In one embodiment, the nucleotide sequence encoding a variable heavy chain region comprises a nucleic acid sequence encoding an amino acid sequence of SEQ ID NO: 95 and the nucleotide sequence encoding a variable light chain region comprises a nucleic acid sequence encoding an amino acid sequence of SEQ ID NO: 97.

In one embodiment, the nucleotide sequence encoding a variable heavy chain region comprises a nucleic acid sequence at least 95% identical to SEQ ID NO: 96 and the nucleotide sequence encoding a variable light chain region comprises a nucleic acid sequence at least 95% identical to SEQ ID NO: 98. In one embodiment, the nucleotide sequence encoding a variable heavy chain region comprises a nucleic acid sequence of SEQ ID NO: 96 and the nucleotide sequence encoding a variable light chain region comprises a nucleic acid of SEQ ID NO: 98.

In one embodiment, the nucleotide sequence encoding a variable heavy chain region comprises a nucleic acid sequence encoding an amino acid sequence at least 95% identical to SEQ ID NO: 99 and the nucleotide sequence encoding a variable light chain region comprises a nucleic acid sequence encoding an amino acid sequence at least 95% identical to SEQ ID NO: 101. In one embodiment, the nucleotide sequence encoding a variable heavy chain region comprises a nucleic acid sequence encoding an amino acid sequence of SEQ ID NO: 99 and the nucleotide sequence encoding a variable light chain region comprises a nucleic acid sequence encoding an amino acid sequence of SEQ ID NO: 101.

In one embodiment, the nucleotide sequence encoding a variable heavy chain region comprises a nucleic acid sequence at least 95% identical to SEQ ID NO: 100 and the nucleotide sequence encoding a variable light chain region comprises a nucleic acid sequence at least 95% identical to SEQ ID NO: 102. In one embodiment, the nucleotide sequence encoding a variable heavy chain region comprises a nucleic acid sequence of SEQ ID NO: 100 and the nucleotide sequence encoding a variable light chain region comprises a nucleic acid of SEQ ID NO: 102.

In one embodiment, the nucleotide sequence encoding a variable heavy chain region comprises a nucleic acid sequence encoding an amino acid sequence at least 95% identical to SEQ ID NO: 103 and the nucleotide sequence encoding a variable light chain region comprises a nucleic acid sequence encoding an amino acid sequence at least 95% identical to SEQ ID NO: 105. In one embodiment, the nucleotide sequence encoding a variable heavy chain region comprises a nucleic acid sequence encoding an amino acid sequence of SEQ ID NO: 103 and the nucleotide sequence encoding a variable light chain region comprises a nucleic acid sequence encoding an amino acid sequence of SEQ ID NO: 105.

In one embodiment, the nucleotide sequence encoding a variable heavy chain region comprises a nucleic acid sequence at least 95% identical to SEQ ID NO: 104 and the nucleotide sequence encoding a variable light chain region comprises a nucleic acid sequence at least 95% identical to SEQ ID NO: 106. In one embodiment, the nucleotide sequence encoding a variable heavy chain region comprises a nucleic acid sequence of SEQ ID NO: 104 and the nucleotide sequence encoding a variable light chain region comprises a nucleic acid of SEQ ID NO: 106.

In one embodiment, the nucleotide sequence encoding a variable heavy chain region comprises a nucleic acid sequence encoding an amino acid sequence at least 95% identical to SEQ ID NO: 107 and the nucleotide sequence encoding a variable light chain region comprises a nucleic acid sequence encoding an amino acid sequence at least 95% identical to SEQ ID NO: 109. In one embodiment, the nucleotide sequence encoding a variable heavy chain region comprises a nucleic acid sequence encoding an amino acid sequence of SEQ ID NO: 107 and the nucleotide sequence encoding a variable light chain region comprises a nucleic acid sequence encoding an amino acid sequence of SEQ ID NO: 109.

In one embodiment, the nucleotide sequence encoding a variable heavy chain region comprises a nucleic acid sequence at least 95% identical to SEQ ID NO: 108 and the nucleotide sequence encoding a variable light chain region comprises a nucleic acid sequence at least 95% identical to SEQ ID NO: 110. In one embodiment, the nucleotide sequence encoding a variable heavy chain region comprises a nucleic acid sequence of SEQ ID NO: 108 and the nucleotide sequence encoding a variable light chain region comprises a nucleic acid of SEQ ID NO: 110.

In one embodiment, the nucleotide sequence encoding a variable heavy chain region comprises a nucleic acid sequence encoding an amino acid sequence at least 95% identical to SEQ ID NO: 111 and the nucleotide sequence encoding a variable light chain region comprises a nucleic acid sequence encoding an amino acid sequence at least 95% identical to SEQ ID NO: 113. In one embodiment, the nucleotide sequence encoding a variable heavy chain region comprises a nucleic acid sequence encoding an amino acid sequence of SEQ ID NO: 111 and the nucleotide sequence encoding a variable light chain region comprises a nucleic acid sequence encoding an amino acid sequence of SEQ ID NO: 113.

In one embodiment, the nucleotide sequence encoding a variable heavy chain region comprises a nucleic acid sequence at least 95% identical to SEQ ID NO: 112 and the nucleotide sequence encoding a variable light chain region comprises a nucleic acid sequence at least 95% identical to SEQ ID NO: 114. In one embodiment, the nucleotide sequence encoding a variable heavy chain region comprises a nucleic acid sequence of SEQ ID NO: 112 and the nucleotide sequence encoding a variable light chain region comprises a nucleic acid of SEQ ID NO: 114.

In one embodiment, the nucleotide sequence encoding a variable heavy chain region comprises a nucleic acid sequence encoding an amino acid sequence at least 95% identical to SEQ ID NO: 115 and the nucleotide sequence encoding a variable light chain region comprises a nucleic acid sequence encoding an amino acid sequence at least 95% identical to SEQ ID NO: 117. In one embodiment, the nucleotide sequence encoding a variable heavy chain region comprises a nucleic acid sequence encoding an amino acid sequence of SEQ ID NO: 115 and the nucleotide sequence encoding a variable light chain region comprises a nucleic acid sequence encoding an amino acid sequence of SEQ ID NO: 117.

In one embodiment, the nucleotide sequence encoding a variable heavy chain region comprises a nucleic acid sequence at least 95% identical to SEQ ID NO: 116 and the nucleotide sequence encoding a variable light chain region comprises a nucleic acid sequence at least 95% identical to SEQ ID NO: 118. In one embodiment, the nucleotide sequence encoding a variable heavy chain region comprises a nucleic acid sequence of SEQ ID NO: 116 and the nucleotide sequence encoding a variable light chain region comprises a nucleic acid of SEQ ID NO: 118.

In one embodiment, the nucleotide sequence encoding a variable heavy chain region comprises a nucleic acid sequence encoding an amino acid sequence at least 95% identical to SEQ ID NO: 119 and the nucleotide sequence encoding a variable light chain region comprises a nucleic acid sequence encoding an amino acid sequence at least 95% identical to SEQ ID NO: 121. In one embodiment, the nucleotide sequence encoding a variable heavy chain region comprises a nucleic acid sequence encoding an amino acid sequence of SEQ ID NO: 119 and the nucleotide sequence encoding a variable light chain region comprises a nucleic acid sequence encoding an amino acid sequence of SEQ ID NO: 121.

In one embodiment, the nucleotide sequence encoding a variable heavy chain region comprises a nucleic acid sequence at least 95% identical to SEQ ID NO: 120 and the nucleotide sequence encoding a variable light chain region comprises a nucleic acid sequence at least 95% identical to SEQ ID NO: 122. In one embodiment, the nucleotide sequence encoding a variable heavy chain region comprises a nucleic acid sequence of SEQ ID NO: 120 and the nucleotide sequence encoding a variable light chain region comprises a nucleic acid of SEQ ID NO: 122.

In one embodiment, the nucleotide sequence encoding a variable heavy chain region comprises a nucleic acid sequence encoding an amino acid sequence at least 95% identical to SEQ ID NO: 123 and the nucleotide sequence encoding a variable light chain region comprises a nucleic acid sequence encoding an amino acid sequence at least 95% identical to SEQ ID NO: 125. In one embodiment, the nucleotide sequence encoding a variable heavy chain region comprises a nucleic acid sequence encoding an amino acid sequence of SEQ ID NO: 123 and the nucleotide sequence encoding a variable light chain region comprises a nucleic acid sequence encoding an amino acid sequence of SEQ ID NO: 125.

In one embodiment, the nucleotide sequence encoding a variable heavy chain region comprises a nucleic acid sequence at least 95% identical to SEQ ID NO: 124 and the nucleotide sequence encoding a variable light chain region comprises a nucleic acid sequence at least 95% identical to SEQ ID NO: 126. In one embodiment, the nucleotide sequence encoding a variable heavy chain region comprises a nucleic acid sequence of SEQ ID NO: 124 and the nucleotide sequence encoding a variable light chain region comprises a nucleic acid of SEQ ID NO: 126.

In one embodiment, the nucleotide sequence encoding a variable heavy chain region comprises a nucleic acid sequence encoding an amino acid sequence at least 95% identical to SEQ ID NO: 127 and the nucleotide sequence encoding a variable light chain region comprises a nucleic acid sequence encoding an amino acid sequence at least 95% identical to SEQ ID NO: 129. In one embodiment, the nucleotide sequence encoding a variable heavy chain region comprises a nucleic acid sequence encoding an amino acid sequence of SEQ ID NO: 127 and the nucleotide sequence encoding a variable light chain region comprises a nucleic acid sequence encoding an amino acid sequence of SEQ ID NO: 129.

In one embodiment, the nucleotide sequence encoding a variable heavy chain region comprises a nucleic acid sequence at least 95% identical to SEQ ID NO: 128 and the nucleotide sequence encoding a variable light chain region comprises a nucleic acid sequence at least 95% identical to SEQ ID NO: 130. In one embodiment, the nucleotide sequence encoding a variable heavy chain region comprises a nucleic acid sequence of SEQ ID NO: 128 and the nucleotide sequence encoding a variable light chain region comprises a nucleic acid of SEQ ID NO: 130.

In one embodiment, the nucleotide sequence encoding a variable heavy chain region comprises a nucleic acid sequence encoding an amino acid sequence at least 95% identical to SEQ ID NO: 131 and the nucleotide sequence encoding a variable light chain region comprises a nucleic acid sequence encoding an amino acid sequence at least 95% identical to SEQ ID NO: 133. In one embodiment, the nucleotide sequence encoding a variable heavy chain region comprises a nucleic acid sequence encoding an amino acid sequence of SEQ ID NO: 131 and the nucleotide sequence encoding a variable light chain region comprises a nucleic acid sequence encoding an amino acid sequence of SEQ ID NO: 133.

In one embodiment, the nucleotide sequence encoding a variable heavy chain region comprises a nucleic acid sequence at least 95% identical to SEQ ID NO: 132 and the nucleotide sequence encoding a variable light chain region comprises a nucleic acid sequence at least 95% identical to SEQ ID NO: 134. In one embodiment, the nucleotide sequence encoding a variable heavy chain region comprises a nucleic acid sequence of SEQ ID NO: 132 and the nucleotide sequence encoding a variable light chain region comprises a nucleic acid of SEQ ID NO: 134.

In one embodiment, the nucleotide sequence encoding a variable heavy chain region comprises a nucleic acid sequence encoding an amino acid sequence at least 95% identical to SEQ ID NO: 135 and the nucleotide sequence encoding a variable light chain region comprises a nucleic acid sequence encoding an amino acid sequence at least 95% identical to SEQ ID NO: 137. In one embodiment, the nucleotide sequence encoding a variable heavy chain region comprises a nucleic acid sequence encoding an amino acid sequence of SEQ ID NO: 135 and the nucleotide sequence encoding a variable light chain region comprises a nucleic acid sequence encoding an amino acid sequence of SEQ ID NO: 137.

In one embodiment, the nucleotide sequence encoding a variable heavy chain region comprises a nucleic acid sequence at least 95% identical to SEQ ID NO: 136 and the nucleotide sequence encoding a variable light chain region comprises a nucleic acid sequence at least 95% identical to SEQ ID NO: 138. In one embodiment, the nucleotide sequence encoding a variable heavy chain region comprises a nucleic acid sequence of SEQ ID NO: 136 and the nucleotide sequence encoding a variable light chain region comprises a nucleic acid of SEQ ID NO: 138.

In one embodiment, the nucleotide sequence encoding a variable heavy chain region comprises a nucleic acid sequence encoding an amino acid sequence at least 95% identical to SEQ ID NO: 139 and the nucleotide sequence encoding a variable light chain region comprises a nucleic acid sequence encoding an amino acid sequence at least 95% identical to SEQ ID NO: 141. In one embodiment, the nucleotide sequence encoding a variable heavy chain region comprises a nucleic acid sequence encoding an amino acid sequence of SEQ ID NO: 139 and the nucleotide sequence encoding a variable light chain region comprises a nucleic acid sequence encoding an amino acid sequence of SEQ ID NO: 141.

In one embodiment, the nucleotide sequence encoding a variable heavy chain region comprises a nucleic acid sequence at least 95% identical to SEQ ID NO: 140 and the nucleotide sequence encoding a variable light chain region comprises a nucleic acid sequence at least 95% identical to SEQ ID NO: 142. In one embodiment, the nucleotide sequence encoding a variable heavy chain region comprises a nucleic acid sequence of SEQ ID NO: 140 and the nucleotide sequence encoding a variable light chain region comprises a nucleic acid of SEQ ID NO: 142.

In one embodiment, the nucleotide sequence encoding a variable heavy chain region comprises a nucleic acid sequence encoding an amino acid sequence at least 95% identical to SEQ ID NO: 143 and the nucleotide sequence encoding a variable light chain region comprises a nucleic acid sequence encoding an amino acid sequence at least 95% identical to SEQ ID NO: 145. In one embodiment, the nucleotide sequence encoding a variable heavy chain region comprises a nucleic acid sequence encoding an amino acid sequence of SEQ ID NO: 143 and the nucleotide sequence encoding a variable light chain region comprises a nucleic acid sequence encoding an amino acid sequence of SEQ ID NO: 145.

In one embodiment, the nucleotide sequence encoding a variable heavy chain region comprises a nucleic acid sequence at least 95% identical to SEQ ID NO: 144 and the nucleotide sequence encoding a variable light chain region comprises a nucleic acid sequence at least 95% identical to SEQ ID NO: 146. In one embodiment, the nucleotide sequence encoding a variable heavy chain region comprises a nucleic acid sequence of SEQ ID NO: 144 and the nucleotide sequence encoding a variable light chain region comprises a nucleic acid of SEQ ID NO: 146.

In one embodiment, the nucleotide sequence encoding a variable heavy chain region comprises a nucleic acid sequence encoding an amino acid sequence at least 95% identical to SEQ ID NO: 147 and the nucleotide sequence encoding a variable light chain region comprises a nucleic acid sequence encoding an amino acid sequence at least 95% identical to SEQ ID NO: 149. In one embodiment, the nucleotide sequence encoding a variable heavy chain region comprises a nucleic acid sequence encoding an amino acid sequence of SEQ ID NO: 147 and the nucleotide sequence encoding a variable light chain region comprises a nucleic acid sequence encoding an amino acid sequence of SEQ ID NO: 149.

In one embodiment, the nucleotide sequence encoding a variable heavy chain region comprises a nucleic acid sequence at least 95% identical to SEQ ID NO: 148 and the nucleotide sequence encoding a variable light chain region comprises a nucleic acid sequence at least 95% identical to SEQ ID NO: 150. In one embodiment, the nucleotide sequence encoding a variable heavy chain region comprises a nucleic acid sequence of SEQ ID NO: 148 and the nucleotide sequence encoding a variable light chain region comprises a nucleic acid of SEQ ID NO: 150.

In one embodiment, the nucleotide sequence encoding a variable heavy chain region comprises a nucleic acid sequence encoding an amino acid sequence at least 95% identical to SEQ ID NO: 151 and the nucleotide sequence encoding a variable light chain region comprises a nucleic acid sequence encoding an amino acid sequence at least 95% identical to SEQ ID NO: 153. In one embodiment, the nucleotide sequence encoding a variable heavy chain region comprises a nucleic acid sequence encoding an amino acid sequence of SEQ ID NO: 151 and the nucleotide sequence encoding a variable light chain region comprises a nucleic acid sequence encoding an amino acid sequence of SEQ ID NO: 153.

In one embodiment, the nucleotide sequence encoding a variable heavy chain region comprises a nucleic acid sequence at least 95% identical to SEQ ID NO: 152 and the nucleotide sequence encoding a variable light chain region comprises a nucleic acid sequence at least 95% identical to SEQ ID NO: 154. In one embodiment, the nucleotide sequence encoding a variable heavy chain region comprises a nucleic acid sequence of SEQ ID NO: 152 and the nucleotide sequence encoding a variable light chain region comprises a nucleic acid of SEQ ID NO: 154.

In one embodiment, the nucleotide sequence encoding a variable heavy chain region comprises a nucleic acid sequence encoding an amino acid sequence at least 95% identical to SEQ ID NO: 155 and the nucleotide sequence encoding a variable light chain region comprises a nucleic acid sequence encoding an amino acid sequence at least 95% identical to SEQ ID NO: 157. In one embodiment, the nucleotide sequence encoding a variable heavy chain region comprises a nucleic acid sequence encoding an amino acid sequence of SEQ ID NO: 155 and the nucleotide sequence encoding a variable light chain region comprises a nucleic acid sequence encoding an amino acid sequence of SEQ ID NO: 157.

In one embodiment, the nucleotide sequence encoding a variable heavy chain region comprises a nucleic acid sequence at least 95% identical to SEQ ID NO: 156 and the nucleotide sequence encoding a variable light chain region comprises a nucleic acid sequence at least 95% identical to SEQ ID NO: 158. In one embodiment, the nucleotide sequence encoding a variable heavy chain region comprises a nucleic acid sequence of SEQ ID NO: 156 and the nucleotide sequence encoding a variable light chain region comprises a nucleic acid of SEQ ID NO: 158.

In one embodiment, the nucleotide sequence encoding a variable heavy chain region comprises a nucleic acid sequence encoding an amino acid sequence at least 95% identical to SEQ ID NO: 159 and the nucleotide sequence encoding a variable light chain region comprises a nucleic acid sequence encoding an amino acid sequence at least 95% identical to SEQ ID NO: 161. In one embodiment, the nucleotide sequence encoding a variable heavy chain region comprises a nucleic acid sequence encoding an amino acid sequence of SEQ ID NO: 159 and the nucleotide sequence encoding a variable light chain region comprises a nucleic acid sequence encoding an amino acid sequence of SEQ ID NO: 161.

In one embodiment, the nucleotide sequence encoding a variable heavy chain region comprises a nucleic acid sequence at least 95% identical to SEQ ID NO: 160 and the nucleotide sequence encoding a variable light chain region comprises a nucleic acid sequence at least 95% identical to SEQ ID NO: 162. In one embodiment, the nucleotide sequence encoding a variable heavy chain region comprises a nucleic acid sequence of SEQ ID NO: 160 and the nucleotide sequence encoding a variable light chain region comprises a nucleic acid of SEQ ID NO: 162.

In one embodiment, the nucleotide sequence encoding a variable heavy chain region comprises a nucleic acid sequence encoding an amino acid sequence at least 95% identical to SEQ ID NO: 163 and the nucleotide sequence encoding a variable light chain region comprises a nucleic acid sequence encoding an amino acid sequence at least 95% identical to SEQ ID NO: 165. In one embodiment, the nucleotide sequence encoding a variable heavy chain region comprises a nucleic acid sequence encoding an amino acid sequence of SEQ ID NO: 163 and the nucleotide sequence encoding a variable light chain region comprises a nucleic acid sequence encoding an amino acid sequence of SEQ ID NO: 165.

In one embodiment, the nucleotide sequence encoding a variable heavy chain region comprises a nucleic acid sequence at least 95% identical to SEQ ID NO: 164 and the nucleotide sequence encoding a variable light chain region comprises a nucleic acid sequence at least 95% identical to SEQ ID NO: 166. In one embodiment, the nucleotide sequence encoding a variable heavy chain region comprises a nucleic acid sequence of SEQ ID NO: 164 and the nucleotide sequence encoding a variable light chain region comprises a nucleic acid of SEQ ID NO: 166.

In one embodiment, the nucleotide sequence encoding a variable heavy chain region comprises a nucleic acid sequence encoding an amino acid sequence at least 95% identical to SEQ ID NO: 167 and the nucleotide sequence encoding a variable light chain region comprises a nucleic acid sequence encoding an amino acid sequence at least 95% identical to SEQ ID NO: 169. In one embodiment, the nucleotide sequence encoding a variable heavy chain region comprises a nucleic acid sequence encoding an amino acid sequence of SEQ ID NO: 167 and the nucleotide sequence encoding a variable light chain region comprises a nucleic acid sequence encoding an amino acid sequence of SEQ ID NO: 169.

In one embodiment, the nucleotide sequence encoding a variable heavy chain region comprises a nucleic acid sequence at least 95% identical to SEQ ID NO: 168 and the nucleotide sequence encoding a variable light chain region comprises a nucleic acid sequence at least 95% identical to SEQ ID NO: 170. In one embodiment, the nucleotide sequence encoding a variable heavy chain region comprises a nucleic acid sequence of SEQ ID NO: 168 and the nucleotide sequence encoding a variable light chain region comprises a nucleic acid of SEQ ID NO: 170.

The composition of the invention can treat, prevent and/or protect against any disease, disorder, or condition associated with Ebola infection. In certain embodiments, the composition can treat, prevent, and or/protect against viral infection. In certain embodiments, the composition can treat, prevent, and or/protect against condition associated with Ebola infection.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. RECOMBINANT NUCLEIC ACID SEQUENCE

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region.

Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(12) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide. For example, in one embodiment, the first recombinant nucleic acid sequence encodes a heavy chain polypeptide having an amino acid sequence at least 95% homologous to one of SEQ ID NO: 15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO: 103, SEQ ID NO: 107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, and SEQ ID NO:167. In one embodiment, the first recombinant nucleic acid sequence comprises a nucleic acid sequence at least 95% homologous to one of SEQ ID NO: 16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO: 100, SEQ ID NO: 104, SEQ ID NO: 108, SEQ ID NO: 112, SEQ ID NO: 116, SEQ ID NO:120, SEQ ID NO: 124, SEQ ID NO: 128, SEQ ID NO: 132, SEQ ID NO:136, SEQ ID NO: 140, SEQ ID NO:144, SEQ ID NO:148, SEQ ID NO:152, SEQ ID NO:156, SEQ ID NO:160, SEQ ID NO:164, and SEQ ID NO:168. In one embodiment, the second recombinant nucleic acid sequence encodes a light chain polypeptide having an amino acid sequence at least 95% homologous to one of SEQ ID NO: 17, SEQ ID NO:21, SEQ ID NO:25, SEQ ID NO:29, SEQ ID NO:33, SEQ ID NO:37, SEQ ID NO:41, SEQ ID NO:45, SEQ ID NO:49, SEQ ID NO:53, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO: 105, SEQ ID NO: 109, SEQ ID NO:113, SEQ ID NO:117, SEQ ID NO:121, SEQ ID NO:125, SEQ ID NO:129, SEQ ID NO:133, SEQ ID NO:137, SEQ ID NO:141, SEQ ID NO:145, SEQ ID NO:149, SEQ ID NO:153, SEQ ID NO:157, SEQ ID NO:161, SEQ ID NO:165, and SEQ ID NO:169. In one embodiment, the second recombinant nucleic acid sequence comprises a nucleic acid sequence at least 95% homologous to one of SEQ ID NO: 18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, SEQ ID NO:62, SEQ ID NO:66, SEQ ID NO:70, SEQ ID NO:74, SEQ ID NO:78, SEQ ID NO:82, SEQ ID NO:86, SEQ ID NO:90, SEQ ID NO:94, SEQ ID NO:98, SEQ ID NO: 102, SEQ ID NO: 106, SEQ ID NO: 110, SEQ ID NO: 114, SEQ ID NO:118, SEQ ID NO: 122, SEQ ID NO: 126, SEQ ID NO: 130, SEQ ID NO:134, SEQ ID NO:138, SEQ ID NO:142, SEQ ID NO:146, SEQ ID NO:150, SEQ ID NO:154, SEQ ID NO:158, SEQ ID NO:162, SEQ ID NO:166, and SEQ ID NO:170.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(13) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(14) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(15) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA1 or pcDNA3 (Invitrogen, San Diego, Calif.), which may be used for protein production in mammalian cells such as Chinese hamster ovary (CHO) cells.

(16) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID Nos.: 2, 4, 6, 8, 10, 12, 14, 16, 18, 20, 22, 24, 26, 28, 30, 32, 34, 38, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 138, 140, 142, 144, 146, 148, 150, 152, 154, 156, 158, 160, 162, 164, 166, 168, or 170. In another embodiment, the nucleotide sequence comprises an RNA sequence transcribed by a DNA sequence encoding a polypeptide sequence of SEQ ID Nos.: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, or 169. or a variant thereof or a fragment thereof. Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(17) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be pcrM2. The LEC can be pcrNP. pcrNP and pcrMR can be derived from pNP (Puerto Rico/34) and pM2 (New Caledonia/99), respectively.

(18) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(19) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. ANTIBODY

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

In one embodiment, the antibody binds an ebolavirus antigen. In one embodiment, the antibody binds an ebolavirus glycoprotein. In one embodiment, the antibody binds at least one an epitope of an ebolavirus glycoprotein. For example, in one embodiment, the antibody binds ebolavirus glycoprotein epitope comprising the reside W531, 1527, or both.

The antibody may be modified to reduce or prevent antibody-dependent enhancement (ADE) of disease associated with the antigen as described in more detail below.

Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

The invention provides novel bispecific antibodies comprising a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

In one embodiment, the bispecific antibody is a bivalent antibody comprising a) a first light chain and a first heavy chain of an antibody specifically binding to a first antigen, and b) a second light chain and a second heavy chain of an antibody specifically binding to a second antigen.

A bispecific antibody molecule according to the invention may have two binding sites of any desired specificity. In some embodiments one of the binding sites is capable of binding a tumor associated antigen. In some embodiments, the binding site included in the Fab fragment is a binding site specific for a Ebolavirus antigen. In some embodiments, the binding site included in the single chain Fv fragment is a binding site specific for a Ebolavirus antigen such as a Ebolavirus glycoprotein antigen.

In some embodiments, one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally monovalent, encompassing .alpha.- and .beta.-chains, in some embodiments it encompasses .gamma.-chains and .delta.-chains (supra). Accordingly, in some embodiments the TCR is TCR (alpha/beta) and in some embodiments it is TCR (gamma/delta). The T cell receptor forms a complex with the CD3 T-Cell co-receptor. CD3 is a protein complex and is composed of four distinct chains. In mammals, the complex contains a CD3γ chain, a CD3δ chain, and two CD3ε chains. These chains associate with a molecule known as the T cell receptor (TCR) and the c-chain to generate an activation signal in T lymphocytes. Hence, in some embodiments a T-cell specific receptor is the CD3 T-Cell co-receptor. In some embodiments, a T-cell specific receptor is CD28, a protein that is also expressed on T cells. CD28 can provide co-stimulatory signals, which are required for T cell activation. CD28 plays important roles in T-cell proliferation and survival, cytokine production, and T-helper type-2 development. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments, the first binding site of the antibody molecule binds a Ebolavirus antigen and the second binding site binds a T cell specific receptor molecule and/or a natural killer (NK) cell specific receptor molecule.

In some embodiments, the first binding site of the antibody molecule binds one of Ebolavirus GP glycan cap, Ebolavirus GP fusion loop, or Ebolavirus GP chalice base, and the second binding site binds a T cell specific receptor molecule and/or a natural killer (NK) cell specific receptor molecule. In some embodiments, the first binding site of the antibody molecule binds a Ebolavirus antigen and the second binding site binds one of CD3, the T cell receptor (TCR), CD28, CD16, NKG2D, Ox40, 4-1BB, CD2, CD5 and CD95.

In some embodiments, the first binding site of the antibody molecule binds a T cell specific receptor molecule and/or a natural killer (NK) cell specific receptor molecule and the second binding site binds an Ebolavirus antigen. In some embodiments, the first binding site of the antibody binds a T cell specific receptor molecule and/or a natural killer (NK) cell specific receptor molecule and the second binding site binds one of Ebolavirus GP glycan cap, Ebolavirus GP fusion loop, or Ebolavirus GP chalice base. In some embodiments, the first binding site of the antibody binds one of CD3, the T cell receptor (TCR), CD28, CD16, NKG2D, Ox40, 4-1BB, CD2, CD5 and CD95, and the second binding site binds an Ebolavirus antigen.

Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

5. ANTIGEN

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with Ebola infection. In one embodiment, the antigen can be an Ebola glycoprotein.

In one embodiment, the antigen can be a fragment of an Ebola glycoprotein. For example, in one embodiment, the antigen is a fragment of an Ebola glycoprotein, wherein the fragment comprises the amino acid Trp531. In one embodiment, the antigen is a fragment of an Ebola glycoprotein, wherein the fragment comprises the amino acid Ile527. In one embodiment, the antigen is a fragment of an Ebola glycoprotein, wherein the fragment comprises the amino acids Trp531 and Ile527.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

Viral Antigens

The viral antigen can be a viral antigen or fragment or variant thereof. The virus can be a disease causing virus. The virus can be the Ebola virus.

The antigen may be a Ebola viral antigen, or fragment thereof, or variant thereof. The Ebola antigen can be from a factor that allows the virus to replicate, infect or survive. Factors that allow a Ebola virus to replicate or survive include, but are not limited to structural proteins and non-structural proteins. Such a protein can be an envelope protein or a glycoprotein.

In one embodiment, an envelope protein is Ebola GP.

6. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Serial No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and U.S. Provisional Application Ser. No. 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. METHOD OF TREATMENT

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing a Ebola Virus infection. In one embodiment, the method treats, protects against, and/or prevents a disease associated with Ebola Virus.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. In one embodiment, the synthetic antibody can provide increased survival of the disease in the subject over the expected survival of a subject having the disease who has not been administered the synthetic antibody. In various embodiments, the synthetic antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the synthetic antibody can provide increased protection against the disease in the subject over the expected protection of a subject who has not been administered the synthetic antibody. In various embodiments, the synthetic antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. USE IN COMBINATION

The present invention also provides a method of treating, protecting against, and/or preventing disease in a subject in need thereof by administering a combination of the synthetic antibody and a therapeutic agent. In one embodiment, the therapeutic agent is an antiviral agent. In one embodiment, the therapeutic is an antibiotic agent.

The synthetic antibody and a therapeutic agent may be administered using any suitable method such that a combination of the synthetic antibody and therapeutic agent are both present in the subject. In one embodiment, the method may comprise administration of a first composition comprising a synthetic antibody of the invention by any of the methods described in detail above and administration of a second composition comprising a therapeutic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising a therapeutic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising a therapeutic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the therapeutic agent. In one embodiment, the method may comprise administration of a first composition comprising a therapeutic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the therapeutic agent. In one embodiment, the method may comprise administration of a first composition comprising a synthetic antibody of the invention by any of the methods described in detail above and a second composition comprising a therapeutic agent concurrently. In one embodiment, the method may comprise administration of a first composition comprising a synthetic antibody of the invention by any of the methods described in detail above and a second composition comprising a therapeutic agent concurrently. In one embodiment, the method may comprise administration of a single composition comprising a synthetic antibody of the invention and a therapeutic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

12. GENERATION OF SYNTHETIC ANTIBODIES IN VITRO AND EX VIVO

In one embodiment, the synthetic antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

The present invention has multiple aspects, illustrated by the following non-limiting examples.

13. EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The studies presented herein demonstrate the generation of functional anti-Ebola "DNA monoclonal antibodies" (DMAb) via intramuscular electroporation of plasmid DNA.

As described herein, an optimized, synthetic DNA vector platform (DMAb) to deliver encoded mAb heavy and light chains directly into skeletal muscle was designed, employing the cells as biological factories that will secrete a functional antibody at detectable levels in systemic circulation. DMAbs encoding anti-GP mAbs that target the GP glycan cap, fusion loop, and chalice base were developed. BALB/c mice were administered individual DMAbs or a combination of multiple DMAbs by intramuscular (IM) DNA injection, followed by in vivo electroporation (EP). EVD DMAbs were detected in mouse serum for >3 months, with Cmax serum levels comparable to protein-delivered human IgG1. In the field, EVD DMAbs could be administered in advance during a possible EVD outbreak.

An illustration of DMAb delivery, as compared to traditional protein MAb delivery, is depicted in FIG. 1. For example, FIG. 1A depicts protein MAb production and delivery. HEK293 or CHO cells are transfected with DNA encoding IgG heavy and light chains using optimized methods. Cell supernatants are harvested and purified to obtain purified protein IgG. Protein IgG is delivered to mice by injection. In contrast, FIG. 1B depicts DMAb delivery. DMAb sequence is nucleotide and amino acid optimized before insertion into a highly optimized plasmid backbone. DMAbs are administered directly into mouse muscle by IM injection, followed by electroporation. Mouse muscle expresses, assembles, and secretes functional mAb in vivo at levels detectable in systemic circulation.

Figures 2A, 2B, 2C, 2D:
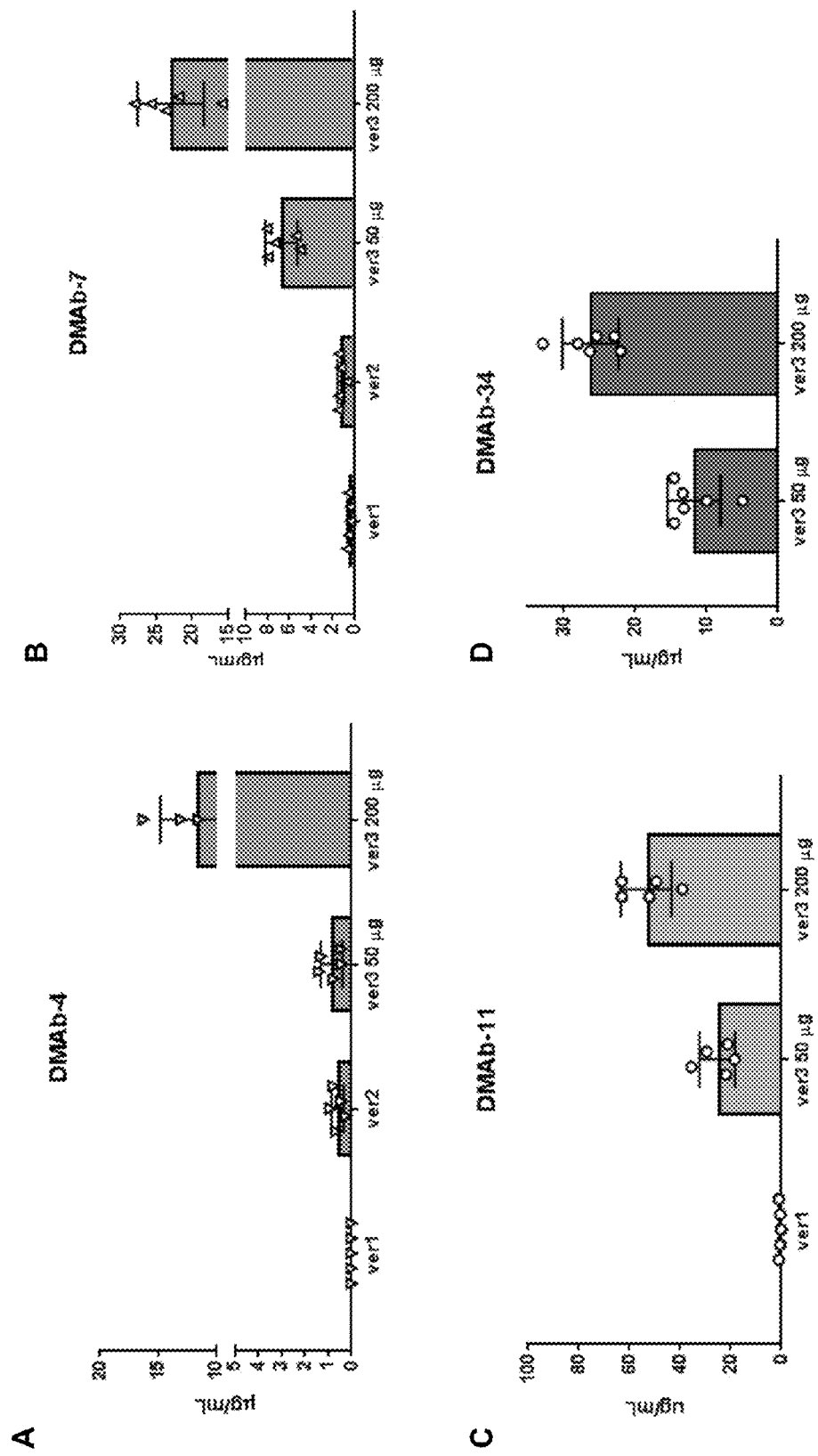
FIG. 2A depicts the in vivo expression of different optimizations of DMAb-4.
FIG. 2B depicts the in vivo expression of different optimizations of DMAb-7.
FIG. 2C depicts the in vivo expression of different optimizations of DMAb-11.
FIG. 2D depicts the in vivo expression of different optimizations of DMAb-34. BALB/c mice (n=5 mice/group) received injections with different optimized variants and formulations of each anti-GP DMAb. ver1=nucleotide optimization, ver2=stabilizing amino acid modifications, ver3=HYA formulation. The bar graphs display the Cmax expression levels and error bars represent the standard deviation.

FIG. 2 illustrates the expression of DMAbs in muscle. FIG. 2 depicts immunofluorescence images of sections of the TA muscle treated with DMAb or pGX0001 empty vector backbone delivered with electroporation, and harvested 72 hours later. Human IgG was detected with anti-human IgG followed by a FITC-labelled secondary antibody (green). DAPI stain in blue. Panel 1. No treatment. Panel 2. pVax. Panels 3 & 4. DMAb. Panels 1-3 display a cross-sectional image perpendicular to muscle fibers, and in Panel 4 the image is along the muscle fibers.

Figures 3A, 3B, 3C, 3D, 3E, 3F:
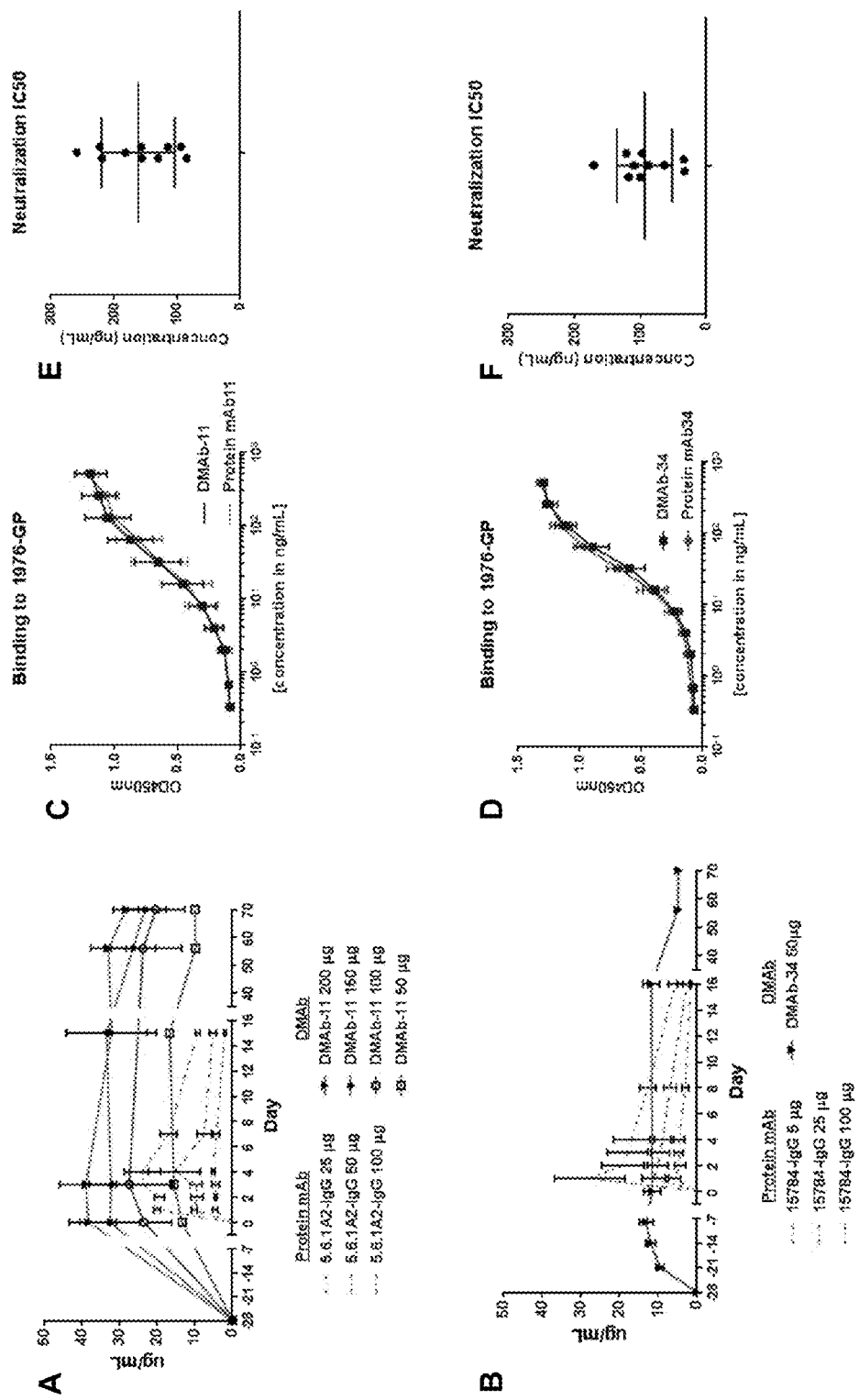
FIG. 3A depicts a comparison of DMAb-11 expression kinetics with protein IgG 5.6.1A2. Different doses of DMAb-11 (50 μg-200 μg plasmid DNA IM-EP) and mAb 5.6.1A2 (25 μg-100 g protein i.p.) were administered to mice and serum human IgG1 levels were monitored over time (n=5/group).
FIG. 3B depicts a comparison of DMAb-34 expression kinetics with protein IgG 15784. A dose of 50 μg plasmid/mouse of DMAb-34 and different doses of mAb 15784 (25 μg-100 μg protein) were administered to mice and serum human IgG1 levels were monitored over time (n=5/group).
FIG. 3C depicts the binding of DMAb-11 to EBOV-GP in comparison with mAb 5.6.1A2.
FIG. 3D depicts the binding of DMAb-34 to EBOV-GP in comparison with mAb 15784.
FIG. 3E depicts Ebola virus neutralization IC50 for DMAb-11.
FIG. 3F depicts Ebola virus neutralization IC50 for DMAb-34. The neutralization assays were performed with EBOV (strain Mayinga) expressing green fluorescent protein.

The in vitro expression of Ebola Virus Disease (EVD) DMAbs is shown in FIG. 3. FIG. 3A depicts the structure of the glycan cap (GP) and fusion loop (Lee et al. 2009). HEK293 T cells were transfected with EVD DMAb, and a Western blot was performed to detect the presence of DMAb heavy and light chains. FIG. 3B demonstrates that the heavy and light chains are detected in lysates from EVD DMAb-transfected HEK293T cells.

Figures 4A, 4B:
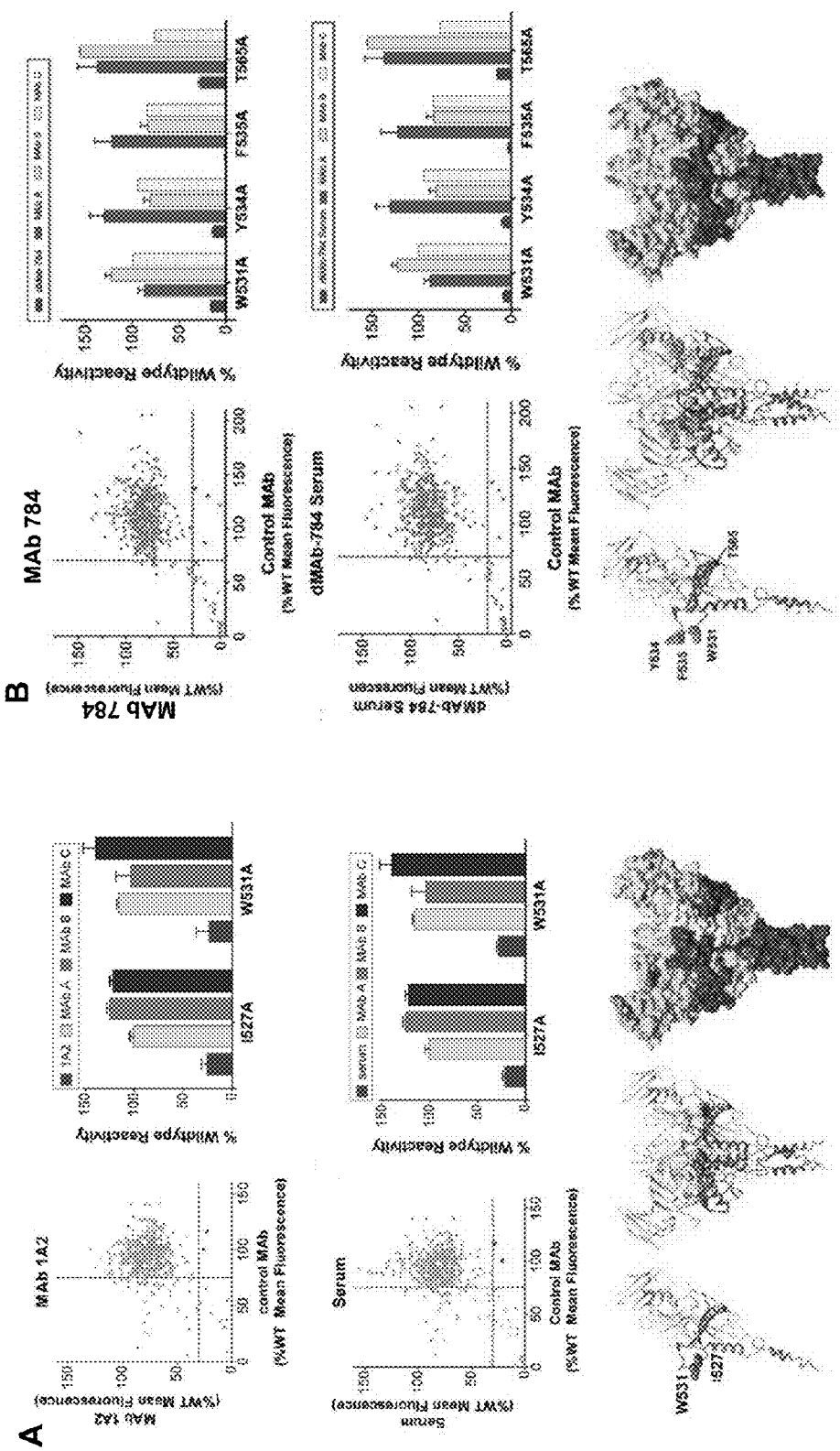
FIG. 4A and FIG. 4B, depicts experimental results of shotgun mutagenesis epitope mapping by alanine scanning of a EBOV Δmucin GP library. Protein IgG and mouse serum were mapped on an EBOV Δmucin GP mutation library expressed in HEK 293T cells and assayed by flow cytometry.

The in vivo expression of EVD DMAbs were investigated in BALB/c mice. BALB/c mice received 400 µg of the various indicated EVD DMAbs by intramuscular injection, followed by electroporation (FIG. 4A). The peak expression level of human IgG1 in the mouse serum was detected, which is depicted in FIG. 4A. As shown in FIG. 4B, optimization of the formulation and delivery of DMAb-11 can enhance DMAb circulating levels.

Example 2

The data presented herein describes DMAbs encoding highly potent anti-Zaire Ebolavirus (EBOV) glycoprotein (GP) mAb clones that were isolated from EVD survivors. Twenty-six human IgG1 DMabs targeting the GP glycan cap, chalice base, fusion loop, HR2 region, MPER, and mucin-like domain were engineered through a series of sequence modifications and formulation studies designed to increase in vivo delivery and pharmacokinetic expression. Anti-GP DMAb pharmacokinetics are independent of in silico mAb liability predictions for cell-culture mAb bio-processing. It was observed that novel sequence modifications using in silico design combined with enhanced DNA formulation development can lead to high levels of anti-GP human IgG DMAb expression in vivo in mouse models. Two anti-GP DMAbs, DMAb-11 (targeting the GP-fusion loop) and DMAb-34 (targeting the GP base), were selected for further demonstration that DMAbs have comparable GP epitope binding to protein Ig. The data demonstrate that in vivo delivery of DMAb-11 and DMAb-34 GP-DMAbs resulted in consistent human Ig mAb production, affording protection individually as well as in combination against lethal mouse-adapted EBOV challenge in mice. Taken together, these results demonstrate that facilitated DMAb delivery is a promising approach for in vivo production of fully human anti-EBOV mAb clones and support further preclinical evaluation.

The materials and methods are now described.

Samples Size and Power Calculations

Sample size and power analysis calculations were performed in SPSS Statistics software and the !NSize macro. For in vivo DMAb expression experiments in mice, sample sizes were calculated for two independent proportions, $\alpha=0.05$ and minimum power of 0.80. Based on these parameters, a minimum of five mice per group was calculated to be necessary to achieve adequate power in the experiments. For survival studies, ten mice per group was determined to be the minimum sample size needed. Independent repeats of challenge experiments were performed in order to increase statistical power.

Data Inclusion and Outliers

All data points were included in the analysis and outliers were included in the figures and data tables. Data from individual animals is included as Supplementary Information.

Endpoint Determination

Anti-GP DMAb expression levels in mice were followed from the time of IM-EP delivery until human IgG1 was undetectable in mouse serum. For survival experiments, endpoints were determined as a terminal point due to course of disease or at day 21 post-challenge, once all surviving animals had recovered. Animals were euthanized if they lost more than twenty percent starting body weight or reached a pre-defined clinical score.

Replicates

All in vitro transfections were performed with three technical replicates and one independent repeat was performed for all samples. In vivo experiments for DMAb expression pharmacokinetics in mice were performed once in order to minimize the use of animals. Following analysis of the data, the top expressing DMAbs were selected for repeats to increase statistical power and demonstrate the consistency of the in vivo DMAb approach. DMAb-11 expression was repeated in at least six independent studies and three independent protection studies. DMAb-34 expression was repeated in at least four independent studies and two independent protection studies.

Experimental Design

Controlled laboratory experiments were performed to evaluate all the anti-GP DMAbs described in this manuscript. These included studies evaluating pharmacokinetic levels of human IgG circulation in mouse serum following human DMAb administration, comparison studies with control protein mAb (binding, epitope mapping, neutralization), and protection studies evaluating different anti-GP DMAb doses in a mouse lethal challenge model.

Research Animals

All in vivo experiments were performed using mouse models. No randomization was performed with the mouse groups in this study.

Cell Lines and Viruses

Human embryonic kidney (HEK) 293 T cells (ATCC #CRL-3216) and African green monkey Vero E6 cells (ATCC #CR1-1586) were maintained in Dulbecco's Modified Eagles Medium (DMEM, Gibco) at 37° C., 5% $CO_2$. All cell lines were tested to be mycoplasma negative.

All infectious work with Zaire ebolavirus was performed in the biosafety level 4 (BSL-4) facility at the National Microbiology Laboratory, Public Health Agency of Canada (NML/PHAC, Winnipeg, Manitoba, Canada). Zaire Ebola virus expressing enhanced green fluorescent protein (EBOV-GFP) stocks were titered by plaque assay to determine the Plaque Forming Unit (PFU) using a final concentration of 0.7% Agarose (SeaPlaque, Lonza, Switzerland). Mouse-adapted Zaire Ebolavirus (EBOV) virus stocks were originally obtained by serial passage in mice and titered using a focus-forming unit (FFU) assay.

In Silico Analysis

In silico analysis of mAb sequence liabilities was performed in Biovia Discovery Studio and SAbPred. Further sequence analysis was performed using MEGA7.0 and germline protein display datasets obtained from the IMGT repertoire database. VH and VL family analysis was performed using the IMGT DomainGapAlign database.

DMAb Construction

The sequences of twenty-six anti-GP monoclonal antibodies were obtained (Flyak et al., 2016, Cell 164:392-405; Bomholdt et al., 2016, Science 351:1078-83). These clones bind to different regions of EBOV GP: glycan cap, HR2 region, fusion loop, chalice base, and the mucin domain. The nucleotide sequences for each heavy chain and light chain Fab and Fc regions were codon-optimized (mouse and human) to enhance transgene expression and RNA-optimized for improved stability. To further enhance expression, stabilizing amino acid mutations were introduced for several anti-GP DMAbs. These amino acid changes were selected based on analysis of the germline Ig protein sequence available from the IMGT repertoire database (Lefranc, 2001, NAR 29:207-099; Scaviner et al., 1999; Exp Clin immunogenet 16:234-40). The optimized human IgG1 HC and LC were inserted into the pVax1 plasmid DNA expression vector, under the control of the human cytomegalovirus (hCMV) promoter and bovine grown hormone (BGH) polyA signal. The single-plasmid construct encoded both HC and LC genes in cis, separated by a furin cleavage site (RGRKRRS) and a porcine teschovirus-1 2A peptide (P2A). The dual-plasmid construct was encoded on separate plasmids.

DMAb Expression In Vitro

HEK 293T cells were transfected with the DMAb DNA single-plasmid or equal mass of HC and LC plasmids (HC+LC) using GeneJammer transfection reagent. Cell supernatants and cell lysates were harvested 40 hours post-transfection to be assayed for human IgG1 production.

Mice

Female, six to eight week old BALB/c mice were purchased from Charles River Laboratories. Mice received intramuscular injections (50 µg/leg dual-plasmid, 25 µg heavy-chain plus 25 µg light chain or 100 µg/leg single-plasmid) in the tibilais anterior or quadriceps muscles of anti-GP DMAb DNA co-formulated with hyaluronidase (200 U/L), followed by electroporation (IM-EP) using the CELLECTRA® 3P adaptive constant current device. BALB/c mice were transiently conditioned using T cell depleting antibodies to evaluate human IgG DMAb expression, unrestricted by the murine host immune system. Full immune function is restored 14-21 days post-conditioning. Serum was collected longitudinally to monitor in vivo expression.

For the lethal challenge experiments, mice received bilateral IP injections at a total volume of 100 µl consisting of 1000 LD50 of mouse-adapted EBOV (strain Mayinga). The challenge stock titer is $1.29 \times 10^7$ FFU/mL and one LD50 is 0.01 FFU/animal. Mice were weighed and scored for clinical signs daily for 21 days and animals were euthanized when their percent weight loss reached 75%.

Mouse Muscle Tissue Immunofluorescence

BALB/c mice were injected with 50 µg of anti-GP DMAb dual-plasmid DNA by IM injection in the quad muscle followed by IM-EP. Muscles were harvest 2 days post-injection and embedded in optimal cutting temperature compound and snap-frozen on dry-ice. Muscles were sectioned and fixed with 100% methanol for ten minutes at −20° C. Slides were washed for three minutes with phosphate buffered saline (PBS)+0.02% Tween 20 (PBST) and then placed in 0.03% Trixon-X100 in 0.05% PBST for fifteen minutes at room temperature. Slides were then washed three times for five minutes/wash with 0.05% PBST and blocked with 5% horse serum in 0.05% PBST for 1 hour. Following incubation, the serum was aspirated and 150 µl of unconjugated purified goat anti-human IgG-Fc (A-80-104, Bethyl, Montgomery, TX) was added to the slides (1:200 dilution in 10% BSA+0.05% PBST) and incubated overnight at 4° C. The following day, slides were washed three times for five minutes/wash with 0.05% PBST and a donkey anti-goat IgG (H+L) cross-adsorbed secondary antibody conjugated to Alexa Fluor 488 (Thermo Fisher Scientific) was added (1:200 dilution in 0.05% PBST) for thirty minutes at room temperature. A final three washes for five minutes/wash was performed and slides were mounted with ProLong Gold Antifade reagent with DAPI before adding coverslips. In vivo expression was imaged with a Nikon 80i upright fluorescent microscope at 40× magnification.

Human IgG Quantification by ELISA

Ninety-six well, high-binding immunosorbent plates were coated with 1 µg mL$^{-1}$ purified anti-Human IgG-Fc (A-80-104A, Bethyl Laboratories, Montgomery, TX) and incubated overnight at 4° C. On the next day, plates were blocked with PBS containing 10% FBS for 1 hour at room temperature. Plates were washed with PBS containing 0.05% Tween-20 in between each incubation steps. Plates were incubated with a standard and samples for 1 hour at room temperature. Purified Human IgG/Kappa (P80-111, Bethyl Laboratories, Montgomery, TX) was used as a standard. Samples were diluted in PBS containing 1% FBS and 0.02% Tween-20. Following the incubation, samples were probed with anti-human Kappa light chain antibody conjugated to horseradish peroxidase (A80-115P, Bethyl Laboratories, Montgomery, TX) in 1:20,000 dilution and incubated for 1 hour at room temperature. After incubation, plates were developed with o-Phenylenediamine dihydrochloride (OPD) substrate (SIGMAFAST™ OPD, Sigma Aldrich, St. Louis, MO) for 25 minutes in the dark and stopped with 2N $H_2SO_4$. A BioTek Synergy2 plate reader was used to read plates at 450 nm wavelength.

Binding ELISA

Ninety-six well, high-binding immunosorbent plates were coated with 1 µg mL$^{-1}$ Ebola virus Glycoprotein (strain Mayinga 1976) (40304-V08B1, Sino Biological, Beijing, China) and incubated overnight at 4° C. Alternatively, Ebola virus Glycoprotein (strain *H. sapiens*-wt/GIN/2014/Kissidougou-C 15) (40442-V08B1, Sino Biological, Beijing, China) was used. On the next day, plates were blocked using PBS containing 5% non-fat milk and 0.02% Tween-20 for 90 minutes at 37° C. Plates were washed with PBS containing 0.05% Tween-20 in between each incubation steps. After being blocked, plates were incubated with samples in series of dilution for 1 hour at 37° C. Following incubation, samples were probed with anti-human IgG (H+L) conjugated to horseradish peroxidase (SAB3701359, Sigma Aldrich, St. Louis, MO) for 1 hour at 37° C. Plates were developed using OPD substrate for 25 minutes in the dark and stopped using 2N $H_2SO_4$. A BioTek Synergy2 plate reader was used to read plates at OD 450 nm.

Western Blot

Cell lysate was collected in transfected cells in cell lysis buffer. Samples were centrifuged at 16,000×g and the supernatant containing the protein fraction was collected. Total protein concentration of each sample was measured using Bicinchoninic acid (BCA) assay. Samples were reduced for 10 minutes at 70° C. using NuPAGE™ Sample Reducing Agent (10x). 10 μg of samples were loaded on a NuPAGE™ 4-12% Bris-Tris gel SeeBlue™ Pre-stained Protein Standard was used as standard markers. The gel was transferred to a PVDF membrane Immobilon-FL (IPFL07810, EMD Millipore, MA) using iBlot™ 2 system. The membrane was blocked with Odyssey® Blocking Buffer in PBS (LI-COR, NE) for 1 hour. Beta Actin Monoclonal Antibody in 1:5,000 dilution was added as a positive control. Following incubation, the membrane was incubated with Anti-Human IRDye 800CW (LI-COR, NE) in OBB containing 0.1% Tween-20 and 0.01% SDS for 1 hour in the dark. Alternatively, anti-Mouse IRDye 680RD (LI-COR, NE) was used as a secondary antibody. After being washed with PBS, the membrane was scanned using Odyssey® CLx Imager (LI-COR, NE).

Neutralization Assay

Neutralization assays were performed using live EBOV-GFP. The day before the assay, Vero E6 cells were plated in ninety-six well black plates with a transparent bottom. Serum from DMAb-administered mice was heat inactivated at 56° C. for 30 minutes and diluted 1 into 10 and then serially diluted two-fold in DMEM down a 96 well plate and incubated with 100 PFU of EBOV-GFP per well for one hour at 37° C., 5% $CO_2$. The serum:virus mixture was then added to Vero E6 cells (85-90% confluent) and incubated for one hour at 37° C., 5% $CO_2$. After incubation, the mixture was removed and 100 μl of DMEM plus 2% Bovine Growth Serum. Cells were then incubated at 37° C., 5% $CO_2$ for up to 144 hours until the GFP signal became saturated. Plates were read for GFP fluorescence daily from the bottom using a Bio-Tek Synergy HT plate reader.

Shotgun Mutagenesis Epitope Mapping

Shotgun Mutagenesis epitope mapping on EBOV-GP was performed as described previously (Davidson et al., 2015, J Virol 89:10982-92). Briefly, alanine scanning mutagenesis was carried out on an expression construct for EBOV-GP (strain Mayinga-76; UniProt accession #Q05320) lacking the mucin-like domain (residues 311-461). Residues 33-310 and 462-676 of the EBOV delta (A) mucin GP were mutagenized to create a library of clones, each with an individual point mutant. Residues were changed to alanine, with alanine residues changed to serine. GP residues 1-32, which constitute the GP signal peptide, were not mutagenized. The resulting EBOV GP alanine-scan library covered 492 of 493 of target residues (99.9%). Each mutation was confirmed by DNA sequencing, and clones were arrayed into 384-well plates, one mutant per well. Each library plate also contained negative control wells with vector alone, and positive control wells containing wild-type EBOV Δmucin GP.

Before epitope mapping on the mutation library, we confirmed that MAb 5.6.1A2 and 15784 and mouse DMAb-11 and DMAb-34 serum showed reactivity with EBOV-GP, and identified an appropriate MAb concentration and serum dilution for screening the mutation library. MAb 5.6.1A2 and 15784 and pooled DMAb-11 and DMAb-34 mouse serum were tested for binding to wild-type EBOV Δmucin GP expressed in HEK-293T cells. After addition of a fluorescent secondary antibody, the mean cellular fluorescence was detected using an Intellicyt flow cytometer. The entire EBOV Δmucin GP library expressed in HEK-293T cells was screened for binding of mutant clones to MAb 5.6.1A2 and 15784, or to DMAb-11 and DMAb-34 mouse serum, by detecting mean cellular fluorescence. Mutations within clones were identified as critical to the MAb epitope if they did not support reactivity of the MAb, but did support reactivity of other conformation-dependent MAbs. This counter-screen strategy facilitates the exclusion of GP mutants that are globally or locally misfolded or that have an expression defect. Validated critical residues represent amino acids whose side chains make the highest energetic contributions to the MAb-epitope interaction (Bogan and Thorn, 1998; Lo Conte et al., 1999).

Statistics

Statistical analyses were performed using GraphPad Prism 7.0 software or SPSS. Sample size calculations were performed for two-independent proportions, alpha 0.05 and power 0.80. Protection study data was represented by a Kaplan-Meier survival curve and log-rank test analysis, followed by two-way ANOVA with correction for multiple comparisons. Samples and animal groups with a p value <0.05 were considered statistically. All bar graphs and line graphs display individual animals or the mean value and error bars represent the standard deviation The results are now described.

Anti-GP DMAb Engineering and Delivery

Twenty-six different anti-EVD mAb clones that target the Ebola virus GP glycan cap, fusion loop, chalice base, HR2 region, and mucin-like domain were selected for development into DMAbs. The sequences of the human Ig heavy and light chains were analyzed in silico. A series of optimizations were performed to reduce potential RNA secondary structure and to increase translation efficiency via mouse and human codon bias. The full-length heavy and light chains were each encoded into a single modified-pVax1 DNA expression vector plasmid, separated by furin and P2A peptide cleavage sites (single-plasmid), or encoded as two separate plasmid constructs (dual-plasmid) (FIG. 1A). For all constructs, initial in vitro transfection assays were performed to confirm expression before administering anti-GP DMAb constructs in vivo (Table 1).

The DMAb single-plasmid or dual-plasmid (equal ratio (μg) of heavy and light chain (HC/LC) plasmids) were administered to mice by in vivo intramuscular (IM) injection followed by facilitated CELLECTRA-3P®electroporation (IM-EP). This resulted in DMAb expression and secretion directly into systemic circulation. Quadriceps muscle slices from mice injected with an anti-GP DMAb were harvested and stained for human IgG (FIG. 1B) indicating expression of DMAb in muscle cells and fibers (Green=human IgG, Blue=DAPI nuclear stain).

Anti-GP DMAb Optimization

It is well-known that sequence liabilities of IgG can limit bioprocessed mAb production, frequently leading to discarding of an otherwise highly potent mAb clone. In certain cases, it was necessary to further engineer DMAbs through nucleotide optimizations (version 1), framework amino acid changes in order to stabilize the Ig molecule (version 2), and using formulations (version 3) in order to enhance in vivo expression. The mAb genes for clones 4G7 (DMAb-4), 13c6 (DMAb-7), 5.6.1A2 (DMab-11), and 15784 (DMAb-34) were optimized (FIG. 2, n=5 mice/group). Clones 4G7 (mouse VH 1-42, VK 12-44) and 13c6 (mouse VH 8-8, VK 6-13) are two clones found in the ZMapp cocktail that were isolated from vaccinated mice. Clone 5.6. 1A2 (human VH 3-53, VK 2-28) was isolated from a 2014-EVD survivor that was treated at Emory University. This clone was isolated from an EVD survivor at the 6 month time point post-treatment. Clone 15784 (human VH 1-18, VK 2-28) was isolated among hundreds of survivor-derived mAb clones from a different 2014-EVD survivor (Bomhold et al., 2016, Science 351:1078-83). Based on this strong expression data, further characterization studies focused on DMAb-11 and DMAb-34.

Equivalency of DMAb-11 and DMAb-34 to Conventional Protein mAb

Figures 9A, 9B:
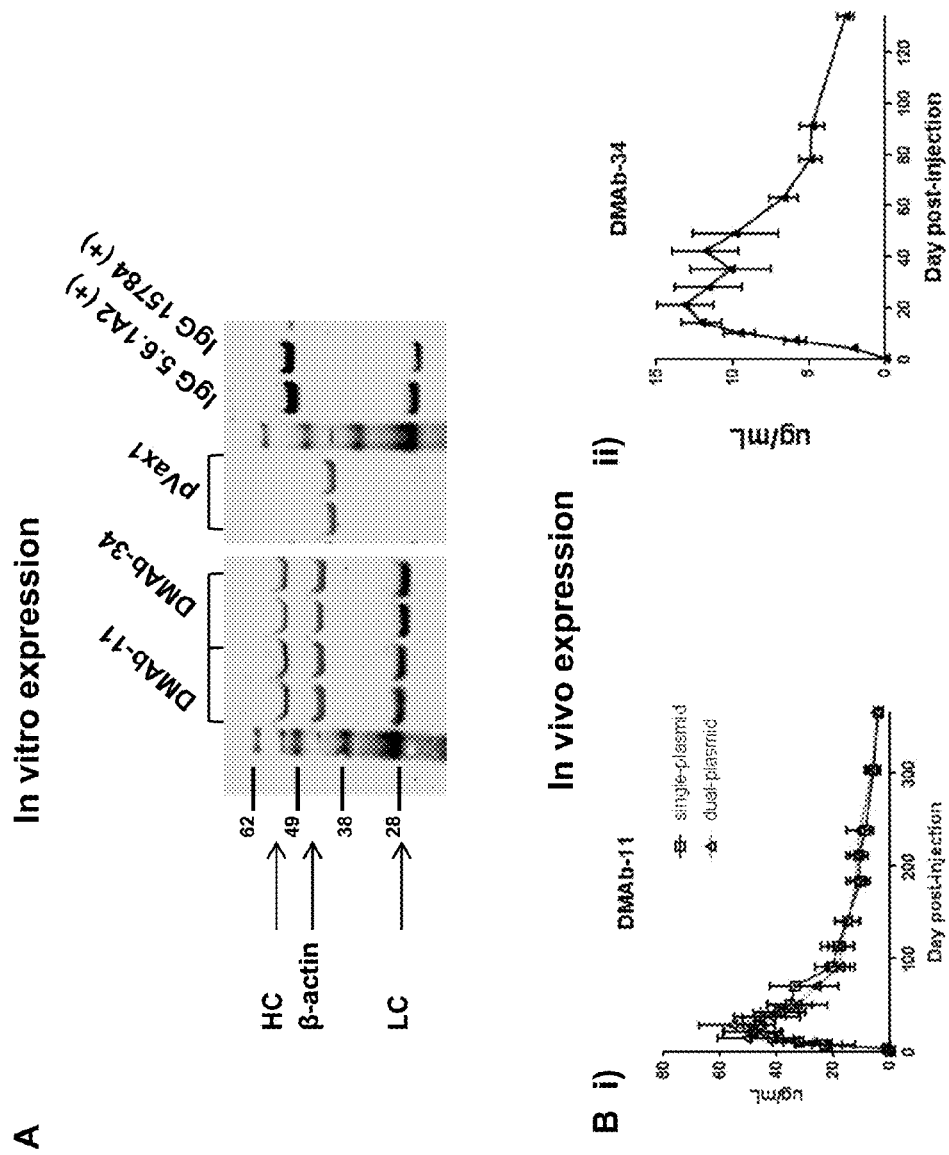
FIG. 9A, and FIG. 9B, depicts the in vitro expression and in vivo expression pharmacokinetics of DMAb-11 and DMAb-34.

In vitro expression of DMAb-11 and DMAb-34 was quantified in cell lysates of human embryonic kidney (HEK) 293T cells (FIG. 9A), harvested 40 hours after transfection. The expected band sizes for the heavy and light chains of DMAb-11 and DMAb-34 were observed at approximately 50 kDa and 25 kDa, respectively. The banding pattern for each antibody was comparable to those observed for protein counterpart mAbs 5.6.1A2 and 15784. DMAb-11 encoded as a single-plasmid (400 µg dose) or dual-plasmid constructs (200 µg dose total DNA) was administered to BALB/c mice (n=8-9 mice/group) and followed for 365 days following administration (FIG. 9B). Long-term expression at high levels was observed and administration of a single-plasmid or dual-plasmids did not impact overall expression kinetics. Dual-plasmid DMab-34 expression is ongoing and had reached 168 days at time of manuscript submission (FIG. 9C, 50 µg dose total DNA).

Comparison of DMAb-11 and DMAb-34 with Protein IgG 5.6.1A2 and 15784

Long-term expression of different doses of DMAb-11 (dual-plasmid, 25-100 µg total DNA, n=5 mice/group) or DMAb-34 (dual-plasmid, 50 µg total DNA, n=5 mice/group) were monitored in parallel with single injection of different doses of protein 5.6.1A2 or 15784 (25 µg-100 µg, n=5 mice/group) (FIG. 3A-3B). Both DMAb-11 and DMAb-34 bound to 1976 EBOV-GP (strain Mayinga) comparably to protein mAb (FIG. 3C-3D, n=10 mice/group). Both DMAbs also neutralized live EBOV-GFP (strain Mayinga) virus in a neutralization assay (FIG. 3E-3F, n=10 mice/group), highlighting the comparable activity of DMAb and conventional protein mAb.

Anti-GP DMAb Epitope Mapping

To further address the question of anti-GP DMAb equivalency to protein IgG, shotgun mutagenesis epitope mapping (Davidson, 2015, J Virol 89:10982-92) was performed using HEK 293 cells expressing EBOV-GP with alanine (Ala) mutations at each position in the glycoprotein. First, protein mAb 5.6.1A2 or protein mAb 15784 were run on the library to set up conditions and identify dropout mutations correlating with binding to GP. Pooled serum from mice administered DMAb-11 or DMAb-34 were run using the same assay, with identical conditions. For protein 5.6.1A2, drop out mutations I527A and W531A were pulled out utilizing the epitope mapping assay (FIG. 4A). The identical drop out mutations were identified for DMAb-11. Drop out mutations W531A, Y534A, F535A, and T565A were identified for protein 15784. Identical dropout mutations were also observed for DMAb-34 (FIG. 4B). Representations of GP and binding sites are shown (FIG. 4, PDB 5JQ3, Zhao et al 2016). This indicates that the in vivo produced DMAb and its respective protein mAb have the same binding characteristics at the molecular level.

Anti-GP DMAb Protection Against Ebola Virus in a Mouse Challenge Model

Figures 5A, 5B, 5C, 5D:
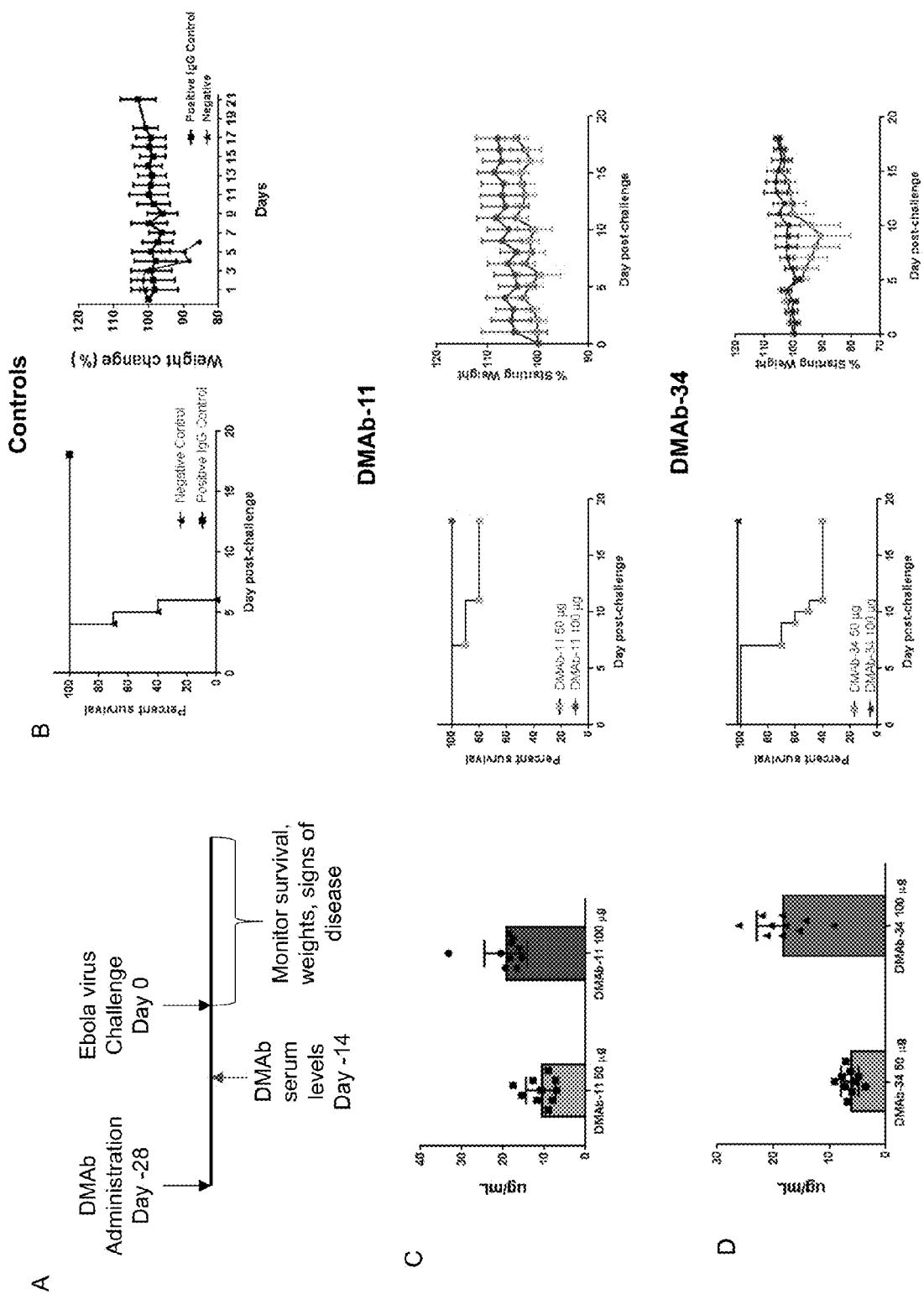
FIG. 5A through FIG. 5D, depicts in vivo protection by anti-GP DMAb-11 and DMAb-34.
Figures 10A, 10B, 10C, 10D:
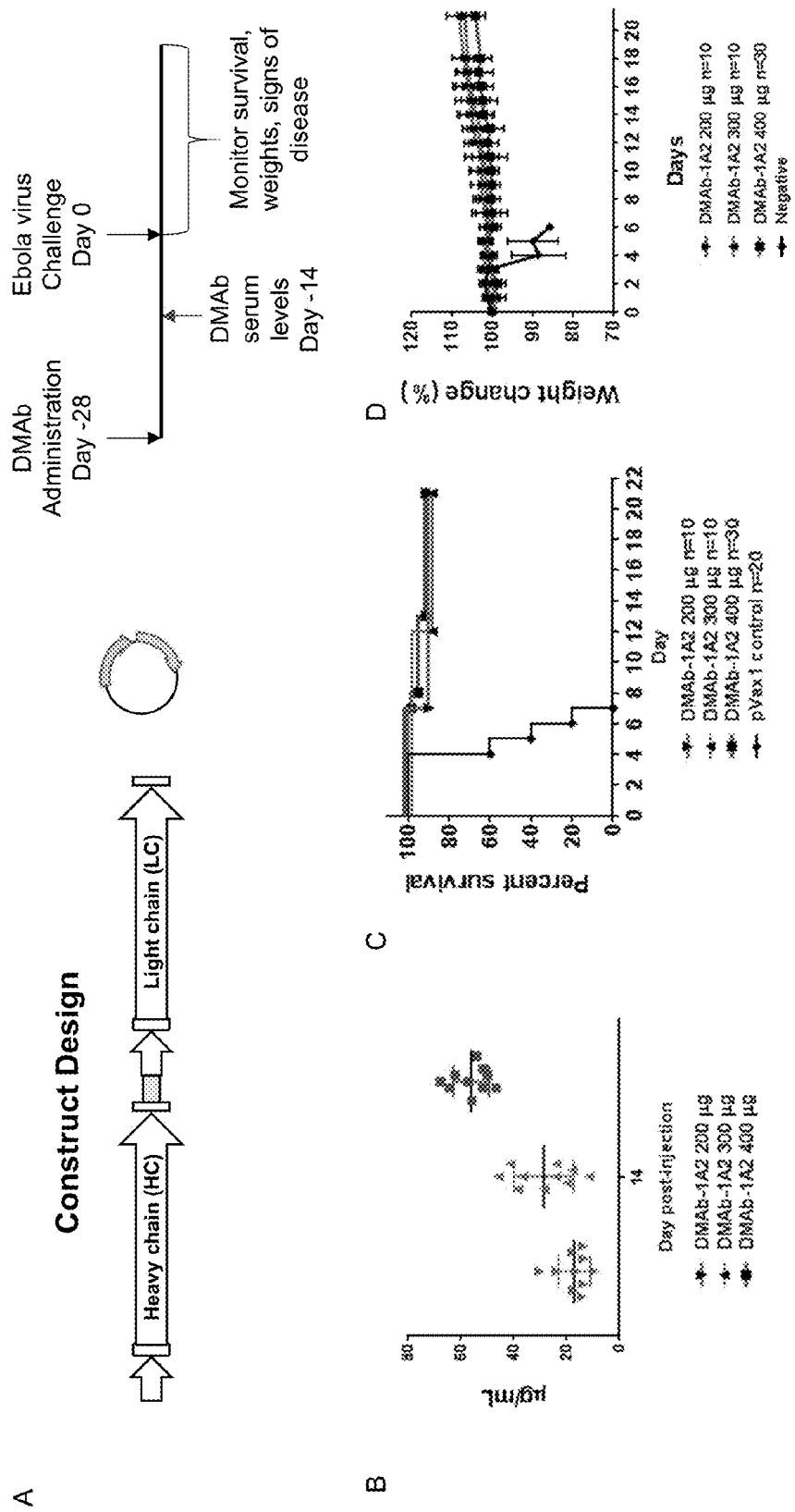
FIG. 10A through FIG. 10D, depicts experimental results demonstrating DMAb-11 single-plasmid protection.

Doses of DMAb-11 and DMAb-34 were administered to groups of transiently conditioned BALB/c mice 28 days prior to infection (Day −28). On day −14, serum was harvested from animals before they were shipped to the biosafety level 4 (BSL4) containment laboratory at the Public Health Agency of Canada (PHAC, Winnipeg, Manitoba, Canada). DMAb-injected mice received 1000 times the median lethal dose (1000LD50) challenge of mouse-adapted EBOV (strain Mayinga) on Day 0 (FIG. 5A). A negative control group (n=10) and positive protein IgG clone 2G4 (n=10) groups were included (FIG. 5B). DMAb expression levels increased in a dose-dependent manner (FIGS. 5C and 5D). DMAb-11 was 100% protective at the 100 µg dose and 80% protective at the lower 50 µg dose. No signs of disease were observed in surviving animals. Full protection (100%) was observed with the 100 µg dose of DMAb-34. A break in DMAb-34 protection was observed at the 50 µg dose, where only 40% of animals survived. DMAb-11 was also protective as a single plasmid. The single-plasmid construct was administered in different doses to conditioned BALB/c mice (FIG. 10). Animals received 200 µg, 300 µg, or 400 µg of total DMAb-11 single-plasmid DNA. High levels of protection (90-100% and no signs of morbidity) were observed with each of the three doses.

Anti-GP DMAb Co-Delivery

Figures 6A, 6B, 6C, 6D:
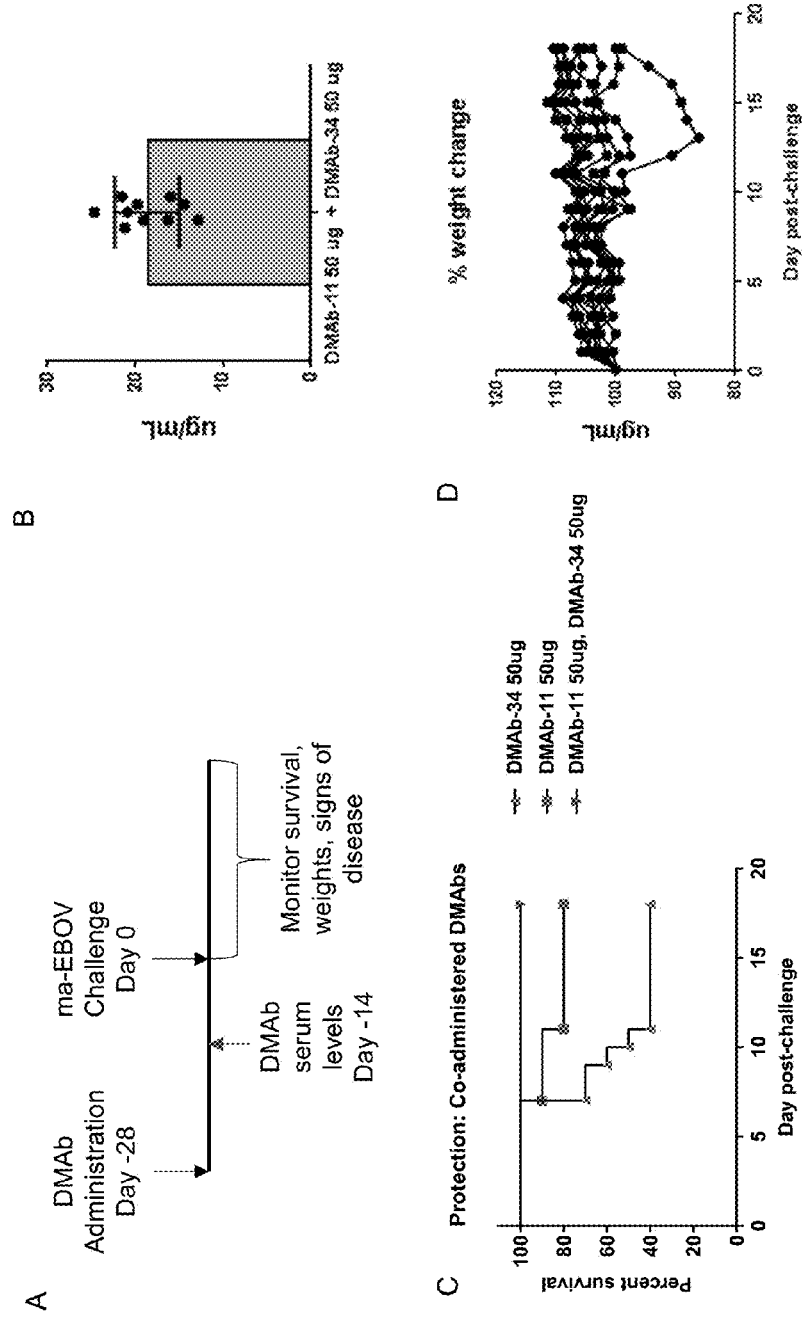
FIG. 6A through FIG. 6D, depicts experimental results of co-administration of DMAb-11 and DMAb-34. Anti-GP DMAb-11 and DMAb-34 were co-administered to BALB/c mice. Each DMAb was injected in separate legs (1 injection site/DMAb=2 sites total, 50 μg/DMAb)) on day −28 and serum was collected on day −14 before lethal challenge with 1000 LD50 of mouse-adapted EBOV (Mayinga). Animals were monitored for 21 days post-challenge for signs of disease and weight loss.

The potential for pathogen escape is a concern for anti-GP mAbs (Kugelman et al., 2015, cell Rep 12:2111-20; Miler et al., 2016, Peerj 4). One strategy is co-delivery of more than one antibody clone targeting different epitopes. Accordingly, both DMAb-11 and DMAb-34 were co-delivered at separate injections sites on the mouse leg. Animals received 50 µg DMAb-11 in one hind limb and 50 µg DMAb-34 in the opposite hind limb (FIG. 6A) on day −28. Total IgG (both DMAb-11 and DMAb-34) was assayed (FIG. 6B). Animals were challenged on Day 0 with 1000LD50 of mouse-adapted EBOV (strain Mayinga). Full protection was observed with no signs of disease (FIG. 6C-6D). One animal lost weight late during challenge however this animal fully recovered. The 50 µg dose groups of DMAb-11 and DMAb-34 from FIG. 5 are duplicated on this graph to aid in comparison of the data.

Rapid Protection with DMAb-11

Figures 7A, 7B, 7C:
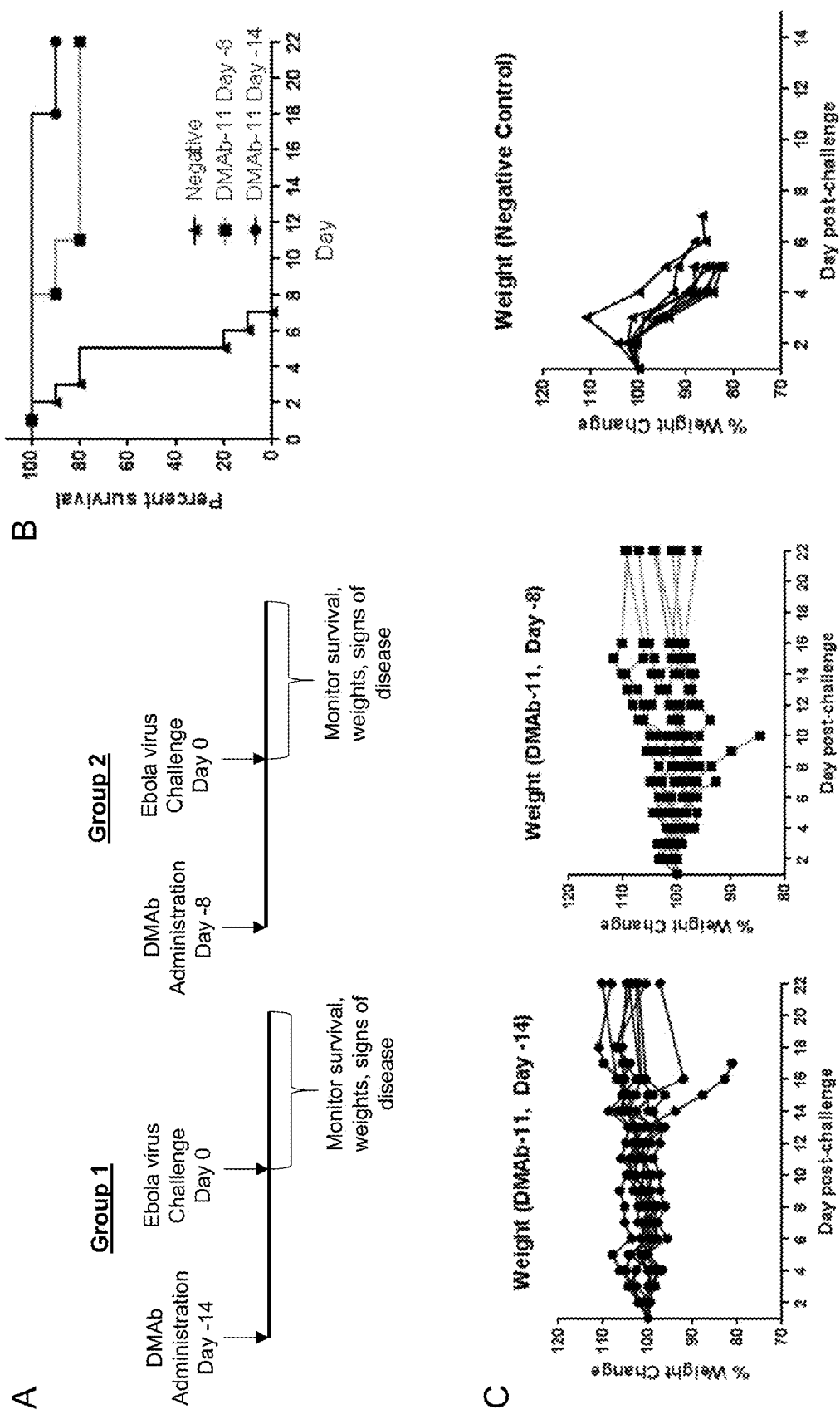
FIG. 7A through FIG. 7C, depicts experimental results demonstrating rapid in vivo protection with DMAb-11.

In all studies, DMAb-11 reliably expressed at high levels and consistent protection was observed when administered 28 days before lethal challenge. To address the question of anti-GP DMAb protection at shorter time frames closer to lethal challenge, BALB/c mice (n=10/group) were injected with 200 µg/mouse of DMAb-11 on days −14 and −8 before lethal challenge (FIG. 7). Mice were challenged on Day 0 with 1000LD5— of mouse-adapted EBOV (strain Mayinga). The higher 200 µg/mouse dose was selected to observe optimal survival in this short-term experiment. A 90% and 80% protection was observed in both groups, respectively, with only signs of disease in one surviving animals. The other surviving animals did not have any signs of disease. The high protection levels support the hypothesis that the anti-GP DMAbs can deliver antibodies that are protective rapidly delivering protective humoral immunity.

Long-Term Protection

Figures 11A, 11B, 11C, 11D:
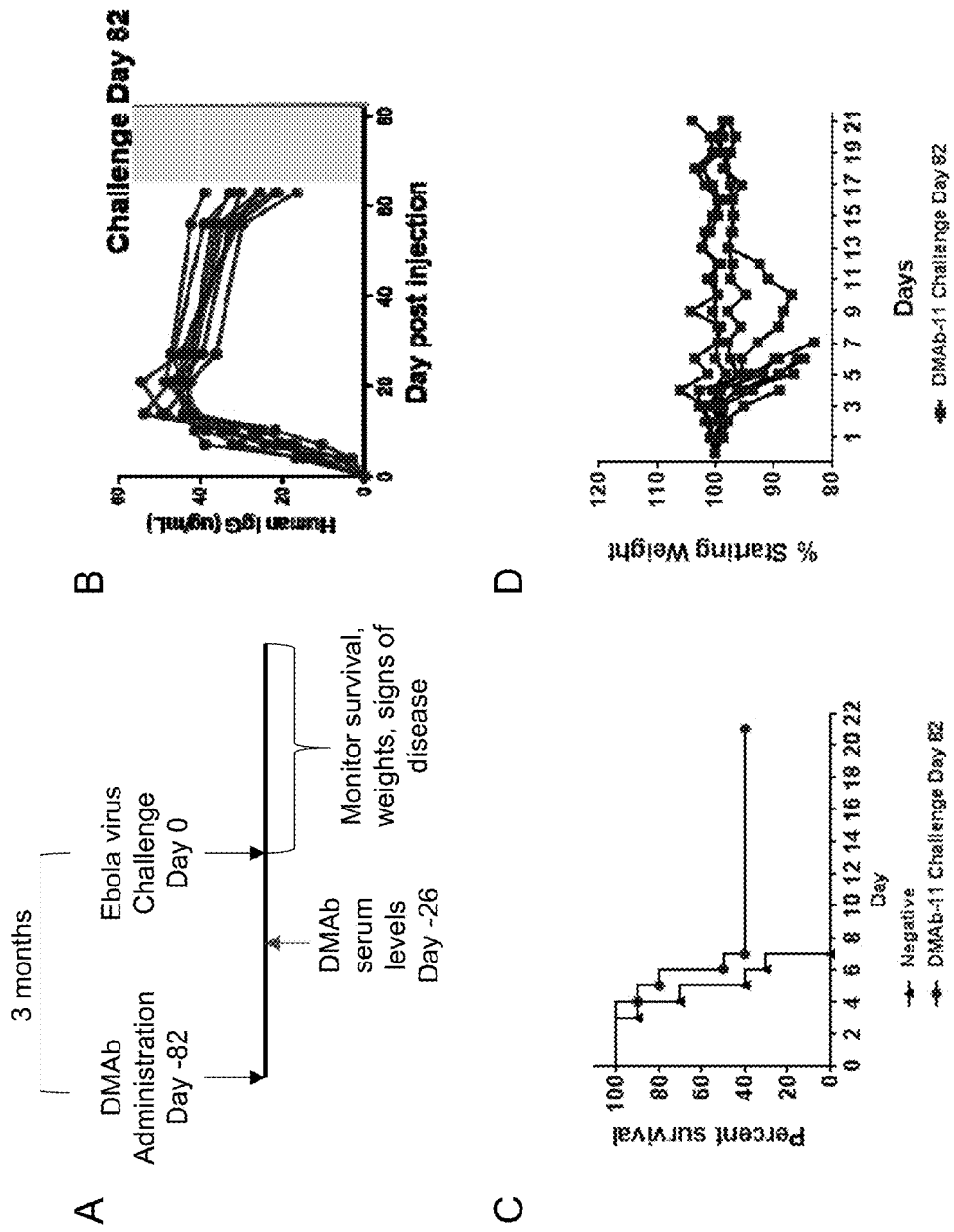
FIG. 11A through FIG. 11D, depicts experimental results demonstrating long-term protection with DMAb-11.

In one set of animals (n=10), DMAb-11 was administered and animals were challenged 82 days following initial DMAb administration. These animals received the single-plasmid DMAb-construct (400 µg/mouse) on day −82. Serum levels were monitored on day −26 before challenge and animals were challenged in Day 0 with 1000LD50 of mouse-adapted EBOV (strain Mayinga). Based on the data in FIG. 3 it is likely that the animals had levels below 10 µg/mL at the time of challenge. Remarkably, 40% survival was observed in these animals suggesting that DMAbs can afford long-term protection (FIG. 11). This would be particularly beneficial during a vaccination regimen that requires multiple boosts in order to achieve optimal efficacy and supports evaluation of a potential co-administration approach with DMAb and vaccine, which could provide rapid as well as long term protection in a field setting.

Developability Index Evaluation

Highly potent antibodies may be excluded from manufacturing due to intrinsic properties that could negatively impact production. Analysis of these parameters has been collectively termed the developability index (DI) (Lauer et al., 2012, J Pharm Sci 101:102-15). This represents a tremendous challenge for difficult-to-treat infectious diseases and highly pathogenic viral infections such as EVD where a potent clone may be excluded in favour of another clone that is easier to manufacture but has a weaker potency profile. Based on sequence information, the predicted DI was calculated for eight mAb clones utilizing in silico algorithms available in Biovia Discovery Studio (Accelyrs) and the SAbPred algorithm (Dunbar et al., 2016, NAR 44:W474-8) to compare this profile (Table 1) with in vivo DMAb expression. Using the DMAb platform, in vivo anti-GP mAb clones were successfully delivered with low DI scores. For example, based on DI analysis, DMAb-11 and DMAb-34 scored in the middle of the in silico DI ranking and are characterized with moderate to high biochemical features including Trp oxidation, Asn deamidation, Met oxidation, Asp isomerization, as well as aggregation scores that may be less favourable for bioprocessed mAb production compared with other candidates. Even so, strong in vivo DMAb expression was observed of both DMAb-11 and DMAb-34, supporting a unique aspect of direct in vivo DMAb antibody production.

TABLE 1

Developability index comparison

| DMAb | †Predicted in vitro DI (Ranked Highest = 1, Lowest = 8) | *In vitro Biochemical liabilities | Expression In vivo (Cmax Dose #1) µg/mL |
|---|---|---|---|
| DMAb-4 | 1 | Low | 3.01 |
| DMAb-9 | 2 | Low | 8.10 |
| DMAb-7 | 3 | Moderate | 6.74 |
| DMAb-11 | 4 | High | 9.44 |
| DMAb-34 | 5 | Moderate | 6.59 |
| DMAb-13 | 6 | High | 7.10 |
| DMAb-12 | 7 | Moderate | 7.00 |
| DMAb-30 | 8 | High | 1.02 |

Rapid Screening of Anti-GP DMAbs

Figure 8:
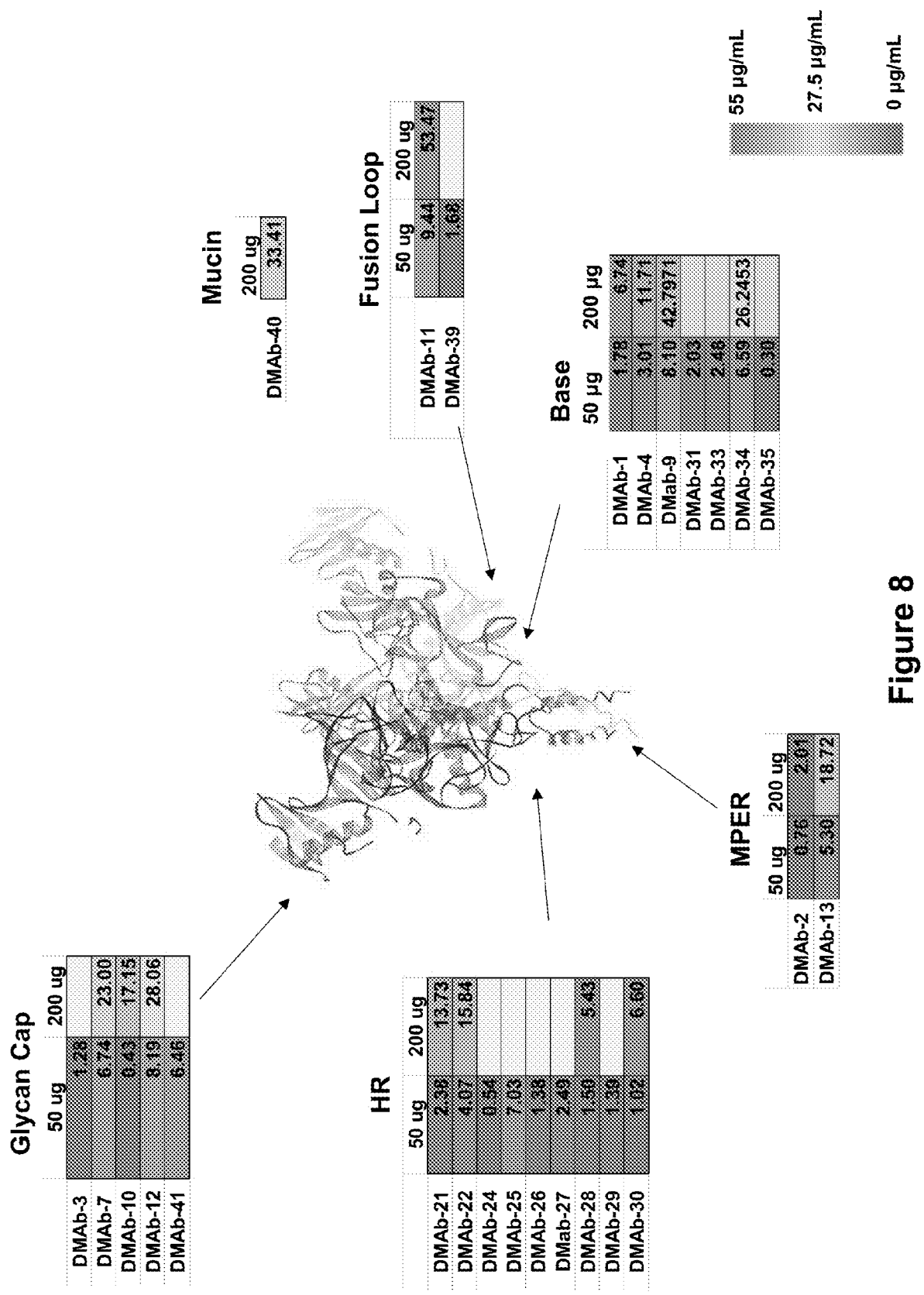
FIG. 8 depicts the Cmax expression levels for 26 different optimized DMAbs targeting various regions of EBOV GP. Optimized anti-GP DMAbs targeting the glycan cap, HR region, MPER, base, fusion loop, and mucin-like domain were evaluated at 50 μg/mouse and 200 μg/mouse. Gray box represents groups that were not evaluated for Dose #2. (Ebola virus GP PDB id 5JQ3, Zhao et al, 2016). A heat map scale bar is included for colorimetric reference (0-55 μg/mL).

Rapid in vivo screening of potent mAb clones is one advantage of the DMAb platform. In total, twenty-six different optimized anti-GP DMAbs at 50 µg/mouse and/or 200 µg/mouse doses (Cmax expression shown in FIG. 8, data from individual mice and standard deviations are listed in Table 2).

TABLE 2

Variable heavy and light chain families expressed as DMAbs

| GP-DMAb | Species | VH* | VL* |
|---|---|---|---|
| DMAb-1 | mouse | VH3-7 | Vκ1-5 |
| DMAb-2 | human | VH4-34 | Vκ3-20 |
| DMAb-3 | human | VH1-69 | Vκ3-15 |
| DMAb-4 | mouse | VH1-42 | Vκ12-44 |
| DMAb-5 | mouse | VH3-2 | Vκ1-135 |
| DMAb-6 | mouse | VH14-3 | Vκ4-55 |
| DMAb-7 | mouse | VH 8-8 | Vκ6-13 |
| DMAb-8 | human | VH4-59 | Vλ3-19 |
| DMAb-9 | human | VH3-13 | Vκ1-27 |
| DMAb-10 | human | VH3-13 | Vκ1-39 |
| DMAb-11 | human | VH3-53 | Vκ2-28 |
| DMAb-12 | human | VH1-69 | Vλ3-19 |
| DMAb-13 | human | VH3-30 | Vκ4-1 |
| DMAb-21 | human | VH4-4 | Vκ1-39 |
| DMAb-22 | human | VH1-46 | Vκ3-11 |

TABLE 2-continued

Variable heavy and light chain families expressed as DMAbs

| GP-DMAb | Species | VH* | VL* |
|---|---|---|---|
| DMAb-24 | human | VH1-46 | Vκ3-11 |
| DMAb-25 | human | VH4-59 | Vκ3-11 |
| DMAb-26 | human | VH1-46 | Vκ3-11 |
| DMAb-27 | human | VH1-46 | Vκ3-11 |
| DMAb-28 | human | VH1-46 | Vκ3-11 |
| DMAb-29 | human | VH3-23 | Vκ3-20 |
| DMAb-30 | human | VH1-46 | Vκ3-11 |
| DMAb-31 | human | VH3-48 | Vκ1-5 |
| DMAb-34 | human | VH1-18 | Vκ2-28 |
| DMAb-35 | human | VH3-23 | Vκ1-5 |
| DMAb-38 | human | VH3-23 | Vκ3-20 |
| DMAb-39 | human | VH1-46 | Vλ2-23 |
| DMAb-40 | human | VH1-46 | Vλ3-25 |
| DMAb-41 | human | VH3-20 | Vκ1-16 |

Figure 13:
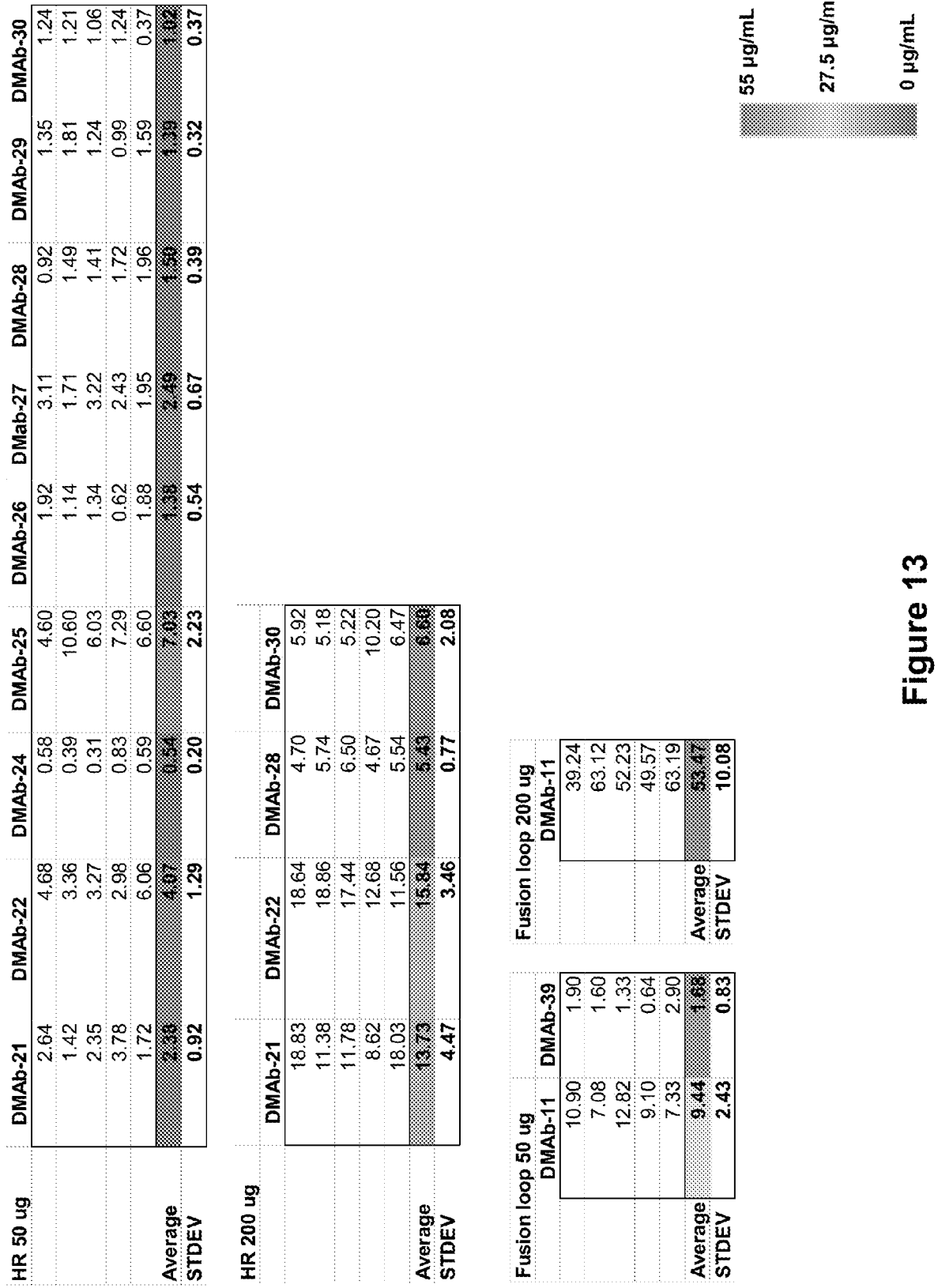
FIG. 13 depicts in vivo Cmax expression data for individual mice receiving anti-GP DMAbs.
Figure 14:
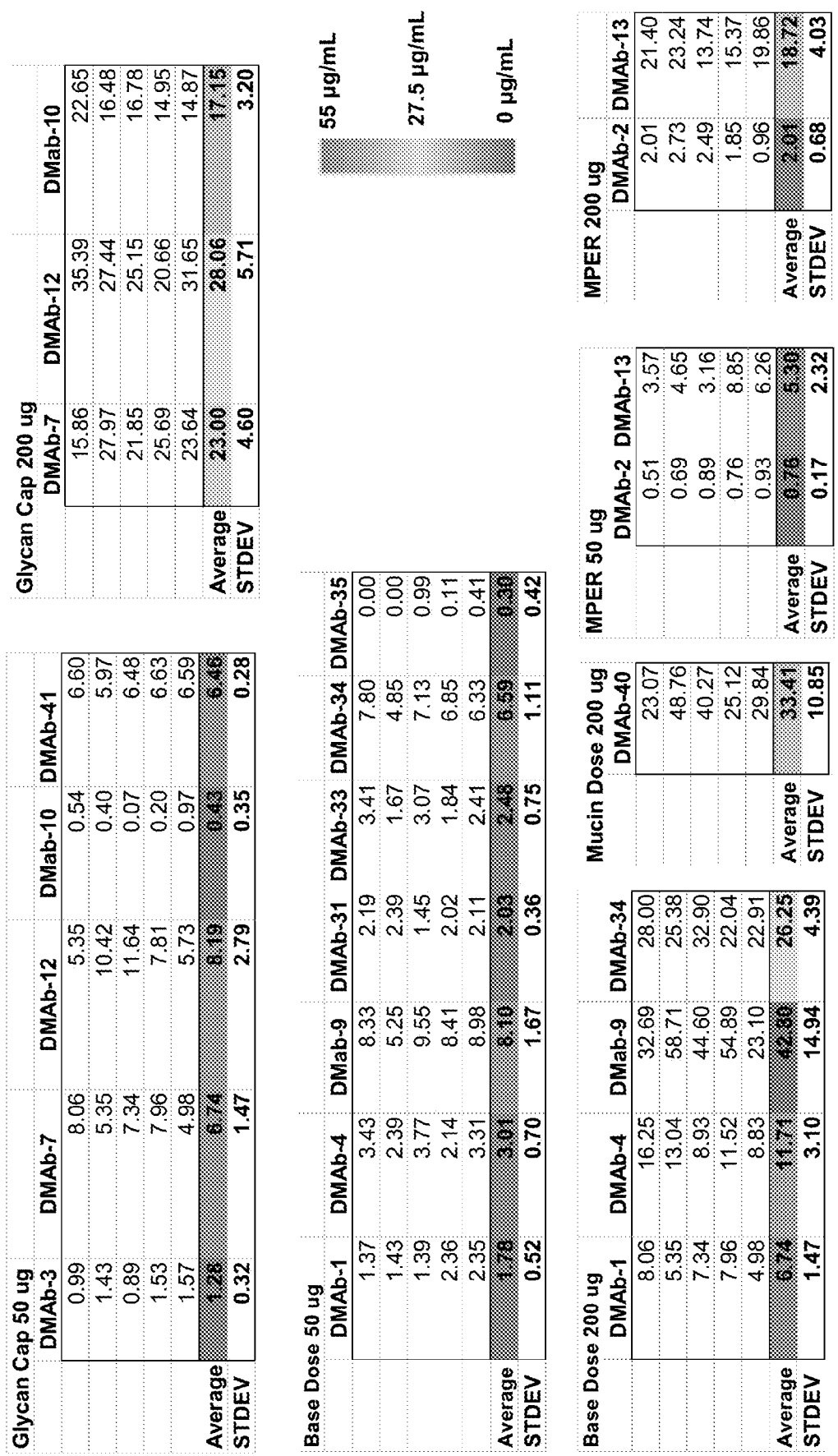
FIG. 14 depicts in vivo Cmax expression data for individual mice receiving anti-GP DMAbs.

Three DMAbs were mouse-human chimeras (DMAb-1, DMAb-4, DMAb7) and twenty-three were fully human IgG1 DMAbs. Successful in vivo DMAb production was detected for clones with a poor in vitro DI score and efficient expression of both chimeric and fully-human clones. These DMAbs expressed clones with different VH and VL families including robust expression of the more frequently used human VH1, VH3, VH4, Vκ1, Vκ2, Vκ3, and Vλ3 families (Table 2 and FIGS. 13-14).

There have been important challenges which have slowed the uptake of mAb technologies to prevent or treat viral infections for viral hemorrhagic fever among other infections. In vivo plasmid DNA delivery of engineered expression cassettes encoding highly potent anti-Ebola virus GP mAbs could have a tremendous impact on prevention of infectious diseases like EVD. The DMAb approach fills an important gap between antibody production and in vivo administration, utilizing many of the discovery and technology advancements established through traditional mAb development. The field of bioprocessed IgG production has developed highly sophisticated in silico analysis (Seeliger et al., 2015, Mabs-Austin 7:505-15; Sharma et al., 2014, PNAS 111:18601-6), cell-line based large-scale bioreactors, and refined purification processes. Here, it is demonstrated that, similarly, consistent expression of DMAbs in vivo also requires significant in silico sequence design, reductive antibody engineering, delivery, and formulation modifications to increase systemic human IgG expression. It is shown here that DMAb in vivo pharmacokinetic expression levels are independent of traditional in silico DI predictions which are designed for conventional cell-based protein mAb manufacturing platforms. The efficacy of the DMAb approach is supported by the complete protection observed in mouse-adapted EBOV prophylactic challenge experiments.

The current study demonstrates that it is possible to study protective efficacy of human IgG DMAbs in mice. Mouse studies of bioprocessed mAb and in vivo vector-delivered mAb are hindered by the development of murine anti-human antibody immune responses. One approach is to convert human Fc to mouse Fc Ig, retaining the antigen-binding Fab, to minimize host anti-antibody responses. Not surprisingly, fully mouse IgG2a DNA-encoded mAbs exhibit long-term expression in mouse models and protect against lethal ma-EBOV challenge (Andrews et al., 2017, Methods Clin Dev 7:74-82). Although Fc conversion may afford experimental advantages to mouse IgG mAbs through preferential binding to mouse Fc gamma receptors, translation of murine DNA-encoded Ig candidates to humans is not trivial. As these studies demonstrate, amino acid changes can have significant impact on in vivo expression levels (FIG. 2) and reversion to a human Fc would likely have direct consequences on gene expression. Others have shown that mouse-human chimeric Ig and humanized mouse Fab VH and VL regions may significantly alter expression, binding, ultimately impacting protection against lethal ma-EBOV challenge (Limberis et al., 2016, J Infect Dis 214:1975-9). Altered antibody paratope binding and functionality has been observed with murine mAbs containing identical variable regions but different Fc isotypes (Janda et al., 2012, J Biol Chem 287:35409-17; Yang et al., 2017, Mabs-Austin 9:1231-52), suggesting that the Fc domain may also place physical constraints on Fab allosteric cooperativity (Janda et al., 2016, Front Microbiol 7:22; Yang et al., 2017, Mabs-Austin 9:1231-52) with a potential impact on epitope specificity and virus neutralization (Tudor et al., 2012, PNAS 109:12680-5). In this context, the current anti-GP DMAb approach provides an important stepping stone for evaluation of human DMAb expression and protective efficacy that will likely be enhanced in NHPs and humans with matched antibody-receptor interactions and functional responses.

During the 2014-2016 EVD epidemic, an alternative mAb bioprocessing method utilizing *Nicotiana benthamiana* (tobacco) plants was used to produce the experimental ZMapp cocktail mAbs (Chen et al., 2016, F1000 Research 5). ZMapp was administered as three intravenous infusions of 50 mg/kg, every three days (PIW Group, 2016, NEJM 375:1448-56). Considerable effort and resources went to rapid production of ZMapp cocktail, yet the high dose/patient and number of infusions draws attention to the need for novel strategies to effectively deliver potent mAbs in vivo. MAb protein stability during transport and cold-chain storage are additional hurdles for delivery of anti-GP protein biologics in resource-limited settings such as field clinics and developing countries. In vivo DNA-delivery strategies such as DMAb are potentially enabling for mAb administration utilizing a platform that is safe, non-integrating, and temperature-stable in a diverse range of environments. DMAbs are simple to modify as newer, highly potent mAb clones are identified. Importantly, DMAbs are an important research tool for quick investigation of mAbs targeting Ebola virus and other infectious disease pathogens. The studies described herein can be adapted to greatly expedite the simultaneous evaluation of multiple mAb clones in vivo and delivery of highly potent clones with biochemical liabilities that may be complicated to overcome using cell-culture Ig bioprocessing.

In these studies, it is demonstrated that the window for protection with anti-GP DMAbs ranges from short-term expression to months of sustained levels, enabling potential administration with immunization campaigns to provide early protection during the time it takes to establish vaccine-induced memory responses (Muthumani et al., 2016, J Infect Dis 214:369-78). DMAbs can be easily administered to various demographic populations including deployable personnel, populations that are contraindicated for other treatments, and those living and working in resource-limited settings. These studies provide an important foundation for DMAb development and translation of anti-GP DMAbs to larger animal of Ebola virus infection. Overall, the anti-GP DMAb approach provides a simple, transient in vivo delivery strategy for highly potent anti-EVD mAb clones that can be applied to the engineering and screening of pan-filovirus and clones targeting other infectious diseases.

Example 3

Figure 15:
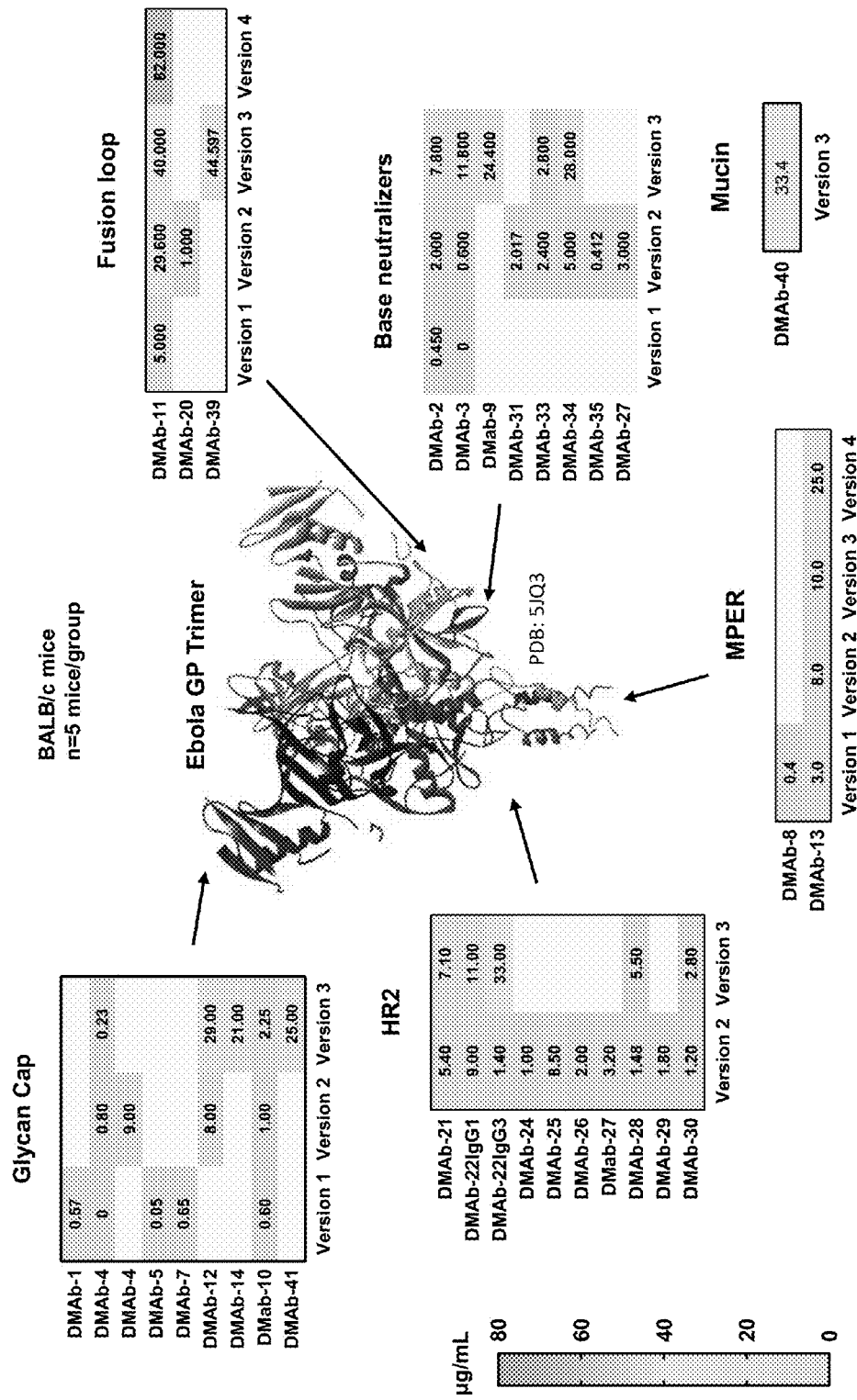
FIG. 15 depicts experimental results demonstrating Cmax expression levels in BALB/c mice (μg/mL).
Figure 16:
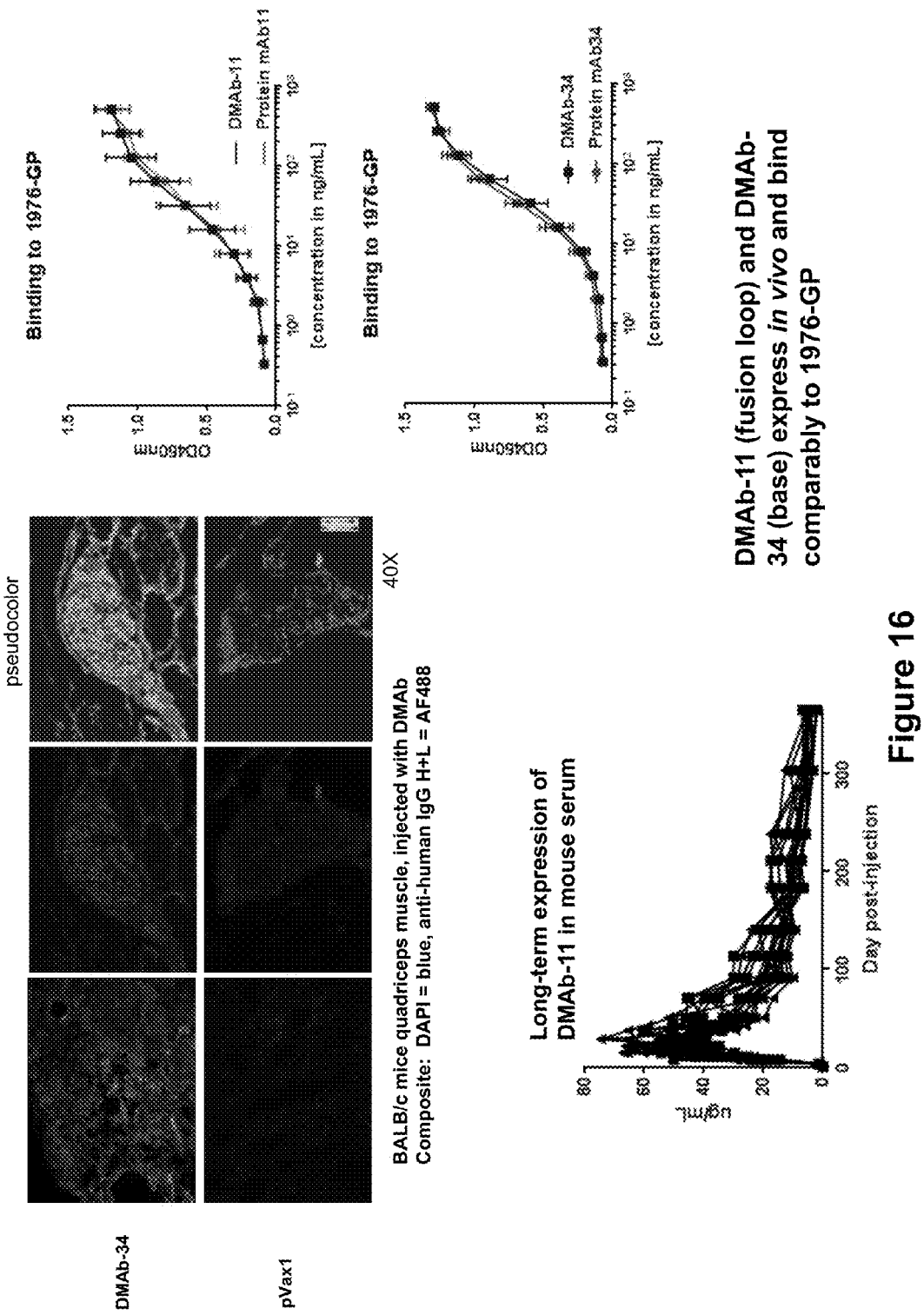
FIG. 16 depicts experimental results demonstrating the in vivo expression and characterization of DMAb-11 and DMAb-34.
Figure 17:
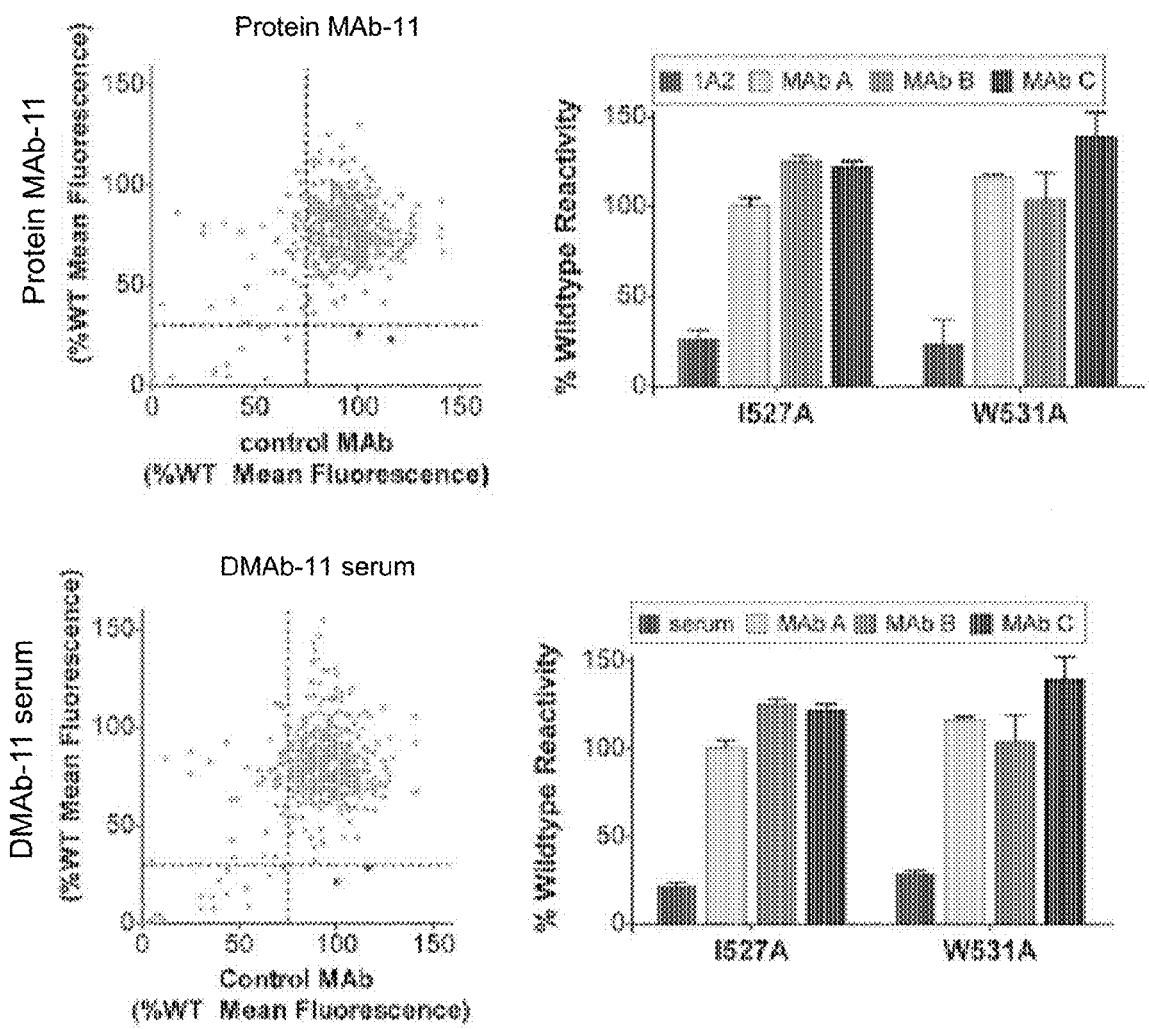
FIG. 17 depicts experimental results demonstrating EVD DMAb-11 epitope mapping.
Figure 17:
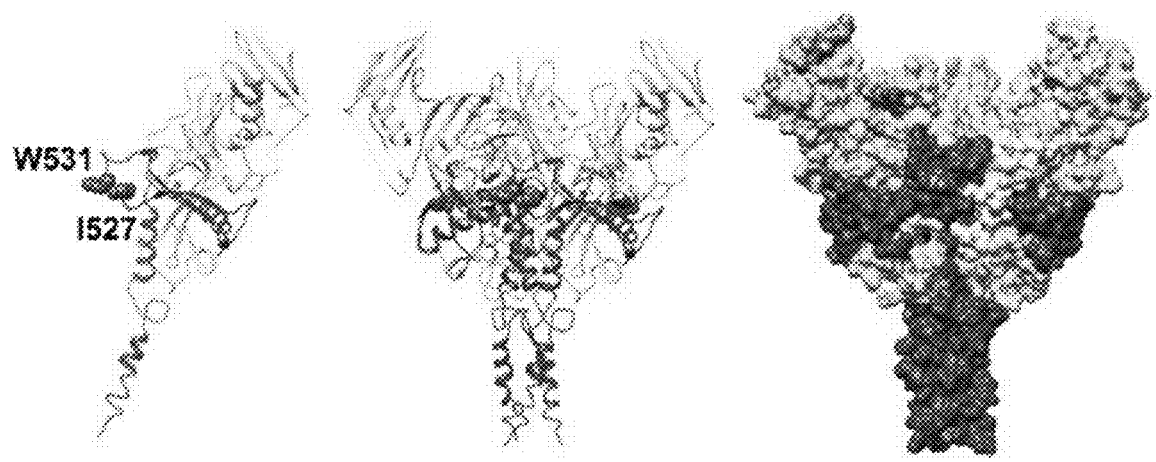
Figure 18:
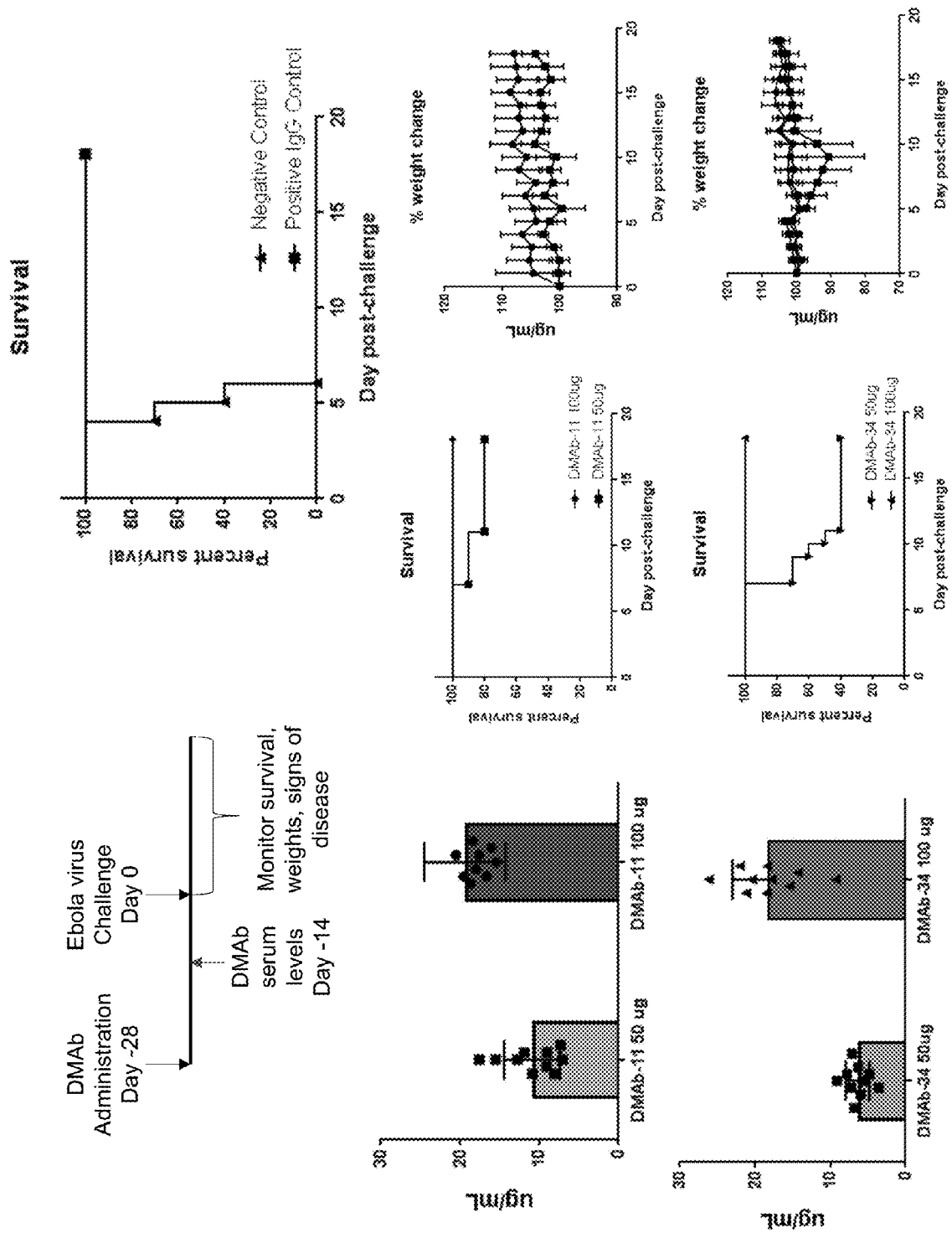
FIG. 18 depicts experimental results demonstrating that EVD DMAb-11 and EVD-34 protect against lethal mouse-adapted Mayinga challenge.

The studies presented herein demonstrate that EVD DMAbs are protective in mice challenged with ma-EBOV. EVD DMAbs are expressed in mice (FIG. 15). DMAb-11 (fusion loop) and DMAb-34 (base) express in vivo and bind comparably to 1976-GP (FIG. 16). Shotgun mutagenesis epitope mapping was performed by alanine scanning of EBOV GP using HEK 293T cells (FIG. 17). Both EVD DMAb-11 and EVD-34 protect against lethal mouse-adapted Mayinga challenge ($1000LD_{50}$) (FIG. 18).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule or a combination of nucleic acid molecules encoding one or more synthetic antibodies, wherein the one or more nucleic acid molecule comprises a nucleotide sequence encoding an anti-Ebola GP antibody or an antigen-binding fragment thereof, wherein the anti Ebola GP antibody or an antigen-binding fragment thereof comprises one or more amino acid sequences that have at least 95% sequence identity in the regions outside the complementarity-determining regions (CDRs) to the amino acid sequence(s) selected from the group consisting of:

a) the sequence as set forth in SEQ ID NO: 9, b) an antigen-binding fragment of SEQ ID NO:9, c) the combination of the heavy chain of SEQ ID NO: 27, and the light chain of SEQ ID NO: 29, and d) antigen binding fragments of the heavy chain of SEQ ID NO: 27, and the light chain of SEQ ID NO: 29.

2. The nucleic acid molecule of claim 1, further comprising a nucleotide sequence encoding a cleavage domain.

3. The nucleic acid molecule of claim 1, comprising a nucleotide sequence encoding an anti-Ebola GP antibody.

4. The nucleic acid molecule(s) of claim 1, wherein the nucleotide sequence(s) comprises a nucleotide sequence(s) having at least 95% sequence identity to the nucleotide sequence selected from the group consisting of:
  a) SEQ ID NO:10,
  b) a fragment of SEQ ID NO: 10 encoding an antigen-binding fragment of SEQ ID NO: 9,
  c) the combination of SEQ ID NO:28, and SEQ ID NO:30, and
  d) a combination of a fragment of SEQ ID NO:28 and a fragment of SEQ ID NO: 30, wherein the fragments encode an antigen-binding molecule;
  wherein the encoded amino acid molecule, or antigen-binding fragment thereof has 100% identity to the CDR sequences of SEQ ID NO:9 or to the CDR sequences of the combination of SEQ ID NO:28 and SEQ ID NO:30.

5. The nucleic acid molecule(s) of claim 1, wherein the nucleic acid molecule(s) comprises a nucleotide sequence having at least about 95% identity in the regions outside of the CDRs over an entire length of the nucleic acid sequence to:
  a) a nucleotide sequence encoding SEQ ID NO:9, and
  b) a combination of nucleotide sequences encoding the combination of SEQ ID NO:27, and SEQ ID NO:29.

6. The nucleic acid molecule(s) of claim 1, wherein the nucleic acid molecule comprises:
  a) a nucleotide sequence having at least about 95% identity over the fragment of SEQ ID NO: 10 encoding SEQ ID NO:9, or
  b) a combination of nucleotide sequences having at least about 95% identity to the combination of SEQ ID NO:28, and SEQ ID NO:30,
  wherein the encoded amino acid molecule has 100% identity to the CDR sequences of SEQ ID NO:9 or to the CDR sequences of the combination of SEQ ID NO: 28 and SEQ ID NO:30.

7. The nucleic acid molecule(s) of claim 1, wherein the nucleotide sequences encoding an anti-Ebola glycoprotein (GP) protein synthetic antibody comprises a nucleotide sequence encoding a variable heavy chain region and a nucleotide sequence encoding a variable light chain region.

8. The nucleic acid molecule(s) of claim 7, wherein the nucleotide sequence encoding a variable heavy chain region encodes SEQ ID NO:27 and further wherein the nucleotide sequence encoding a variable light chain region encodes SEQ ID NO:29.

9. The nucleic acid molecule(s) of claim 8, wherein the nucleotide sequence encoding a variable heavy chain region comprises SEQ ID NO:28 and further wherein the nucleotide sequence encoding a variable light chain region comprises SEQ ID NO: 30.

10. The nucleic acid molecule of claim 1, wherein the nucleotide sequence encodes a leader sequence.

11. The nucleic acid molecule of claim 1, wherein the nucleic acid molecule comprises an expression vector.

12. A composition comprising the nucleic acid molecule or the combination of nucleic acid molecules of claim 1.

13. The composition of claim 12, further comprising a pharmaceutically acceptable excipient.

* * * * *

SEQUENCE LISTING

```
<160> NUMBER OF SEQ ID NOS: 170

<210> SEQ ID NO 1
<211> LENGTH: 732
<212> TYPE: PRT
<213> ORGANISM: Artificial Sequence
<220> FEATURE:
<223> OTHER INFORMATION: DMAb-2G4

<400> SEQUENCE: 1

Met Asp Trp Thr Trp Arg Ile Leu Phe Leu Val Ala Ala Ala Thr Gly
1               5                   10                  15

Thr His Ala Glu Val Gln Leu Gln Glu Ser Gly Gly Gly Leu Met Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60
```

```
Glu Trp Val Ala Glu Ile Arg Leu Lys Ser Asn Asn Tyr Ala Thr His
 65                  70                  75                  80

Tyr Ala Glu Ser Val Lys Gly Arg Phe Thr Ile Ser Arg Asp Asp Ser
             85                  90                  95

Lys Arg Ser Val Tyr Leu Gln Met Asn Thr Leu Arg Ala Glu Asp Thr
            100                 105                 110

Gly Ile Tyr Tyr Cys Thr Arg Gly Asn Gly Asn Tyr Arg Ala Met Asp
        115                 120                 125

Tyr Trp Gly Gln Gly Thr Ser Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
```

```
            485                 490                 495
Pro Gly Pro Met Val Leu Gln Thr Gln Val Phe Ile Ser Leu Leu Leu
            500                 505                 510

Trp Ile Ser Gly Ala Tyr Gly Asp Ile Gln Met Thr Gln Ser Pro Ala
            515                 520                 525

Ser Leu Ser Val Ser Val Gly Glu Thr Val Ser Ile Thr Cys Arg Ala
        530                 535                 540

Ser Glu Asn Ile Tyr Ser Ser Leu Ala Trp Tyr Gln Gln Lys Gln Gly
545                 550                 555                 560

Lys Ser Pro Gln Leu Leu Val Tyr Ser Ala Thr Ile Leu Ala Asp Gly
                565                 570                 575

Val Pro Ser Arg Phe Ser Gly Ser Gly Ser Gly Thr Gln Tyr Ser Leu
            580                 585                 590

Lys Ile Asn Ser Leu Gln Ser Glu Asp Phe Gly Thr Tyr Tyr Cys Gln
            595                 600                 605

His Phe Trp Gly Thr Pro Tyr Thr Phe Gly Gly Gly Thr Lys Leu Glu
        610                 615                 620

Ile Lys Thr Val Ala Ala Pro Ser Val Phe Ile Phe Pro Pro Ser Asp
625                 630                 635                 640

Glu Gln Leu Lys Ser Gly Thr Ala Ser Val Val Cys Leu Leu Asn Asn
                645                 650                 655

Phe Tyr Pro Arg Glu Ala Lys Val Gln Trp Lys Val Asp Asn Ala Leu
            660                 665                 670

Gln Ser Gly Asn Ser Gln Glu Ser Val Thr Glu Gln Asp Ser Lys Asp
            675                 680                 685

Ser Thr Tyr Ser Leu Ser Asn Thr Leu Thr Leu Ser Lys Ala Asp Tyr
        690                 695                 700

Glu Lys His Lys Val Tyr Ala Cys Glu Val Thr His Gln Gly Leu Ser
705                 710                 715                 720

Ser Pro Val Thr Lys Ser Phe Asn Arg Gly Glu Cys
                725                 730
```

<210> SEQ ID NO 2
<211> LENGTH: 2202
<212> TYPE: DNA
<213> ORGANISM: Artificial Sequence
<220> FEATURE:
<223> OTHER INFORMATION: PGX9226, DMAb-2G4

<400> SEQUENCE: 2

```
atggattgga catggaggat tctgtttctg gtcgccgccg caactggaac ccacgctgaa      60
gtgcagctgc aggagtcagg aggaggactg atgcagcccg gcggaagcat gaagctgtcc     120
tgcgtggcat ctggcttcac ctttagtaac tactggatga attgggtccg ccagtcacct     180
gagaagggac tggaatgggt ggctgagatc cgactgaaaa gcaacaatta cgccacccac     240
tatgctgagt cagtgaaggg cgcattcaca attagcaggg acgattctaa agaagtgtg      300 tatctgcaga tgaacactct gagagccgaa gacaccggaa tctactattg cacacggggc     360
aacggaaatt accgcgctat ggattattgg ggcagggca cttccgtcac cgtgagctcc      420
gcaagcacaa agggaccctc cgtgtttccc ctggccccctt ctagtaaaag cacctccgga    480
ggaacagcag ctctgggatg tctggtgaag gactacttcc ctgagccagt caccgtgtca    540
tggaacagcg gagccctgac ctctggggtc catacatttc ctgctgtgct gcagtcaagc    600
gggctgtact ccctgtcctc tgtggtcact gtgccaagtt caagcctggg cactcagacc    660
```

-continued

```
tatatctgca acgtgaatca caagcccagc aataccaaag tcgacaagaa agtggagcct      720
aagtcctgtg ataaaacaca tacttgccca ccttgtccag cacctgaact gctgggagga      780
cctagcgtgt tcctgtttcc acccaagcca aaagacacac tgatgatttc ccgcactcct      840
gaggtcacct gtgtggtcgt ggacgtgtct cacgaggacc ccgaagtcaa gttcaactgg      900
tacgtggatg gcgtcgaagt gcataatgcc aagaccaaac ccagggagga acagtacaac      960
tctacctata gggtcgtgag tgtcctgaca gtgctgcacc aggactggct gaacggcaag     1020
gagtataagt gcaaagtgag caataaggct ctgccagcac ccatcgaaaa aactatttcc     1080
aaggccaaag acagccaag agagcccag gtgtacaccc tgcctccatc tcgggacgaa       1140
ctgacaaaga accaggtcag tctgacttgt ctggtgaaag gcttctatcc atccgatatc     1200
gctgtggagt gggaatctaa tggacagccc gagaacaatt acaagaccac acccctgtg      1260
ctggactccg atgggtcttt ctttctgtat agtaagctga ccgtggataa atcacggtgg     1320
cagcagggca acgtcttttc ttgcagtgtg atgcatgaag ccctgcacaa tcattacaca     1380
cagaagtcac tgagcctgtc cccaggcaag cgaggacgaa aaaggagatc tggaagtggg     1440
gctactaact tcagcctgct gaaacaggca ggcgacgtgg aggaaaatcc tggaccaatg     1500
gtcctgcaga cccaggtgtt tatctcactg ctgctgtgga ttagcggggc ttacggcgat     1560
attcagatga cacagtcccc agcatcactg agcgtctccg tgggagaaac agtgtccatc     1620
acttgtcgcg cctctgagaa catctacagc agcctggctt ggtatcagca aagcaggga     1680
aaaagccccc agctgctggt ctactccgca acaatcctgg ccgacggggt gccttctagg     1740
ttctctggca gtggatcagg gacacagtat agcctgaaga ttaatagtct gcagtcagag     1800
gattttggga cttactattg ccagcacttc tggggcacac catacacttt tggcggaggg     1860
actaagctgg agatcaaaac cgtcgcagcc ccctctgtgt tcatttttcc acccagtgac     1920
gaacagctga agagtggcac cgcctcagtc gtgtgtctgc tgaacaattt ctaccctaga     1980
gaggcaaagg tccagtggaa agtggataac gccctgcaga gcggcaattc ccaggaatct     2040
gtgactgagc aggacagtaa ggattcaacc tatagcctgt ccaacaccct gacactgagc     2100
aaagctgact acgaaaagca caaagtctat gcatgcgagg tgacacatca gggactgagt     2160
tcaccagtga ctaagtcctt taatcggggg gagtgttgat aa                        2202
```

<210> SEQ ID NO 3
<211> LENGTH: 711
<212> TYPE: PRT
<213> ORGANISM: Artificial Sequence
<220> FEATURE:
<223> OTHER INFORMATION: DMAb-4G7

<400> SEQUENCE: 3

```
Gln Val Gln Leu Gln Gln Ser Gly Pro Glu Leu Glu Met Pro Gly Ala
1               5                   10                  15

Ser Val Lys Ile Ser Cys Lys Ala Ser Gly Ser Ser Phe Thr Gly Phe
            20                  25                  30

Ser Met Asn Trp Val Lys Gln Ser Asn Gly Lys Ser Leu Glu Trp Ile
        35                  40                  45

Gly Asn Ile Asp Thr Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95
```

```
Ala Arg Ser Ala Tyr Tyr Gly Ser Thr Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Arg Gly Arg Lys Arg Arg Ser Gly Ser Gly Ala Thr Asn Phe Ser
            450                 455                 460

Leu Leu Lys Gln Ala Gly Asp Val Glu Glu Asn Pro Gly Pro Met Val
465                 470                 475                 480

Leu Gln Thr Gln Val Phe Ile Ser Leu Leu Leu Trp Ile Ser Gly Ala
            485                 490                 495

Tyr Gly Asp Ile Gln Met Thr Gln Ser Pro Ala Ser Leu Ser Ala Ser
            500                 505                 510
```

```
Val Gly Glu Thr Val Thr Ile Thr Cys Arg Ala Ser Glu Asn Ile Tyr
            515                 520                 525
Ser Tyr Leu Ala Trp Tyr Gln Gln Lys Gln Gly Lys Ser Pro Gln Leu
        530                 535                 540
Leu Val Tyr Asn Ala Lys Thr Leu Ile Glu Gly Val Pro Ser Arg Phe
545                 550                 555                 560
Ser Gly Ser Gly Ser Gly Thr Gln Phe Ser Leu Lys Ile Asn Ser Leu
                565                 570                 575
Gln Pro Glu Asp Phe Gly Ser Tyr Phe Cys Gln His His Phe Gly Thr
            580                 585                 590
Pro Phe Thr Phe Gly Ser Gly Thr Glu Leu Glu Ile Lys Thr Val Ala
        595                 600                 605
Ala Pro Ser Val Phe Ile Phe Pro Pro Ser Asp Glu Gln Leu Lys Ser
610                 615                 620
Gly Thr Ala Ser Val Val Cys Leu Leu Asn Asn Phe Tyr Pro Arg Glu
625                 630                 635                 640
Ala Lys Val Gln Trp Lys Val Asp Asn Ala Leu Gln Ser Gly Asn Ser
                645                 650                 655
Gln Glu Ser Val Thr Glu Gln Asp Ser Lys Asp Ser Thr Tyr Ser Leu
            660                 665                 670
Ser Asn Thr Leu Thr Leu Ser Lys Ala Asp Tyr Glu Lys His Lys Val
        675                 680                 685
Tyr Ala Cys Glu Val Thr His Gln Gly Leu Ser Ser Pro Val Thr Lys
        690                 695                 700
Ser Phe Asn Arg Gly Glu Cys
705                 710

<210> SEQ ID NO 4
<211> LENGTH: 2196
<212> TYPE: DNA
<213> ORGANISM: Artificial Sequence
<220> FEATURE:
<223> OTHER INFORMATION: pGX9229, DMAb-4G7

<400> SEQUENCE: 4
atggattgga catggaggat tctgtttctg gtcgccgccg ccactggaac ccacgcccag      60
gtgcagctgc agcagtcagg gcctgagctg gaaatgcctg gcgcttctgt gaaaatcagt     120
tgcaaggcat caggaagctc cttcacaggg tttagcatga ctgggtgaa cagagcaat      180 gggaagtccc tggagtggat cggcaacatt gacacctact atggcggaac cacatacaat     240
cagaagttca aggcaaggc tacactgact gtggacaaat ctagttcaac cgcatatatg     300
cagctgaaga gcctgacatc cgaggattct gcagtgtact attgcgctag atcagcatac     360
tatggcagca ctttcgccta ctggggccag ggaaccctgg tcacagtgag ctccgcctcc     420
accaaaggac catctgtgtt tcccctggct ccttctagta agagtacatc aggaggaact     480
gcagctctgg gatgtctggt gaaggattat ttccctgagc cagtcaccgt gagttggaac     540
tcaggcgcac tgacttctgg agtccacacc tttcctgccg tgctgcagtc aagcggcctg     600
tacagcctgt cctctgtggt caccgtgcca agttcaagcc tgggaaccca gacatatatc     660
tgcaacgtga atcacaaacc ctctaataca aaggtcgaca gaaaagtgga acctaaaagc     720
tgtgataaga ctcatacctg cccaccttgt ccagcacctg agctgctggg agggccttcc     780
gtgttcctgt ttcacccaa accaaaggac acactgatga ttagcagaac ccctgaagtc     840
acatgtgtgg tcgtggacgt gtcccacgag accccgaag tcaagttcaa ctggtacgtg     900
```

```
gatggcgtcg aggtgcataa tgctaaaacc aagccccgag aggaacagta caactctact    960
tataggtcg tgagtgtcct gaccgtgctg caccaggact ggctgaacgg caaggagtat   1020
aaatgcaagg tgtctaacaa ggccctgcca gctcccatcg agaagacaat tagcaaagct   1080
aagggacagc caagagaacc ccaggtgtac actctgcctc catctcggga cgagctgacc   1140
aaaaaccagg tcagtctgac atgtctggtg aagggattct atccaagcga tatcgcagtg   1200
gagtgggaat ccaatgggca gcccgaaaac aattacaaga ctaccccccc tgtgctggac   1260
agcgatggca gcttcttcct gtattccaaa ctgacagtgg ataagtctcg gtggcagcag   1320
gggaacgtct ttagctgctc cgtgatgcat gaggccctgc acaatcatta cactcagaag   1380
tctctgagtc tgtcaccagg caaacgagga cgaaagagga gaagcgggtc cggagcaacc   1440
aacttctccc tgctgaagca ggctggagac gtggaggaaa atcctgggcc aatggtcctg   1500
cagacacagg tgtttatctc actgctgctg tggattagcg gggcctacgg cgatattcag   1560
atgactcaga gccccgcatc tctgagtgcc tcagtcggcg agacagtgac tatcacctgt   1620
cgcgcaagtg aaaacatcta ctcatatctg gcctggtacc agcagaaaca ggggaagagc   1680
ccccagctgc tggtctataa tgctaaaacc ctgatcgaag gagtgccttc ccgattcagc   1740
ggcagcgggt ctggcacaca gtttagcctg aagattaact ccctgcagcc agaggacttc   1800
ggcagctact tttgccagca ccatttcgga actcccttca cctttggcag cgggacagag   1860
ctggaaatca aaactgtcgc agcccccagt gtgttcattt ttccaccctc agacgaacag   1920
ctgaagtctg gaccgccag tgtcgtgtgt ctgctgaaca ttttttaccc tcggggaggct   1980
aaagtccagt ggaaggtgga taacgcactg cagtctggaa atagtcagga gtcagtgaca   2040
gaacaggaca gcaaagattc cacttatagt ctgtcaaaca cactgactct gtctaaggcc   2100
gactacgaga aacacaaggt ctatgcttgc gaagtgactc atcaggggct gtcctctcct   2160
gtgaccaaga gcttcaatcg cggcgagtgt tgataa                             2196
```

<210> SEQ ID NO 5
<211> LENGTH: 733
<212> TYPE: PRT
<213> ORGANISM: Artificial Sequence
<220> FEATURE:
<223> OTHER INFORMATION: DMAB4

<400> SEQUENCE: 5

```
Met Asp Trp Thr Trp Arg Ile Leu Phe Leu Val Ala Ala Ala Thr Gly
1               5                   10                  15

Thr His Ala Gln Val Thr Leu Lys Glu Ser Gly Pro Gly Ile Leu Lys
            20                  25                  30

Pro Ser Gln Thr Leu Ser Leu Thr Cys Ser Leu Ser Gly Phe Ser Leu
        35                  40                  45

Ser Thr Ser Gly Val Gly Val Gly Trp Phe Arg Gln Pro Ser Gly Lys
    50                  55                  60

Gly Leu Glu Trp Leu Ala Leu Ile Trp Trp Asp Asp Lys Tyr Tyr
65                  70                  75                  80

Asn Pro Ser Leu Lys Ser Gln Leu Ser Ile Ser Lys Asp Phe Ser Arg
                85                  90                  95

Asn Gln Val Phe Leu Lys Ile Ser Asn Val Asp Ile Ala Asp Thr Ala
            100                 105                 110

Thr Tyr Tyr Cys Ala Arg Arg Asp Pro Phe Gly Tyr Asp Asn Ala Met
        115                 120                 125

Gly Tyr Trp Gly Gln Gly Thr Ser Val Thr Val Ser Ser Ala Ser Thr
```

-continued

```
               130                 135                 140
Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
                485                 490                 495

Asn Pro Gly Pro Met Val Leu Gln Thr Gln Val Phe Ile Ser Leu Leu
            500                 505                 510

Leu Trp Ile Ser Gly Ala Tyr Gly Asp Ile Val Met Thr Gln Ser Gln
        515                 520                 525

Lys Phe Met Ser Thr Ser Val Gly Asp Arg Val Ser Leu Thr Cys Lys
    530                 535                 540

Ala Ser Gln Asn Val Gly Thr Ala Val Ala Trp Tyr Gln Gln Lys Pro
545                 550                 555                 560
```

Gly Gln Ser Pro Lys Leu Leu Ile Tyr Ser Ala Ser Asn Arg Tyr Thr
            565                 570                 575

Gly Val Pro Asp Arg Phe Thr Gly Ser Gly Ser Gly Thr Asp Phe Thr
            580                 585                 590

Leu Thr Ile Ser Asn Met Gln Ser Glu Asp Leu Ala Asp Tyr Phe Cys
            595                 600                 605

Gln Gln Tyr Ser Ser Tyr Pro Leu Thr Phe Gly Ala Gly Thr Lys Leu
            610                 615                 620

Glu Ile Lys Thr Val Ala Ala Pro Ser Val Phe Ile Phe Pro Pro Ser
625                 630                 635                 640

Asp Glu Gln Leu Lys Ser Gly Thr Ala Ser Val Val Cys Leu Leu Asn
            645                 650                 655

Asn Phe Tyr Pro Arg Glu Ala Lys Val Gln Trp Lys Val Asp Asn Ala
            660                 665                 670

Leu Gln Ser Gly Asn Ser Gln Glu Ser Val Thr Glu Gln Asp Ser Lys
            675                 680                 685

Asp Ser Thr Tyr Ser Leu Ser Asn Thr Leu Thr Leu Ser Lys Ala Asp
            690                 695                 700

Tyr Glu Lys His Lys Val Tyr Ala Cys Glu Val Thr His Gln Gly Leu
705                 710                 715                 720

Ser Ser Pro Val Thr Lys Ser Phe Asn Arg Gly Glu Cys
            725                 730

<210> SEQ ID NO 6
<211> LENGTH: 2226
<212> TYPE: DNA
<213> ORGANISM: Artificial Sequence
<220> FEATURE:
<223> OTHER INFORMATION: pGX9230, DMAb4

<400> SEQUENCE: 6

```
ggatccgccg ccaccatgga ctggacttgg agaattctgt tcctggtcgc agcagccact      60
gggacacacg cacaggtgac actgaaagag agcggacccg gaatcctgaa accaagccag     120
actctgtccc tgacctgcag cctgtccggc ttctctctga gtacctcagg agtcggagtg     180
ggatggtttc gacagccaag cggaaaggga ctggagtggc tggccctgat ctggtgggac     240
gatgacaagt actataaccc ttcactgaaa gccagctgag catttccaa ggatttctct      300
cgcaaccagg tctttctgaa gatcagtaat gtggatattg ccgacactgc tacctactat     360
tgcgctagga gagatccatt cggctacgac aatgcaatgg atattgggg ccagggaacc      420
tccgtcacag tgagctccgc atccacaaaa gggccctctg tgtttcccct ggcccttct      480
agtaagtcta caagtggcgg aactgccgct ctgggctgtc tggtgaagga ctacttccct     540
gagccagtca ccgtgtcctg gaactctgga gccctgactt ctggggtcca cccttttcct    600
gctgtgctgc agtcaagcgg actgtacagc ctgtcctctg tggtcaccgt gccaagttca     660
agcctgggga cacagactta tatctgcaac gtgaatcaca agccatctaa tacaaagtc     720
gataagaaag tggaacccaa gagctgtgac aaaacccata catgcccacc ttgtccagca     780
cctgagctgc tgggaggacc aagcgtgttc ctgttccac ccaagcctaa agatacactg      840
atgatttcca ggaccccga agtgacatgt gtggtcgtgg atgtgtctca cgaggaccct      900
gaagtcaagt tcaactggta cgtggacggc gtcgaggtgc ataatgctaa gaccaaacct     960
cgcgaggaac agtacaacag tacatatcga gtcgtgtcag tgctgaccgt cctgcaccag    1020
gactggctga acggaaagga gtataagtgc aaagtgagca caaggcact gccagccccc     1080
```

```
atcgagaaga ctatttccaa ggcaaaaggg cagccaaggg aaccccaggt gtacaccctg    1140
cctccaagca gagatgagct gactaaaaac caggtctccc tgacctgtct ggtgaagggg    1200
ttctatccta gtgacatcgc tgtggagtgg gaatcaaatg ccagccaga aaacaattac     1260 aagaccacac ccctgtgct ggatagtgac ggctcattct ttctgtattc aaagctgacc     1320
gtggataaaa gcagatggca gcagggaaac gtcttctcat gcagcgtgat gcatgaggcc    1380
ctgcacaatc attacactca gaaatccctg tctctgagtc ccggcaagcg aggaaggaaa    1440
cggcgctcag ggagcggcgc tacaaacttt tccctgctga agcaggcagg ggacgtggag    1500
gaaaatcctg cccaatggt cctgcagacc caggtgttca tcagcctgct gctgtggatt     1560 tccgggcct acggcgatat tgtgatgacc cagagccaga agttcatgtc cacatctgtc     1620
ggcgaccggg tgtctctgac ctgtaaggcc agtcagaacg tcggaactgc tgtggcatgg    1680
tatcagcaga agcctgggca gtccccaaaa ctgctgatct acagtgcttc aaacagatat    1740
accggcgtgc ctgatcggtt caccggaagc gggtccggca cagactttac tctgaccatt    1800
tctaatatgc agagtgaaga tctggctgac tacttctgcc agcagtactc ctcttatcca    1860
ctgacatttg gagcagggac taagctgaaa atcaaaacag tcgcagcccc ctccgtgttc    1920
atttttccac cctctgatga gcagctgaag tcaggcactg ccagcgtcgt gtgtctgctg    1980
aacaatttct accccaggga ggccaaggtc cagtggaaag tggacaacgc tctgcagagc    2040
ggaaattccc aggagtctgt gactgaacag gatagtaaag actcaaccta ttctctgagt    2100
aacacactga ctctgtccaa ggcagactac gagaagcaca agtctatgc ctgcgaagtg      2160 acccatcagg gcctgagttc accagtgaca aagtctttta tcgcggaga gtgttgataa      2220 ctcgag                                                                 2226

<210> SEQ ID NO 7
<211> LENGTH: 729
<212> TYPE: PRT
<213> ORGANISM: Artificial Sequence
<220> FEATURE:
<223> OTHER INFORMATION: DMAb-10

<400> SEQUENCE: 7

Met Asp Trp Thr Trp Arg Ile Leu Phe Leu Val Ala Ala Thr Gly
1               5                   10                  15

Thr His Ala Glu Val Gln Leu Val Glu Ser Gly Gly Leu Val Gln
                20                  25                  30

Pro Gly Gly Ser Leu Arg Leu Ser Cys Ala Ala Ser Gly Phe Thr Phe
            35                  40                  45

Arg Ser Tyr Asp Met His Trp Val Arg Gln Ala Thr Gly Lys Gly Leu
        50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Val Arg Phe Gly Asp Thr Ala Val Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
```

-continued

```
            145                 150                 155                 160
        Ala Leu Gly Cys Leu Val Lys Asp Tyr Phe Pro Glu Pro Val Thr Val
                        165                 170                 175
        Ser Trp Asn Ser Gly Ala Leu Thr Ser Gly Val His Thr Phe Pro Ala
                        180                 185                 190
        Val Leu Gln Ser Ser Gly Leu Tyr Ser Leu Ser Ser Val Val Thr Val
                        195                 200                 205
        Pro Ser Ser Ser Leu Gly Thr Gln Thr Tyr Ile Cys Asn Val Asn His
                        210                 215                 220
        Lys Pro Ser Asn Thr Lys Val Asp Lys Val Glu Pro Lys Ser Cys
        225                 230                 235                 240
        Asp Lys Thr His Thr Cys Pro Pro Cys Pro Ala Pro Glu Leu Leu Gly
                        245                 250                 255
        Gly Pro Ser Val Phe Leu Phe Pro Pro Lys Pro Lys Asp Thr Leu Met
                        260                 265                 270
        Ile Ser Arg Thr Pro Glu Val Thr Cys Val Val Val Asp Val Ser His
                        275                 280                 285
        Glu Asp Pro Glu Val Lys Phe Asn Trp Tyr Val Asp Gly Val Glu Val
                        290                 295                 300
        His Asn Ala Lys Thr Lys Pro Arg Glu Glu Gln Tyr Asn Ser Thr Tyr
        305                 310                 315                 320
        Arg Val Val Ser Val Leu Thr Val Leu His Gln Asp Trp Leu Asn Gly
                        325                 330                 335
        Lys Glu Tyr Lys Cys Lys Val Ser Asn Lys Ala Leu Pro Ala Pro Ile
                        340                 345                 350
        Glu Lys Thr Ile Ser Lys Ala Lys Gly Gln Pro Arg Glu Pro Gln Val
                        355                 360                 365
        Tyr Thr Leu Pro Pro Ser Arg Asp Glu Leu Thr Lys Asn Gln Val Ser
                        370                 375                 380
        Leu Thr Cys Leu Val Lys Gly Phe Tyr Pro Ser Asp Ile Ala Val Glu
        385                 390                 395                 400
        Trp Glu Ser Asn Gly Gln Pro Glu Asn Asn Tyr Lys Thr Thr Pro Pro
                        405                 410                 415
        Val Leu Asp Ser Asp Gly Ser Phe Phe Leu Tyr Ser Lys Leu Thr Val
                        420                 425                 430
        Asp Lys Ser Arg Trp Gln Gln Gly Asn Val Phe Ser Cys Ser Val Met
                        435                 440                 445
        His Glu Ala Leu His Asn His Tyr Thr Gln Lys Ser Leu Ser Leu Ser
        450                 455                 460
        Pro Gly Lys Arg Gly Arg Lys Arg Arg Ser Gly Ser Gly Ala Thr Asn
        465                 470                 475                 480
        Phe Ser Leu Leu Lys Gln Ala Gly Asp Val Glu Glu Asn Pro Gly Pro
                        485                 490                 495
        Met Val Leu Gln Thr Gln Val Phe Ile Ser Leu Leu Leu Trp Ile Ser
                        500                 505                 510
        Gly Ala Tyr Gly Asp Ile Gln Met Thr Gln Ser Pro Ser Ser Leu Ser
                        515                 520                 525
        Ala Ser Val Gly Asp Arg Val Thr Ile Thr Cys Arg Ala Ser Gln Ser
                        530                 535                 540
        Ile Ser Ser Phe Leu Asn Trp His Gln Gln Lys Pro Gly Lys Ala Pro
        545                 550                 555                 560
        Lys Leu Leu Ile Tyr Ala Ala Ser Ser Leu Gln Ser Gly Val Pro Ser
                        565                 570                 575
```

```
Arg Phe Ser Gly Ser Gly Ser Gly Thr Asp Phe Thr Leu Thr Ile Ser
                580                 585                 590

Ser Leu Gln Pro Glu Asp Phe Ala Ile Tyr Tyr Cys Gln Gln Ser Tyr
            595                 600                 605

Ile Ser Pro Phe Thr Phe Gly Pro Gly Thr Lys Val Asp Ile Lys Thr
        610                 615                 620

Val Ala Ala Pro Ser Val Phe Ile Phe Pro Pro Ser Asp Glu Gln Leu
625                 630                 635                 640

Lys Ser Gly Thr Ala Ser Val Val Cys Leu Leu Asn Asn Phe Tyr Pro
                645                 650                 655

Arg Glu Ala Lys Val Gln Trp Lys Val Asp Asn Ala Leu Gln Ser Gly
            660                 665                 670

Asn Ser Gln Glu Ser Val Thr Glu Gln Asp Ser Lys Asp Ser Thr Tyr
        675                 680                 685

Ser Leu Ser Ser Thr Leu Thr Leu Ser Lys Ala Asp Tyr Glu Lys His
        690                 695                 700

Lys Val Tyr Ala Cys Glu Val Thr His Gln Gly Leu Ser Ser Pro Val
705                 710                 715                 720

Thr Lys Ser Phe Asn Arg Gly Glu Cys
                725

<210> SEQ ID NO 8
<211> LENGTH: 2214
<212> TYPE: DNA
<213> ORGANISM: Artificial Sequence
<220> FEATURE:
<223> OTHER INFORMATION: pGX9244, DMAb-10

<400> SEQUENCE: 8
ggatccgccg ccaccatgga ctggacttgg agaatcctgt tcctggtcgc cgccgctact    60
gggactcatg ccgaggtgca gctggtcgaa tctggagggg gcctggtgca gcctggcggc   120
agcctgaggc tgtcctgcgc agcatctggc ttcaccttta ggagctacga catgcactgg   180
gtgcgccagg caacaggcaa gggactggag tgggtgtctg ccatcggaac cgcaggcgat   240
acatactatc caggctccgt gaagggcagg ttcaccatct cccgcgagaa cgccaagaat   300
tctctgtacc tgcagatgaa cagcctgaga gccgaggaca ccgccgtgta ctattgcgcc   360
agggtgcgct tcggcgacac agcagtggat tattggggcc agggcaccct ggtgacagtg   420
agctccgcct ccaccaaggg accaagcgtg ttcccactgg caccttctag caagtccacc   480
tctggcggca gcccgccct gggctgtctg gtgaaggatt acttccctga gccagtgaca   540
gtgtcctgga actctggcgc cctgaccagc ggagtgcaca catttcctgc cgtgctgcag   600
tcctctggcc tgtactccct gagctccgtg gtgaccgtgc catctagctc cctgggcacc   660
cagacatata tctgcaacgt gaatcacaag cctagcaata caaaggtgga caagaaggtg   720
gagccaaagt cctgtgataa gacccacaca tgccctccct gtccagcacc tgagctgctg   780
ggcggcccaa gcgtgttcct gttttccaccc aagcccaagg acaccctgat gatcagccgg   840
accccagagg tgacatgcgt ggtggtggac gtgtcccacg aggacccga ggtgaagttt   900 aactggtacg tggatggcgt ggaggtgcac aatgccaaga ccaagccccg ggaggagcag   960
tacaacagca cctatagagt ggtgtccgtg ctgacagtgc tgcaccagga ctggctgaac  1020
ggcaaggagt ataagtgcaa ggtgagcaat aaggccctgc cagcccccat cgagaagacc  1080
atctccaagg caaagggaca gccaagggag ccacaggtgt acacactgcc tccatcccgc  1140
```

```
gacgagctga ccaagaacca ggtgtctctg acatgtctgg tgaagggctt ctatccctct    1200
gatatcgccg tggagtggga gagcaatggc cagcctgaga acaattacaa gaccacaccc    1260
cctgtgctgg acagcgatgg ctccttcttt ctgtattcca agctgaccgt ggacaagtct    1320
cggtggcagc agggcaacgt gtttagctgc tccgtgatgc acgaggccct gcacaatcac    1380
tacacccaga agtctctgag cctgtcccca ggcaagaggg aagaaagcg  gagatctggc    1440 agcggcgcca caaacttcag cctgctgaag caggccggcg atgtggagga gaatcctggc    1500
ccaatggtgc tgcagaccca ggtgtttatc tctctgctgc tgtggatcag cggcgcctat    1560
ggcgacatcc agatgacaca gtccccttct agcctgtccg cctctgtggg cgatcgggtg    1620
accatcacat gtagagccag ccagtccatc tcctctttcc tgaactggca ccagcagaag    1680
cctggcaagg ccccaaagct gctgatctac gcagccagct ccctgcagag cggagtgccc    1740
tccaggttct ctggcagcgg ctccggaacc gactttaccc tgacaatctc tagcctgcag    1800
cctgaggatt ttgccatcta ctattgccag cagtcttata tcagccccct caccttt ggc    1860 cctggcacaa aggtggacat caagaccgtg gccgcccaa gcgtgttcat ctttccaccc    1920
tccgatgagc agctgaagtc tggcacagcc agcgtggtgt gcctgctgaa caatttctac    1980
ccccgcgagg ccaaggtgca gtggaaggtg acaacgccc  tgcagtccgg caattctcag    2040
gagagcgtga ccgagcagga ctccaaggat tctacatatt ctctgagctc taccctgaca    2100
ctgagcaagg ccgattacga gaagcacaag gtgtatgcct gcgaggtcac ccaccagggg    2160
ctgtcaagtc cagtcactaa gtccttcaat cggggcgaat gctgataact cgag           2214
```

<210> SEQ ID NO 9
<211> LENGTH: 739
<212> TYPE: PRT
<213> ORGANISM: Artificial Sequence
<220> FEATURE:
<223> OTHER INFORMATION: DMAb-11

<400> SEQUENCE: 9

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Ala Val
        35                  40                  45

Arg Ser Asn Tyr Leu Ser Trp Val Arg Gln Ala Pro Gly Lys Gly Leu
    50                  55                  60

Glu Trp Val Ser Leu Ile Tyr Ser Gly Gly Leu Thr Ala Tyr Ala Asp
65                  70                  75                  80

Ser Val Glu Gly Arg Phe Thr Ile Ser Arg Asp Asn Ser Lys Asn Thr
                85                  90                  95

Leu Tyr Leu Gln Met Asn Ser Leu Arg Val Glu Asp Thr Ala Leu Tyr
            100                 105                 110

Tyr Cys Ala Arg Val Ala Ser Ala Gly Thr Phe Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

```
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
        210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Asp Glu Leu Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys Arg Gly Arg Lys Arg Arg Ser Gly Ser
465                 470                 475                 480
Gly Ala Thr Asn Phe Ser Leu Leu Lys Gln Ala Gly Asp Val Glu Glu
                485                 490                 495
Asn Pro Gly Pro Met Val Leu Gln Thr Gln Val Phe Ile Ser Leu Leu
            500                 505                 510
Leu Trp Ile Ser Gly Ala Tyr Gly Asp Ile Val Met Thr Gln Ser Pro
        515                 520                 525
Arg Ser Leu Ser Val Thr Pro Gly Glu Pro Ala Ser Ile Ser Cys Arg
    530                 535                 540
Ser Ser Gln Ser Leu Leu His Arg Asn Gly Tyr Asn Tyr Leu Asp Trp
545                 550                 555                 560
Tyr Leu Gln Lys Pro Gly Gln Ser Pro Gln Leu Leu Ile Tyr Leu Gly
                565                 570                 575
Ser Asn Arg Ala Ser Gly Val Pro Asp Arg Phe Ser Gly Ser Gly Ser
            580                 585                 590
Gly Thr Asp Phe Thr Leu Lys Ile Ser Arg Val Glu Ala Glu Asp Val
```

```
            595                 600                 605
Gly Val Tyr Tyr Cys Met Gln Ala Leu Gln Thr Pro Ser Trp Thr Phe
    610                 615                 620

Gly Gln Gly Thr Lys Val Glu Ile Lys Thr Val Ala Ala Pro Ser Val
625                 630                 635                 640

Phe Ile Phe Pro Pro Ser Asp Glu Gln Leu Lys Ser Gly Thr Ala Ser
            645                 650                 655

Val Val Cys Leu Leu Asn Asn Phe Tyr Pro Arg Glu Ala Lys Val Gln
            660                 665                 670

Trp Lys Val Asp Asn Ala Leu Gln Ser Gly Asn Ser Gln Glu Ser Val
            675                 680                 685

Thr Glu Gln Asp Ser Lys Asp Ser Thr Tyr Ser Leu Ser Ser Thr Leu
            690                 695                 700

Thr Leu Ser Lys Ala Asp Tyr Glu Lys His Lys Val Tyr Ala Cys Glu
705                 710                 715                 720

Val Thr His Gln Gly Leu Ser Ser Pro Val Thr Lys Ser Phe Asn Arg
                725                 730                 735

Gly Glu Cys

<210> SEQ ID NO 10
<211> LENGTH: 2244
<212> TYPE: DNA
<213> ORGANISM: Artificial Sequence
<220> FEATURE:
<223> OTHER INFORMATION: pGX9256, DMAb-11

<400> SEQUENCE: 10
ggatccgccg ccaccatgga ctggacctgg agaatcctgt tcctggtggc agcagcaacc      60
ggaacacacg cagaggtgca gctggtggag agcggcggcg ccctgatcca gccaggcggc     120
agcctgaggc tgtcctgcgc agcatctgga tttgccgtga ggagcaacta cctgtcctgg     180
gtgagacagg caccaggcaa gggactggag tgggtgtctc tgatctacag cggcggcctg     240
accgcatatg cagacagcgt ggagggcagg ttcaccatct ccagagataa ctctaagaat     300
acactgtatc tgcagatgaa ttccctgcgg gtggaggaca ccgccctgta ctattgcgcc     360
cgcgtggcca gctccgccgg cacattctac tatggcatgg acgtgtgggg ccagggcacc     420
acagtgaccg tgtctagcgc ctccacaaag ggaccaagcg tgttcccact ggcaccttcc     480
tctaagtcca cctctggcgg cacagccgcc ctgggctgtc tggtgaagga ttacttccct     540
gagccagtga ccgtgtcttg aacagcggcg ccctgaccag cggagtgca cacatttcct     600
gccgtgctgc agagctccgg cctgtactcc ctgtctagcg tggtgaccgt gccatcctct     660
agcctgggca cccagacata tatctgcaac gtgaatcaca agcctagcaa tacaaaggtg     720
gacaagaagg tggagccaaa gtcctgtgat aagacccaca catgccctcc ctgtccagca     780
cctgagctgc tgggcggccc aagcgtgttc ctgtttccac ccaagcccaa ggacacactg     840
atgatctcta ggacccccaga ggtgacatgc gtggtggtgg acgtgagcca cgaggacccc     900
gaggtgaagt ttaactggta cgtggatggc gtggaggtgc acaatgccaa gaccaagcca     960
agggaggagc agtacaacag cacctataga gtggtgtccg tgctgacagt gctgcaccag    1020
gactggctga acggcaagga gtataagtgc aaggtgtcca ataaggccct gccagccccc    1080
atcgagaaga ccatctctaa ggcaaaggga cagccaaggg agccacaggt gtacacactg    1140
cctccatcca gagacgagct gaccaagaac caggtgtctc tgacatgtct ggtgaagggc    1200
ttctatccct ctgatatcgc cgtggagtgg gagagcaatg gccagcctga gaacaattac    1260
```

-continued

```
aagaccacac cccctgtgct ggactccgat ggctctttct ttctgtattc caagctgacc    1320
gtggataagt ctcggtggca gcagggcaac gtgtttagct gctccgtgat gcacgaggcc    1380
ctgcacaatc actacaccca gaagtctctg agcctgtccc ctggcaagag gggaaggaag    1440
aggagatctg gcagcggcgc cacaaacttc agcctgctga agcaggcagg cgacgtggag    1500
gagaatcctg gaccaatggt gctgcagacc caggtgttta tctctctgct gctgtggatc    1560
agcggcgcct acggcgatat cgtgatgacc cagtcccctc gctccctgtc tgtgacacct    1620
ggcgagccag ccagcatctc ctgtcggtcc tctcagtctc tgctgcaccg caacggctac    1680
aattatctgg actggtacct gcagaagccc ggccagtccc ctcagctgct gatctatctg    1740
ggcagcaaca gggcatccgg agtgccagac cgcttctctg gcagcggctc cggaaccgac    1800
ttcaccctga agatcagcag ggtggaggcc gaggatgtgg gcgtgtacta ttgcatgcag    1860
gccctgcaga ccccctcctg gacattcggc cagggcacca aggtggagat caagacagtg    1920 gccgcccta gcgtgttcat ctttccaccc tccgacgagc agctgaagtc tggcaccgcc    1980
agcgtggtgt gcctgctgaa caacttctac cccagagagg ccaaggtgca gtggaaggtg    2040
gataacgccc tgcagagcgg caattcccag gagtctgtga ccgagcagga cagcaaggat    2100
tccacatatt ctctgagctc caccctgaca ctgagcaagg ccgactacga aagcacaag    2160 gtgtatgcct gcgaggtgac ccaccagggc ctgtctagcc ctgtgacaaa gtccttcaac    2220
agaggcgagt gttgataact cgag                                          2244
```

<210> SEQ ID NO 11
<211> LENGTH: 741
<212> TYPE: PRT
<213> ORGANISM: Artificial Sequence
<220> FEATURE:
<223> OTHER INFORMATION: DMAb12

<400> SEQUENCE: 11

```
Met Asp Trp Thr Trp Arg Ile Leu Phe Leu Val Ala Ala Ala Thr Gly
 1               5                  10                  15

Thr His Ala Gln Val Gln Leu Val Gln Ser Gly Ala Glu Val Lys Lys
            20                  25                  30

Pro Gly Ser Ser Val Lys Val Ser Cys Lys Ala Ser Gly Ala Thr Phe
        35                  40                  45

Gly Ser Asp Thr Val Thr Trp Val Arg Gln Ala Pro Gly Gln Gly Leu
    50                  55                  60

Glu Trp Met Gly Gly Ile Ile Pro Phe Gly Glu Ala Asn Tyr Ala
65                  70                  75                  80

Gln Arg Phe Gln Gly Arg Val Thr Ile Thr Ala Asp Lys Ser Thr Asn
                85                  90                  95

Thr Ala Tyr Met Glu Leu Ser Ser Leu Arg Ser Glu Asp Thr Ala Val
            100                 105                 110

Tyr Phe Cys Ala Arg Gln Ile Asn Glu Met Ala Thr Phe Gly Glu Ile
        115                 120                 125

His Tyr Tyr Thr Tyr Met Asp Val Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
```

```
                180                 185                 190
Leu Thr Ser Gly Val His Thr Phe Pro Ala Val Leu Gln Ser Ser Gly
            195                 200                 205

Leu Tyr Ser Leu Ser Ser Val Val Thr Val Pro Ser Ser Ser Leu Gly
            210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Arg Gly Arg
465                 470                 475                 480

Lys Arg Arg Ser Gly Ser Gly Ala Thr Asn Phe Ser Leu Leu Lys Gln
                485                 490                 495

Ala Gly Asp Val Glu Glu Asn Pro Gly Pro Met Val Leu Gln Thr Gln
            500                 505                 510

Val Phe Ile Ser Leu Leu Leu Trp Ile Ser Gly Ala Tyr Gly Gly Ser
        515                 520                 525

Glu Leu Thr Gln Asp Pro Ala Val Ser Val Ala Leu Gly Gln Thr Val
    530                 535                 540

Arg Ile Thr Cys Gln Gly Asp Ser Leu Arg Asn Tyr Tyr Ala Ser Trp
545                 550                 555                 560

Tyr Gln Gln Lys Pro Arg Gln Ala Pro Val Leu Val Phe Tyr Gly Lys
                565                 570                 575

Asn Asn Arg Pro Ser Gly Ile Pro Asp Arg Phe Ser Gly Ser Ser Ser
            580                 585                 590

Gly Asn Thr Ala Ser Leu Thr Ile Ser Gly Ala Gln Ala Glu Asp Glu
        595                 600                 605
```

```
Ala Asp Tyr Tyr Cys Asn Ser Arg Asp Ser Ser Asn His Leu Val
        610                 615                 620
Phe Gly Gly Gly Thr Lys Leu Thr Val Leu Ser Thr Val Ala Ala Pro
625                 630                 635                 640
Ser Val Phe Ile Phe Pro Pro Ser Asp Glu Gln Leu Lys Ser Gly Thr
                645                 650                 655
Ala Ser Val Val Cys Leu Leu Asn Asn Phe Tyr Pro Arg Glu Ala Lys
            660                 665                 670
Val Gln Trp Lys Val Asp Asn Ala Leu Gln Ser Gly Asn Ser Gln Glu
        675                 680                 685
Ser Val Thr Glu Gln Asp Ser Lys Asp Ser Thr Tyr Ser Leu Ser Asn
    690                 695                 700
Thr Leu Thr Leu Ser Lys Ala Asp Tyr Glu Lys His Lys Val Tyr Ala
705                 710                 715                 720
Cys Glu Val Thr His Gln Gly Leu Ser Ser Pro Val Thr Lys Ser Phe
                725                 730                 735
Asn Arg Gly Glu Cys
            740

<210> SEQ ID NO 12
<211> LENGTH: 2232
<212> TYPE: DNA
<213> ORGANISM: Artificial Sequence
<220> FEATURE:
<223> OTHER INFORMATION: pGX9260, DMAb12

<400> SEQUENCE: 12
catggactgg acctggagaa tcctgttcct ggtggcagca gcaaccggaa cacacgcaca      60
ggtgcagctg gtgcagagcg gagcagaggt gaagaagcca ggcagctccg tgaaggtgtc     120
ctgcaaggca tctggagcca ccttcggctc cgataccgtg acatgggtgc gccaggcacc     180
aggacaggga ctggagtgga tgggcggcat catcccttc tttggcgagg ccaactacgc      240
ccagcggttt cagggcagag tgaccatcac agccgacaag tccaccaata gcctacat      300
ggagctgtct agcctgcggt ctgaggatac cgccgtgtat ttctgcgcca gacagatcaa     360
cgagatggcc acctttggcg agatccacta ctatacatac atggacgtgt ggggacaggg     420
caccctggtg acagtgtcct ctgcctccac aagggacct agcgtgttcc cactggcacc      480
tagctccaag tctaccagcg gcggcacagc cgccctggga tgtctggtga aggattattt     540
ccctgagcca gtgacagtgt cctggaactc tggcgccctg accagcggag tgcacacatt     600
tccccgccgtg ctgcagtcta gcggcctgta ctccctgtcc tctgtggtga ccgtgcctag    660
ctcctctctg gcacccagac atatatctg caacgtgaat cacaagccctt ctaatacaaa    720
ggtggacaag aaggtggagc caaagagctg tgataagacc cacacatgcc ctcctgtcc     780
agcacctgag ctgctgggcg gcccaagcgt gttcctgttt ccacccaagc caaggacac     840
cctgatgatc agcaggaccc ctgaggtgac atgcgtggtg gtggacgtgt ccacgagga     900
ccccgaggtg aagttcaact ggtacgtgga tggcgtggag gtgcacaatg ccaagaccaa     960
gccccgggag gagcagtaca acagcaccta tagagtggt tccgtgctga cagtgctgca    1020
ccaggactgg ctgaacggca aggagtataa gtgcaaggtg tctaataagg ccctgccagc    1080
ccccatcgag aagaccatct ccaaggcaaa gggacagcca agggagccac aggtgtacac    1140
actgcctcca agccgcgacg agctgaccaa gaaccaggtg tccctgacat gtctggtgaa    1200
gggcttctat ccatccgata tcgccgtgga gtgggagtct aatggccagc cgagaacaa     1260
```

-continued

```
ttacaagacc acaccccctg tgctggacag cgatggctcc ttctttctgt attccaagct   1320
gaccgtggac aagtctcggt ggcagcaggg caacgtgttt tcctgctctg tgatgcacga   1380
ggccctgcac aatcactaca cccagaagag cctgtccctg tctcctggca gaggggaag    1440 gaagcggaga agcggctccg gagccacaaa cttcagcctg ctgaagcagg ccggcgatgt   1500
ggaggagaat cctggcccaa tggtgctgca gacccaggtg tttatctctc tgctgctgtg   1560
gatcagcgga gcatacggcg gctccgagct gacacaggac ccagccgtga gcgtggccct   1620
gggacagacc gtgaggatca catgtcaggg cgatagcctg cgcaactact atgcctcctg   1680
gtaccagcag aagcctcggc aggccccagt gctggtgttc tatggcaaga caataggcc   1740 ctctggcatc cctgaccgct ttagcggcag ctcctctggc aataccgcaa gcctgacaat   1800
ctccggagca caggcagagg acgaggcaga ttactattgc aacagcagag atagctcctc   1860
taatcacctg gtgttcggcg gcggaaccaa gctgacagtg ctgtctaccg tggccgcccc   1920
aagcgtgttc atctttccac cctccgacga gcagctgaag tctggcacag ccagcgtggt   1980
gtgcctgctg aacaacttct accccgggga ggccaaggtg cagtggaagg tggataacgc   2040
cctgcagtct ggcaatagcc aggagtccgt gaccgagcag gactctaagg atagcacata   2100
ttctctgagc aacaccctga cactgagcaa ggccgactac gagaagcaca aggtgtatgc   2160
atgcgaggtg acccaccagg gactgagctc cccagtgaca aagtccttca atagaggcga   2220
gtgttgataa ct                                                       2232
```

<210> SEQ ID NO 13
<211> LENGTH: 735
<212> TYPE: PRT
<213> ORGANISM: Artificial Sequence
<220> FEATURE:
<223> OTHER INFORMATION: DMAb13

<400> SEQUENCE: 13

```
Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30

Pro Gly Gly Ser Leu Arg Leu Ser Cys Glu Val Ser Gly Leu Thr Phe
        35                  40                  45

Ser Asn Phe Gly Met Gln Trp Val Arg Gln Ala Pro Gly Lys Gly Leu
    50                  55                  60

Glu Trp Val Ala Phe Ile Arg Phe Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Gly Ser Leu Arg Ala Glu Asp Thr Ala Val
            100                 105                 110

Tyr Phe Cys Gly Arg Val Leu Tyr Gly Ala Ala Asp Phe Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
```

```
                180             185             190
Val Leu Gln Ser Ser Gly Leu Tyr Ser Leu Ser Ser Val Val Thr Val
            195             200             205
Pro Ser Ser Leu Gly Thr Gln Thr Tyr Ile Cys Asn Val Asn His
    210             215             220
Lys Pro Ser Asn Thr Lys Val Asp Lys Val Glu Pro Lys Ser Cys
225             230             235             240
Asp Lys Thr His Thr Cys Pro Pro Cys Pro Ala Pro Glu Leu Leu Gly
            245             250             255
Gly Pro Ser Val Phe Leu Phe Pro Pro Lys Pro Lys Asp Thr Leu Met
            260             265             270
Ile Ser Arg Thr Pro Glu Val Thr Cys Val Val Val Asp Val Ser His
            275             280             285
Glu Asp Pro Glu Val Lys Phe Asn Trp Tyr Val Asp Gly Val Glu Val
            290             295             300
His Asn Ala Lys Thr Lys Pro Arg Glu Glu Gln Tyr Asn Ser Thr Tyr
305             310             315             320
Arg Val Val Ser Val Leu Thr Val Leu His Gln Asp Trp Leu Asn Gly
            325             330             335
Lys Glu Tyr Lys Cys Lys Val Ser Asn Lys Ala Leu Pro Ala Pro Ile
            340             345             350
Glu Lys Thr Ile Ser Lys Ala Lys Gly Gln Pro Arg Glu Pro Gln Val
            355             360             365
Tyr Thr Leu Pro Pro Ser Arg Asp Glu Leu Thr Lys Asn Gln Val Ser
            370             375             380
Leu Thr Cys Leu Val Lys Gly Phe Tyr Pro Ser Asp Ile Ala Val Glu
385             390             395             400
Trp Glu Ser Asn Gly Gln Pro Glu Asn Asn Tyr Lys Thr Thr Pro Pro
            405             410             415
Val Leu Asp Ser Asp Gly Ser Phe Phe Leu Tyr Ser Lys Leu Thr Val
            420             425             430
Asp Lys Ser Arg Trp Gln Gln Gly Asn Val Phe Ser Cys Ser Val Met
            435             440             445
His Glu Ala Leu His Asn His Tyr Thr Gln Lys Ser Leu Ser Leu Ser
            450             455             460
Pro Gly Lys Arg Gly Arg Lys Arg Arg Ser Gly Ser Gly Ala Thr Asn
465             470             475             480
Phe Ser Leu Leu Lys Gln Ala Gly Asp Val Glu Glu Asn Pro Gly Pro
            485             490             495
Met Val Leu Gln Thr Gln Val Phe Ile Ser Leu Leu Leu Trp Ile Ser
            500             505             510
Gly Ala Tyr Gly Asp Ile Val Met Thr Gln Ser Pro Asp Ser Leu Ala
            515             520             525
Val Ser Leu Gly Glu Arg Ala Thr Ile Asn Cys Thr Ser Ser His Ser
            530             535             540
Leu Leu Tyr Ser Ser Asp Asn Lys Asn Tyr Leu Thr Trp Tyr Gln Gln
545             550             555             560
Lys Ala Gly Gln Pro Pro Lys Leu Leu Ile Tyr Trp Ala Ser Thr Arg
            565             570             575
Gln Ser Gly Val Pro Asp Arg Phe Ser Gly Ser Gly Ser Gly Thr Glu
            580             585             590
Phe Thr Leu Thr Ile Ser Ser Leu Gln Ala Glu Asp Val Ala Val Tyr
            595             600             605
```

Tyr Cys Gln Gln Tyr Tyr Thr Lys Ser Phe Thr Phe Gly Gln Gly Thr
           610                 615                 620

Lys Val Glu Ile Lys Thr Val Ala Ala Pro Ser Val Phe Ile Phe Pro
625                 630                 635                 640

Pro Ser Asp Glu Gln Leu Lys Ser Gly Thr Ala Ser Val Val Cys Leu
                645                 650                 655

Leu Asn Asn Phe Tyr Pro Arg Glu Ala Lys Val Gln Trp Lys Val Asp
            660                 665                 670

Asn Ala Leu Gln Ser Gly Asn Ser Gln Glu Ser Val Thr Glu Gln Asp
        675                 680                 685

Ser Lys Asp Ser Thr Tyr Ser Leu Ser Asn Thr Leu Thr Leu Ser Lys
    690                 695                 700

Ala Asp Tyr Glu Lys His Lys Val Tyr Ala Cys Glu Val Thr His Gln
705                 710                 715                 720

Gly Leu Ser Ser Pro Val Thr Lys Ser Phe Asn Arg Gly Glu Cys
                725                 730                 735

<210> SEQ ID NO 14
<211> LENGTH: 2214
<212> TYPE: DNA
<213> ORGANISM: Artificial Sequence
<220> FEATURE:
<223> OTHER INFORMATION: pGX9261, DMAb13

<400> SEQUENCE: 14

| | | | |
|---|---|---|---|
| catggactgg acctggagaa tcctgttcct ggtggcagca gcaaccggaa cacacgcaca | 60 |
| ggtgcagctg gtggagagcg gcggcggcgt ggtgcagcct ggcggctctc tgagactgag | 120 |
| ctgcagaggt gtccggcctg accttcagca ctttggaatg cagtgggtga ggcaggcacc | 180 |
| aggcaaggga ctggagtggg tggccttcat ccgctttgac ggctctaata agtactatgc | 240 |
| cgatagcgtg aagggccggt tcaccatctc tagagacaac agcaagaata cagtgtacct | 300 |
| gcagatgggc agcctgaggg cagaggacac cgccgtgtac ttctgcggac gcgtgctgta | 360 |
| tggagcagca gcagattttt ggggacaggg caccctggtg acagtgagct ccgcctctac | 420 |
| aaagggacca agcgtgtttc cactggcacc ctctagcaag tccacctctg cggcacagc | 480 |
| cgccctgggc tgtctggtga aggattactt ccccgagcct gtgaccgtga gctggaactc | 540 |
| cggcgccctg acctccggag tgcacacatt ccagccgtg ctgcagtcct ctggcctgta | 600 |
| cagcctgagc tccgtggtga ccgtgccctc tagctccctg gcacccaga catatatctg | 660 |
| caacgtgaat cacaagccaa gcaatacaaa ggtggacaag aaggtggagc ccaagtcctg | 720 |
| tgataagacc cacacatgcc ctccctgtcc agcaccagag ctgctgggcg gcccaagcgt | 780 |
| gttcctgttt ccacccaagc ctaaggacac cctgatgatc tctagaaccc ccgaggtgac | 840 |
| atgcgtggtg gtggacgtga gccacgagga ccccgaggtg aagttcaact ggtacgtgga | 900 |
| tggcgtggag gtgcacaatg ccaagacaaa gcctcgggag gagcagtaca actccaccta | 960 |
| tagagtggtg tctgtgctga cagtgctgca ccaggactgg ctgaacggca aggagtataa | 1020 |
| gtgcaaggtg tccaataagg ccctgcctgc cccaatcgag aagaccatct ctaaggcaaa | 1080 |
| gggacagcct cgggagccac aggtgtacac actgcctcca tccagagacg agctgaccaa | 1140 |
| gaaccaggtg tctctgacat gtctggtgaa gggcttctat ccttctgata tcgccgtgga | 1200 |
| gtgggagagc aatggccagc cagagaacaa ttacaagacc acccccctg tgctggactc | 1260 |
| tgatggcagc ttctttctgt attccaagct gaccgtggac aagtctcggt ggcagcaggg | 1320 |

```
caacgtgttt agctgctccg tgatgcacga ggccctgcac aatcactaca cccagaagtc    1380
tctgagcctg tccccaggca agaggggaag gaagcggaga tctggcagcg gagccacaaa    1440
cttctccctg ctgaagcagg caggcgatgt ggaggagaat ccaggaccta tggtgctgca    1500
gacccaggtg tttatcagcc tgctgctgtg gatctccggc gcctatggcg acatcgtgat    1560
gacacagtcc ccagattctc tggccgtgtc cctgggagag agggcaacca tcaactgtac    1620
atctagccac agcctgctgt actcctctga caacaagaat tacctgacct ggtatcagca    1680
gaaggccggc cagccaccca agctgctgat ctattgggca tccaccaggc agtctggagt    1740
gccagaccgc ttctccggct ctggcagcgg cacagagttt accctgacaa tcagctccct    1800
gcaggccgag gatgtggccg tgtactattg ccagcagtac tataccaaga gcttcacatt    1860
tggccagggc accaaggtgg agatcaagac agtggccgcc cccagcgtgt tcatctttcc    1920
tccatccgac gagcagctga agagcggaac cgcatccgtg gtgtgcctgc tgaacaattt    1980
ctaccctagg gaggccaagg tgcagtggaa ggtggataac gccctgcaga gcggcaattc    2040
ccaggagtct gtgaccgagc aggacagcaa ggattccaca tattccctgt ctaacaccct    2100
gacactgtcc aaggccgatt acgagaagca caaggtgtat gcctgcgagg tgacccacca    2160
gggcctgtct agccctgtga caaagagctt taatcgcggc gagtgttgat aact           2214
```

<210> SEQ ID NO 15
<211> LENGTH: 468
<212> TYPE: PRT
<213> ORGANISM: Artificial Sequence
<220> FEATURE:
<223> OTHER INFORMATION: DMAb-34 Heavy Chain

<400> SEQUENCE: 15

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Ser Tyr Gly Phe Ser Trp Val Arg Gln Ala Pro Gly Gln Gly Leu
    50                  55                  60

Glu Trp Met Gly Trp Ile Ser Ala Tyr Asn Gly Tyr Thr Lys Tyr Ala
65                  70                  75                  80

Gln Lys Phe Gln Gly Arg Val Thr Met Thr Thr Asp Thr Ser Thr Arg
                85                  90                  95

Thr Ala Tyr Met Glu Leu Arg Ser Leu Arg Ser Asp Asp Ala Ala Val
            100                 105                 110

Tyr Tyr Cys Ala Arg Asp Leu Thr Pro Arg Asp Gly Met Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 16
<211> LENGTH: 1431
<212> TYPE: DNA
<213> ORGANISM: Artificial Sequence
<220> FEATURE:
<223> OTHER INFORMATION: DMAb-34 Heavy Chain

<400> SEQUENCE: 16
ggatccgccg ccaccatgga ctggacatgg agaatcctgt tcctggtggc agcagcaacc      60
ggaacacacg cacaggtgca gctggtgcag tccggagcag aggtgaagaa gccaggagcc     120
tctgtgaagg tgagctgcaa ggcctccggc tataccttca gctcctacgg cttttcttgg     180
gtgcgccagg cacctggaca gggcctggag tggatgggct ggatcagcgc ctacaacggc     240
tatacaaagt acgcccagaa gttccagggc cgggtgacca tgaccacaga caccagcaca     300
cgcaccgcct atatggagct gaggagcctg agaagcgacg atgccgccgt gtactattgc     360
gcccgggatc tgaccccctc cgacggaatg gacgtgtggg gacagggaac cacagtgaca     420
gtgtctagcg cctctaccaa gggcccaagc gtgtttccac tggccccctc ctctaagtcc     480
acatctggcg gcaccgccgc cctgggatgt ctggtgaagg attacttccc agagcccgtg     540

```
accgtgtcct ggaactctgg cgccctgaca agcggcgtgc acacctttcc agccgtgctg    600
cagagctccg gcctgtattc cctgtctagc gtggtgacag tgccctcctc tagcctgggc    660
acacagacct acatctgcaa cgtgaatcac aagccaagca ataccaaggt ggacaagaag    720
gtggagccca agtcctgtga taagacacac acctgccctc cctgtcctgc accagagctg    780 ctggcggcc catccgtgtt cctgtttcca cccaagccta aggacacact gatgatctct    840
aggacacccg aggtgacctg cgtggtggtg gacgtgagcc acgaggaccc cgaggtgaag    900
tttaactggt acgtggatgg cgtggaggtg cacaatgcca agaccaagcc aagggaggag    960
cagtataatt ccacatacag agtggtgtct gtgctgaccg tgctgcacca ggactggctg   1020
aacggcaagg agtacaagtg caaggtgtcc aataaggccc tgcccgcccc tatcgagaag   1080
acaatctcta aggccaaggg ccagcctagg gagccacagg tgtatacccT gcctccatcc   1140
agagacgagc tgacaaagaa ccaggtgtct ctgacctgtc tggtgaaggg cttctaccct   1200
tctgatatcg ccgtggagtg ggagagcaat ggccagccag agaacaatta taagaccaca   1260
ccccctgtgc tggacagcga tggctccttc tttctgtaca gcaagctgac agtggataag   1320
tccagatggc agcagggcaa cgtgtttagc tgttccgtga tgcacgaggc cctgcacaat   1380
cactacaccc agaagtctct gagcctgtcc cctggcaagt gataactcga g             1431
```

<210> SEQ ID NO 17
<211> LENGTH: 238
<212> TYPE: PRT
<213> ORGANISM: Artificial Sequence
<220> FEATURE:
<223> OTHER INFORMATION: DMAb-34 Light Chain

<400> SEQUENCE: 17

```
Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Leu Leu His Ser Asn Gly Tyr Asn Tyr Leu Asp Trp Tyr Leu Gln Lys
    50                  55                  60

Pro Gly Gln Pro Pro Gln Val Leu Ile Ser Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Arg Thr Phe Gly Gln Gly Thr Lys
        115                 120                 125

Val Glu Ile Lys Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205
```

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 18
<211> LENGTH: 741
<212> TYPE: DNA
<213> ORGANISM: Artificial Sequence
<220> FEATURE:
<223> OTHER INFORMATION: DMAb-34 Light Chain

<400> SEQUENCE: 18

```
ggatccgccg ccaccatggt gctgcagacc caggtgttca tctccctgct gctgtggatc      60
tctggcgcct acggcgacat cgtgctgacc cagtctcctc tgagcctgcc tgtgacacca     120
ggagagccag caagcatctc ctgcaggagc tcccagagcc tgctgcactc caacggctac     180
aattatctgg attggtatct gcagaagcca ggacagcccc ctcaggtgct gatctccctg     240
ggctctaaca gggcctctgg cgtgcctgac agattctctg gcagcggctc cggaaccgac     300
ttcaccctga gatcagccg gtggaggca gaggacgtgg gcgtgtacta ttgcatgcag      360
gccctgcaga cccctcgcac attcggccag ggcaccaagg tggagatcaa gacagtggcc     420
gccccaagcg tgttcatctt tccaccctcc gacgagcagc tgaagtctgg cacagccagc     480
gtggtgtgcc tgctgaacaa cttctaccca agggaggcca aggtgcagtg gaaggtggat     540
aacgccctgc agagcggcaa ttcccaggag tctgtgaccg agcaggacag caaggattcc     600
acatattctc tgtctagcac cctgacactg tccaaggccg attacgagaa gcacaaggtg     660
tatgcatgcg aggtgaccca ccagggcctg tcctctcccg tgacaaagag ctttaatcgg     720
ggcgagtgtt gataactcga g                                               741
```

<210> SEQ ID NO 19
<211> LENGTH: 119
<212> TYPE: PRT
<213> ORGANISM: Artificial Sequence
<220> FEATURE:
<223> OTHER INFORMATION: DMAb-4G7 heavy chain

<400> SEQUENCE: 19

Gln Val Gln Leu Gln Gln Ser Gly Pro Glu Leu Glu Met Pro Gly Ala
1               5                   10                  15

Ser Val Lys Ile Ser Cys Lys Ala Ser Gly Ser Ser Phe Thr Gly Phe
            20                  25                  30

Ser Met Asn Trp Val Lys Gln Ser Asn Gly Lys Ser Leu Glu Trp Ile
        35                  40                  45

Gly Asn Ile Asp Thr Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Ala Tyr Tyr Gly Ser Thr Phe Ala Tyr Trp Gly Gln Gly
            100                 105                 110

Thr Leu Val Thr Val Ser Ser
        115

<210> SEQ ID NO 20
<211> LENGTH: 416

```
<212> TYPE: DNA
<213> ORGANISM: Artificial Sequence
<220> FEATURE:
<223> OTHER INFORMATION: DMAb-4G7 heavy chain

<400> SEQUENCE: 20
atggattgga catggaggat tctgtttctg gtcgccgccg ccactggaac ccacgcccag      60
gtgcagctgc agcagtcagg gcctgagctg gaaatgcctg gcgcttctgt gaaaatcagt    120
tgcaaggcat caggaagctc cttcacaggg tttagcatga actgggtgaa acagagcaat    180
gggaagtccc tggagtggat cggcaacatt gacacctact atggcggaac cacatacaat    240
cagaagttca aggcaaggc tacactgact gtggacaaat ctagttcaac cgcatatatg    300
cagctgaaga gcctgacatc cgaggattct gcagtgtact attgcgctag atcagcatac    360
tatggcagca ctttcgccta ctggggccag ggaaccctgg tcacagtgag ctccgc       416

<210> SEQ ID NO 21
<211> LENGTH: 107
<212> TYPE: PRT
<213> ORGANISM: Artificial Sequence
<220> FEATURE:
<223> OTHER INFORMATION: DMAb-4G7 light chain

<400> SEQUENCE: 21

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ile Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Phe Cys Gln His His Phe Gly Thr Pro Phe
                85                  90                  95

Thr Phe Gly Ser Gly Thr Glu Leu Glu Ile Lys
            100                 105

<210> SEQ ID NO 22
<211> LENGTH: 639
<212> TYPE: DNA
<213> ORGANISM: Artificial Sequence
<220> FEATURE:
<223> OTHER INFORMATION: DMAb-4G7 light chain

<400> SEQUENCE: 22
gatattcaga tgactcagag ccccgcatct ctgagtgcct cagtcggcga cagtgact       60 atcacctgtc gcgcaagtga aaacatctac tcatatctgg cctggtacca gcagaaacag   120
gggaagagcc cccagctgct ggtctataat gctaaaaccc tgatcgaagg agtgccttcc   180
cgattcagcg gcagcgggtc tggcacacag tttagcctga gattaactc cctgcagcca    240 gaggacttcg gcagctactt tgccagcac catttcggaa ctcccttcac ctttggcagc    300
gggacagagc tggaaatcaa aactgtcgca gcccccagtg tgttcatttt tccaccctca   360
gacgaacagc tgaagtctgg gaccgccagt gtcgtgtgtc tgctgaacaa ttttttaccct  420 cgggaggcta aagtccagtg gaaggtggat aacgcactgc agtctggaaa tagtcaggag   480
tcagtgacag aacaggacag caaagattcc acttatagtc tgtcaaacac actgactctg   540
```

```
tctaaggccg actacgagaa acacaaggtc tatgcttgcg aagtgactca tcagggctg      600 cctctcctg tgaccaagag cttcaatcgc ggcgagtgt                             639
```

<210> SEQ ID NO 23
<211> LENGTH: 141
<212> TYPE: PRT
<213> ORGANISM: Artificial Sequence
<220> FEATURE:
<223> OTHER INFORMATION: DMAb-4 heavy chain

<400> SEQUENCE: 23

```
Met Asp Trp Thr Trp Arg Ile Leu Phe Leu Val Ala Ala Ala Thr Gly
1               5                   10                  15

Thr His Ala Gln Val Thr Leu Lys Glu Ser Gly Pro Gly Ile Leu Lys
            20                  25                  30

Pro Ser Gln Thr Leu Ser Leu Thr Cys Ser Leu Ser Gly Phe Ser Leu
        35                  40                  45

Ser Thr Ser Gly Val Gly Val Gly Trp Phe Arg Gln Pro Ser Gly Lys
    50                  55                  60

Gly Leu Glu Trp Leu Ala Leu Ile Trp Trp Asp Asp Asp Lys Tyr Tyr
65                  70                  75                  80

Asn Pro Ser Leu Lys Ser Gln Leu Ser Ile Ser Lys Asp Phe Ser Arg
                85                  90                  95

Asn Gln Val Phe Leu Lys Ile Ser Asn Val Asp Ile Ala Asp Thr Ala
            100                 105                 110

Thr Tyr Tyr Cys Ala Arg Arg Asp Pro Phe Gly Tyr Asp Asn Ala Met
        115                 120                 125

Gly Tyr Trp Gly Gln Gly Thr Ser Val Thr Val Ser Ser
    130                 135                 140
```

<210> SEQ ID NO 24
<211> LENGTH: 425
<212> TYPE: DNA
<213> ORGANISM: Artificial Sequence
<220> FEATURE:
<223> OTHER INFORMATION: DMAb-4 heavy chain

<400> SEQUENCE: 24

```
atggactgga cttggagaat tctgttcctg gtcgcagcag ccactgggac acacgcacag      60
gtgacactga agagagcgg acccggaatc ctgaaaccaa gccagactct gtccctgacc      120
tgcagcctgt ccggcttctc tctgagtacc tcaggagtcg gagtgggatg gtttcgacag      180
ccaagcggaa agggactgga gtggctggcc ctgatctggt gggacgatga caagtactat      240 aaccttcac tgaaaagcca gctgagcatt tccaaggatt tctctcgcaa ccaggtcttt      300
ctgaagatca gtaatgtgga tattgccgac actgctacct actattgcgc taggagagat      360
ccattcggct acgacaatgc aatgggatat tggggccagg gaacctccgt cacagtgagc      420
tccgc                                                                  425
```

<210> SEQ ID NO 25
<211> LENGTH: 107
<212> TYPE: PRT
<213> ORGANISM: Artificial Sequence
<220> FEATURE:
<223> OTHER INFORMATION: DMAb-4 light chain

<400> SEQUENCE: 25

Asp Ile Val Met Thr Gln Ser Gln Lys Phe Met Ser Thr Ser Val Gly

```
              1               5                  10                   15
           Asp Arg Val Ser Leu Thr Cys Lys Ala Ser Gln Asn Val Gly Thr Ala
                             20                  25                  30

Val Ala Trp Tyr Gln Gln Lys Pro Gly Gln Ser Pro Lys Leu Leu Ile
                       35                  40                  45

Tyr Ser Ala Ser Asn Arg Tyr Thr Gly Val Pro Asp Arg Phe Thr Gly
                       50                  55                  60

Ser Gly Ser Gly Thr Asp Phe Thr Leu Thr Ile Ser Asn Met Gln Ser
            65                 70                  75                  80

Glu Asp Leu Ala Asp Tyr Phe Cys Gln Gln Tyr Ser Ser Tyr Pro Leu
                             85                  90                  95

Thr Phe Gly Ala Gly Thr Lys Leu Glu Ile Lys
                             100                 105

<210> SEQ ID NO 26
<211> LENGTH: 639
<212> TYPE: DNA
<213> ORGANISM: Artificial Sequence
<220> FEATURE:
<223> OTHER INFORMATION: DMAb-4 light chain

<400> SEQUENCE: 26
gatattgtga tgacccagag ccagaagttc atgtccacat ctgtcggcga ccgggtgtct      60
ctgacctgta aggccagtca gaacgtcgga actgctgtgg catggtatca gcagaagcct    120
gggcagtccc caaaactgct gatctacagt gcttcaaaca gatataccgg cgtgcctgat    180
cggttcaccg gaagcgggtc cggcacagac tttactctga ccatttctaa tatgcagagt    240
gaagatctgg ctgactactt ctgccagcag tactcctctt atccactgac atttggagca    300
gggactaagc tggaaatcaa aacagtcgca gccccctccg tgttcatttt tccaccctct    360
gatgagcagc tgaagtcagg cactgccagc gtcgtgtgtc tgctgaacaa tttctacccc    420
agggaggcca aggtccagtg gaaagtggac aacgctctgc agagcggaaa ttcccaggag    480
tctgtgactg aacaggatag taaagactca acctattctc tgagtaacac actgactctg    540
tccaaggcag actacgagaa gcacaaagtc tatgcctgcg aagtgaccca tcagggcctg    600
agttcaccag tgacaaagtc tttttaatcg cggagagtgt                          639

<210> SEQ ID NO 27
<211> LENGTH: 471
<212> TYPE: PRT
<213> ORGANISM: Artificial Sequence
<220> FEATURE:
<223> OTHER INFORMATION: DMAb-11 Heavy Chain

<400> SEQUENCE: 27

Met Asp Trp Thr Trp Arg Ile Leu Phe Leu Val Ala Ala Ala Thr Gly
            1               5                  10                  15

Thr His Ala Glu Val Gln Leu Val Glu Ser Gly Gly Gly Leu Ile Gln
                             20                  25                  30

Pro Gly Gly Ser Leu Arg Leu Ser Cys Ala Ala Ser Gly Phe Ala Val
                       35                  40                  45

Arg Ser Asn Tyr Leu Ser Trp Val Arg Gln Ala Pro Gly Lys Gly Leu
                       50                  55                  60

Glu Trp Val Ser Leu Ile Tyr Ser Gly Gly Leu Thr Ala Tyr Ala Asp
            65                 70                  75                  80

Ser Val Glu Gly Arg Phe Thr Ile Ser Arg Asp Asn Ser Lys Asn Thr
                             85                  90                  95
```

Leu Tyr Leu Gln Met Asn Ser Leu Arg Val Glu Asp Thr Ala Leu Tyr
            100                 105                 110

Tyr Cys Ala Arg Val Ala Ser Ala Gly Thr Phe Tyr Tyr Gly Met
        115                 120                 125

Asp Val Trp Gly Gln Gly Thr Thr Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
        180                 185                 190

Thr Phe Pro Ala Val Leu Gln Ser Ser Gly Leu Tyr Ser Leu Ser Ser
    195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 28
<211> LENGTH: 1413
<212> TYPE: DNA
<213> ORGANISM: Artificial Sequence
<220> FEATURE:

<223> OTHER INFORMATION: DMAb-11 Heavy Chain

<400> SEQUENCE: 28

```
atggactgga cctggagaat cctgttcctg gtggcagcag caaccggaac acacgcagag    60
gtgcagctgg tggagagcgg cggcggcctg atccagcctg gcggcagcct gaggctgtcc   120
tgcgcagcat ctggatttgc cgtgcggagc aactacctgt cctgggtgcg ccaggcacca   180
ggcaagggcc tggagtgggt gtctctgatc tacagcggcg gcctgaccgc atatgcagac   240
tccgtggagg gcaggttcac catctccaga gataactcta agaatacact gtatctgcag   300
atgaatagcc tgcgggtgga ggacaccgcc ctgtactatt gcgcccgcgt ggccagctcc   360
gccggcacat tctactatgg catggacgtg tggggccagg gcaccacagt gaccgtgtct   420
agcgccagca caagggacc atccgtgttt ccactggcac cctcctctaa gtccacctct   480
ggcggcacag ccgccctggg ctgtctggtg aaggattact cccagagcc cgtgaccgtg   540
tcttggaaca gcggcgccct gacctccgga gtgcacacat tccagccgt gctgcagagc   600
tccggcctgt acagcctgtc tagcgtggtg accgtgccct cctctagcct gggcacccag   660
acatatatct gcaacgtgaa tcacaagcca tccaatacaa aggtggacaa gaaggtggag   720
cccaagtctt gtgataagac ccacacatgc cctccctgtc ctgcaccaga gctgctgggc   780
ggcccaagcg tgttcctgtt tccacccaag cctaaggaca ccctgatgat cagcaggacc   840
cccgaggtga catgcgtggt ggtggacgtg tcccacgagg accccgaggt gaagtttaac   900
tggtacgtgg atggcgtgga ggtgcacaat gccaagacaa agcccaggga ggagcagtac   960
aactctacct atagagtggt gagcgtgctg acagtgctgc accaggactg gctgaacggc  1020
aaggagtata agtgcaaggt gtctaataag gccctgcccg cccctatcga aagaccatc  1080
agcaaggcca agggccagcc tagggagcca caggtgtaca cactgcctcc atctagagac  1140
gagctgacca gaaccaggt gagcctgaca tgtctggtga agggcttcta tcctagcgat  1200
atcgccgtgg agtgggagtc caatggccag ccagagaaca attacaagac cacacccct  1260
gtgctggact ccgatggctc tttctttctg tattccaagc tgaccgtgga taagtctaga  1320
tggcagcagg gcaacgtgtt tagctgttcc gtgatgcacg aggccctgca caatcactac  1380
acacagaagt ctctgagcct gtcccctggc aag                              1413
```

<210> SEQ ID NO 29
<211> LENGTH: 239
<212> TYPE: PRT
<213> ORGANISM: Artificial Sequence
<220> FEATURE:
<223> OTHER INFORMATION: DMAb-11 Light Chain

<400> SEQUENCE: 29

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Arg Ser Leu Ser
            20                  25                  30

Val Thr Pro Gly Glu Pro Ala Ser Ile Ser Cys Arg Ser Ser Gln Ser
        35                  40                  45

Leu Leu His Arg Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95
```

```
Thr Leu Lys Ile Ser Arg Val Glu Ala Glu Asp Val Gly Val Tyr Tyr
            100                 105                 110

Cys Met Gln Ala Leu Gln Thr Pro Ser Trp Thr Phe Gly Gln Gly Thr
            115                 120                 125

Lys Val Glu Ile Lys Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 30
<211> LENGTH: 717
<212> TYPE: DNA
<213> ORGANISM: Artificial Sequence
<220> FEATURE:
<223> OTHER INFORMATION: DMAb-11 Light Chain

<400> SEQUENCE: 30
atggtgctgc agacccaggt gttcatctct ctgctgctgt ggatcagcgg cgcctacggc      60
gacatcgtga tgacccagtc cccacggagc ctgtccgtga caccaggaga gccagcatct     120
atcagctgcc ggagctccca gagcctgctg caccgcaacg gctacaatta tctggattgg     180
tacctgcaga agcctggcca gtccccacag ctgctgatct atctgggctc caacagggca     240
tctggagtgc cagacagatt ctccggctct ggcagcggaa ccgacttcac cctgaagatc     300
tctagggtgg aggccgagga cgtgggcgtg tactattgca tgcaggccct gcagaccccc     360
agctggacat tcggccaggg caccaaggtg gagatcaaga cagtggccgc ccccttccgtg     420
ttcatctttc cccctcctga cgagcagctg aagagcggca cagcctccgt ggtgtgcctg     480
ctgaacaact ctaccctag agaggccaag gtgcagtgga aggtggataa cgccctgcag     540
tccggcaatt ctcaggagag cgtgaccgag caggactcca aggattctac atatagcctg     600
tctagcaccc tgacactgtc caaggccgat tacgagaagc acaaggtgta tgcatgcgag     660
gtgacccacc agggcctgtc ctctcccgtg acaaagagct taatcgcgg cgagtgt         717

<210> SEQ ID NO 31
<211> LENGTH: 473
<212> TYPE: PRT
<213> ORGANISM: Artificial Sequence
<220> FEATURE:
<223> OTHER INFORMATION: DMAb-30 Heavy Chain

<400> SEQUENCE: 31

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Thr Lys
            20                  25                  30

Pro Gly Ala Ser Val Lys Val Ser Cys Lys Ala Ser Gly Tyr Thr Phe
```

```
            35                  40                  45
Thr Thr Tyr Tyr Met His Trp Val Arg Gln Ala Pro Gly Gln Gly Leu
 50                  55                  60

Glu Trp Val Gly Ile Ile Asn Pro Ser Gly Gly Ile Thr Arg Tyr Ala
 65                  70                  75                  80

Gln Lys Phe Gln Gly Arg Val Thr Leu Thr Arg Asp Thr Ser Thr Thr
                 85                  90                  95

Thr Val Tyr Met Glu Leu Ser Ser Leu Arg Ser Glu Asp Thr Ala Val
                100                 105                 110

Tyr Tyr Cys Ala Arg Asp Arg Tyr Pro Val Leu Phe Ala Thr Asp Tyr
            115                 120                 125

Gly Met Asp Val Trp Gly Gln Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460
```

Lys Ser Leu Ser Leu Ser Pro Gly Lys
465                 470

<210> SEQ ID NO 32
<211> LENGTH: 1419
<212> TYPE: DNA
<213> ORGANISM: Artificial Sequence
<220> FEATURE:
<223> OTHER INFORMATION: DMAb-30 Heavy Chain

<400> SEQUENCE: 32

| | | | | | |
|---|---|---|---|---|---|
| atggactgga | cctggagaat | cctgttcctg | gtggcagcag | caacaggaac | ccacgcacag | 60 |
| gtgcagctgg | tgcagtccgg | agcagaggtg | acaaagccag | agccagcgt | gaaggtgtcc | 120 |
| tgcaaggcct | ctggctacac | cttcaccaca | tactatatgc | actgggtgag | gcaggcacct | 180 |
| ggacagggcc | tggagtgggt | gggcatcatc | aacccaagcg | gcggcatcac | aagatacgcc | 240 |
| cagaagtttc | agggaagggt | gacactgacc | cgcgacacca | gcaccacaac | cgtgtatatg | 300 |
| gagctgagct | ccctgcgctc | cgaggacaca | gccgtgtact | attgcgccag | ggatagatac | 360 |
| cccgtgctgt | tcgccaccga | ctatggcatg | gacgtgtggg | gccagggcac | aaccgtgaca | 420 |
| gtgtctagcg | ccagcaccaa | gggcccttcc | gtgtttccac | tggccccctc | ctctaagtcc | 480 |
| acatctggcg | gcaccgccgc | cctgggatgt | ctggtgaagg | attatttccc | agagcccgtg | 540 |
| accgtgtctt | ggaacagcgg | cgccctgaca | tccggagtgc | acaccttcc | tgccgtgctg | 600 |
| cagagctccg | gcctgtacag | cctgtctagc | gtggtcacag | tgccatcctc | tagcctgggc | 660 |
| acacagacct | atatctgcaa | cgtgaatcac | aagccatcca | ataccaaggt | ggacaagaag | 720 |
| gtggagccca | gtcttgtga | taagacacac | acctgccctc | cctgtcctgc | accagagctg | 780 |
| ctgggcggcc | caagcgtgtt | cctgtttcca | cccaagccta | ggacaccct | gatgatctct | 840 |
| aggacaccag | aggtgacctg | cgtggtggtg | gacgtgagcc | acgaggaccc | cgaggtgaag | 900 |
| tttaactggt | acgtggatgg | cgtggaggtg | cacaatgcca | gaccaagcc | aagggaggag | 960 |
| cagtacaatt | ctacatatag | agtggtgagc | gtgctgaccg | tgctgcacca | ggactggctg | 1020 |
| aacggcaagg | agtataagtg | caaggtgtcc | aataaggccc | tgcccgcccc | tatcgagaag | 1080 |
| acaatctcta | aggcaaaggg | acagcctcgg | gagccacagg | tgtacaccct | gcctccatct | 1140 |
| cgcgacgagc | tgacaaagaa | ccaggtgagc | ctgacctgtc | tggtgaaggg | cttctatccc | 1200 |
| agcgatatcg | ccgtggagtg | ggagtccaat | ggccagcctg | agaacaatta | caagacaacc | 1260 |
| cctcccgtgc | tggactccga | tggctctttc | tttctgtatt | ccaagctgac | agtggataag | 1320 |
| tctagatggc | agcagggcaa | cgtgtttagc | tgttccgtga | tgcacgaggc | cctgcacaat | 1380 |
| cactacaccc | agaagtctct | gagcctgtcc | cctggcaag | | | 1419 |

<210> SEQ ID NO 33
<211> LENGTH: 234
<212> TYPE: PRT
<213> ORGANISM: Artificial Sequence
<220> FEATURE:
<223> OTHER INFORMATION: DMAb-30 Light Chain

<400> SEQUENCE: 33

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Ala Thr Leu Ser
            20                  25                  30

Leu Ser Pro Gly Glu Arg Ala Thr Leu Ser Cys Arg Ala Ser Gln Ser

```
                35                  40                  45
Val Ser Gly Tyr Leu Ala Trp Tyr Gln Gln Lys Pro Gly Gln Ala Pro
 50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
                100                 105                 110

Ile Trp Pro Pro Gly Val Thr Phe Gly Gly Gly Thr Lys Val Glu Ile
                115                 120                 125

Lys Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 34
<211> LENGTH: 702
<212> TYPE: DNA
<213> ORGANISM: Artificial Sequence
<220> FEATURE:
<223> OTHER INFORMATION: DMAb-30 Light Chain

<400> SEQUENCE: 34
atggtgctgc agacccaggt gttcatcagc ctgctgctgt ggatctccgg cgcctacggc      60
gacatcgtga tgacccagtc cccagccaca ctgagcctgt cccctggaga gagggccacc     120
ctgtcttgca gagcctctca gagcgtgtcc ggctacctgg cctggtatca gcagaagcct     180
ggccaggccc caaggctgct gatctatgat gcatctaaca gggcaaccgg catcccagca     240
cgcttctctg gcagcggctc cggcacagac tttaccctga caatcagctc cctggagccc     300
gaggatttcg ccgtgtacta ttgccagcag agaagcatct ggccccctgg agtgaccttc     360
ggcggcggca caaggtgga gatcaagacc gtggccgccc ctagcgtgtt catctttcca     420
cccagcgacg agcagctgaa gtccggcaca gcctctgtgg tgtgcctgct gaacaatttc     480
tacccacggg aggccaaggt gcagtggaag gtggataacg ccctgcagtc tggcaatagc     540
caggagtccg tgaccgagca ggacaaggat tctacatata gcctgtctag caccctgaca     600
ctgagcaagg ccgactacga gaagcacaag gtgtatgcat gcgaggtgac ccaccagggc     660
ctgtcctctc ccgtgacaaa gtcctttaat cgcggcgagt gt                        702

<210> SEQ ID NO 35
<211> LENGTH: 119
<212> TYPE: PRT
<213> ORGANISM: Artificial Sequence
<220> FEATURE:
<223> OTHER INFORMATION: DMAb
```

<400> SEQUENCE: 35

Gln Leu Gln Glu Ser Gly Gly Gly Leu Met Gln Pro Gly Gly Ser Met
1               5                   10                  15

Lys Leu Ser Cys Val Ala Ser Gly Phe Thr Phe Ser Asn Tyr Trp Met
            20                  25                  30

Asn Trp Val Arg Gln Ser Pro Glu Lys Gly Leu Glu Trp Val Ala Glu
        35                  40                  45

Ile Arg Leu Lys Ser Asn Asn Tyr Ala Thr His Tyr Ala Glu Ser Val
    50                  55                  60

Lys Gly Arg Phe Thr Ile Ser Arg Asp Asp Ser Lys Arg Ser Val Tyr
65                  70                  75                  80

Leu Gln Met Asn Thr Leu Arg Ala Glu Asp Thr Gly Ile Tyr Tyr Cys
                85                  90                  95

Thr Arg Gly Asn Gly Asn Tyr Arg Ala Met Asp Tyr Trp Gly Gln Gly
            100                 105                 110

Thr Ser Val Thr Val Ser Ser
            115

<210> SEQ ID NO 36
<211> LENGTH: 421
<212> TYPE: DNA
<213> ORGANISM: Artificial Sequence
<220> FEATURE:
<223> OTHER INFORMATION: DMAb

<400> SEQUENCE: 36

```
atggattgga catggaggat tctgtttctg gtcgccgccg caactggaac ccacgctgaa    60
gtgcagctgc aggagtcagg aggaggactg atgcagcccg gcggaagcat gaagctgtcc   120
tgcgtggcat ctggcttcac ctttagtaac tactggatga attgggtccg ccagtcacct   180
gagaagggac tggaatgggt ggctgagatc cgactgaaaa gcaacaatta cgccacccac   240
tatgctgagt cagtgaaggg cgcattcaca attagcaggg acgattctaa agaagtgtg   300
tatctgcaga tgaacactct gagagccgaa gacaccggaa tctactattg cacgggggc   360
aacggaaatt accgcgctat ggattattgg gggcagggca cttccgtcac cgtgagctcc   420
g                                                                   421
```

<210> SEQ ID NO 37
<211> LENGTH: 107
<212> TYPE: PRT
<213> ORGANISM: Artificial Sequence
<220> FEATURE:
<223> OTHER INFORMATION: DMAb

<400> SEQUENCE: 37

Asp Ile Gln Met Thr Gln Ser Pro Ala Ser Leu Ser Val Ser Val Gly
1               5                   10                  15

Glu Thr Val Ser Ile Thr Cys Arg Ala Ser Glu Asn Ile Tyr Ser Ser
            20                  25                  30

Leu Ala Trp Tyr Gln Gln Lys Gln Gly Lys Ser Pro Gln Leu Leu Val
        35                  40                  45

Tyr Ser Ala Thr Ile Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Tyr

Thr Phe Gly Gly Gly Thr Lys Leu Glu Ile Lys
            100                 105

<210> SEQ ID NO 38
<211> LENGTH: 699
<212> TYPE: DNA
<213> ORGANISM: Artificial Sequence
<220> FEATURE:
<223> OTHER INFORMATION: DMAb

<400> SEQUENCE: 38

| | | | | |
|---|---|---|---|---|
| atggtcctgc | agacccaggt | gtttatctca | ctgctgctgt | ggattagcgg | ggcttacggc | 60 |
| gatattcaga | tgacacagtc | cccagcatca | ctgagcgtct | ccgtgggaga | aacagtgtcc | 120 |
| atcacttgtc | gcgcctctga | aacatctac | agcagcctgg | cttggtatca | gcagaagcag | 180 |
| ggaaaaagcc | cccagctgct | ggtctactcc | gcaacaatcc | tggccgacgg | ggtgccttct | 240 |
| aggttctctg | gcagtggatc | agggacacag | tatagcctga | gattaatag | tctgcagtca | 300 |
| gaggattttg | gacttacta | ttgccagcac | ttctggggca | ccatacac | ttttggcgga | 360 |
| gggactaagc | tggagatcaa | aaccgtcgca | gccccctctg | tgttcatttt | tccacccagt | 420 |
| gacgaacagc | tgaagagtgg | caccgcctca | gtcgtgtgtc | tgctgaacaa | tttctaccct | 480 |
| agagaggcaa | aggtccagtg | gaaagtggat | aacgccctgc | agagcggcaa | ttcccaggaa | 540 |
| tctgtgactg | agcaggacag | taaggattca | acctatagcc | tgtccaacac | cctgacactg | 600 |
| agcaaagctg | actacgaaaa | gcacaaagtc | tatgcatgcg | aggtgacaca | tcagggactg | 660 |
| agttcaccag | tgactaagtc | ctttaatcgg | ggggagtgt | | | 699 |

<210> SEQ ID NO 39
<211> LENGTH: 122
<212> TYPE: PRT
<213> ORGANISM: Artificial Sequence
<220> FEATURE:
<223> OTHER INFORMATION: DMAb

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Thr Thr Thr
            20                  25                  30

Tyr Trp Asn Trp Ile Arg Gln Pro Pro Gly Lys Gly Leu Glu Trp Ile
        35                  40                  45

Gly Glu Val Asn Tyr Ser Gly Asn Ala Asn Tyr Asn Pro Ser Leu Lys
    50                  55                  60

Gly Arg Val Ala Ile Ser Val Asp Thr Ser Lys Asn Gln Phe Ser Leu
65                  70                  75                  80

Arg Leu Asn Ser Val Thr Ala Ala Asp Thr Ala Ile Tyr Tyr Cys Thr
                85                  90                  95

Ser Arg Ile Arg Ser His Ile Ala Tyr Ser Trp Lys Gly Asp Val Trp
            100                 105                 110

Gly Lys Gly Thr Thr Val Thr Val Ser Ser
        115                 120

<210> SEQ ID NO 40
<211> LENGTH: 424
<212> TYPE: DNA
<213> ORGANISM: Artificial Sequence
<220> FEATURE:

<223> OTHER INFORMATION: DMAb

<400> SEQUENCE: 40

| atggattgga cttggagaat tctgtttctg gtggccgccg ctacaggaac tcacgctcag | 60 |
| gtgcagctgc agcagtgggg agccgggctg ctgaagccaa gcgagacact gtccctgact | 120 |
| tgcgccgtgt acggcggaag cttcaccaca acttattgga attggatcag gcagcccct | 180 |
| ggcaagggac tggagtggat tggggaagtg aactacagcg gcaacgctaa ttataacccc | 240 |
| tccctgaagg gccgagtcgc aatctctgtg gacactagta aaaatcagtt tagtctgagg | 300 |
| ctgaactcag tgaccgccgc tgatacagca atctactatt gcaccagcag gatcaggagc | 360 |
| cacattgcct actcctggaa gggagacgtg tgggggaaag gcaccacagt caccgtgagc | 420 |
| tccg | 424 |

<210> SEQ ID NO 41
<211> LENGTH: 108
<212> TYPE: PRT
<213> ORGANISM: Artificial Sequence
<220> FEATURE:
<223> OTHER INFORMATION: DMAb

<400> SEQUENCE: 41

Glu Ile Val Met Thr Gln Ser Pro Gly Thr Leu Ser Leu Ser Pro Gly
1               5                   10                  15
Glu Arg Ala Thr Leu Ser Cys Arg Ala Ser Gln Ser Val Pro Arg Asn
            20                  25                  30
Tyr Ile Gly Trp Phe Gln Gln Lys Pro Gly Gln Ala Pro Arg Leu Leu
        35                  40                  45
Ile Tyr Gly Ala Ser Ser Arg Ala Ala Gly Phe Pro Asp Arg Phe Ser
    50                  55                  60
Gly Ser Gly Ser Gly Thr Asp Phe Thr Leu Thr Ile Thr Arg Leu Glu
65                  70                  75                  80
Pro Glu Asp Phe Ala Met Tyr Tyr Cys His Gln Tyr Asp Arg Leu Pro
                85                  90                  95
Tyr Thr Phe Gly Gln Gly Thr Lys Leu Glu Ile Lys
            100                 105

<210> SEQ ID NO 42
<211> LENGTH: 702
<212> TYPE: DNA
<213> ORGANISM: Artificial Sequence
<220> FEATURE:
<223> OTHER INFORMATION: DMAb

<400> SEQUENCE: 42

| atggtcctgc agacacaggt gtttatctca ctgctgctgt ggattagcgg agcctacggg | 60 |
| gaaatcgtga tgactcagag cccaggcacc ctgtctctga gtcccggaga gagagctaca | 120 |
| ctgtcctgtc gggcatcaca gagcgtgccc agaaattaca tcggatggtt ccagcagaag | 180 |
| ccaggacagg cccctcggct gctgatctac ggagcttcct ctcgcgctgc agggttccct | 240 |
| gaccgatttt ccggctctgg aagtgggacc gatttcactc tgaccatcac acgcctggag | 300 |
| cccgaagact tgccatgta ctattgccac cagtacgatc gactgcctta cattcggc | 360 |
| cagggaacta agctggaaat caaaacagtc gccgctccta gcgtgttcat ctttcctcca | 420 |
| tcagacgagc agctgaagtc cggaactgct tctgtggtgt gcctgctgaa caacttctac | 480 |
| ccacgcgaag ctaaggtcca gtggaaagtg ataatgcac tgcagagcgg caactcccag | 540 |

```
gagtctgtga ccgaacagga cagtaaggat tcaacatatt cactgagcaa cactctgacc    600
ctgtccaaag ccgactacga gaagcataaa gtgtatgctt gcgaggtcac ccaccagggg    660
ctgtcatctc cagtcactaa gtccttcaat agaggcgaat gt                      702
```

```
<210> SEQ ID NO 43
<211> LENGTH: 123
<212> TYPE: PRT
<213> ORGANISM: Artificial Sequence
<220> FEATURE:
<223> OTHER INFORMATION: DMAb

<400> SEQUENCE: 43

Gln Val Gln Leu Val Gln Ser Gly Ala Glu Val Lys Lys Pro Gly Ser
1               5                   10                  15

Ser Val Lys Val Ser Cys Arg Ala Ser Gly Asp Ser Phe Ser Arg Lys
            20                  25                  30

Tyr Gly Ile Ser Trp Val Arg Gln Ala Pro Gly Gln Gly Phe Glu Trp
        35                  40                  45

Met Gly Thr Ile Met Pro Ile Val Gly Leu Thr Thr Ser Ala Gln Lys
    50                  55                  60

Phe Gln Gly Arg Val Thr Ile Thr Ala Asp Lys Ser Thr Ser Thr Ala
65                  70                  75                  80

His Met Glu Leu Asn Ser Leu Thr Ser Glu Asp Thr Ala Ile Tyr Tyr
                85                  90                  95

Cys Ala Arg Asp Glu Ile Ile Gly Ala Arg Pro His Trp Phe Asp Ser
            100                 105                 110

Trp Gly Gln Gly Thr Leu Val Thr Val Ser Ser
        115                 120
```

```
<210> SEQ ID NO 44
<211> LENGTH: 428
<212> TYPE: DNA
<213> ORGANISM: Artificial Sequence
<220> FEATURE:
<223> OTHER INFORMATION: DMAb

<400> SEQUENCE: 44
atggattgga catggaggat tctgtttctg gtcgccgccg ctactggaac tcacgctcag    60
gtgcagctgg tgcagtcagg ggccgaagtg aagaaacccg gcagtccgt caaggtgtct   120 tgccgggcta gtggcgactc attcagccgc aaatacggaa tcagctgggt gcgacaggca   180
ccaggacagg ggtttgaatg gatgggcacc atcatgccta ttgtgggact gaccacatcc   240
gcccagaagt tccagggacg cgtcacaatc actgccgaca atccacctc tacagctcac   300 atggagctga actccctgac ttctgaagac accgccatct actattgcgc tagagatgag   360
atcattggcg ctcggcctca ttggttcgat agctggggcc agggaacact ggtcaccgtg   420
agcagcgc                                                            428
```

```
<210> SEQ ID NO 45
<211> LENGTH: 107
<212> TYPE: PRT
<213> ORGANISM: Artificial Sequence
<220> FEATURE:
<223> OTHER INFORMATION: DMAb

<400> SEQUENCE: 45

Glu Ile Val Met Thr Gln Ser Pro Ala Ile Met Ser Val Ser Pro Gly
1               5                   10                  15
```

```
Lys Arg Ala Thr Leu Ser Cys Arg Ala Ser Gln Ser Val Ser Ser Asn
            20                  25                  30

Leu Ala Trp Tyr Gln Arg Lys Pro Gly Gln Ala Pro Arg Leu Leu Ile
        35                  40                  45

Tyr Gly Ser Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Leu Gln Tyr Tyr Asn Trp Pro Arg
                85                  90                  95

Thr Phe Gly Gln Gly Thr Lys Val Glu Ile Lys
                100                 105
```

<210> SEQ ID NO 46
<211> LENGTH: 699
<212> TYPE: DNA
<213> ORGANISM: Artificial Sequence
<220> FEATURE:
<223> OTHER INFORMATION: DMAb

<400> SEQUENCE: 46

| | | | | | |
|---|---|---|---|---|---|
| atggtcctgc | agacccaggt | gtttatcagc | ctgctgctgt | ggatttccgg | ggcatatggc | 60 |
| gagatcgtga | tgactcagag | ccccgccatt | atgtctgtca | gtcctggcaa | gcgagctacc | 120 |
| ctgtcctgta | gggcatcaca | gagcgtgagt | tcaaacctgg | cttggtacca | gcgcaaacct | 180 |
| ggacaggcac | cacgactgct | gatctatgga | agctccacca | gggcaacagg | gattcccgcc | 240 |
| agattctccg | gatctgggag | tggcaccgag | tttaccctga | caatctctag | tctgcagtct | 300 |
| gaagacttcg | ccgtgtacta | ttgcctgcag | tactataatt | ggccccgaac | atttggacag | 360 |
| gggactaagg | tcgaaatcaa | aacagtggca | gcccttcag | tcttcatttt | tccacccagc | 420 |
| gacgagcagc | tgaagtcagg | gactgctagc | gtggtgtgcc | tgctgaacaa | tttctaccct | 480 |
| agggaagcca | aggtccagtg | gaaagtggat | aacgctctgc | agtctggcaa | tagtcaggag | 540 |
| tcagtgacag | aacaggacag | caaggattcc | acttattcac | tgagcaacac | tctgacccctg | 600 |
| agcaaagcag | attacgagaa | gcacaaagtg | tatgcctgcg | aggtcaccca | ccaggggctg | 660 |
| agcagtccag | tcactaagtc | cttcaacagg | ggagaatgt | | | 699 |

<210> SEQ ID NO 47
<211> LENGTH: 118
<212> TYPE: PRT
<213> ORGANISM: Artificial Sequence
<220> FEATURE:
<223> OTHER INFORMATION: DMAb

<400> SEQUENCE: 47

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Glu Asp Thr Ala Val Tyr Tyr Cys Ala
                85                  90                  95
```

```
Arg Val Arg Phe Gly Asp Thr Ala Val Asp Tyr Trp Gly Gln Gly Thr
                100                 105                 110

Leu Val Thr Val Ser Ser
        115
```

<210> SEQ ID NO 48
<211> LENGTH: 413
<212> TYPE: DNA
<213> ORGANISM: Artificial Sequence
<220> FEATURE:
<223> OTHER INFORMATION: DMAb

<400> SEQUENCE: 48

```
atggactgga cttggagaat cctgttcctg gtcgccgccg ctactgggac tcatgccgag    60
gtgcagctgg tcgaatctgg agggggcctg gtgcagcctg gcggcagcct gaggctgtcc   120
tgcgcagcat ctggcttcac ctttaggagc tacgacatgc actgggtgcg ccaggcaaca   180
ggcaagggac tggagtgggt gtctgccatc ggaaccgcag gcgatacata ctatccaggc   240
tccgtgaagg gcaggttcac catctcccgc gagaacgcca agaattctct gtacctgcag   300
atgaacagcc tgagagccga ggacaccgcc gtgtactatt gcgccagggt gcgcttcggc   360
gacacagcag tggattattg gggccagggc accctggtga cagtgagctc cgc          413
```

<210> SEQ ID NO 49
<211> LENGTH: 213
<212> TYPE: PRT
<213> ORGANISM: Artificial Sequence
<220> FEATURE:
<223> OTHER INFORMATION: DMAb

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp His Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ser Tyr Ile Ser Pro Phe
                85                  90                  95

Thr Phe Gly Pro Gly Thr Lys Val Asp Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

-continued

Asn Arg Gly Glu Cys
    210

<210> SEQ ID NO 50
<211> LENGTH: 699
<212> TYPE: DNA
<213> ORGANISM: Artificial Sequence
<220> FEATURE:
<223> OTHER INFORMATION: DMAb

<400> SEQUENCE: 50

```
atggtgctgc agacccaggt gtttatctct ctgctgctgt ggatcagcgg cgcctatggc      60
gacatccaga tgacacagtc cccttctagc ctgtccgcct ctgtgggcga tcgggtgacc     120
atcacatgta gagccagcca gtccatctcc tctttcctga actggcacca gcagaagcct     180
ggcaaggccc caaagctgct gatctacgca gccagctccc tgcagagcgg agtgccctcc     240
aggttctctg gcagcggctc cggaaccgac tttaccctga caatctctag cctgcagcct     300
gaggattttg ccatctacta ttgccagcag tcttatatca gccccttcac ctttggccct     360
ggcacaaagg tggacatcaa gaccgtggcc gccccaagcg tgttcatctt ccaccctcc      420
gatgagcagc tgaagtctgg cacagccagc gtggtgtgcc tgctgaacaa tttctacccc     480
cgcgaggcca aggtgcagtg gaaggtggac aacgccctgc agtccggcaa ttctcaggag     540
agcgtgaccg agcaggactc caaggattct acatattctc tgagctctac cctgacactg     600
agcaaggccg attacgagaa gcacaaggtg tatgcctgcg aggtcaccca ccaggggctg     660
tcaagtccag tcactaagtc cttcaatcgg ggcgaatgc                            699
```

<210> SEQ ID NO 51
<211> LENGTH: 113
<212> TYPE: PRT
<213> ORGANISM: Artificial Sequence
<220> FEATURE:
<223> OTHER INFORMATION: DMAb

<400> SEQUENCE: 51

Glu Val Gln Leu Gln Glu Ser Gly Pro Gly Leu Val Arg Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Leu Gly Tyr Ile Thr Asn Thr Gly Ser Thr Gly Phe Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ile Ser Val Thr Thr Glu Asp Thr Ala Thr Tyr His Cys
                85                  90                  95

Ala Arg Gly Leu Ala Tyr Trp Gly Gln Gly Thr Leu Val Thr Val Ser
            100                 105                 110

Ser

<210> SEQ ID NO 52
<211> LENGTH: 398
<212> TYPE: DNA
<213> ORGANISM: Artificial Sequence
<220> FEATURE:
<223> OTHER INFORMATION: DMAb -continued

```
<400> SEQUENCE: 52
atggattgga cttggaggat tctgtttctg gtcgccgccg ctactgggac acacgccgag    60
gtgcagctgc aggagagtgg gcctggactg gtgcgaccca gccagtccct gtctctgaca   120
tgcactgtga ccggctacag tatcacatca gactatgcct ggaactggat tcgccagttc   180
ccaggcaata agctggaatg ctgggatac atcacaaaca ctggcagcac cgggtttaat    240
cccagcctga gtcccgaat ctctattaca agggacactt ctaaaaacca gttctttctg    300
cagctgatta gtgtgaccac agaggatacc gcaacatacc actgcgcccg gggactggct   360
tattggggac aggggaccct ggtcacagtg agctccgc                           398

<210> SEQ ID NO 53
<211> LENGTH: 112
<212> TYPE: PRT
<213> ORGANISM: Artificial Sequence
<220> FEATURE:
<223> OTHER INFORMATION: DMAb

<400> SEQUENCE: 53

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Thr
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Phe Thr Phe Gly Ser Gly Thr Lys Leu Glu Ile Lys
            100                 105                 110

<210> SEQ ID NO 54
<211> LENGTH: 714
<212> TYPE: DNA
<213> ORGANISM: Artificial Sequence
<220> FEATURE:
<223> OTHER INFORMATION: DMAb

<400> SEQUENCE: 54
atggtcctgc agacccaggt gtttatctct ctgctgctgt ggattagtgg ggcctatggc    60
gatgtcgtgc tgacccagac accactgact ctgagcgtga ccatcggaca gcccgcttct   120
attagttgta gtcctctca gtctctgctg acagtgatg gcaaaaccta cctgaactgg    180
ctgctgcaga gacctggaca gtccccaaag cggctgatct atctggtctc aaaactggac   240
agcggcgtga cagatcggtt cactgggtca ggcagcggaa ctgactttac cctgaagatt   300
tctcgcgtcg aggctgaaga tctgggagtg tactattgct ggcaggggac tcactcacct   360
ttcacctttg ggagcggcac aaagctggaa atcaaaaccg tcgcagcccc aagtgtgttc   420 attttccac cctcagacga gcagctgaag tccgggacag catctgtcgt gtgtctgctg    480
aacaatttct accctaggga ggctaaggtc cagtggaaag tggataacgc actgcagtct   540
ggcaatagtc aggagtcagt gaccgaacag gacagcaagg attccacata ttccctgtct   600
aacactctga ccctgagcaa agccgactac gagaagcaca aagtctatgc ttgcgaagtg   660
```
actcatcagg ggctgagttc accagtgacc aagagcttta atagaggcga gtgt 714

<210> SEQ ID NO 55
<211> LENGTH: 124
<212> TYPE: PRT
<213> ORGANISM: Artificial Sequence
<220> FEATURE:
<223> OTHER INFORMATION: DMAb

<400> SEQUENCE: 55

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Gly Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Gly Leu Thr Ser Glu Asp Thr Ala Val Tyr Tyr Cys
                85                  90                  95

Ala Arg Glu Ser Arg Ile Ser Thr Met Leu Thr Thr Gly Tyr Phe Asp
            100                 105                 110

Tyr Trp Gly Gln Gly Thr Thr Leu Thr Val Ser Ser
        115                 120

<210> SEQ ID NO 56
<211> LENGTH: 431
<212> TYPE: DNA
<213> ORGANISM: Artificial Sequence
<220> FEATURE:
<223> OTHER INFORMATION: DMAb

<400> SEQUENCE: 56
atggattgga catggagaat cctgttcctg gtcgccgccg ctactgggac acacgccgaa     60
gtgcagctgc agcagagtgg agccgagctg gtcaaacctg gggcatccgt gaagctgtct    120
tgcactgcca gtggcttcaa catcaaagac acctacattc actgggtgaa gcagggccca    180
gagcagggac tggaatggat cggacggatt gacccagcaa acgggaatac caagtatgat    240
cccaaatttc aggggaaggc aaccatcaca gccgacacaa gctccaatac tgcctacctg    300
cagctgtcag gcctgaccag cgaggataca gccgtgtact attgcgccag ggagagcagg    360
atttccacca tgctgaccac aggatatttc gactactggg gacaggggac taccctgacc    420
gtctctagtg c                                                         431

<210> SEQ ID NO 57
<211> LENGTH: 212
<212> TYPE: PRT
<213> ORGANISM: Artificial Sequence
<220> FEATURE:
<223> OTHER INFORMATION: DMAb

<400> SEQUENCE: 57

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr

```
                  35                  40                  45
Asp Thr Ser Asn Leu Ala Ser Gly Val Pro Val Arg Phe Ser Gly Ser
                 50                  55                  60
Gly Ser Gly Thr Ser Tyr Ser Leu Thr Ile Ser Arg Met Glu Ala Glu
 65                  70                  75                  80
Asp Ala Ala Thr Tyr Tyr Cys Gln Gln Trp Ser Ser Tyr Pro Tyr Thr
                     85                  90                  95
Phe Gly Gly Gly Thr Lys Leu Glu Ile Lys Thr Val Ala Ala Pro Ser
                100                 105                 110
Val Phe Ile Phe Pro Pro Ser Asp Glu Gln Leu Lys Ser Gly Thr Ala
            115                 120                 125
Ser Val Val Cys Leu Leu Asn Asn Phe Tyr Pro Arg Glu Ala Lys Val
        130                 135                 140
Gln Trp Lys Val Asp Asn Ala Leu Gln Ser Gly Asn Ser Gln Glu Ser
145                 150                 155                 160
Val Thr Glu Gln Asp Ser Lys Asp Ser Thr Tyr Ser Leu Ser Asn Thr
                165                 170                 175
Leu Thr Leu Ser Lys Ala Asp Tyr Glu Lys His Lys Val Tyr Ala Cys
            180                 185                 190
Glu Val Thr His Gln Gly Leu Ser Ser Pro Val Thr Lys Ser Phe Asn
        195                 200                 205
Arg Gly Glu Cys
    210

<210> SEQ ID NO 58
<211> LENGTH: 696
<212> TYPE: DNA
<213> ORGANISM: Artificial Sequence
<220> FEATURE:
<223> OTHER INFORMATION: DMAb

<400> SEQUENCE: 58
atggtcctgc agactcaggt gtttatctca ctgctgctgt ggattagcgg agcctacgga     60
cagatcgtgc tgacccagtc cccagctatt atgtccgcat ctcctggcga gaaagtgacc    120
atgacatgtt ccgctagttc aagcgtgtct tacatgtatt ggtaccagca gaagcctggc    180
agcagcccaa ggctgctgat ctatgacacc tccaacctgg cttctggggt ccccgtgaga    240
ttcagtgggt caggcagcgg aacttcctac tctctgacca tttcccggat ggaggcagaa    300
gatgcagcca catactattg ccagcagtgg agttcatatc cctacacatt tggaggggc     360 actaaactgg aaatcaagac agtcgctgca ccttctgtgt tcatttttcc acccagtgac    420
gagcagctga gagtggcac tgcctcagtc gtgtgtctgc tgaacaattt ctatccccgc    480
gaggccaaag tccagtggaa ggtggataac gctctgcagt ccggcaattc tcaggagagt    540
gtgaccgaac aggactcaaa agatagcaca tacagtctgt caaacactct gaccctgagc    600
aaggcagact atgagaagca caaagtctac gcctgcgaag tgacacatca gggactgagc    660 tccctgtga ctaagtcctt taatcgaggg gagtgt                              696

<210> SEQ ID NO 59
<211> LENGTH: 122
<212> TYPE: PRT
<213> ORGANISM: Artificial Sequence
<220> FEATURE:
<223> OTHER INFORMATION: DMAb

<400> SEQUENCE: 59
```

-continued

Gln Val Thr Leu Lys Glu Ser Gly Pro Gly Ile Leu Lys Pro Ser Gln
1               5                   10                  15

Thr Leu Ser Leu Thr Cys Ser Leu Ser Gly Phe Ser Leu Ser Thr Ser
            20                  25                  30

Gly Val Gly Val Gly Trp Phe Arg Gln Pro Ser Gly Lys Gly Leu Glu
        35                  40                  45

Trp Leu Ala Leu Ile Trp Trp Asp Asp Lys Tyr Tyr Asn Pro Ser
50                  55                  60

Leu Lys Ser Gln Leu Ser Ile Ser Lys Asp Phe Ser Arg Asn Gln Val
65                  70                  75                  80

Phe Leu Lys Ile Ser Asn Val Asp Ile Ala Asp Thr Ala Thr Tyr Tyr
                85                  90                  95

Cys Ala Arg Arg Asp Pro Phe Gly Tyr Asp Asn Ala Met Gly Tyr Trp
            100                 105                 110

Gly Gln Gly Thr Ser Val Thr Val Ser Ser
            115                 120

<210> SEQ ID NO 60
<211> LENGTH: 425
<212> TYPE: DNA
<213> ORGANISM: Artificial Sequence
<220> FEATURE:
<223> OTHER INFORMATION: DMAb

<400> SEQUENCE: 60
atggactgga cttggagaat tctgttcctg gtcgcagcag ccactgggac acacgcacag      60
gtgacactga agagagcgg acccggaatc ctgaaaccaa gccagactct gtccctgacc     120
tgcagcctgt ccggcttctc tctgagtacc tcaggagtcg gagtgggatg gtttcgacag     180
ccaagcggaa agggactgga gtggctggcc ctgatctggt gggacgatga caagtactat     240
aacccttcac tgaaaagcca gctgagcatt tccaaggatt tctctcgcaa ccaggtcttt     300
ctgaagatca gtaatgtgga tattgccgac actgctacct actattgcgc taggagagat     360
ccattcggct acgacaatgc aatgggatat tggggccagg gaacctccgt cacagtgagc     420
tccgc                                                                 425

<210> SEQ ID NO 61
<211> LENGTH: 213
<212> TYPE: PRT
<213> ORGANISM: Artificial Sequence
<220> FEATURE:
<223> OTHER INFORMATION: DMAb

<400> SEQUENCE: 61

Asp Ile Val Met Thr Gln Ser Gln Lys Phe Met Ser Thr Ser Val Gly
1               5                   10                  15

Asp Arg Val Ser Leu Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Ile Lys Thr Val Ala Ala Pro

|  |  |  | 100 |  |  |  | 105 |  |  |  | 110 |  |
|---|---|---|---|---|---|---|---|---|---|---|---|---|

Ser Val Phe Ile Phe Pro Pro Ser Asp Glu Gln Leu Lys Ser Gly Thr
    115                120                125

Ala Ser Val Val Cys Leu Leu Asn Asn Phe Tyr Pro Arg Glu Ala Lys
    130                135                140

Val Gln Trp Lys Val Asp Asn Ala Leu Gln Ser Gly Asn Ser Gln Glu
145                150                155                160

Ser Val Thr Glu Gln Asp Ser Lys Asp Ser Thr Tyr Ser Leu Ser Asn
    165                170                175

Thr Leu Thr Leu Ser Lys Ala Asp Tyr Glu Lys His Lys Val Tyr Ala
    180                185                190

Cys Glu Val Thr His Gln Gly Leu Ser Ser Pro Val Thr Lys Ser Phe
    195                200                205

Asn Arg Gly Glu Cys
    210

<210> SEQ ID NO 62
<211> LENGTH: 699
<212> TYPE: DNA
<213> ORGANISM: Artificial Sequence
<220> FEATURE:
<223> OTHER INFORMATION: DMAb

<400> SEQUENCE: 62

```
atggtcctgc agacccaggt gttcatcagc ctgctgctgt ggatttccgg ggcctacggc    60
gatattgtga tgacccagag ccagaagttc atgtccacat ctgtcggcga ccgggtgtct   120
ctgacctgta aggccagtca gaacgtcgga actgctgtgg catggtatca gcagaagcct   180
gggcagtccc caaaactgct gatctacagt gcttcaaaca gatataccgg cgtgcctgat   240
cggttcaccg gaagcgggtc cggcacagac tttactctga ccatttctaa tatgcagagt   300
gaagatctgg ctgactactt ctgccagcag tactcctctt atccactgac atttggagca   360
gggactaagc tggaaatcaa aacagtcgca gccccctccg tgttcatttt tccaccctct   420
gatgagcagc tgaagtcagg cactgccagc gtcgtgtgtc tgctgaacaa tttctacccc   480
agggaggcca aggtccagtg gaaagtggac aacgctctgc agagcggaaa ttcccaggag   540
tctgtgactg aacaggatag taaagactca acctattctc tgagtaacac actgactctg   600
tccaaggcag actacgagaa gcacaaagtc tatgcctgcg aagtgaccca tcagggcctg   660
agttcaccag tgacaaagtc ttttaatcgc ggagagtgt                          699
```

<210> SEQ ID NO 63
<211> LENGTH: 125
<212> TYPE: PRT
<213> ORGANISM: Artificial Sequence
<220> FEATURE:
<223> OTHER INFORMATION: DMAb

<400> SEQUENCE: 63

Gln Val Gln Leu Gln Glu Ser Gly Pro Gly Leu Val Lys Pro Ser Asp
1                5                  10                15

Thr Leu Ser Leu Thr Cys Thr Val Ser Gly Gly Ser Leu Ser Ser Phe
    20                25                30

Tyr Trp Ser Trp Ile Arg Gln Pro Pro Gly Lys Gly Leu Glu Trp Ile
    35                40                45

Gly Tyr Ile Tyr Tyr Ser Gly Ser Pro Asn Tyr Ser Pro Ser Leu Glu
    50                55                60

```
Ser Arg Val Thr Met Ser Val Asp Thr Thr Arg Asn Gln Ile Ser Leu
 65                  70                  75                  80

Lys Leu Asp Ser Val Thr Ala Ala Asp Thr Ala Val Tyr Tyr Cys Val
                 85                  90                  95

Arg Ala Ser Arg Ser Tyr Tyr Trp Gly Ser Tyr Arg Pro Thr Ala Phe
            100                 105                 110

Asp Ser Trp Gly Gln Gly Thr Leu Val Thr Val Ser Ser
        115                 120                 125

<210> SEQ ID NO 64
<211> LENGTH: 433
<212> TYPE: DNA
<213> ORGANISM: Artificial Sequence
<220> FEATURE:
<223> OTHER INFORMATION: DMAb

<400> SEQUENCE: 64
atggattgga cttggagaat tctgtttctg gtcgccgccg ccactggaac ccacgcccag      60
gtgcagctgc aggaatcagg acccggactg gtgaagccaa cgacaccct gtccctgaca     120 tgcaccgtga cggcggcag cctgagctcc ttctactgga gctggatcag cagcccct      180 ggcaaaggac tggaatggat cggatacatc tactattcag ggagcccca ctattcccct     240 tctctggagt cacgcgtcac aatgagcgtg acaccacac gaaatcagat ttccctgaag     300
ctggactctg tgacagccgc tgatactgcc gtctactatt gcgtgcgagc tagtaggtca     360
tactattggg gctcctaccg cccaaccgcc ttcgattctt gggggcaggg cacactggtc     420
accgtgagca gcg                                                        433

<210> SEQ ID NO 65
<211> LENGTH: 206
<212> TYPE: PRT
<213> ORGANISM: Artificial Sequence
<220> FEATURE:
<223> OTHER INFORMATION: DMAb

<400> SEQUENCE: 65

Ser Tyr Glu Leu Thr Gln Pro Leu Ser Val Ser Val Ser Pro Gly Gln
 1               5                  10                  15

Thr Ala Ile Phe Thr Cys Ser Gly Asp Asn Leu Gly Asp Lys Tyr Val
             20                  25                  30

Cys Trp Phe Gln Gln Arg Pro Gly Gln Ser Pro Met Leu Leu Ile Tyr
         35                  40                  45

Gln Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ser Thr
 65                  70                  75                  80

Asp Glu Ala Asp Tyr Tyr Cys Gln Thr Trp Asp Ser Thr Val Val Phe
                 85                  90                  95

Gly Gly Gly Thr Lys Leu Thr Val Leu Ala Pro Ser Val Thr Leu Phe
            100                 105                 110

Pro Pro Ser Ser Glu Glu Leu Gln Ala Asn Lys Ala Thr Leu Val Cys
        115                 120                 125

Leu Ile Ser Asp Phe Tyr Pro Gly Ala Val Thr Val Ala Trp Lys Ala
    130                 135                 140

Asp Ser Ser Pro Val Lys Ala Gly Val Glu Thr Thr Thr Pro Ser Lys
145                 150                 155                 160

Gln Ser Asn Asn Lys Tyr Ala Ala Ser Ser Tyr Leu Ser Leu Thr Pro
```

```
                165                 170                 175
Glu Gln Trp Lys Ser His Arg Ser Tyr Ser Cys Gln Val Thr His Glu
            180                 185                 190

Gly Ser Thr Val Glu Lys Thr Val Ala Pro Thr Glu Cys Ser
        195                 200                 205

<210> SEQ ID NO 66
<211> LENGTH: 678
<212> TYPE: DNA
<213> ORGANISM: Artificial Sequence
<220> FEATURE:
<223> OTHER INFORMATION: DMAb

<400> SEQUENCE: 66
atggtcctgc agactcaggt gtttatcagc ctgctgctgt ggattagcgg ggcctacggc      60
tcctatgagc tgacccagcc cctgtcagtc agcgtgtccc tggacagac agctatcttc     120 acttgctccg agacaaacct gggggataag tacgtgtgct ggtttcagca gagaccaggc     180
cagagcccca tgctgctgat ctatcaggac aacaagagac cttccggaat tccagaacgg     240
ttctctggca gtaactcagg aaatacagca actctgacca tttctggcac ccagagtaca     300
gacgaggcca ttactattg ccagacctgg atagcacag tcgtgttcgg cggagggact      360
aagctgaccg tcctggcccc ttccgtgacc ctgtttcctc caagttcaga ggaactgcag     420
gcaaacaaag ccaccctggt gtgcctgatc agcgactttt acccaggggc tgtcaccgtg     480
gcttggaagg cagatagctc ccctgtcaaa gcaggcgtgg aaacaactac ccctagtaag     540
cagtcaaaca caagtacgc tgcatctagt tatctgagcc tgaccctga gcagtggaag       600 tcccatcgca gctactcctg tcaggtcacc catgaaggct caaccgtgga aaaaacagtg     660
gcaccaaccg aatgctca                                                   678

<210> SEQ ID NO 67
<211> LENGTH: 119
<212> TYPE: PRT
<213> ORGANISM: Artificial Sequence
<220> FEATURE:
<223> OTHER INFORMATION: DMAb

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ala Leu Arg Met Tyr
            20                  25                  30

Asp Met His Trp Val Arg Gln Thr Ile Asp Lys Arg Leu Glu Trp Val
        35                  40                  45

Ser Ala Val Gly Pro Ser Gly Asp Thr Tyr Tyr Ala Asp Ser Val Lys
    50                  55                  60

Gly Arg Phe Ala Val Ser Arg Glu Asn Ala Lys Asn Ser Leu Ser Leu
65                  70                  75                  80

Gln Met Asn Ser Leu Thr Ala Gly Asp Thr Ala Ile Tyr Tyr Cys Val
            85                  90                  95

Arg Ser Asp Arg Gly Val Ala Gly Leu Phe Asp Ser Trp Gly Gln Gly
            100                 105                 110

Ile Leu Val Thr Val Ser Ser
        115

<210> SEQ ID NO 68
<211> LENGTH: 416
```

```
<212> TYPE: DNA
<213> ORGANISM: Artificial Sequence
<220> FEATURE:
<223> OTHER INFORMATION: DMAb

<400> SEQUENCE: 68
atggactgga catggagaat cctgttcctg gtcgccgccg ctactgggac tcacgccgag      60
gtgcagctgg tcgaaagtgg agggggactg atccagccag gcggaagcct gcgactgtcc    120
tgcgcagctt ctggattcgc actgcgcatg tacgacatgc actgggtgcg ccagacaatt    180
gataagcgac tggaatgggt cagcgccgtg ggaccatccg ggacactta ctatgctgat     240 tctgtgaagg ggagatttgc tgtcagtcgg gagaacgcaa aaattctct gagtctgcag    300 atgaactctc tgaccgcagg cgacacagcc atctactatt gcgtgcgatc cgacaggggc    360
gtcgcaggac tgttcgattc ttggggccag ggaattctgg tcacagtgag ctccgc        416

<210> SEQ ID NO 69
<211> LENGTH: 213
<212> TYPE: PRT
<213> ORGANISM: Artificial Sequence
<220> FEATURE:
<223> OTHER INFORMATION: DMAb

<400> SEQUENCE: 69

Asp Ile Gln Met Thr Gln Ser Pro Ser Leu Ser Ala Ser Val Gly
1               5                   10                  15

Asp Arg Ile Thr Ile Thr Cys Arg Ala Ser Gln Ala Phe Asp Asn Tyr
            20                  25                  30

Val Ala Trp Tyr Gln Gln Arg Pro Gly Lys Val Pro Lys Leu Leu Ile
        35                  40                  45

Ser Ala Ala Ser Ala Leu His Ala Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 70
<211> LENGTH: 630
<212> TYPE: DNA
<213> ORGANISM: Artificial Sequence
<220> FEATURE:
```

<223> OTHER INFORMATION: DMAb

<400> SEQUENCE: 70

```
atgacacagt ctccttcctc tctgagtgct tcagtgggcg acaggatcac cattacatgt      60
agagctagcc aggcattcga taactacgtg gcctggtatc agcagcggcc tgggaaggtg     120
ccaaaactgc tgatctctgc tgcaagtgcc ctgcacgctg gagtgccaag ccgcttcagc     180
ggcagcgggt ctggaactca cttcaccctg accattagtt cactgcagcc agaggacgtg     240
gctacctact attgccagaa ctacaattcc gcacccctga ctttcggcgg agggaccaag     300
gtcgaaatca aaactgtggc cgctcccagc gtcttcattt ttccaccctc cgacgagcag     360
ctgaagagtg gcaccgcctc agtggtgtgc ctgctgaaca acttctaccc tagagaagca     420
aaggtccagt ggaaagtgga taacgccctg cagtcaggaa atagccagga gtccgtgaca     480
gaacaggact ctaaggatag tacttattca ctgagctcca cactgactct gtccaaagct     540
gactacgaga agcacaaagt gtatgcatgc gaagtgaccc accagggact gagcagcccc     600
gtgaccaaga gctttaatag aggagaatgt                                      630
```

<210> SEQ ID NO 71
<211> LENGTH: 477
<212> TYPE: PRT
<213> ORGANISM: Artificial Sequence
<220> FEATURE:
<223> OTHER INFORMATION: DMAb

<400> SEQUENCE: 71

```
Met Asp Trp Thr Trp Arg Ile Leu Phe Leu Val Ala Ala Thr Gly
 1               5                  10                  15

Thr His Ala Gln Val Gln Leu Val Gln Ser Gly Ala Glu Val Lys Lys
            20                  25                  30

Pro Gly Ser Ser Val Lys Val Ser Cys Lys Ala Ser Gly Ala Thr Phe
        35                  40                  45

Gly Ser Asp Thr Val Thr Trp Val Arg Gln Ala Pro Gly Gln Gly Leu
    50                  55                  60

Glu Trp Met Gly Gly Ile Ile Pro Phe Phe Gly Glu Ala Asn Tyr Ala
65                  70                  75                  80

Gln Arg Phe Gln Gly Arg Val Thr Ile Thr Ala Asp Lys Ser Thr Asn
                85                  90                  95

Thr Ala Tyr Met Glu Leu Ser Ser Leu Arg Ser Glu Asp Thr Ala Val
            100                 105                 110

Tyr Phe Cys Ala Arg Gln Ile Asn Glu Met Ala Thr Phe Gly Glu Ile
        115                 120                 125

His Tyr Tyr Thr Tyr Met Asp Val Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
```

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
            245                 250                 255

Phe Pro Pro Lys Pro Lys Asp Thr Leu Met Ile Ser Arg Thr Pro Glu
        260                 265                 270

Val Thr Cys Val Val Val Asp Val Ser His Glu Asp Pro Glu Val Lys
    275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
        340                 345                 350

Ala Lys Gly Gln Pro Arg Glu Pro Gln Val Tyr Thr Leu Pro Pro Ser
    355                 360                 365

Arg Asp Glu Leu Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
        420                 425                 430

Gln Gly Asn Val Phe Ser Cys Ser Val Met His Glu Ala Leu His Asn
    435                 440                 445

His Tyr Thr Gln Lys Ser Leu Ser Leu Ser Pro Gly Lys
450                 455                 460

465                 470                 475

<210> SEQ ID NO 72
<211> LENGTH: 1431
<212> TYPE: DNA
<213> ORGANISM: Artificial Sequence
<220> FEATURE:
<223> OTHER INFORMATION: DMAb

<400> SEQUENCE: 72

```
atggactgga cctggagaat cctgttcctg gtggcagcag caaccggaac acacgcacag      60
gtgcagctgg tgcagagcgg agcagaggtg aagaagccag gcagctccgt gaaggtgtcc     120
tgcaaggcat ctggagccac cttcggctcc gataccgtga catgggtgcg ccaggcacca     180
ggacagggac tggagtggat gggcggcatc atccctttct ttggcgaggc caactacgcc     240
cagcggtttc agggcagagt gaccatcaca gccgacaagt ccaccaatac agcctacatg     300
gagctgtcta gcctgcggtc tgaggatacc gccgtgtatt tctgcgccag acagatcaac     360
gagatggcca cctttggcga gatccactac tatacataca tggacgtgtg gggacagggc     420
accctggtga cagtgtcctc tgcctccacc aagggaccta gcgtgttccc actggcacct     480
agctccaagt ctaccagcgg cggcacagcc gccctgggat gtctggtgaa ggattatttc     540
cctgagccag tgacagtgtc ctggaactct ggcgccctga ccagcggagt gcacacattt     600
cccgccgtgc tgcagtctag cggcctgtac tccctgtcct ctgtggtgac cgtgcctagc     660
```

```
tcctctctgg gcacccagac atatatctgc aacgtgaatc acaagccttc taatacaaag    720
gtggacaaga aggtggagcc aaagagctgt gataagaccc acacatgccc tccctgtcca    780
gcacctgagc tgctgggcgg cccaagcgtg ttcctgtttc acccaagcc caaggacacc     840 ctgatgatca gcaggacccc tgaggtgaca tgcgtggtgg tggacgtgtc ccacgaggac    900
cccgaggtga agttcaactg gtacgtggat ggcgtggagg tgcacaatgc caagaccaag    960
ccccgggagg agcagtacaa cagcacctat agagtggtgt ccgtgctgac agtgctgcac   1020
caggactggc tgaacggcaa ggagtataag tgcaaggtgt ctaataaggc cctgccagcc   1080
cccatcgaga agaccatctc caaggcaaag ggacagccaa gggagccaca ggtgtacaca   1140
ctgcctccaa gccgcgacga gctgaccaag aaccaggtgt ccctgacatg tctggtgaag   1200
ggcttctatc catccgatat cgccgtggag tgggagtcta atggccagcc cgagaacaat   1260
tacaagacca caccccctgt gctggacagc gatggctcct ctttctgta ttccaagctg    1320 accgtggaca gtctcggtg gcagcagggc aacgtgtttt cctgctctgt gatgcacgag    1380
gccctgcaca atcactacac ccagaagagc ctgtccctgt ctcctggcaa g            1431
```

<210> SEQ ID NO 73
<211> LENGTH: 235
<212> TYPE: PRT
<213> ORGANISM: Artificial Sequence
<220> FEATURE:
<223> OTHER INFORMATION: DMAb

<400> SEQUENCE: 73

```
Met Val Leu Gln Thr Gln Val Phe Ile Ser Leu Leu Trp Ile Ser
1               5                   10                  15

Gly Ala Tyr Gly Gly Ser Glu Leu Thr Gln Asp Pro Ala Val Ser Val
            20                  25                  30

Ala Leu Gly Gln Thr Val Arg Ile Thr Cys Gln Gly Asp Ser Leu Arg
        35                  40                  45

Asn Tyr Tyr Ala Ser Trp Tyr Gln Gln Lys Pro Arg Gln Ala Pro Val
    50                  55                  60

Leu Val Phe Tyr Gly Lys Asn Asn Arg Pro Ser Gly Ile Pro Asp Arg
65                  70                  75                  80

Phe Ser Gly Ser Ser Gly Asn Thr Ala Ser Leu Thr Ile Ser Gly
                85                  90                  95

Ala Gln Ala Glu Asp Glu Ala Asp Tyr Tyr Cys Asn Ser Arg Asp Ser
            100                 105                 110

Ser Ser Asn His Leu Val Phe Gly Gly Gly Thr Lys Leu Thr Val Leu
        115                 120                 125

Ser Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Asn Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

225          230          235

<210> SEQ ID NO 74
<211> LENGTH: 705
<212> TYPE: DNA
<213> ORGANISM: Artificial Sequence
<220> FEATURE:
<223> OTHER INFORMATION: DMAb

<400> SEQUENCE: 74

```
atggtgctgc agacccaggt gtttatctct ctgctgctgt ggatcagcgg agcatacggc    60
ggctccgagc tgacacagga cccagccgtg agcgtggccc tgggacagac cgtgaggatc   120
acatgtcagg gcgatagcct gcgcaactac tatgcctcct ggtaccagca gaagcctcgg   180
caggccccag tgctggtgtt ctatggcaag aacaataggc cctctggcat ccctgaccgc   240
tttagcggca gctcctctgg caataccgca agcctgacaa tctccggagc acaggcagag   300
gacgaggcag attactattg caacagcaga gatagctcct ctaatcacct ggtgttcggc   360
ggcggaacca agctgacagt gctgtctacc gtggccgccc aagcgtgtt catctttcca   420
ccctccgacg agcagctgaa gtctggcaca gccagcgtgg tgtgcctgct gaacaacttc   480
taccccgga aggccaaggt gcagtggaag gtggataacg ccctgcagtc tggcaatagc   540
caggagtccg tgaccgagca ggactctaag gatagcacat attctctgag caacaccctg   600
acactgagca aggccgacta cgagaagcac aaggtgtatg catgcgaggt gacccaccag   660
ggactgagct ccccagtgac aaagtccttc aatagaggcg agtgt              705
```

<210> SEQ ID NO 75
<211> LENGTH: 467
<212> TYPE: PRT
<213> ORGANISM: Artificial Sequence
<220> FEATURE:
<223> OTHER INFORMATION: DMAb

<400> SEQUENCE: 75

```
Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30

Pro Gly Gly Ser Leu Arg Leu Ser Cys Glu Val Ser Gly Leu Thr Phe
        35                  40                  45

Ser Asn Phe Gly Met Gln Trp Val Arg Gln Ala Pro Gly Lys Gly Leu
    50                  55                  60

Glu Trp Val Ala Phe Ile Arg Phe Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Gly Ser Leu Arg Ala Glu Asp Thr Ala Val
            100                 105                 110

Tyr Phe Cys Gly Arg Val Leu Tyr Gly Ala Ala Asp Phe Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Val Val Thr Val
        195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 76
<211> LENGTH: 1401
<212> TYPE: DNA
<213> ORGANISM: Artificial Sequence
<220> FEATURE:
<223> OTHER INFORMATION: DMAb

<400> SEQUENCE: 76
atggactgga cctggagaat cctgttcctg gtggcagcag caaccggaac acacgcacag      60
gtgcagctgg tggagagcgg cggcggcgtg gtgcagcctg gcggctctct gagactgagc     120
tgcgaggtgt ccggcctgac cttcagcaac tttggaatgc agtgggtgag gcaggcacca     180
ggcaagggac tggagtgggt ggccttcatc cgctttgacg gctctaataa gtactatgcc     240
gatagcgtga aggccggtt caccatctct agagacaaca gcaagaatac agtgtacctg     300
cagatgggca gcctgagggc agaggacacc gccgtgtact tctgcggacg cgtgctgtat     360

```
ggagcagcag cagattttg gggacagggc accctggtga cagtgagctc cgcctctaca    420
aagggaccaa gcgtgtttcc actggcaccc tctagcaagt ccacctctgg cggcacagcc    480
gccctgggct gtctggtgaa ggattacttc cccgagcctg tgaccgtgag ctggaactcc    540
ggcgccctga cctccggagt gcacacattt ccagccgtgc tgcagtcctc tggcctgtac    600
agcctgagct ccgtggtgac cgtgccctct agctccctgg gcacccagac atatatctgc    660
aacgtgaatc acaagccaag caatacaaag gtggacaaga aggtggagcc caagtcctgt    720
gataagaccc acacatgccc tcctgtcca gcaccagagc tgctgggcgg cccaagcgtg    780
ttcctgtttc cacccaagcc taaggacacc ctgatgatct ctagaacccc cgaggtgaca    840
tgcgtggtgg tggacgtgag ccacgaggac cccgaggtga agttcaactg gtacgtggat    900
ggcgtggagg tgcacaatgc caagacaaag cctcgggagg agcagtacaa ctccacctat    960
agagtggtgt ctgtgctgac agtgctgcac caggactggc tgaacggcaa ggagtataag   1020
tgcaaggtgt ccaataaggc cctgcctgcc ccaatcgaga agaccatctc taaggcaaag   1080
ggacagcctc gggagccaca ggtgtacaca ctgcctccat ccagagacga gctgaccaag   1140
aaccaggtgt ctctgacatg tctggtgaag ggcttctatc cttctgatat cgccgtggag   1200
tgggagagca atggccagcc agagaacaat tacaagacca cccccctgt gctggactct   1260
gatggcagct tctttctgta ttccaagctg accgtggaca gtctcggtg cagcagggc   1320
aacgtgttta gctgctccgt gatgcacgag gccctgcaca tcactacac ccagaagtct   1380
ctgagcctgt ccccaggcaa g                                              1401
```

<210> SEQ ID NO 77
<211> LENGTH: 239
<212> TYPE: PRT
<213> ORGANISM: Artificial Sequence
<220> FEATURE:
<223> OTHER INFORMATION: DMAb

<400> SEQUENCE: 77

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Thr Ser Ser His Ser
            35                  40                  45

Leu Leu Tyr Ser Ser Asp Asn Lys Asn Tyr Leu Thr Trp Tyr Gln Gln
        50                  55                  60

Lys Ala Gly Gln Pro Pro Lys Leu Leu Ile Tyr Trp Ala Ser Thr Arg
65                  70                  75                  80

Gln Ser Gly Val Pro Asp Arg Phe Ser Gly Ser Gly Ser Gly Thr Glu
                85                  90                  95

Phe Thr Leu Thr Ile Ser Ser Leu Gln Ala Glu Asp Val Ala Val Tyr
            100                 105                 110

Tyr Cys Gln Gln Tyr Tyr Thr Lys Ser Phe Thr Phe Gly Gln Gly Thr
        115                 120                 125

Lys Val Glu Ile Lys Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Asn Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 78
<211> LENGTH: 717
<212> TYPE: DNA
<213> ORGANISM: Artificial Sequence
<220> FEATURE:
<223> OTHER INFORMATION: DMAb

<400> SEQUENCE: 78
atggtgctgc agacccaggt gtttatcagc ctgctgctgt ggatctccgg cgcctatggc      60
gacatcgtga tgacacagtc cccagattct ctggccgtgt ccctgggaga gagggcaacc     120
atcaactgta catctagcca cagcctgctg tactcctctg acaacaagaa ttacctgacc     180
tggtatcagc agaaggccgg ccagccaccc aagctgctga tctattgggc atccaccagg     240
cagtctggag tgccagaccg cttctccggc tctggcagcg gcacagagtt taccctgaca     300
atcagctccc tgcaggccga ggatgtggcc gtgtactatt gccagcagta ctataccaag     360
agcttcacat ttggccaggg caccaaggtg gagatcaaga cagtggccgc ccccagcgtg     420
ttcatctttc ctccatccga cgagcagctg aagagcggaa ccgcatccgt ggtgtgcctg     480
ctgaacaatt tctaccctag ggaggccaag gtgcagtgga aggtggataa cgccctgcag     540
agcggcaatt cccaggagtc tgtgaccgag caggacagca aggattccac atattccctg     600
tctaacaccc tgacactgtc caaggccgat tacgagaagc acaaggtgta tgcctgcgag     660
gtgacccacc agggcctgtc tagccctgtg acaaagagct ttaatcgcgg cgagtgt       717

<210> SEQ ID NO 79
<211> LENGTH: 476
<212> TYPE: PRT
<213> ORGANISM: Artificial Sequence
<220> FEATURE:
<223> OTHER INFORMATION: DMAb

<400> SEQUENCE: 79

Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Glu Ile Asn Trp Val Arg Gln Ala Pro Gly Arg Gly Leu
    50                  55                  60

Glu Trp Val Ser Tyr Ile Ser Ser Ser Gly Arg Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Pro Tyr Val Asp Gly Ile Leu Tyr Gly Ala
        115                 120                 125

Gly Asp Ser Tyr Phe Asp Tyr Trp Gly Gln Gly Thr Leu Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
                180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 80
<211> LENGTH: 1428
<212> TYPE: DNA
<213> ORGANISM: Artificial Sequence
<220> FEATURE:
<223> OTHER INFORMATION: DMAb

<400> SEQUENCE: 80
atggactgga cctggagaat cctgttcctg gtggcagcag caaccggaac acacgcacag    60

-continued

| | |
|---|---|
| gtgcagctgg tgcagagcgg cggcggcctg gtgcagcccg gcggcagcct gagactgtcc | 120 |
| tgcgccgcct ctggcttcac ctttagctcc tacgagatca actgggtgcg gcaggcacct | 180 |
| ggaagaggac tggagtgggt gagctatatc tctagctccg gcaggaccat ctactatgcc | 240 |
| gactccgtga agggcaggtt tacaatctct cgcgataacg ccaagaatag cctgtacctg | 300 |
| cagatgaatt ccctgagggc agaggacacc gccgtgtact attgcgccag agagccttac | 360 |
| gtggatggca tcctgtatgg cgccggcgac agctacttcg attattgggg ccagggcacc | 420 |
| ctggtgacag tgtctagcgc ctctaccaag ggcccaagcg tgtttccact ggcccctcc | 480 |
| tctaagtcta ccagcggcgg cacagccgcc ctgggatgtc tggtgaagga ctacttcccc | 540 |
| gagcctgtga cagtgagctg gaactccggc gccctgacca gcggagtgca cacatttcct | 600 |
| gccgtgctgc agagctccgg cctgtactcc ctgtctagcg tggtgaccgt gccatcctct | 660 |
| agcctgggca cccagacata tatctgcaac gtgaatcaca agccttccaa tacaaaggtg | 720 |
| gacaagaagg tggagccaaa gtcttgtgat aagacccaca catgcccctc ctgtccagca | 780 |
| ccagagctgc tgggcggccc aagcgtgttc ctgtttccac ccaagcccaa ggacaccctg | 840 |
| atgatcagcc gcaccccaga ggtgacatgc gtggtggtgg acgtgtccca cgaggacccc | 900 |
| gaggtgaagt tcaactggta cgtggatggc gtggaggtgc acaatgccaa gaccaagccc | 960 |
| agggaggagc agtacaactc cacctatcgc gtggtgtctg tgctgacagt gctgcaccag | 1020 |
| gattggctga acggcaagga gtataagtgc aaggtgtcta ataagccct gcctgcccca | 1080 |
| atcgagaaga ccatctccaa ggccaagggc cagcctaggg agccacaggt gtacacactg | 1140 |
| cctccatctc gcgacgagct gaccaagaac caggtgagcc tgacatgtct ggtgaagggc | 1200 |
| ttctatccca gcgatatcgc cgtggagtgg gagtccaatg ccagcctga aacaattac | 1260 |
| aagaccacac cccctgtgct ggactctgat ggcagcttct ttctgtattc taagctgacc | 1320 |
| gtggacaaga gccggtggca gcagggcaac gtgttttcct gctctgtgat gcacgaggcc | 1380 |
| ctgcacaatc actacaccca gaagagcctg tccctgtctc caggcaag | 1428 |

<210> SEQ ID NO 81
<211> LENGTH: 234
<212> TYPE: PRT
<213> ORGANISM: Artificial Sequence
<220> FEATURE:
<223> OTHER INFORMATION: DMAb

<400> SEQUENCE: 81

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Ser
            35                  40                  45

Ile Ser Asn Tyr Leu Asn Trp Tyr Gln Gln Lys Pro Gly Lys Ala Pro
        50                  55                  60

Lys Val Leu Ile Tyr Ala Ala Ser Ser Leu Gln Ser Gly Val Ser Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Phe Cys Gln Gln Ser Tyr
            100                 105                 110

Asn Thr Pro Pro Val Thr Phe Gly Gln Gly Thr Arg Leu Glu Ile Lys
        115                 120                 125
```

```
Thr Val Ala Ala Pro Ser Val Phe Ile Phe Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Asn Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

<210> SEQ ID NO 82
<211> LENGTH: 702
<212> TYPE: DNA
<213> ORGANISM: Artificial Sequence
<220> FEATURE:
<223> OTHER INFORMATION: DMAb

<400> SEQUENCE: 82

```
atggtgctgc agacccaggt gtttatcagc ctgctgctgt ggatctccgg cgcctacggc    60
gacatccaga tgacacagtc ccttcctctc tgtctgcca gcgtgggcga tcgggtgacc   120
atcacatgta gagcctccca gtctatcagc aactacctga attggtatca gcagaagccc   180
ggcaaggccc ctaaggtgct gatctatgca gccagctccc tgcagagcgg cgtgtctagc   240
agattctccg gctctggcag cggcaccgac tttacccctga caatctcctc tctgcagcca   300
gaggatttcg ccacatactt ttgccagcag tcctataaca ccccaccgt gacattcggc   360
cagggcacca ggctggagat caagacagtg gccgcccat ccgtgttcat ctttcctcca   420
tctgacgagc agctgaagag cggaaccgca tccgtggtgt gcctgctgaa caacttctac   480
ccccgcgagg ccaaggtgca gtggaaggtg ataacgccc tgcagtccgg caattctcag   540
gagagcgtga ccgagcagga ctccaaggat tctacatatt ccctgtctaa caccctgaca   600
ctgagcaagg ccgactacga aaagcacaag gtgtatgcat gcgaggtgac ccaccaggga   660
ctgagctccc ctgtgacaaa gtccttcaat cggggcgagt gt                     702
```

<210> SEQ ID NO 83
<211> LENGTH: 475
<212> TYPE: PRT
<213> ORGANISM: Artificial Sequence
<220> FEATURE:
<223> OTHER INFORMATION: DMAb

<400> SEQUENCE: 83

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Thr Asn Ala Trp Met Asn Trp Val Arg Gln Ala Pro Gly Lys Gly Leu
    50                  55                  60

Glu Trp Val Gly Arg Ile Lys Ser Asn Thr Asp Gly Gly Thr Thr Asp
```

```
              65                  70                  75                  80
Tyr Ala Ala Pro Val Lys Gly Arg Phe Thr Ile Ser Arg Asp Asp Ser
                85                  90                  95
Lys Lys Thr Leu Tyr Leu Gln Met Asn Ser Leu Lys Thr Glu Asp Thr
               100                 105                 110
Ala Val Tyr Tyr Cys Thr Thr Gly Lys Ser Asp Cys Ser Gly Gly Asn
               115                 120                 125
Cys Tyr Val Val Asp Tyr Trp Gly Gln Gly Thr Leu Val Thr Val Ser
               130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                    165                 170                 175
Tyr Phe Pro Glu Pro Val Thr Val Ser Trp Asn Ser Gly Ala Leu Thr
                180                 185                 190
Ser Gly Val His Thr Phe Pro Ala Val Leu Gln Ser Ser Gly Leu Tyr
                195                 200                 205
Ser Leu Ser Ser Val Val Thr Val Pro Ser Ser Ser Leu Gly Thr Gln
210                 215                 220
Thr Tyr Ile Cys Asn Val Asn His Lys Pro Ser Asn Thr Lys Val Asp
225                 230                 235                 240
Lys Lys Val Glu Pro Lys Ser Cys Asp Lys Thr His Thr Cys Pro Pro
                245                 250                 255
Cys Pro Ala Pro Glu Leu Leu Gly Gly Pro Ser Val Phe Leu Phe Pro
                260                 265                 270
Pro Lys Pro Lys Asp Thr Leu Met Ile Ser Arg Thr Pro Glu Val Thr
            275                 280                 285
Cys Val Val Val Asp Val Ser His Glu Asp Pro Glu Val Lys Phe Asn
                290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
                340                 345                 350
Asn Lys Ala Leu Pro Ala Pro Ile Glu Lys Thr Ile Ser Lys Ala Lys
                355                 360                 365
Gly Gln Pro Arg Glu Pro Gln Val Tyr Thr Leu Pro Pro Ser Arg Asp
                370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                    405                 410                 415
Asn Asn Tyr Lys Thr Thr Pro Pro Val Leu Asp Ser Asp Gly Ser Phe
                420                 425                 430
Phe Leu Tyr Ser Lys Leu Thr Val Asp Lys Ser Arg Trp Gln Gln Gly
                435                 440                 445
Asn Val Phe Ser Cys Ser Val Met His Glu Ala Leu His Asn His Tyr
                450                 455                 460
Thr Gln Lys Ser Leu Ser Leu Ser Pro Gly Lys
465                 470                 475

<210> SEQ ID NO 84
```

<211> LENGTH: 1425
<212> TYPE: DNA
<213> ORGANISM: Artificial Sequence
<220> FEATURE:
<223> OTHER INFORMATION: DMAb

<400> SEQUENCE: 84

```
atggactgga cctggagaat cctgttcctg gtggcagcag caaccggaac acacgcacag      60
gtgcagctgg tgcagagcgg cggcggcctg gtgaagccag gcggctctct gagactgagc     120
tgcgcagcat ccggcttcac ctttacaaat gcctggatga actgggtgag gcaggcacca     180
ggcaagggac tggagtgggt gggacgcatc aagtccaaca ccgacggcgg aaccacagat     240
tacgccgccc ccgtgaaggg caggttcaca atctctcgcg acgatagcaa gaagaccctg     300
tatctgcaga tgaatagcct gaagaccgag gacacagccg tgtactattg caccaccggc     360
aagtccgact gctctggcgg caactgttac gtggtggatt attggggcca gggcaccctg     420
gtgacagtga gctccgccag cacaaagggc ccttccgtgt tccactggcc ccctctagc      480
aagtccacat ctggcggcac cgccgccctg ggatgtctgg tgaaggatta cttccccgag     540
cctgtgaccg tgagctggaa ttccggcgcc ctgacatccg gagtgcacac ctttccagcc     600
gtgctgcagt cctctggcct gtacagcctg agctccgtgg tgacagtgcc ttctagctcc     660
ctgggcaccc agacatatat ctgcaatgtg aaccacaagc ccagcaacac caaggtggac     720
aagaaggtgg agcctaagtc ctgtgataag acccacacat gccctccctg tccagcacca     780
gagctgctgg gcggcccttc cgtgttcctg tttccaccca agccaaagga caccctgatg     840
atctctagaa cacctgaggt gacctgcgtg gtggtggacg tgagccacga ggaccccgag     900
gtgaagttca attggtacgt ggatggcgtg gaggtgcaca acgccaagac caagcccagg     960
gaggagcagt acaattctac atatcgcgtg gtgagcgtgc tgaccgtgct gcaccaggat    1020
tggctgaatg gcaaggagta taagtgcaag gtgtccaaca aggccctgcc tgccccaatc    1080
gagaagacaa tctctaaggc aaagggacag cctcgggagc cacaggtgta caccctgcct    1140
ccatccagag acgagctgac aaagaatcag gtgtctctga cctgtctggt gaagggcttc    1200
tatccatctg atatcgcagt ggagtgggag agcaacggac agcccgagaa caattacaag    1260
accacacccc ctgtgctgga ctctgatggc agcttctttc tgtattccaa gctgaccgtg    1320
gacaagtctc ggtggcagca gggcaacgtg ttcagctgct ccgtgatgca cgaggccctg    1380
cacaaccact acacacagaa gtctctgagc ctgtccccag gcaag                    1425
```

<210> SEQ ID NO 85
<211> LENGTH: 238
<212> TYPE: PRT
<213> ORGANISM: Artificial Sequence
<220> FEATURE:
<223> OTHER INFORMATION: DMAb

<400> SEQUENCE: 85

Met Val Leu Gln Thr Gln Val Phe Ile Ser Leu Leu Trp Ile Ser
1               5                   10                  15

Gly Ala Tyr Gly Gln Ser Val Leu Thr Gln Pro Pro Ser Val Ser Gly
                20                  25                  30

Ala Pro Gly Gln Arg Val Thr Ile Ser Cys Thr Gly Ser Ser Ser Asn
            35                  40                  45

Ile Gly Ala Gly Tyr Asp Val Lys Trp Tyr Gln Gln Leu Pro Gly Ala
        50                  55                  60

Ala Pro Lys Leu Leu Ile Tyr Gly Asn Asn Asn Arg Pro Ser Gly Val

```
                65                  70                  75                  80
Pro Asp Arg Phe Ser Ala Ser Lys Ser Gly Thr Ser Ala Ser Leu Ala
                        85                  90                  95
Ile Thr Gly Leu Gln Ala Glu Asp Glu Ala Asp Tyr Tyr Cys Gln Ser
                    100                 105                 110
Tyr Asp Ser Arg Leu Arg Asp His Trp Val Phe Gly Gly Thr Lys
                115                 120                 125
Leu Thr Val Leu Thr Val Ala Ala Pro Ser Val Phe Ile Phe Pro Pro
        130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Asn Thr Leu Thr Leu Ser Lys Ala
            195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235
```

```
<210> SEQ ID NO 86
<211> LENGTH: 714
<212> TYPE: DNA
<213> ORGANISM: Artificial Sequence
<220> FEATURE:
<223> OTHER INFORMATION: DMAb

<400> SEQUENCE: 86
atggtgctgc agacacaggt gtttatctcc ctgctgctgt ggatctctgg agcatacgga      60
cagagcgtgc tgacccagcc accctccgtg tctggagcac tggacagag ggtgacaatc     120 tcctgtaccg gctctagctc caacatcggc gccggctacg acgtgaagtg gtatcagcag    180
ctgccaggag cagcacctaa gctgctgatc tacggcaaca ataaccggcc aagcggcgtg    240
cccgatagat tcagcgcctc caagtctggc acaagcgcct ccctggcaat caccggactg    300
caggccgagg acgaggccga ttactattgc cagtcctatg actctcggct gagagatcac    360
tgggtgtttg gcggcggaac caagctgaca gtgctgaccg tggccgcccc tagcgtgttc    420
atctttcctc catccgacga gcagctgaag tccggcaccg cctctgtggt gtgcctgctg    480
aataacttct acccaaggga ggccaaggtg cagtggaagg tggataatgc cctgcagagc    540
ggcaactccc aggagtctgt gacagagcag gacagcaagg attccaccta ttctctgagc    600
aataccctga cactgtccaa ggccgactac gagaagcaca aggtgtatgc ctgcgaggtg    660
acacaccagg gcctgtctag ccccgtgacc aagagcttta ccgcggcga gtgt           714

<210> SEQ ID NO 87
<211> LENGTH: 480
<212> TYPE: PRT
<213> ORGANISM: Artificial Sequence
<220> FEATURE:
<223> OTHER INFORMATION: DMAb

<400> SEQUENCE: 87

Met Asp Trp Thr Trp Arg Ile Leu Phe Leu Val Ala Ala Ala Thr Gly
1               5                   10                  15
```

```
Thr His Ala Gln Val Gln Leu Val Gln Ser Gly Ala Glu Val Lys Lys
                20                  25                  30

Pro Gly Ala Ser Val Lys Val Ser Cys Lys Thr Ser Gly Tyr Thr Phe
        35                  40                  45

Thr Ser Phe Glu Ile His Trp Val Arg Gln Gly Ser Gly Gln Gly Leu
    50                  55                  60

Glu Trp Met Gly Arg Met Asn Pro Lys Ser Gly Asp Thr Val Ser Ala
65                  70                  75                  80

Gln Lys Phe Gln Gly Arg Val Thr Leu Thr Arg Asp Thr Ser Ile Asn
                85                  90                  95

Ala Ala Tyr Met Glu Leu Gly Ser Leu Ser Ser Glu Asp Thr Ala Val
            100                 105                 110

Tyr Tyr Cys Ala Arg Gly Pro His Val Gly Glu Val Val Pro Gly Leu
        115                 120                 125

Met Ala Gly Thr Tyr Tyr Phe Pro Leu Asp Val Trp Gly Gln Gly Thr
    130                 135                 140

Leu Val Thr Val Ser Ser Ala Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
    210                 215                 220

Ser Leu Gly Thr Gln Thr Tyr Ile Cys Asn Val Asn His Lys Pro Ser
225                 230                 235                 240

Asn Thr Lys Val Asp Lys Lys Val Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
```

```
            435                 440                 445
Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

<210> SEQ ID NO 88
<211> LENGTH: 1440
<212> TYPE: DNA
<213> ORGANISM: Artificial Sequence
<220> FEATURE:
<223> OTHER INFORMATION: DMAb

<400> SEQUENCE: 88
atggactgga catggagaat cctgttcctg gtggcagcag caaccggaac acacgcacag      60
gtgcagctgg tgcagagcgg agcagaggtg aagaagccag agcctctgt gaaggtgagc     120 tgcaagacct ccggctacac cttcacaagc tttgagatcc actgggtgcg gcagggctcc     180
ggacagggac tggagtggat gggcagaatg aaccctaagt ccggcgacac cgtgtctgcc     240
cagaagtttc agggccgggt gaccctgaca agagatacat ctatcaatgc cgcctatatg     300
gagctgggca gcctgagctc cgaggacacc gccgtgtact attgcgccag aggcccacac     360
gtgggagagg tggtgcctgg actgatggca ggcacctact atttcccact ggacgtgtgg     420
ggacagggca cctggtgac agtgtctagc gccagcacaa aggaccatc cgtgtttcca     480 ctggcacctt cctctaagag cacctccggc ggcacagccg ccctgggctg tctggtgaag     540
gattacttcc ctgagccagt gaccgtgtct tggaacagcg gcgccctgac cagcggagtg     600
cacacatttc cagccgtgct gcagagctcc ggactgtact ccctgtctag cgtggtgacc     660
gtgccttcct ctagcctggg cacccagaca tatatctgca acgtgaatca caagcctagc     720
aatacaaagg tggacaagaa ggtggagcca agtcctgtg ataagaccca cacatgccct     780
ccctgtccag cacctgagct gctgggcggc caagcgtgt tcctgttccc acccaagccc     840
aaggatcccc tgatgatctc tcggaccca gaggtgacat gcgtggtggt ggacgtgtcc     900
cacgaggacc ccgaggtgaa gttcaactgg tacgtggacg gcgtggaggt gcacaatgcc     960
aagaccaagc ctcgggagga gcagtacaac tctacctata gagtggtgag cgtgctgaca    1020
gtgctgcacc aggactggct gaacggcaag gagtataagt gcaaggtgag caataaggcc    1080
ctgccagccc ccatcgagaa gaccatctcc aaggcaaagg gacagccaag ggagccacag    1140
gtgtacacac tgcctccatc ccgcgacgag ctgaccaaga accaggtgtc tctgacatgt    1200
ctggtgaagg gcttctatcc ctccgatatc gccgtggagt gggagtctaa tggccagcct    1260
gagaacaatt acaagaccac accccctgtg ctggactccg atggctcttt ctttctgtat    1320
agcaagctga ccgtggataa gtcccggtgg cagcagggca acgtgttttc ttgcagcgtg    1380
atgcacgagg ccctgcacaa tcactacacc cagaagtccc tgtctctgag cccaggcaag    1440

<210> SEQ ID NO 89
<211> LENGTH: 233
<212> TYPE: PRT
<213> ORGANISM: Artificial Sequence
<220> FEATURE:
<223> OTHER INFORMATION: DMAb

<400> SEQUENCE: 89

Met Val Leu Gln Thr Gln Val Phe Ile Ser Leu Leu Leu Trp Ile Ser
1               5                   10                  15
```

```
Gly Ala Tyr Gly Asp Ile Gln Met Thr Gln Ser Pro Ser Thr Leu Ser
            20                  25                  30

Ala Ser Ile Gly Asp Arg Val Thr Ile Thr Cys Arg Ala Ser Gln Ser
        35                  40                  45

Ile Ser Arg Trp Leu Ala Trp Tyr Gln Gln Lys Pro Gly Lys Ala Pro
    50                  55                  60

Lys Leu Leu Ile Tyr Lys Val Ser Asp Leu Gln Ser Gly Val Pro Ser
65                  70                  75                  80

Arg Phe Ser Gly Ser Gly Tyr Gly Thr Glu Phe Thr Leu Thr Ile Gly
                85                  90                  95

Ser Leu Gln Pro Asp Asp Leu Ala Thr Tyr Tyr Cys Gln Gln Tyr Asp
            100                 105                 110

Thr Tyr Pro Trp Thr Phe Gly Gln Gly Thr Lys Leu Glu Ile Lys Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Asn Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 90
<211> LENGTH: 699
<212> TYPE: DNA
<213> ORGANISM: Artificial Sequence
<220> FEATURE:
<223> OTHER INFORMATION: DMAb

<400> SEQUENCE: 90
atggtgctgc agacccaggt gtttatctcc ctgctgctgt ggatctctgg cgcctatggc      60
gacatccaga tgacccagag cccatccaca ctgtctgcca gcatcggcga tagggtgacc     120
atcacatgtc gcgcctccca gtctatcagc aggtggctgg cctggtacca gcagaagcct     180
ggcaaggccc caaagctgct gatctataag gtgtctgatc tgcagagcgg agtgccctcc     240
cgcttctccg gctctggata cggaaccgag tttacccctga caatcggctc cctgcagcct     300
gacgatctgg ccacatacta ttgccagcag tacgacacct atccatggac attcggccag     360
ggcaccaagc tggagatcaa gacagtggcc gcccctagcg tgttcatctt cccacccagc     420
gatgagcagc tgaagtctgg caccgccagc gtggtgtgcc tgctgaacaa cttctaccca     480
cgggaggcca aggtgcagtg gaaggtggac aacgccctgc agagcggcaa ttcccaggag     540
tctgtgaccg agcaggacag caaggattcc acatatagcc tgtccaacac cctgacactg     600
agcaaggccg actacgagaa gcacaaggtg tatgcatgcg aggtgaccca ccagggactg     660
tcctctcccg tgacaaagtc cttcaataga ggcgagtgt                             699

<210> SEQ ID NO 91
<211> LENGTH: 474
```

```
<212> TYPE: PRT
<213> ORGANISM: Artificial Sequence
<220> FEATURE:
<223> OTHER INFORMATION: DMAb

<400> SEQUENCE: 91

Met Asp Trp Thr Trp Arg Ile Leu Phe Leu Val Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Ser Phe Gly Ile Ser Trp Val Arg Gln Ala Pro Gly Gln Gly Leu
    50                  55                  60

Glu Trp Leu Gly Trp Ile Asn Thr Tyr Asn Gly Asp Thr Asn Tyr Ala
65              70                  75                  80

Gln Lys Phe Gln Gly Arg Val Thr Met Thr Thr Asp Thr Ser Thr Ser
                85                  90                  95

Thr Gly Phe Met Glu Leu Arg Ser Leu Arg Ser Asp Asp Thr Ala Val
                100                 105                 110

Tyr Tyr Cys Ala Arg Asp Ser His Leu Ile Ser Ile Ala Val Ala Asn
                115                 120                 125

Thr Pro Asn Asp Phe Trp Gly Gln Gly Thr Leu Val Thr Val Ser Ser
            130                 135                 140

Ala Ser Thr Lys Gly Pro Ser Val Phe Pro Leu Ala Pro Ser Ser Lys
145             150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
            210                 215                 220

Tyr Ile Cys Asn Val Asn His Lys Pro Ser Asn Thr Lys Val Asp Lys
225             230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305             310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
            370                 375                 380
```

```
Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470
```

<210> SEQ ID NO 92
<211> LENGTH: 1422
<212> TYPE: DNA
<213> ORGANISM: Artificial Sequence
<220> FEATURE:
<223> OTHER INFORMATION: DMAb

<400> SEQUENCE: 92

```
atggattgga cctggagaat cctgttcctg gtggcagcag caaccggaac acacgcacag      60
gtgcagctgg tgcagagcgg agcagaggtg aagaagcctg agcctccgt gaaggtgtct     120
tgcaaggcca gcggctacac cttcacatcc tttggcatct cttgggtgag gcaggcacca     180
ggacagggac tggagtggct gggatggatc aacacataca atggcgatac caactatgcc     240
cagaagttcc agggccgcgt gacaatgacc acagacacca gcacatccac cggctttatg     300
gagctgcggt ctctgagaag cgacgatacc gccgtgtact attgcgcccg cgatagccac     360
ctgatctcca tcgccgtggc caacacaccc aatgacttct ggggccaggg cacactggtg     420
accgtgagct ccgcctccac caagggacct agcgtgttcc cactggcacc ttctagcaag     480
tctacaagcg gcggcaccgc cgccctggga tgtctggtga aggactactt ccctgagcca     540
gtgaccgtgt cctggaactc tggcgccctg acatccggcg tgcacacctt cctgccgtg     600
ctgcagtcct ctggcctgta cagcctgagc tccgtggtga cagtgccatc tagctccctg     660
ggcacacaga cctatatctg caacgtgaat cacaagcctt caataccaa ggtggacaag     720
aaggtggagc caaagagctg tgataagaca cacacctgcc ctcctgtcc agcacctgag     780
ctgctgggcg gcccaagcgt gttcctgttt ccacccaagc caaggatac cctgatgatc     840
tccagaacac cagaggtgac ctgcgtggtg gtggacgtgt ctcacgagga ccccgaggtg     900
aagttcaact ggtacgtgga cggcgtggag gtgcacaatg ccaagaccaa gccaagggag     960
gagcagtaca atagcacata cgcgtggtg tccgtgctga ccgtgctgca ccaggattgg    1020
ctgaacggca aggagtataa gtgcaaggtg tccaataagg ccctgccagc ccccatcgag    1080
aagacaatca gcaaggcaaa gggacagcca cgggagccac aggtgtacac cctgcctcca    1140
agcagagatg agctgacaaa gaaccaggtg tccctgacct gtctggtgaa gggcttctat    1200
ccctctgaca tcgccgtgga gtgggagagc aatggccagc ctgagaacaa ttacaagacc    1260
acacccctg tgctgacag cgatggctcc ttctttctgt attccaagct gaccgtggac    1320
aagtctcggt ggcagcaggg caacgtgttt cctgctctg tgatgcacga ggccctgcac    1380
aatcactaca cacagaagag cctgtccctg tctcctggca ag                      1422
```

<210> SEQ ID NO 93
<211> LENGTH: 236

<212> TYPE: PRT
<213> ORGANISM: Artificial Sequence
<220> FEATURE:
<223> OTHER INFORMATION: DMAb

<400> SEQUENCE: 93

```
Met Val Leu Gln Thr Gln Val Phe Ile Ser Leu Leu Trp Ile Ser
1               5                   10                  15

Gly Ala Tyr Gly Glu Ile Val Met Thr Gln Ser Pro Gly Thr Leu Ser
            20                  25                  30

Leu Ser Pro Gly Asp Arg Val Thr Leu Ser Cys Arg Ala Ser Gln Ser
            35                  40                  45

Val Tyr Ser Tyr Tyr Leu Ala Trp Tyr Gln Gln Lys Pro Gly Gln Ala
        50                  55                  60

Pro Arg Leu Leu Met Tyr Asp Ala Ser Ile Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Tyr Tyr
            100                 105                 110

Gly Asn Ser His Gln Gly Ala Ala Phe Gly Gly Thr Lys Val Glu
        115                 120                 125

Val Lys Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Asn Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 94
<211> LENGTH: 708
<212> TYPE: DNA
<213> ORGANISM: Artificial Sequence
<220> FEATURE:
<223> OTHER INFORMATION: DMAb

<400> SEQUENCE: 94

```
atggtgctgc agacacaggt gtttatctct ctgctgctgt ggatcagcgg cgcctacggc      60
gagatcgtga tgacacagag cccaggcacc ctgtctctga gccctggcga cagggtgacc     120
ctgtcctgta gggcatccca gagcgtgtac tcttactatc tggcctggta tcagcagaag     180
cctggacagg ccccacggct gctgatgtat gacgcctcca tccgggccac aggcatccca     240
gatagattca gcggctccgg ctctggcacc gactttacac tgaccatctc tagcctggag     300
cccgaggatt tcgccgtgta ctattgccag tactatggaa acagccacca gggagcagcc     360
tttggccagg gcacaaaggt ggaggtgaag accgtggcag caccaagcgt gttcatcttt     420
ccaccctccg atgagcagct gaagtctggc accgccagcg tggtgtgcct gctgaacaat     480
ttctaccctc gggaggccaa ggtgcagtgg aaggtggaca acgccctgca gtctggcaat     540
```

```
agccaggagt ccgtgacaga gcaggactct aaggatagca cctatagcct gtccaacaca    600
ctgaccctgt ccaaggccga ctacgagaag cacaaggtgt atgcctgcga ggtgacacac    660
cagggcctgt cctctcccgt gaccaagagc tttaatagag gcgagtgt                 708
```

<210> SEQ ID NO 95
<211> LENGTH: 116
<212> TYPE: PRT
<213> ORGANISM: Artificial Sequence
<220> FEATURE:
<223> OTHER INFORMATION: DMAb

<400> SEQUENCE: 95

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Thr
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Leu Asp Lys Ser Lys Asp Gln Phe Ser
65                  70                  75                  80

Leu Lys Leu Ser Ser Val Thr Ala Ala Asp Thr Ala Val Tyr Tyr Cys
                85                  90                  95

Ala Tyr Ser Asn Thr Trp Thr Gly Gly Trp Gly Gln Gly Thr Leu Val
            100                 105                 110

Thr Val Ser Ser
        115
```

<210> SEQ ID NO 96
<211> LENGTH: 1536
<212> TYPE: DNA
<213> ORGANISM: Artificial Sequence
<220> FEATURE:
<223> OTHER INFORMATION: DMAb

<400> SEQUENCE: 96

```
atggattgga cctggagaat cctgttcctg gtggcagcag caaccggaac acacgcacag    60
gtgcagctgc aggagagcgg accaggcctg gtgaagccta gcggcacact gtccctgacc    120
tgtgccgtgt ccggcggctc tatcagctcc accaactggt ggtcctgggt gcggcagccc    180
cctggcaagg gctggagtg atcggcgag atctaccaca gcggctccac aaactataat      240
cccagcctga agtcccgcgt gaccatctct ctggacaaga gcaaggatca gttcagcctg    300
aagctgtcta gcgtgacagc cgccgatacc gccgtgtact attgcgccta ctccaatacc    360
tggacaggcg gctggggaca gggcacactg gtgaccgtgt cctctgcctc caccaaggga    420
ccaagcgtgt tcccactggc accatgctct aggagcacat ccgcggcac cgccgccctg    480 ggatgtctgg tgaaggacta tttcccagag cccgtgacag tgtcttggaa cagcggcgcc    540
ctgacatccg gagtgcacac ctttcctgcc gtgctgcaga gctccggcct gtactctctg    600
tctagcgtgg tgaccgtgcc ttcctctagc ctgggcaccc agacatatac ctgtaacgtg    660
aatcacaagc caagcaatac aaaggtggac aagagagtgg agctgaagac accactgggc    720
gataccacac acacctgccc caggtgtcct gagccaaagt cctgcgacac accacccct    780 tgccctagat gtcccgagcc taagtcttgt gatacccac cccccttgccc aaggtgtcca    840
```

```
gagcccaaga gttgtgatac accaccccct tgtccaaggt gtcctgcacc agagctgctg    900
ggcggccctt ccgtgttcct gtttccaccc aagccaaagg atacccctgat gatcagccgc    960 acaccagagg tgacctgcgt ggtggtggac gtgtcccacg aggaccccga ggtgcagttc   1020
aagtggtacg tggacggcgt ggaggtgcac aacgccaaga ccaagccaag ggaggagcag   1080
tataatagca ccttcagggt ggtgtccgtg ctgaccgtgc tgcaccagga ctggctgaac   1140
ggcaaggagt acaagtgtaa ggtgtctaat aaggccctgc ccgcccctat cgagaagaca   1200
atcagcaaga ccaagggcca gcctcgggag ccacaggtgt acaccctgcc tccatcccgc   1260
gaggagatga caaagaacca ggtgtctctg acctgcctgg tgaagggctt ttatcccagc   1320
gatatcgcag tggagtggga gtcctctgga cagcctgaga caattacaa taccacaccc   1380 cctatgctgg actccgatgg ctcttttcttt ctgtattcta agctgaccgt ggacaagagc   1440
aggtggcagc agggcaacat cttctcttgt agcgtgatgc acgaggccct gcacaatagg   1500
ttcacccaga gtccctgtc tctgagccct ggcaag                               1536
```

<210> SEQ ID NO 97
<211> LENGTH: 107
<212> TYPE: PRT
<213> ORGANISM: Artificial Sequence
<220> FEATURE:
<223> OTHER INFORMATION: DMAb

<400> SEQUENCE: 97

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ser Ala Phe Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

<210> SEQ ID NO 98
<211> LENGTH: 699
<212> TYPE: DNA
<213> ORGANISM: Artificial Sequence
<220> FEATURE:
<223> OTHER INFORMATION: DMAb

<400> SEQUENCE: 98

```
atggtgctgc agacccaggt gttcatctct ctgctgctgt ggatcagcgg cgcctacggc     60
gacatccaga tgacacagtc cccaagctcc ctgtccgcct ctgtgggcga tagggtgacc    120
atcacatgca gagccagcca gtccatctct agctacctga actggtatca gcagaagcca    180
ggcaaggccc ccaaggtgct gatctactcc gccttttctc tgcagaatgg agtgcccagc    240
cggttctctg gcagcggctc cggcaccgac tttaccctga caatctcctc tctgcagcct    300
gaggatttcg ccacatacta ttgccagcag tcttatagca ccccacgcac atttggccag    360
ggcaccaagg tggagatcaa gacagtggcc gccccctccg tgttcatctt tccccttct    420
```

-continued

| | |
|---|---|
| gacgagcagc tgaagagcgg aaccgcatcc gtggtgtgcc tgctgaacaa tttctaccct | 480 |
| agggaggcca aggtgcagtg gaaggtggat aacgccctgc agagcggcaa ttcccaggag | 540 |
| tctgtgaccg agcaggacag caaggattcc acatattctc tgagctccac cctgacactg | 600 |
| tccaaggccg actacgagaa gcacaaggtg tatgcctgcg aggtgaccca ccagggcctg | 660 |
| tctagccccg tgacaaagag ctttaaccgg ggcgagtgt | 699 |

<210> SEQ ID NO 99
<211> LENGTH: 115
<212> TYPE: PRT
<213> ORGANISM: Artificial Sequence
<220> FEATURE:
<223> OTHER INFORMATION: DMAb

<400> SEQUENCE: 99

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Asn Glu Tyr
            20                  25                  30

Met Met Asn Trp Val Arg Gln Pro Pro Gly Lys Gly Leu Glu Trp Val
        35                  40                  45

Ser Ser Ile Ser Gly Thr Ser Thr Tyr Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Asp Asp Thr Ala Met Tyr Tyr Cys
                85                  90                  95

Ala Arg Gly Ser Thr Gly Gly Tyr Trp Gly Gln Gly Thr Leu Ile Thr
            100                 105                 110

Val Ser Ser
        115

<210> SEQ ID NO 100
<211> LENGTH: 1392
<212> TYPE: DNA
<213> ORGANISM: Artificial Sequence
<220> FEATURE:
<223> OTHER INFORMATION: DMAb

<400> SEQUENCE: 100

| | |
|---|---|
| atggactgga cctggagaat cctgttcctg gtggcagcag caaccggaac acacgcagag | 60 |
| gtgcagctgc tggagagcgg cggcggcctg gtgaagcccg gcggctccct gaggctgtct | 120 |
| tgcgccgcca gcggcttcac ctttaacgag tacatgatga attgggtgag acagcccct | 180 |
| ggcaagggcc tggagtgggt gagctccatc tctggcacca gcacatacat caactatgcc | 240 |
| gactccgtga agggcaggtt caccatctct agagataacg ccaagaatag cctgtacctg | 300 |
| cagatgaatt ccctgaggtc tgacgatacc gccatgtact attgcgccag aggcagcaca | 360 |
| ggcggctatt ggggacaggg caccctgatc acagtgtcta gcgcctccac caagggccct | 420 |
| agcgtgttcc ctctggcccc atcctctaag tccacctctg gcggcacagc cgccctgggc | 480 |
| tgtctggtga aggattattt ccctgagcca gtgacagtga ctggaactc cggcgccctg | 540 |
| acctccggag tgcacacatt cctgccgtg ctgcagagct ccggcctgta cagcctgtct | 600 |
| agcgtggtga ccgtgccatc ctctagcctg gcacccaga catatatctg caacgtgaat | 660 |
| cacaagcctt ccaatacaaa ggtggacaag aaggtggagc caaagtcttg tgataagacc | 720 |
| cacacatgcc caccctgtcc agcacctgag ctgctgggcg gcccaagcgt gttcctgttt | 780 |

```
cctccaaagc caaggacacc ctgatgatc agccggaccc cagaggtgac atgcgtggtg      840
gtggacgtgt cccacgagga ccccgaggtg aagtttaact ggtacgtgga tggcgtggag      900
gtgcacaatg ccaagacaaa gccacgggag gagcagtaca acagcaccta tcgcgtggtg      960
tccgtgctga cagtgctgca ccaggactgg ctgaacggca aggagtataa gtgcaaggtg     1020
tctaataagg ccctgccagc ccccatcgag aagaccatca gcaaggcaaa gggacagccc     1080
cgggagcctc aggtgtacac actgccccct tctcgcgacg agctgaccaa gaaccaggtg     1140
agcctgacat gtctggtgaa gggcttctat cccagcgata tcgccgtgga gtgggagtcc     1200
aatggccagc ctgagaacaa ttacaagacc acaccacccg tgctggactc tgatggcagc     1260
ttctttctgt attccaagct gaccgtggat aagtctcgct ggcagcaggg caacgtgttt     1320
agctgttccg tgatgcacga ggccctgcac aatcactaca cacagaagtc tctgagcctg     1380 tccctggca ag                                                          1392
```

<210> SEQ ID NO 101
<211> LENGTH: 113
<212> TYPE: PRT
<213> ORGANISM: Artificial Sequence
<220> FEATURE:
<223> OTHER INFORMATION: DMAb

<400> SEQUENCE: 101

```
Gly Asp Ile Val Met Thr Gln Thr Pro Leu Ser Ser Ala Val Thr Leu
1               5                  10                  15
Gly Gln Pro Ala Ser Ile Ser Cys Arg Ser Ser Gln Arg Leu Val His
            20                  25                  30
Ser Asp Gly Asn Thr Tyr Leu Ser Trp Leu His Gln Arg Pro Gly Gln
        35                  40                  45
Pro Pro Arg Leu Leu Ile Tyr Lys Val Ser Leu Arg Phe Ser Gly Val
    50                  55                  60
Pro Asp Arg Phe Ser Gly Ser Gly Ala Gly Thr Asp Phe Thr Leu Lys
65                  70                  75                  80
Ile Ser Arg Val Glu Ala Glu Asp Val Gly Ile Tyr Tyr Cys Met Gln
                85                  90                  95
Ala Thr Gln Phe Pro Leu Thr Phe Gly Gly Gly Thr Lys Val Glu Ile
            100                 105                 110
Lys
```

<210> SEQ ID NO 102
<211> LENGTH: 714
<212> TYPE: DNA
<213> ORGANISM: Artificial Sequence
<220> FEATURE:
<223> OTHER INFORMATION: DMAb

<400> SEQUENCE: 102

```
atggtgctgc agacccaggt gttcatctcc ctgctgctgt ggatctctgg cgcctacggc       60
gacatcgtga tgacccagac acctctgagc tccgccgtga cactgggaca gccagcctct      120
atcagctgca ggtctagcca gagactggtg cacagcgatg gcaacaccta cctgtcctgg      180
ctgcaccagc ggccaggaca gccccctcgc ctgctgatct ataaggtgag cctgaggttc      240
tccggcgtgc ccgacagatt ttccggctct ggcgccggca ccgatttcac actgaagatc      300
agccgggtgg aggcagagga cgtgggcatc tactattgca tgcaggcaac ccagttccca      360
ctgaccttcg gcggcggcac caaggtggag atcaagacag tggccgcccc tagcgtgttc      420
```

```
atctttccac ccagcgacga gcagctgaag tctggcaccg ccagcgtggt gtgcctgctg    480
aacaacttct accctcgcga ggccaaggtg cagtggaagt tggataacgc cctgcagagc    540
ggcaattccc aggagtctgt gacagagcag gacagcaagg attccaccta ttctctgtcc    600
tctaccctga cactgtccaa ggccgattac gagaagcaca aggtgtatgc ctgcgaggtg    660
acacaccagg gcctgagctc ccccgtgacc aagtctttta ataggggcga gtgt          714
```

<210> SEQ ID NO 103
<211> LENGTH: 124
<212> TYPE: PRT
<213> ORGANISM: Artificial Sequence
<220> FEATURE:
<223> OTHER INFORMATION: DMAb

<400> SEQUENCE: 103

```
Gln Val Gln Leu Val Gln Ser Gly Ala Glu Val Lys Lys Pro Gly Ala
1               5                   10                  15

Ser Val Asn Leu Ser Cys Lys Gly Ser Gly Tyr Ser Phe Arg Thr Tyr
            20                  25                  30

Tyr Ile His Trp Val Arg Gln Ala Pro Gly Gln Gly Leu Glu Trp Met
        35                  40                  45

Gly Ile Ile Asn Ser Ser Gly Gly Thr Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Arg Ser Leu Lys Tyr Glu Asp Thr Ala Met Tyr Tyr Cys
                85                  90                  95

Ala Arg Asp Arg Phe Pro Thr Val Ser Gly Glu Pro Phe Ala Met Asp
            100                 105                 110

Val Trp Gly Gln Gly Thr Thr Val Thr Val Ser Ser
        115                 120
```

<210> SEQ ID NO 104
<211> LENGTH: 1098
<212> TYPE: DNA
<213> ORGANISM: Artificial Sequence
<220> FEATURE:
<223> OTHER INFORMATION: DMAb

<400> SEQUENCE: 104

```
atggactgga catggagaat cctgttcctg gtggcagcag caaccggaac acacgcacag     60
gtgcagctgg tgcagtccgg agcagaggtg aagaagcctg agccagcgt gaacctgtcc    120 tgcaagggct ctggctacag cttcaggacc tactatatcc actgggtgag acaggcacca    180
ggacagggcc tggagtggat gggcatcatc aacagcagcg gcggcggcac cacatatgcc    240
cagaagtttc agggccgggt gaccatgaca cgcgacacct ccacatctac cgtgtacatg    300
gagctgagga gcctgaagta tgaggacaca gccatgtact attgcgccag ggatagattc    360
cccaccgtga gcggcgagcc ttttgccatg gacgtgtggg gccagggcac cacagtgaca    420
gtgtctagcg cctctaccaa gggcccagc gtgtttcctc tggccccatc ctctaagagc    480
acatccggcg gcaccgccgc cctgggatgt ctggtgaagg actacttccc tgagccagtg    540
accgtgtcct ggaactctgg cgccctgaca agcggcgtgc acacctttcc agccgtgctg    600
cagagctccg gcctgtactc cctgtctagc gtggtgacag tgccctcctc tagcctgggc    660
acacagacct atatctgcaa cgtgaatcac aagcctagca ataccaaggt ggacaagaag    720
```

```
gtggagccaa agtcctgtga taagacacac acctgccctc cctgtccagc acctgagctg    780
ctgggcggcc caagcgtgtt cctgtttcca cccaagccca aggacacact gatgatctct    840
agaacacccg aggtgacctg cgtggtggtg acgtgagcc acgaggaccc cgaggtgaag    900
ttcaactggt acgtggatgg cgtggaggtg cacaatgcca agaccaagcc tcggaggag    960 cagtacaact ccacatatcg cgtggtgtct gtgctgaccg tgctgcacca ggattggctg   1020
aacggcaagg agtataagtg taaggtgtcc aataaggccc tgccagcccc catcgagaag   1080
accatctcta aggccaag                                                 1098
```

<210> SEQ ID NO 105
<211> LENGTH: 107
<212> TYPE: PRT
<213> ORGANISM: Artificial Sequence
<220> FEATURE:
<223> OTHER INFORMATION: DMAb

<400> SEQUENCE: 105

```
Glu Val Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

Leu Ala Trp Tyr Gln Gln Lys Pro Gly Gln Val Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Thr Ile Glu Pro
65                  70                  75                  80

Glu Asp Phe Ala Val Tyr Tyr Cys Gln Gln Arg Ser Lys Trp Gly Val
                85                  90                  95

Thr Phe Gly Gly Gly Thr Lys Val Asp Ile Lys
            100                 105
```

<210> SEQ ID NO 106
<211> LENGTH: 699
<212> TYPE: DNA
<213> ORGANISM: Artificial Sequence
<220> FEATURE:
<223> OTHER INFORMATION: DMAb

<400> SEQUENCE: 106

```
atggtgctgc agacccaggt gttcatctct ctgctgctgt ggatcagcgg agcatacgga     60
gaggtggtgc tgacccagag ccctgtgaca ctgtccctgt ctccaggaga gagggccacc    120
ctgtcctgca gagcaagcca gtccgtgtct ggctacctgg cctggtatca gcagaagcca    180
ggccaggtgc ccaggctgct gatctatgac accagcaacc gggccacagg catccccgca    240
cgcttcagcg gctccggctc tggcaccgac tttaccctga caatctctac aatcgagcct    300
gaggatttcg ccgtgtacta ttgccagcag agaagcaagt ggggcgtgac cttcggcggc    360
ggcacaaagg tggacatcaa gaccgtggcc gcccatccg tgttcatctt ccccccttct    420
gatgagcagc tgaagagcgg cacagcctcc gtggtgtgcc tgctgaacaa tttctacccc    480
cgggaggcca aggtgcagtg gaaggtggac aacgccctgc agagcggcaa ttcccaggag    540
tctgtgaccg agcaggacag caaggattcc acatattctc tgagctccac cctgacactg    600
tccaaggccg attacgagaa gcacaaggtg tatgcctgcg aggtgaccca ccagggcctg    660
tctagccccg tgacaaagtc ttttaatcgc ggcgagtgt                           699
```

<210> SEQ ID NO 107
<211> LENGTH: 123
<212> TYPE: PRT
<213> ORGANISM: Artificial Sequence
<220> FEATURE:
<223> OTHER INFORMATION: DMAb

<400> SEQUENCE: 107

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Asp Arg Tyr Pro Thr Val Val Asn Tyr Phe Gly Met Asp Val
                100                 105                 110

Trp Gly Gln Gly Thr Thr Val Thr Val Ser Ser
        115                 120
```

<210> SEQ ID NO 108
<211> LENGTH: 1416
<212> TYPE: DNA
<213> ORGANISM: Artificial Sequence
<220> FEATURE:
<223> OTHER INFORMATION: DMAb

<400> SEQUENCE: 108

```
atggactgga cctggagaat cctgttcctg gtggcagcag caaccggaac acacgcacag      60
gtgcagctgg tggagtccgg agcagaggtg aagaagccag agcctccgt gaaggtgtct     120
tgcaaggcca gcggctacac cttcaccaca tactatatgc actgggtgag gcaggcacct    180
ggacagggcc tggagtggat gggcatcatc aacccatccg gcggtctac cacatatgcc    240
cagaagtttc agggccgggt gaccatgaca cgcgacacct ccacatctac cgtgtacatg    300
gagctgagct ccctgagaag cgaggacaca gccgtgtatt tctgcgccag ggatagatac    360
cccaccgtgg tgaattattt tggcatggac gtgtggggcc agggcaccac agtgacagtg    420
tctagcgcct ccaccaaggg acctagcgtg ttcccactgg caccctcctc taagagcaca    480
tccggcggca ccgccgccct gggatgtctg gtgaaggatt acttcccaga gccagtgacc    540
gtgagctgga actccggcgc cctgacatct ggcgtgcaca ccttcctgc cgtgctgcag    600
agctccggcc tgtacagcct gtctagcgtg gtgacagtgc catcctctag cctgggcaca    660
cagacctata tctgcaacgt gaatcacaag ccatctaata ccaaggtgga caagaaggtg    720
gagcccaaga gctgtgataa gacacacacc tgccctccct gtcctgcacc agagctgctg    780
ggcggcccat ccgtgttcct gtttccaccc aagcctaagg acacactgat gatctcccgg    840
acaccagagg tgacctgcgt ggtggtggac gtgtctcacg aggaccccga ggtgaagttc    900
aactggtacg tggatggcgt ggaggtgcac aatgccaaga ccaagccaag ggaggagcag    960
tacaacagca catatagagt ggtgtccgtg ctgaccgtgc tgcaccagga ctggctgaac   1020
ggcaaggagt ataagtgcaa ggtgagcaat aaggccctgc cgcccctat cgagaagaca   1080
```

```
atctccaagg caaagggaca gcctcgggag ccacaggtgt acaccctgcc tccaagccgc    1140
gacgagctga caaagaacca ggtgtccctg acctgtctgg tgaagggctt ctatccctcc    1200
gatatcgccg tggagtggga gtctaatggc cagcctgaga caattacaa gaccacaccc    1260 cctgtgctgg actctgatgg cagcttcttt ctgtattcta agctgacagt ggataagagc    1320
cgctggcagc agggcaacgt gttttcttgt agcgtgatgc acgaggccct gcacaatcac    1380
tacacccaga gtccctgtc tctgagccct ggcaag                              1416
```

<210> SEQ ID NO 109
<211> LENGTH: 109
<212> TYPE: PRT
<213> ORGANISM: Artificial Sequence
<220> FEATURE:
<223> OTHER INFORMATION: DMAb

<400> SEQUENCE: 109

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

Leu Ala Trp Tyr Gln Gln Thr Pro Gly Gln Ala Pro Arg Leu Leu Ile
        35                  40                  45

Phe Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ser Ile Thr Phe Gly His Gly Thr Arg Leu Glu Ile Lys
            100                 105
```

<210> SEQ ID NO 110
<211> LENGTH: 705
<212> TYPE: DNA
<213> ORGANISM: Artificial Sequence
<220> FEATURE:
<223> OTHER INFORMATION: DMAb

<400> SEQUENCE: 110

```
atggtgctgc agacccaggt gttcatcagc ctgctgctgt ggatctccgg agcatacgga     60
gagatcgtgc tgacccagtc cccagccaca ctgagcctgt ccctggaga gagggccacc    120 ctgtcttgca gagcctctca gagcgtgtcc ggctacctgg cctggtatca gcagacacct    180
ggccaggccc caaggctgct gatctttgac accagcaaca gggcaacagg catcccagca    240
cgcttctctg gcagcggctc cggcaccgac tttaccctga caatcagctc cctggagccc    300
gaggatttcg ccgtgtacta ttgccagcag aggtccaatt ggccccttc tatcaccttt    360 ggccacggca agactgga gatcaagacc gtggccgccc ctagcgtgtt catctttcca    420
cccagcgacg agcagctgaa gtctggcaca gccagcgtgg tgtgcctgct gaacaatttc    480
tacccacggg aggccaaggt gcagtggaag gtggataacg ccctgcagtc tggcaatagc    540
caggagtccg tgaccgagca ggactctaag gatagcacat attccctgtc tagcaccctg    600
acactgagca aggccgatta cgagaagcac aaggtgtatg catgcgaggt gacccaccag    660
ggcctgtcct ctcccgtgac aaagtccttt aaccgcggcg agtgt                    705
```

```
<210> SEQ ID NO 111
<211> LENGTH: 122
<212> TYPE: PRT
<213> ORGANISM: Artificial Sequence
<220> FEATURE:
<223> OTHER INFORMATION: DMAb

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr His Ser Gly Lys Ser Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Thr Pro Ile Arg Tyr Ser Ser Gly Trp Tyr Leu Asp Tyr Trp
            100                 105                 110

Gly Gln Gly Thr Leu Val Thr Val Ser Ser
        115                 120

<210> SEQ ID NO 112
<211> LENGTH: 1363
<212> TYPE: DNA
<213> ORGANISM: Artificial Sequence
<220> FEATURE:
<223> OTHER INFORMATION: DMAb

<400> SEQUENCE: 112
acacgcacag gtgcagctgc aggagagcgg accaggcctg gtgaagccat ccgagacact     60
gtctctgacc tgcacagtga gcggcgcctc catcagctcc tactattggt cctggatcag    120 gcagcccct ggcaagggcc tggagtggat cggctacatc tatcactctg gcaagagcaa    180
ctacaatccc tccctgaagt ctcgcgtgac catcagcgtg gacacatcca agaaccagtt    240
cagcctgaag ctgtctagcg tgaccgccgc cgatacagcc gtgtactatt gcgccaggca    300 cacccaatc agatattcct ctggctggta cctggactat tggggccagg gcaccctggt    360
gacagtgagc tccgcctcta caaagggccc cagcgtgttt cctctggccc catctagcaa    420
gtctaccagc ggcggcacag ccgccctggg atgtctggtg aaggattact ccctgagcc    480 agtgaccgtg agctggaact ccggcgccct gaccagcgga gtgcacacat tcccgccgt    540 gctgcagtcc tctggcctgt actccctgag ctccgtggtg accgtgcctt ctagctccct    600
gggcacccag acatatatct gcaacgtgaa tcacaagccc agcaatacaa aggtggacaa    660
gaaggtggag cctaagtcct gtgataagac ccacacatgc ccaccctgtc agcacctga    720 gctgctgggc ggcccttccg tgttcctgtt tcctccaaag ccaaaggaca ccctgatgat    780
ctctaggacc cctgaggtga catgcgtggt ggtggacgtg agccacgagg acccccgaggt    840 gaagtttaac tggtacgtgg atggcgtgga ggtgcacaat gccaagacca gcctcgggga    900
ggagcagtac aattccacct atcgcgtggt gtctgtgctg acagtgctgc accaggactg    960
gctgaacggc aaggagtata agtgcaaggt gtccaataag gccctgccag cccccatcga   1020
gaagaccatc tctaaggcaa agggacagcc cagggagcct caggtgtaca cactgccccc   1080
```

```
ttccagagac gagctgacta agaaccaggt gtctctgaca tgtctggtga agggcttcta   1140
tccatctgat atcgccgtgg agtgggagag caatggccag cccgagaaca attacaagac   1200
cacaccaccc gtgctggact ctgatggcag cttctttctg tatagcaagc tgaccgtgga   1260
taagtccagg tggcagcagg gcaacgtgtt ttcctgttct gtgatgcacg aggccctgca   1320
caatcactac acacagaaga gcctgtccct gtctccaggc aag                      1363
```

<210> SEQ ID NO 113
<211> LENGTH: 109
<212> TYPE: PRT
<213> ORGANISM: Artificial Sequence
<220> FEATURE:
<223> OTHER INFORMATION: DMAb

<400> SEQUENCE: 113

```
Asp Ile Arg Leu Thr Gln Ser Pro Ala Thr Leu Ser Leu Ser Pro Gly
1               5                  10                  15

Glu Arg Ala Thr Leu Ser Cys Arg Ala Ser Gln Ser Ile Ser Gly Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Ile Thr Phe Gly Gln Gly Thr Arg Leu Glu Ile Lys
            100                 105
```

<210> SEQ ID NO 114
<211> LENGTH: 705
<212> TYPE: DNA
<213> ORGANISM: Artificial Sequence
<220> FEATURE:
<223> OTHER INFORMATION: DMAb

<400> SEQUENCE: 114

```
atggtgctgc agacccaggt gttcatctcc ctgctgctgt ggatctctgg agcatacggc    60
gacatcaggc tgacccagtc tccagccaca ctgagcctgt cccctggaga gagggccacc   120
ctgagctgca gagcatctca gagcatctcc ggctacctgg cctggtatca gcagaagcct   180
ggacaggccc cacgcctgct gatctatgat gcaagcaaca gggcaaccgg catcccagca   240
cgcttctctg gcagcggctc cggcacagac tttaccctga caatcagctc cctggagccc   300
gaggatttcg ccgtgtacta ttgccagcag aggtccaatt ggccccctgc catcaccttt   360
ggccagggca agactggaga tcaagaccc gtggccgccc ctagcgtgtt catctttcca   420
ccctccgacg agcagctgaa gtctggcaca gccagcgtgg tgtgcctgct gaacaatttc   480
tacccaaggg aggccaaggt gcagtggaag gtggataacg ccctgcagtc tggcaatagc   540
caggagtccg tgaccgagca ggactctaag gatagcacat attccctgtc tagcaccctg   600
acactgtcca aggccgacta cgagaagcac aaggtgtatg catgcgaggt gacccaccag   660
ggcctgtcct ctcccgtgac aaagtctttt aacaggggcg agtgt                    705
```

<210> SEQ ID NO 115
<211> LENGTH: 124
<212> TYPE: PRT

```
<213> ORGANISM: Artificial Sequence
<220> FEATURE:
<223> OTHER INFORMATION: DMAb

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Arg Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Tyr Pro Val Leu Val Ala Thr Asp Tyr Gly Met Asp
            100                 105                 110

Val Trp Gly Gln Gly Thr Thr Val Thr Val Ser Ser
        115                 120

<210> SEQ ID NO 116
<211> LENGTH: 1419
<212> TYPE: DNA
<213> ORGANISM: Artificial Sequence
<220> FEATURE:
<223> OTHER INFORMATION: DMAb

<400> SEQUENCE: 116
atggactgga cctggagaat cctgttcctg gtggcagcag caaccggaac acacgcacag      60
gtgcagctgg tgcagtccgg agcagaggtg aagaagccag gagcctctgt gaaggtgagc     120
tgcaaggcct ccggctacac attcaccaca tactatatgc actgggtgag gcaggcacct     180
ggacagggcc tggagtggat gggcatcatc aacccatctg gcggcagaac cagctacgcc     240
cagaagtttc agggccgggt gaccatgaca cgcgacacct ccacatctac cgtgtatatg     300
gagctgagct ccctgcgcag cgaggacaca gccgtgtact attgcgccag ggatagatac     360
cccgtgctgg tggccaccga ctatggcatg gacgtgtggg gccagggcac cacagtgaca     420
gtgtctagcg cctccaccaa gggacctagc gtgttccac tggcacccte ctctaagagc     480 acatccggcg gcaccgccgc cctgggatgt ctggtgaagg attatttccc agagcccgtg     540
accgtgtcct ggaactctgg cgccctgaca tctggcgtgc acacctttcc tgccgtgctg     600
cagagctccg gcctgtacag cctgtctagc gtggtgacag tgccatcctc tagcctgggc     660
acacagacct atatctgcaa cgtgaatcac aagccatcta taccaaggt ggacaagaag      720 gtggagccca gagctgtgga taagacacac acctgcccct cctgtcctgc accagagctg     780
ctgggcggcc catccgtgtt cctgtttcca cccaagccta ggacacact gatgatctcc      840 aggacaccag aggtgacctg cgtggtggtg acgtgtctc acgaggaccc cgaggtgaag      900
ttcaactggt acgtggatgg cgtggaggtg cacaatgcca agaccaagcc aagggaggag     960
cagtacaata gcacatatag agtggtgtcc gtgctgaccg tgctgcacca ggactggctg     1020
aacggcaagg agtataagtg caaggtgagc aataaggccc tgcccgcccc tatcgagaag     1080
acaatctcca aggcaagggg acagcctcgg gagccacagg tgtacaccct gcctccaagc     1140
cgcgacgagc tgacaaagaa ccaggtgtcc ctgacctgtc tggtgaaggg cttctatccc     1200
```

-continued

| | |
|---|---|
| tccgatatcg ccgtggagtg ggagtctaat ggccagcctg agaacaatta caagaccaca | 1260 |
| cccctgtgc tggacagcga tggctccttc tttctgtatt ctaagctgac agtggataag | 1320 |
| agcagatggc agcagggcaa cgtgttttct tgtagcgtga tgcacgaggc cctgcacaat | 1380 |
| cactacaccc agaagtccct gtctctgagc cctggcaag | 1419 |

<210> SEQ ID NO 117
<211> LENGTH: 109
<212> TYPE: PRT
<213> ORGANISM: Artificial Sequence
<220> FEATURE:
<223> OTHER INFORMATION: DMAb

<400> SEQUENCE: 117

Asp Ile Val Leu Thr Gln Thr Pro Ala Thr Leu Ser Leu Ser Pro Gly
1               5                   10                  15

Glu Arg Ala Thr Leu Ser Cys Gly Ala Ser Gln Ser Val Arg Asn Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ile Trp Pro Pro
                85                  90                  95

Gly Val Thr Phe Gly Gly Gly Thr Lys Leu Glu Ile Lys
            100                 105

<210> SEQ ID NO 118
<211> LENGTH: 705
<212> TYPE: DNA
<213> ORGANISM: Artificial Sequence
<220> FEATURE:
<223> OTHER INFORMATION: DMAb

<400> SEQUENCE: 118

| | |
|---|---|
| atggtgctgc agacccaggt gttcatcagc ctgctgctgt ggatctccgg agcatacggc | 60 |
| gacatcgtgc tgacccagac accagccacc ctgagcctgt cccctggaga gagggccaca | 120 |
| ctgtcctgcg gagcatctca gagcgtgcgc aactacctgg cctggtatca gcagaagcct | 180 |
| ggccaggccc caaggctgct gatctttgat gccagcaata gggccaccgg catcccagcc | 240 |
| agattctccg gctctggcag cggcacagac tttaccctga caatcagctc cctggagccc | 300 |
| gaggatttcg ccgtgtacta ttgccagcag agatccatct ggccccctgg agtgaccttc | 360 |
| ggcggcggca aaagctgga gatcaagacc gtggccgccc ctagcgtgtt catctttcca | 420 |
| cccagcgacg agcagctgaa gtccggcaca gcctctgtgg tgtgcctgct gaacaatttc | 480 |
| tacccacggg aggccaaggt gcagtggaag gtggataacg ccctgcagtc cggcaattct | 540 |
| caggagagcg tgaccgagca ggactccaag gattctacat atagcctgtc tagcacctg | 600 |
| acactgtcca aggccgacta cgagaagcac aaggtgtatg catgcgaggt gacccaccag | 660 |
| ggcctgtcct ctcccgtgac aaagtctttt aaccgcggcg agtgt | 705 |

<210> SEQ ID NO 119
<211> LENGTH: 123
<212> TYPE: PRT
<213> ORGANISM: Artificial Sequence
<220> FEATURE:
<223> OTHER INFORMATION: DMAb

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Thr Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Tyr Pro Thr Val Val Lys Tyr Phe Gly Met Asp Val
                100                 105                 110

Trp Gly Gln Gly Thr Thr Val Thr Val Ser Ser
            115                 120

<210> SEQ ID NO 120
<211> LENGTH: 1416
<212> TYPE: DNA
<213> ORGANISM: Artificial Sequence
<220> FEATURE:
<223> OTHER INFORMATION: DMAb

<400> SEQUENCE: 120
atggactgga cctggagaat cctgttcctg gtggcagcag caaccggaac acacgcacag      60
gtgcagctgg tgcagtccgg agcagaggtg aagaagccag gagcctccgt gaaggtgtct     120
tgcaaggcca gcggctacac cttcacaagc tactatatgc actgggtgag gcaggcacct     180
ggacagggcc tggagtggat gggcatcatc aacccatccg gcggctctac cacatacgcc     240
cagaagtttc agggccgggt gaccatgaca cgcgacacct ccacatctac cgtgtatatg     300
gagctgagct ccctgagatc cgaggacaca gccgtgtact attgcgccag ggatagatac     360
cccaccgtgg tgaagtattt cggaatggac gtgtggggac agggaaccac agtgacagtg     420
tctagcgcct ccaccaaggg acctagcgtg ttcccactgg cacctcctc taagagcaca     480 tccggcggca cgccgcccct gggatgtctg gtgaaggatt atttcccaga gccagtgacc     540
gtgagctgga actccggcgc cctgacatct ggcgtgcaca cctttcctgc cgtgctgcag     600
agctccggcc tgtacagcct gtctagcgtg gtgacagtgc catcctctag cctgggcaca     660
cagacctata tctgcaacgt gaatcacaag ccatctaata ccaaggtgga caagaaggtg     720
gagcccaaga gctgtgataa gacacacacc tgccctccct gtcctgcacc agagctgctg     780
ggcggcccaa gcgtgttcct gtttccaccc aagcctaagg acacactgat gatctcccgg     840
acaccagagg tgacctgcgt ggtggtggac gtgtctcacg aggaccccga ggtgaagttt     900
aactggtacg tggatggcgt ggaggtgcac aatgccaaga ccaagccaag ggaggagcag     960
tacaatagca catatagagt ggtgtccgtg ctgaccgtgc tgcaccagga ctggctgaac    1020
ggcaaggagt ataagtgcaa ggtgagcaat aaggccctgc ccgcccctat cgagaagaca    1080
atctccaagg caaagggaca gcctcgggag ccacaggtgt acaccctgcc tccaagccgc    1140
gacgagctga caaagaacca ggtgtccctg acctgtctgg tgaagggctt ctatccctcc    1200

```
gatatcgccg tggagtggga gtctaatggc cagcctgaga acaattacaa gaccacaccc   1260
cctgtgctgg actctgatgg cagcttcttt ctgtattcta agctgacagt ggataagagc   1320
cgctggcagc agggcaacgt gttttcttgt agcgtgatgc acgaggccct gcacaatcac   1380
tacacccaga gtccctgtc tctgagccct ggcaag                              1416
```

<210> SEQ ID NO 121
<211> LENGTH: 109
<212> TYPE: PRT
<213> ORGANISM: Artificial Sequence
<220> FEATURE:
<223> OTHER INFORMATION: DMAb

<400> SEQUENCE: 121

```
Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

Leu Ala Trp Tyr Gln Gln Thr Pro Gly Gln Ala Pro Arg Leu Leu Ile
        35                  40                  45

Phe Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ser Ile Thr Phe Gly His Gly Thr Lys Val Asp Ile Lys
            100                 105
```

<210> SEQ ID NO 122
<211> LENGTH: 702
<212> TYPE: DNA
<213> ORGANISM: Artificial Sequence
<220> FEATURE:
<223> OTHER INFORMATION: DMAb

<400> SEQUENCE: 122

```
atggtgctgc agacccaggt gttcatctct ctgctgctgt ggatcagcgg agcatacgga    60
gagactacgc tgacccagag cccagccaca ctgagcctgt ccctggaga gagggccacc   120 ctgtcctgca gagcatctca gagcgtgtcc ggctacctgg cctggtatca gcagacacct   180
ggccaggccc caaggctgct gatctttgac gcatccaaca gggcaaccgg catcccagca   240
cgcttctctg gcagcggctc cggcacagac tttaccctga caatcagctc cctggagccc   300
gaggatttcg ccgtgtacta ttgccagcag agaagcaatt ggccccttc catcaccttt   360 ggccacggca aaggtgga catcaagacc gtggccgccc cttccgtgtt catctttcca   420
ccctctgatg agcagctgaa gtccggcaca gcctctgtgg tgtgcctgct gaacaatttc   480
tacccacggg aggccaaggt gcagtggaag gtggacaacg ccctgcagtc tggcaatagc   540
caggagtccg tgaccgagca ggacaaggat tctacatata gcctgtctag caccctgaca   600
ctgtctaagg ccgattacga gaagcacaag gtgtatgcat gcgaggtgac ccaccagggc   660
ctgtcctctc ccgtgacaaa gagctttaac cgcggcgagt gt                      702
```

<210> SEQ ID NO 123
<211> LENGTH: 123
<212> TYPE: PRT
<213> ORGANISM: Artificial Sequence
<220> FEATURE:

<223> OTHER INFORMATION: DMAb

<400> SEQUENCE: 123

```
Gln Val Gln Leu Val Gln Ser Gly Ala Glu Val Lys Lys Pro Gly Ala
1               5                   10                  15

Ser Val Lys Leu Ser Cys Lys Val Ser Gly Phe Thr Phe Thr Thr Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Phe
    50                  55                  60

Gln Gly Gly Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Tyr Pro Thr Val Thr Lys Tyr Phe Gly Met Asp Val
            100                 105                 110

Trp Gly Gln Gly Thr Thr Val Thr Val Ser Ser
        115                 120
```

<210> SEQ ID NO 124
<211> LENGTH: 1416
<212> TYPE: DNA
<213> ORGANISM: Artificial Sequence
<220> FEATURE:
<223> OTHER INFORMATION: DMAb

<400> SEQUENCE: 124

```
atggactgga cctggagaat cctgttcctg gtggcagcag caaccggaac acacgcacag        60
gtgcagctgg tgcagtccgg agcagaggtg aagaagccag gagcctccgt gaagctgtct       120
tgcaaggtga gcggcttcac ctttaccaca tactatatcc actgggtgag acaggcacct       180
ggacagggcc tggagtggat gggcatcatc aacccatccg gcggctctac cacatacgcc       240
cagaagtttc agggcggcgt gaccctgaca cgggacacct ccacatctac cgtgtatatg       300
gagctgagct ccctgcgcag cgaggacacc gccgtgtact attgcgccag ggatagatac       360
cccacagtga ccaagtattt cggaatggac gtgtgggaca gggaaccac agtgacagtg        420
tctagcgcct ccaccaaggg acctagcgtg ttcccactgg cacccctcc taagagcaca        480
tccggcggca ccgccgccct gggatgtctg gtgaaggatt acttcccaga gccagtgacc       540
gtgagctgga ctccggcgc cctgacatct ggcgtgcaca ccttcctgc cgtgctgcag        600
agctccggcc tgtacagcct gtctagcgtg gtgacagtgc catcctctag cctgggcaca       660
cagacctata tctgcaacgt gaatcacaag ccatctaata ccaaggtgga caagaaggtg       720
gagcccaaga gctgtgataa gacacacacc tgccctccct gtcctgcacc agagctgctg       780
ggcggcccat ccgtgttcct gtttccaccc aagcctaagg acacactgat gatctcccgg       840
acaccagagg tgacctgcgt ggtggtggac gtgtctcacg aggaccccga ggtgaagttc       900
aactggtacg tggatggcgt ggaggtgcac aatgccaaga ccaagccacg ggaggagcag       960
tacaatagca catatcgcgt ggtgtccgtg ctgaccgtgc tgcaccagga ctggctgaac      1020
ggcaaggagt ataagtgcaa ggtgagcaat aaggccctgc cgcccctat cgagaagaca       1080
atctccaagg ccaagggcca gcctaggag ccacaggtgt acaccctgcc tccaagcaga      1140
gacgagctga caaagaacca ggtgtccctg acctgtctgg tgaagggctt ctatccctcc      1200
gatatcgccg tggagtggga gtctaatggc cagcctgaga caattacaa gaccacaccc       1260
```

```
cctgtgctgg actctgatgg cagcttcttt ctgtattcta agctgacagt ggataagagc    1320
cgctggcagc agggcaacgt gttttcttgt agcgtgatgc acgaggccct gcacaatcac    1380
tacacccaga agtccctgtc tctgagccct ggcaag                              1416
```

<210> SEQ ID NO 125
<211> LENGTH: 109
<212> TYPE: PRT
<213> ORGANISM: Artificial Sequence
<220> FEATURE:
<223> OTHER INFORMATION: DMAb

<400> SEQUENCE: 125

```
Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

Leu Ala Trp Tyr Gln His Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ser Ile Thr Phe Gly Gln Gly Thr Arg Leu Glu Ile Lys
            100                 105
```

<210> SEQ ID NO 126
<211> LENGTH: 702
<212> TYPE: DNA
<213> ORGANISM: Artificial Sequence
<220> FEATURE:
<223> OTHER INFORMATION: DMAb

<400> SEQUENCE: 126

```
atggtgctgc agacccaggt gttcatctct ctgctgctgt ggatcagcgg agcatacgga     60
gagactacgc tgacccagag cccagccaca ctgagcctgt cccctggaga gagggccaca    120
ctgtcctgca gagcctctca gagcgtgtcc ggctacctgg cctggtatca gcacaagcct    180
ggccaggccc caaggctgct gatctatgac gcatccaccc gggccacagg catcccagca    240
cgcttctctg gcagcggctc cggcaccgac tttaccctga caatcagctc cctggagccc    300
gaggatttcg ccgtgtacta ttgccagcag aggagcaact ggccccgttc catcaccttt    360
ggccagggca aagactgga gatcaagacc gtggccgccc cttccgtgtt catctttcca    420
ccctctgacg agcagctgaa gtccggcaca gcctctgtgg tgtgcctgct gaacaatttc    480
tacccacggg aggccaaggt gcagtggaag gtggataacg ccctgcagtc tggcaatagc    540
caggagtccg tgaccgagca ggacaaggat tctacatata gcctgtctag caccctgaca    600
ctgtctaagg ccgattacga gaagcacaag gtgtatgcat gcgaggtgac ccaccagggc    660
ctgtcctctc ccgtgacaaa gagctttaat cgcggcgagt gt                       702
```

<210> SEQ ID NO 127
<211> LENGTH: 115
<212> TYPE: PRT
<213> ORGANISM: Artificial Sequence
<220> FEATURE:
<223> OTHER INFORMATION: DMAb

<400> SEQUENCE: 127

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Pro Leu Ser Trp Val Arg Gln Ala Pro Gly Lys Gly Leu Glu Trp Val
        35                  40                  45

Ser Thr Ile Ser Gly Ser Gly Ser Thr Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Ser Ser Ala Trp Gly Gln Gly Thr Leu Val Thr
            100                 105                 110

Val Ser Ser
        115
```

<210> SEQ ID NO 128
<211> LENGTH: 1392
<212> TYPE: DNA
<213> ORGANISM: Artificial Sequence
<220> FEATURE:
<223> OTHER INFORMATION: DMAb

<400> SEQUENCE: 128

| | |
|---|---|
| atggactgga cctggagaat cctgttcctg gtggcagcag caaccggaac acacgcagag | 60 |
| gtgcagctgg tggagagcgg cggcggcctg gtgcagcccg gcggctctct gaggctgagc | 120 |
| tgcgcagcat ccggcttcac ctttccgat taccccctgt cttgggtgag acaggcacct | 180 |
| ggcaagggcc tggagtgggt gagcaccatc tccggctctg cggctccac atactctgcc | 240 |
| gacagcgtga aggcaggtt caccatctct agagataaca gcaagaatac actgtatctg | 300 |
| cagatgaact ccctgagggc agaggacacc gccgtgtact attgcgccaa gggacgcaca | 360 |
| agctccgcct ggggacaggg caccctggtg acagtgtcta gcgccagcac caagggcccc | 420 |
| tccgtgtttc cactggcacc ctcctctaag agcacctccg gcggcacagc cgccctgggc | 480 |
| tgtctggtga aggattattt cccagagccc gtgacagtgt cctggaactc tggcgccctg | 540 |
| accagcggag tgcacacatt cctgccgtg ctgcagagct ccggcctgta ctccctgtct | 600 |
| agcgtggtga ccgtgccatc ctctagcctg ggcacccaga catatatctg caacgtgaat | 660 |
| cacaagcctt ccaatacaaa ggtggacaag aaggtggagc caaagtcttg tgataagacc | 720 |
| cacacatgcc ctccctgtcc tgcaccagag ctgctgggcg gcccaagcgt gttcctgttt | 780 |
| ccacccaagc caaggacac cctgatgatc agccggaccc cagaggtgac atgcgtggtg | 840 |
| gtggacgtgt cccacgagga ccccgaggtg aagtttaact ggtacgtgga tggcgtggag | 900 |
| gtgcacaatg ccaagaccaa gccacgggag gagcagtaca ttctaccta cgcgtggtg | 960 |
| agcgtgctga cagtgctgca ccaggactgg ctgaacggca aggagtataa gtgcaaggtg | 1020 |
| tctaataagg ccctgcccgc ccctatcgag aagaccatct ccaaggccaa ggccagcct | 1080 |
| agggagccac aggtgtacac actgcctcca tctagagacg agctgaccaa gaaccaggtg | 1140 |
| agcctgacat gtctggtgaa gggcttctat cccagcgata tcgccgtgga gtgggagtcc | 1200 |
| aatggccagc ctgagaacaa ttacaagacc acacccctg tgctggacag cgatggctcc | 1260 |

```
ttctttctgt attccaagct gaccgtggat aagtctcgct ggcagcaggg caacgtgttt    1320
tcttgtagcg tgatgcacga ggccctgcac aatcactaca cacagaagtc cctgtctctg    1380
agccctggca ag                                                         1392
```

<210> SEQ ID NO 129
<211> LENGTH: 108
<212> TYPE: PRT
<213> ORGANISM: Artificial Sequence
<220> FEATURE:
<223> OTHER INFORMATION: DMAb

<400> SEQUENCE: 129

```
Asp Ile Val Met Thr Gln Thr Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Phe Val Ala Ser Ile Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Thr Ser Pro
                85                  90                  95

Trp Thr Phe Gly Gln Gly Thr Lys Val Glu Ile Lys
            100                 105
```

<210> SEQ ID NO 130
<211> LENGTH: 699
<212> TYPE: DNA
<213> ORGANISM: Artificial Sequence
<220> FEATURE:
<223> OTHER INFORMATION: DMAb

<400> SEQUENCE: 130

```
atggtgctgc agacccaggt gttcatcagc ctgctgctgt ggatctccgg cgcctacggc     60
gacatcgtga tgacccagac acctggcacc ctgtccctgt ctccaggcga gagggccaca    120
ctgtcttgca gagccagcca gtccgtgagc tcctctttcc tggcctggta tcagcagaag    180
ccaggacagg cccccaggct gctgatcttt gtggcaagca tcagggcagc aggcatccct    240
gaccgcttct ctggcagcgg ctccggaacc gacttcaccc tgacaatctc cagactggag    300
cccgaggatt tcgccgtgta ctattgccac cagtacggca cctctccttg gacatttggc    360
cagggcacca aggtggagat caagacagtg gccgccccaa gcgtgttcat ctttcccccct   420 agcgacgagc agctgaagtc cggcacagcc tctgtggtgt gcctgctgaa caatttctac    480
ccccgggagg ccaaggtgca gtggaaggtg ataacgccc tgcagtctgg caatagccag     540
gagtccgtga ccgagcagga caaggattct acatatagcc tgagctccac cctgacactg    600
agcaaggccg actacgagaa gcacaaggtg tatgcctgcg aggtgaccca ccagggcctg    660
tctagccccg tgacaaagtc ctttaaccgc ggcgagtgt                            699
```

<210> SEQ ID NO 131
<211> LENGTH: 129
<212> TYPE: PRT
<213> ORGANISM: Artificial Sequence
<220> FEATURE:
<223> OTHER INFORMATION: DMAb

<400> SEQUENCE: 131

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg Ser Phe
            20                  25                  30
Glu Met Asn Trp Val Arg Arg Ala Pro Gly Lys Gly Leu Glu Trp Val
        35                  40                  45
Ser Tyr Ile Ser Ser Ser Gly Ser Ser Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Thr Leu Gly Tyr Cys Ser Gly Gly Ser Cys Tyr Ser Val Ser
            100                 105                 110
His Asp Ala Phe Asp Ile Trp Gly Gln Gly Thr Thr Val Thr Val Ser
        115                 120                 125
Ser

<210> SEQ ID NO 132
<211> LENGTH: 1434
<212> TYPE: DNA
<213> ORGANISM: Artificial Sequence
<220> FEATURE:
<223> OTHER INFORMATION: DMAb

<400> SEQUENCE: 132

```
atggactgga cctggagaat cctgttcctg gtggcagcag caaccggaac acacgcagag    60
gtgcagctgg tggagagcgg cggcggcctg gtgcagcctg gcggctccct gaggctgtct   120
tgcgcagcaa gcggcttcac ctttcgcagc ttcgagatga actgggtgag gagagcacca   180
ggcaagggcc tggagtgggt gtcttacatc agctcctctg gcagctccat ctactatgcc   240
gacagcgtga agggccggtt taccatctct cgcgataacg ccaagaatag cctgtatctg   300
cagatgaatt ccctgagggc cgaggacacc gccgtgtact attgcgccag aacactgggc   360
tactgctccg gcggctcttg ttattccgtg tctcacgacg ccttcgatat ctggggccag   420
ggcaccacag tgaccgtgtc tagcgcctcc acaaagggac caagcgtgtt cccactggca   480
ccctcctcta agagcacctc cggcggcaca gccgccctgg gctgtctggt gaaggattac   540
ttcccagagc cagtgaccgt gagctggaac tccggcgccc tgacctccgg agtgcacaca   600
tttccagccg tgctgcagag ctccggcctg tacagcctgt ctagcgtggt gaccgtgccc   660
tcctctagcc tgggcaccca gacatatatc tgcaacgtga atcacaagcc atctaataca   720
aaggtggaca agaaggtgga gcccaagagc tgtgataaga cccacacatg ccctccctgt   780
cctgcaccag agctgctggg cggcccatcc gtgttcctgt tccacccaa gcctaaggac    840
accctgatga tctccaggac ccccgaggtg acatgcgtgg tggtggacgt gtctcacgag   900
gaccccgagg tgaagtttaa ctggtacgtg gatggcgtgg aggtgcacaa tgccaagaca   960
aagcccaggg aggagcagta caacagcacc tatagagtgg tgtccgtgct gacagtgctg  1020
caccaggact ggctgaacgg caaggagtat aagtgcaagg tgagcaataa ggccctgccc  1080
gcccctatcg agaagaccat ctccaaggca aagggacagc ctcgggagcc acaggtgtac  1140
acactgcctc caagccgcga cgagctgacc aagaaccagg tgtccctgac atgtctggtg  1200
aagggcttct atccttccga tatcgccgtg gagtgggagt ctaatgggca gccagagaac  1260
```

```
aattacaaga ccacacccc tgtgctggac tctgatggca gcttctttct gtattctaag    1320
ctgaccgtgg ataagagcag atggcagcag ggcaacgtgt tttcttgtag cgtgatgcac    1380
gaggccctgc acaatcacta cacacagaag tccctgtctc tgagccctgg caag          1434
```

<210> SEQ ID NO 133
<211> LENGTH: 107
<212> TYPE: PRT
<213> ORGANISM: Artificial Sequence
<220> FEATURE:
<223> OTHER INFORMATION: DMAb

<400> SEQUENCE: 133

```
Glu Ile Val Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Thr Trp
             20                  25                  30

Leu Ala Trp Tyr Gln Gln Lys Pro Gly Lys Ala Pro Lys Leu Leu Ile
         35                  40                  45

Phe Asp Ala Ser Arg Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ser Tyr Pro Trp
                 85                  90                  95

Thr Phe Gly Gln Gly Thr Lys Val Glu Ile Lys
            100                 105
```

<210> SEQ ID NO 134
<211> LENGTH: 699
<212> TYPE: DNA
<213> ORGANISM: Artificial Sequence
<220> FEATURE:
<223> OTHER INFORMATION: DMAb

<400> SEQUENCE: 134

```
atggtgctgc agacccaggt gttcatctct ctgctgctgt ggatcagcgg cgcctacggc     60
gagatcgtga tgacccagag cccatccaca ctgtctgcca gcgtgggcga tagggtgacc    120
atcacatgca gagcctccca gtctatcggc acctggctgg cctggtatca gcagaagcca    180
ggcaaggccc ccaagctgct gatctttgac gccagccggc tggagtccgg agtgccctct    240
cgcttcagcg gctccggctc tggaaccgag tttaccctga caatcagctc cctgcagcct    300
gacgatttcg ccacatacta ttgccagcag tacgacagct atccatggac ctttggccag    360
ggcacaaagg tggagatcaa gaccgtggcc gcccctccg tgttcatctt cccccttct     420 gatgagcagc tgaagagcgg cacagcctcc gtggtgtgcc tgctgaacaa tttctaccct    480
agggaggcca aggtgcagtg gaaggtggac aacgccctgc agagcggcaa ttcccaggag    540
tctgtgaccg agcaggacag caaggattcc acatattctc tgtctagcac cctgacactg    600
agcaaggccg attacgagaa gcacaaggtg tatgcatgcg aggtgaccca ccagggcctg    660
tcctctcccg tgacaaagtc ctttaaccgg ggcgagtgt                            699
```

<210> SEQ ID NO 135
<211> LENGTH: 122
<212> TYPE: PRT
<213> ORGANISM: Artificial Sequence
<220> FEATURE:
<223> OTHER INFORMATION: DMAb

<400> SEQUENCE: 135

```
Gln Val Gln Leu Val Gln Ser Gly Val Thr Leu Val Gln Pro Gly Gly
1               5                   10                  15

Ser Leu Arg Val Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Leu Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Arg Val Trp Ala Ala Gly Tyr His Phe Asp Tyr Trp
            100                 105                 110

Gly Gln Gly Ala Leu Val Thr Val Ser Ser
        115                 120
```

<210> SEQ ID NO 136
<211> LENGTH: 1413
<212> TYPE: DNA
<213> ORGANISM: Artificial Sequence
<220> FEATURE:
<223> OTHER INFORMATION: DMAb

<400> SEQUENCE: 136

```
atggactgga cctggagaat cctgttcctg gtggcagcag caaccggaac acacgcacag      60
gtgcagctgg tgcagtccgg agtgaccctg gtgcagcctg gcggctctct gagggtgagc     120
tgcgcagcat ccggcttcac cttcagcagc tacgccatga gctgggtgag acaggcacca     180
ggcaagggcc tggagtgggt gtctgccatc agcggcctgg gcggcagcac ctactatgca     240
gactccgtga agggcaggtt taccatctct agagataaca gcaagaatac actgtatctg     300
cagatgaact ccctgcgggc cgaggacaca gccgtgtact attgcgcaaa ggatcaccgc     360
gtgtgggcag caggatacca cttcgactat tggggacagg gcgccctggt gaccgtgtct     420
agcgcctcca caagggacc aagcgtgttc ccactggcac ctcctctaa gtccacctct     480
ggcggcacag ccgccctggg ctgtctggtg aaggattact ccagagagcc cgtgaccgtg     540
tcctggaact ctggcgccct gacctccgga gtgcacacat tccagccgt gctgcagagc     600
tccggcctgt acagcctgtc tagcgtggtg accgtgccct cctctagcct gggcacccag     660
acatatatct gcaacgtgaa tcacaagcca tccaatacaa aggtggacaa gaaggtggag     720
cccaagtctt gtgataagac ccacacatgc cctccctgtc ctgcaccaga gctgctgggc     780
ggcccaagcg tgttcctgtt ccacccaag cctaaggaca ccctgatgat cagccggacc     840
ccagaggtga catgcgtggt ggtggacgtg tcccacgagg accccgaggt gaagttcaac     900
tggtacgtgg atggcgtgga ggtgcacaat gccaagacca gccccggga ggagcagtac     960
aattctacct atcgcgtggt gagcgtgctg acagtgctgc accaggactg gctgaacggc    1020
aaggagtata agtgcaaggt gtctaataag gccctgcccg cccctatcga aagaccatc    1080
agcaaggcca agggccagcc tagggagcca caggtgtaca cactgcctcc atctagagac    1140
gagctgacca gaaccaggt gagcctgaca tgtctggtga agggcttcta tcctagcgat    1200
atcgccgtgg agtgggagtc caatggccag ccagagaaca attacaagac cacacccct    1260
```

```
gtgctggaca gcgatggctc cttctttctg tattccaagc tgaccgtgga taagtctcgc    1320
tggcagcagg gcaacgtgtt tagctgttcc gtgatgcacg aggccctgca caatcactac    1380
acacagaagt ctctgagcct gtcccctggc aag                                 1413
```

<210> SEQ ID NO 137
<211> LENGTH: 106
<212> TYPE: PRT
<213> ORGANISM: Artificial Sequence
<220> FEATURE:
<223> OTHER INFORMATION: DMAb

<400> SEQUENCE: 137

```
Asp Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Glu Ala Pro Lys Leu Leu Ile
        35                  40                  45

Ser Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Ser Pro Thr
                85                  90                  95

Phe Gly Gly Gly Thr Lys Val Glu Ile Lys
            100                 105
```

<210> SEQ ID NO 138
<211> LENGTH: 693
<212> TYPE: DNA
<213> ORGANISM: Artificial Sequence
<220> FEATURE:
<223> OTHER INFORMATION: DMAb

<400> SEQUENCE: 138

```
atggtgctgc agacccaggt gttcatcagc ctgctgctgt ggatctccgg agcatacggc     60
gacatcgtgc tgacccagag cccatccaca ctgtctgcca gcgtgggcga tagggtgacc    120
atcacatgca gagcctccca gtctatcagc tcctggctgg cctggtatca gcagaagcca    180
ggcgaggccc ccaagctgct gatcagcgac gcctctagcc tggagtctgg agtgcccagc    240
aggttcagcg gctccggctc tggaaccgag tttacccctg caatctcctc tctgcagcct    300
gacgatttcg ccacatacta ttgccagcag tactatagct ccccaccctt cggcggcggc    360
acaaaggtgg agatcaagac cgtggccgcc ccagcgtgt tcatctttcc cccttccgac    420
gagcagctga gtccggcac agcctctgtg gtgtgcctgc tgaacaattt ctaccctcgg    480
gaggccaagg tgcagtggaa ggtggataac gccctgcaga gcggcaattc ccaggagtct    540
gtgaccgagc aggacaagga tagcacatat tccctgtcta gcaccctgac actgagcaag    600
gccgattacg agaagcacaa ggtgtatgca tgcgaggtga cccaccaggg cctgtcctct    660
cccgtgacaa agtcctttaa ccgcggcgag tgt                                 693
```

<210> SEQ ID NO 139
<211> LENGTH: 119
<212> TYPE: PRT
<213> ORGANISM: Artificial Sequence
<220> FEATURE:
<223> OTHER INFORMATION: DMAb

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Tyr Thr Lys Tyr Pro Arg Lys Phe
    50                  55                  60

Gln Gly Arg Val Thr Met Thr Thr Asp Thr Ser Thr Ser Thr Ala Tyr
65                  70                  75                  80

Met Asp Leu Arg Ser Leu Arg Ser Asp Thr Ala Val Tyr Tyr Cys
                85                  90                  95

Ala Arg Asp Leu Thr Pro Arg Tyr Gly Leu Asp Val Trp Gly Gln Gly
            100                 105                 110

Thr Thr Val Thr Val Ser Ser
        115

<210> SEQ ID NO 140
<211> LENGTH: 1404
<212> TYPE: DNA
<213> ORGANISM: Artificial Sequence
<220> FEATURE:
<223> OTHER INFORMATION: DMAb

<400> SEQUENCE: 140

```
atggactgga cctggagaat cctgttcctg gtggcagcag caaccggaac acacgcacag      60
gtgcagctgg tgcagtccgg agcagaggtg aagaagccag gagcctctgt gaaggtgagc     120
tgcaaggcct ccggctatac cttccggaac tacggaatct cctgggtgcg ccaggcacct     180
ggacagggcc tggagtggat gggctggatc agcgcctaca atggctatac aaagtaccca     240
cggaagtttc agggccgcgt gaccatgacc acagacacct ctacaagcac cgcctatatg     300
gatctgagga gcctgagaag cgacgataca gccgtgtact attgcgccag ggacctgacc     360
cccagatacg gcctggacgt gtggggacag ggaaccacag tgacagtgag ctccgcctct     420
accaagggcc tagcgtgtt tccactggcc cctctagca agtccacatc tggcggcacc     480
gccgccctgg gatgtctggt gaaggattat ttcccagagc ccgtgaccgt gtcctggaac     540
tctggcgccc tgacatccgg cgtgcacacc tttccagccg tgctgcagtc ctctggcctg     600
tatagcctga gctccgtggt gacagtgccc tctagctccc tgggcacaca gacctacatc     660
tgcaacgtga atcacaagcc aagcaatacc aaggtggaca gaaggtgga gcccaagtcc     720
tgtgataaga cacacacctg ccctccctgt cctgcaccag agctgctggg cggcccaagc     780
gtgttcctgt tccacccaa gcctaaggac acactgatga tctctaggac acccgaggtg     840
acctgcgtgg tggtggacgt gagccacgag accccgagg tgaagttcaa ctggtacgtg     900
gatggcgtgg aggtgcacaa tgccaagacc aagccaaggg aggagcagta taactccaca     960
tacagagtgg tgtctgtgct gaccgtgctg caccaggact ggctgaacgg caaggagtac    1020
aagtgcaagg tgtccaataa ggccctgccc gccctatcg agaagacaat ctctaaggca    1080
aagggacagc ctcgggagcc acaggtgtat accctgcctc catcccgcga cgagctgaca    1140
aagaaccagg tgtctctgac ctgtctggtg aagggcttct acccttctga tatcgccgtg    1200
gagtgggaga gcaatggcca gccagagaac aattataaga ccacacccccc tgtgctggac    1260
agcgatggct ccttctttct gtacagcaag ctgacagtgg ataagtccag atggcagcag    1320
```

```
ggcaacgtgt ttagctgttc cgtgatgcac gaggccctgc acaatcacta cacccagaag    1380
tctctgagcc tgtcccctgg caag                                           1404

<210> SEQ ID NO 141
<211> LENGTH: 112
<212> TYPE: PRT
<213> ORGANISM: Artificial Sequence
<220> FEATURE:
<223> OTHER INFORMATION: DMAb

<400> SEQUENCE: 141

Asp Ile Val Leu Thr Gln Ser Pro Leu Ser Leu Pro Val Thr Pro Gly
1               5                  10                  15

Glu Pro Ala Ser Ile Ser Cys Arg Ser Gln Ser Leu Leu His Ser
            20                  25                  30

Asn Gly Tyr Asn Tyr Leu Asp Trp Tyr Val Gln Lys Pro Gly Gln Ser
        35                  40                  45

Pro Gln Val Leu Ile Tyr Leu Gly Ser Asp Arg Ala Ser Gly Val Pro
    50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Ala
                85                  90                  95

Leu Gln Ser Pro Trp Thr Phe Gly Gln Gly Thr Lys Val Glu Ile Lys
            100                 105                 110

<210> SEQ ID NO 142
<211> LENGTH: 711
<212> TYPE: DNA
<213> ORGANISM: Artificial Sequence
<220> FEATURE:
<223> OTHER INFORMATION: DMAb

<400> SEQUENCE: 142
atggtgctgc agacccaggt gttcatctct ctgctgctgt ggatcagcgg agcatacggc     60
gacatcgtgc tgacccagtc tcccctgagc ctgccagtga caccaggaga gcctgcaagc    120
atctcctgcc ggagctccca gagcctgctg cactccaacg gctacaatta tctggattgg    180
tacgtgcaga agccaggcca gagccccag gtgctgatct atctgggctc tgacagggca    240
agcggagtgc ctgatagatt ctctggcagc ggctccggca cagactttc cctgaagatc    300 tctcgcgtgg aggccgagga tgtgggcgtg tactattgca tgcaggccct gcagtcccct    360
tggaccttcg gccagggcac aaaggtggag atcaagaccg tggccgcccc atccgtgttc    420
atctttcccc cttctgacga gcagctgaag agcggcacag cctccgtggt gtgcctgctg    480
aacaacttct acccaaggga ggccaaggtg cagtggaagg tggataacgc cctgcagtcc    540
ggcaattctc aggagagcgt gaccgagcag gacaaggatt ccacatattc tctgtctagc    600
accctgacac tgagcaaggc cgactacgag aagcacaagg tgtatgcatg cgaggtgacc    660
caccagggcc tgtcctctcc cgtgacaaag tcctttaacc ggggcgagtg t             711

<210> SEQ ID NO 143
<211> LENGTH: 122
<212> TYPE: PRT
<213> ORGANISM: Artificial Sequence
<220> FEATURE:
<223> OTHER INFORMATION: DMAb

<400> SEQUENCE: 143
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Glu Ile Ser Gly Leu Gly Gly Ser Thr Tyr Tyr Ala Asp Ser Ala
50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Arg Val Trp Ala Pro Gly Tyr Tyr Phe Asp His Trp
            100                 105                 110

Gly Gln Gly Thr Leu Val Thr Val Ser Ser
            115                 120

<210> SEQ ID NO 144
<211> LENGTH: 1413
<212> TYPE: DNA
<213> ORGANISM: Artificial Sequence
<220> FEATURE:
<223> OTHER INFORMATION: DMAb

<400> SEQUENCE: 144

```
atggactgga cctggagaat cctgttcctg gtggcagcag caaccggaac acacgcagag      60
gtgcagctgg tggagagcgg cggcggcctg gtgcagcccg gcggctccct gaggctgtct     120
tgcgccgcca gcggcttcac ctttagctcc tacgccatga gctgggtgag acaggcacct     180
ggcaagggcc tggagtgggt gtccgagatc tctggcctgg gcggcagcac atactatgcc     240
gactccgcca agggcaggtt taccatctcc agagataact ccaagtctac actgtatctg     300
cagatgaatt ctctgcgggc cgaggacacc gccgtgtact attgcgcaaa ggatcaccgc     360
gtgtgggcac ctggctacta tttcgaccac tggggacagg gcaccctggt gacagtgtct     420
agcgcctcca caagggacc aagcgtgttc ccactggcac cctcctctaa gagcacctcc     480
ggcggcacag ccgccctggg ctgtctggtg aaggattact cccagagcc agtgaccgtg     540 agctggaact ccgcgccct gacctccgga gtgcacacat tccagccgt gctgcagagc     600 tccggcctgt acagcctgtc tagcgtggtg accgtgccct cctctagcct gggcacccag     660
acatatatct gcaacgtgaa tcacaagcca tccaatacaa aggtggacaa gaaggtggag     720
cccaagtctt gtgataagac ccacacatgc cctccctgtc ctgcaccaga gctgctgggc     780
ggcccaagcg tgttcctgtt ccacccaag cctaaggaca ccctgatgat cagccggacc     840
ccagaggtga catgcgtggt ggtggacgtg tcccacgagg accccgaggt gaagttcaac     900
tggtacgtgg atggcgtgga ggtgcacaat gccaagacca gccacgggga ggagcagtac     960
aactctacct atcgcgtggt gagcgtgctg acagtgctgc accaggactg gctgaacggc    1020
aaggagtata agtgcaaggt gtctaataag gccctgcccg ccctatcga agaccatc      1080 agcaaggcca agggccagcc tagggagcca caggtgtaca cactgcctcc atctagagac    1140
gagctgacca gaaccaggt gagcctgaca tgtctggtga agggcttcta tcctagcgat    1200
atcgccgtgg agtgggagtc caatggccag ccagagaaca attacaagac cacacccct    1260 gtgctggact ctgatggcag cttctttctg tattccaagc tgaccgtgga taagtctcgc    1320
```

```
tggcagcagg gcaacgtgtt ttcttgtagc gtgatgcacg aggccctgca caatcactac    1380
acacagaagt ccctgtctct gagccctggc aag                                 1413

<210> SEQ ID NO 145
<211> LENGTH: 106
<212> TYPE: PRT
<213> ORGANISM: Artificial Sequence
<220> FEATURE:
<223> OTHER INFORMATION: DMAb

<400> SEQUENCE: 145

Asp Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asn Arg Ser Pro Thr
                85                  90                  95

Phe Gly Gly Gly Thr Lys Val Glu Ile Lys
            100                 105

<210> SEQ ID NO 146
<211> LENGTH: 696
<212> TYPE: DNA
<213> ORGANISM: Artificial Sequence
<220> FEATURE:
<223> OTHER INFORMATION: DMAb

<400> SEQUENCE: 146
atggtgctgc agacccaggt gttcatctct ctgctgctgt ggatcagcgg agcatacggc      60
gacatcgtgc tgacccagtc cccatctaca ctgagcgcct ccgtgggcga tagggtgacc    120
atcacatgca gagcctctca gagcatcagc tcctggctgg cctggtacca gcagaagcca    180
ggcaaggccc ccaagctgct gatctatgac gcctctagcc tggagtccgg agtgccctct    240
cggttctccg gctctggcag cggaaccgag tttaccctga caatctcctc tctgcagcct    300
gacgatttcg ccacatactt ttgccagcag tataacagga gccccacctt cggcggcggc    360
acaaaggtgg agatcaagac cgtggccgcc ccctccgtgt tcatctttcc cccttctgac    420
gagcagctga gagcggcac agcctccgtg gtgtgcctgc tgaacaactt ctaccctagg    480
gaggccaagg tgcagtggaa ggtggataac gccctgcagt ccggcaattc tcaggagagc    540
gtgaccgagc aggactccaa ggattctaca tatagcctga gctccaccct gacactgtcc    600
aaggccgatt acgagaagca caaggtgtat gcctgcgagg tgacccacca gggcctgtct    660
agccccgtga caaagagctt taatcggggc gagtgt                              696

<210> SEQ ID NO 147
<211> LENGTH: 123
<212> TYPE: PRT
<213> ORGANISM: Artificial Sequence
<220> FEATURE:
<223> OTHER INFORMATION: DMAb

<400> SEQUENCE: 147
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Gly Met Asn Trp Val Arg Gln Ala Pro Gly Lys Gly Leu Glu Trp Val
        35                  40                  45

Ser Ser Ile Ser Thr Arg Ser Asn Tyr Ile Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Asp Ile Leu Ile Val Pro Ala Ala Phe Asp Tyr
            100                 105                 110

Trp Gly Gln Gly Thr Leu Val Thr Val Ser Ser
            115                 120

<210> SEQ ID NO 148
<211> LENGTH: 1416
<212> TYPE: DNA
<213> ORGANISM: Artificial Sequence
<220> FEATURE:
<223> OTHER INFORMATION: DMAb

<400> SEQUENCE: 148

```
atggactgga cctggagaat cctgttcctg gtggcagcag caaccggaac acacgcagag     60
gtgcagctgg tggagagcgg cggcggcctg gtgaagcccg gcggctccct gaggctgtct    120
tgcgcagcaa gcggcttcac ctttagctcc ttcggcatga actgggtgag gcaggcacct    180
ggcaagggcc tggagtgggt gtctagcatc tccaccagat ctaattacat ctactatgcc    240
gactccgtga agggcaggtt tacaatctct agagataacg ccaagaatag cctgtatctg    300
cagatgaact ccctgagggc cgaggacacc gccgtgtact attgcgccag ggacctgggc    360
gatatcctga tcgtgcctgc cgccttcgat tactggggcc agggcaccct ggtgacagtg    420
tcctctgcct ccacaaaggg accaagcgtg ttcccactgg cacccagctc aagagcacc    480
tccggcggca gccgcccct gggctgtctg gtgaaggatt atttcccaga gccagtgacc    540
gtgagctgga actccggcgc cctgaccagc ggagtgcaca catttccagc cgtgctgcag    600
tctagcggcc tgtactccct gtcctctgtg gtgaccgtgc ccagctcctc tctgggcacc    660
cagacatata tctgcaacgt gaatcacaag ccatctaata caaggtgga caagaaggtg    720
gagcccaaga gctgtgataa gacccacaca tgccctccct gtcctgcacc agagctgctg    780
ggcggcccaa gcgtgttcct gtttccaccc aagcctaagg acacactgat gatctccagg    840
accccgagg tgacatgcgt ggtggtggac gtgtctcacg aggaccccga ggtgaagttt    900
aactggtacg tggatggcgt ggaggtgcac aatgccaaga ccaagccacg ggaggagcag    960
tacaacagca cctatcgcgt ggtgtccgtg ctgacagtgc tgcaccagga ctggctgaac   1020
ggcaaggagt ataagtgcaa ggtgagcaat aaggccctgc cgcccctat cgagaagacc   1080
atctccaagg caaagggaca gcctcgggag ccacaggtgt acacactgcc tccaagccgc   1140
gacgagctga ccaagaacca ggtgtccctg acatgtctgg tgaagggctt ctatccttcc   1200
gatatcgccg tggagtggga gtctaatggc cagccagaga caattacaa gaccacaccc   1260
cctgtgctgg actctgatgg cagcttcttt ctgtattcta agctgaccgt ggataagagc   1320
agatggcagc agggcaacgt gttttcttgt agcgtgatgc acgaggccct gcacaatcac   1380
```
tacacacaga agtccctgtc tctgagccct ggcaag                               1416

<210> SEQ ID NO 149
<211> LENGTH: 111
<212> TYPE: PRT
<213> ORGANISM: Artificial Sequence
<220> FEATURE:
<223> OTHER INFORMATION: DMAb

<400> SEQUENCE: 149

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Thr Val Asn Trp Tyr Gln Gln Leu Pro Gly Thr Ala Pro Lys Leu Leu
        35                  40                  45

Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Pro Val Phe Gly Thr Gly Thr Lys Leu Thr Val Leu Ser
            100                 105                 110

<210> SEQ ID NO 150
<211> LENGTH: 696
<212> TYPE: DNA
<213> ORGANISM: Artificial Sequence
<220> FEATURE:
<223> OTHER INFORMATION: DMAb

<400> SEQUENCE: 150
atggcctgga cccctctgct gctgccactg ctgacattct gcaccgtgtc cgaggcatct     60
cagcccgtgc tgacacagcc ccctagcgcc tccggaaccc ctggacagcg ggtgacaatc    120
tcttgtagcg gcagctcctc taacatcggc cgcaacaccg tgaattggta ccagcagctg    180
cccggcacag cccctaagct gctgatctat tccaattctc agaggccaag cggagtgcca    240
gacaggttca gcggctccaa gtctggcacc agcgcctccc tggcaatctc cggcctgcag    300
tctgaggacg aggccgatta ctattgcgcc acctgggacg attccctgaa cggcccagtg    360
ttcggcacag gaaccaagct gaccgtgctg agcgccccat ccgtgacact gtttccaccc    420
agctccgagg agctgcaggc caataaggcc accctggtgt gcctgatcag cgacttctac    480
ccaggagcag tgacagtggc atggaaggcc gattctagcc ctgtgaaggc cggcgtggag    540
acaacaaccc catctaagca gagcaacaat aagtacgccg cctcctctta tctgagcctg    600
acccctgagc agtggaagtc ccacaggtct tatagctgcc aggtgacaca cgagggctct    660
acagtggaga agaccgtggc cccaacagag tgttcc                              696

<210> SEQ ID NO 151
<211> LENGTH: 119
<212> TYPE: PRT
<213> ORGANISM: Artificial Sequence
<220> FEATURE:
<223> OTHER INFORMATION: DMAb

<400> SEQUENCE: 151

Gln Val Gln Leu Val Gln Ser Gly Ala Glu Val Lys Lys Pro Gly Ala

```
  1               5                  10                 15
Ser Val Lys Val Ser Cys Lys Ala Ser Gly Tyr Thr Phe Thr Thr Tyr
             20                 25                 30
Gly Phe Ser Trp Val Arg Gln Ala Pro Gly Gln Gly Leu Glu Trp Leu
             35                 40                 45
Gly Trp Ile Ser Ala Tyr Asn Gly Asn Thr Asn Tyr Gly Gln Lys Val
         50                 55                 60
Gln Gly Arg Val Thr Met Thr Thr Asp Lys Ser Thr Ser Thr Ala Tyr
65                 70                 75                 80
Met Glu Leu Arg Ser Leu Arg Ser Asp Asp Thr Ala Val Tyr Tyr Cys
             85                 90                 95
Ala Arg Asp Leu Thr Pro Arg Tyr Gly Met Asp Val Trp Gly Gln Gly
            100                105                110
Thr Thr Val Thr Val Ser Ser
            115
```

<210> SEQ ID NO 152
<211> LENGTH: 1404
<212> TYPE: DNA
<213> ORGANISM: Artificial Sequence
<220> FEATURE:
<223> OTHER INFORMATION: DMAb

<400> SEQUENCE: 152

| | | | | | |
|---|---|---|---|---|---|
| atggactgga | cctggagaat | cctgttcctg | gtggcagcag | caaccggaac | acacgcacag | 60 |
| gtgcagctgg | tgcagtccgg | agcagaggtg | aagaagccag | agcctctgt | gaaggtgagc | 120 |
| tgcaaggcct | ccggctacac | cttcaccaca | tatggctttt | cctgggtgag | gcaggcacct | 180 |
| ggacagggcc | tggagtggct | gggatggatc | agcgcctaca | acggcaatac | caactatggc | 240 |
| cagaaggtgc | agggcagagt | gacaatgacc | acagacaagt | ctaccagcac | agcctacatg | 300 |
| gagctgagga | gcctgagaag | cgacgatacc | gccgtgtact | attgcgcccg | ggacctgaca | 360 |
| cctcgctatg | gcatggacgt | gtggggccag | ggcaccacag | tgaccgtgag | ctccgcctct | 420 |
| acaaagggcc | caagcgtgtt | tccactggcc | ccctctagca | agtccacctc | tggcggcaca | 480 |
| gccgccctgg | gctgtctggt | gaaggattac | ttcccagagc | ccgtgaccgt | gtcctggaat | 540 |
| tctggcgccc | tgaccteegg | cgtgcacaca | tttccagccg | tgctgcagtc | ctctggcctg | 600 |
| tacagcctga | gctccgtggt | gaccgtgccc | tctagctccc | tgggcaccca | gacatatatc | 660 |
| tgcaatgtga | accacaagcc | aagcaacaca | aaggtggaca | agaaggtgga | gcccaagtcc | 720 |
| tgtgataaga | cccacacatg | ccctccctgt | cctgcaccag | agctgctggg | cggcccaagc | 780 |
| gtgttcctgt | tccacccaa | gcctaaggac | accctgatga | tctctcggac | ccccgaggtg | 840 |
| acatgcgtgt | ggtggacgt | gagccacgag | gaccccgagg | tgaagttcaa | ttggtacgtg | 900 |
| gatggcgtgg | aggtgcacaa | cgccaagaca | aagccaaggg | aggagcagta | caattccacc | 960 |
| tatagagtgg | tgtctgtgct | gacagtgctg | caccaggact | ggctgaatgg | caaggagtat | 1020 |
| aagtgcaagg | tgtccaacaa | ggccctgccc | gcccctatcg | agaagaccat | ctctaaggca | 1080 |
| aagggacagc | ctcgggagcc | acaggtgtac | acactgcctc | catcccgcga | cgagctgacc | 1140 |
| aagaatcagg | tgtctctgac | atgtctggtg | aagggcttct | atccttctga | tatcgcagtg | 1200 |
| gagtgggaga | gcaacggaca | gccagagaac | aattacaaga | ccacaccccc | tgtgctggac | 1260 |
| agcgatggct | ccttctttct | gtatagcaag | ctgaccgtgg | ataagtcccg | ctggcagcag | 1320 |
| ggcaacgtgt | tcagctgttc | cgtgatgcac | gaggccctgc | acaaccacta | cacacagaag | 1380 |

```
tctctgagcc tgtcccctgg caag                                          1404
```

<210> SEQ ID NO 153
<211> LENGTH: 112
<212> TYPE: PRT
<213> ORGANISM: Artificial Sequence
<220> FEATURE:
<223> OTHER INFORMATION: DMAb

<400> SEQUENCE: 153

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu His Lys Pro Gly Gln Ser
        35                  40                  45

Pro Gln Val Leu Ile Phe Leu Gly Ser Asp Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110
```

<210> SEQ ID NO 154
<211> LENGTH: 714
<212> TYPE: DNA
<213> ORGANISM: Artificial Sequence
<220> FEATURE:
<223> OTHER INFORMATION: DMAb

<400> SEQUENCE: 154

```
atggtgctgc agacccaggt gttcatctcc ctgctgctgt ggatctctgg cgcctacggc    60
gacatcgtga tgacccagtc tcccctgagc ctgccagtga caccaggaga gcctgcaagc   120
atctcctgca ggagctccca gtccctgctg cactctaacg gctacaatta tctggattgg   180
tatctgcaca agccaggcca gagcccccag gtgctgatct ttctgggcag cgacagggca   240
tccggagtgc ctgatagatt ctctggcagc ggctccggca ccgactttac actgaagatc   300
agccgggtgg aggcagagga tgtgggcgtg tactattgca tgcaggccct gcagaccccg   360
cgcacattcg gccagggcac caagctggag atcaagacag tggccgcccc aagcgtgttc   420
atctttcccc cttccgacga gcagctgaag tctggcacag ccagcgtggt gtgcctgctg   480
aacaacttct acccaaggga ggccaaggtg cagtggaagg tggataacgc cctgcagtcc   540
ggcaattctc aggagagcgt gaccgagcag gactccaagg attctacata tagcctgtct   600
agcaccctga cactgtctaa ggccgactac gagaagcaca aggtgtatgc atgcgaggtg   660
acccaccagg gcctgtcctc tcccgtgaca aagagcttca ccggggcga gtgt           714
```

<210> SEQ ID NO 155
<211> LENGTH: 125
<212> TYPE: PRT
<213> ORGANISM: Artificial Sequence
<220> FEATURE:
<223> OTHER INFORMATION: DMAb

<400> SEQUENCE: 155

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Ala Phe Ser Thr Tyr
         20                  25                  30

Ala Met Ser Trp Val Arg Gln Ala Pro Gly Lys Gly Leu Glu Trp Val
         35                  40                  45

Ser Ala Ile Thr Gly Ser Gly Tyr Ser Thr Tyr Tyr Ala Asp Ser Val
 50                  55                  60

Lys Gly Arg Phe Thr Ile Ser Gly Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Val Gly Glu Tyr Tyr Asp Phe Trp Ser Gly Tyr Ser Pro Phe
                100                 105                 110

Asp Ser Trp Gly Gln Gly Thr Leu Val Thr Val Ser Ser
        115                 120                 125

<210> SEQ ID NO 156
<211> LENGTH: 1422
<212> TYPE: DNA
<213> ORGANISM: Artificial Sequence
<220> FEATURE:
<223> OTHER INFORMATION: DMAb

<400> SEQUENCE: 156
```

| | |
|---|---:|
| atggactgga cctggagaat cctgttcctg gtggcagcag caaccggaac acacgcagag | 60 |
| gtgcagctgg tggagagcgg cggcggcctg gtgcagcccg gcggctctct gaggctgagc | 120 |
| tgcgcagcat ccggattcgc cttttccacc tacgccatgt cttgggtgag acaggcacct | 180 |
| ggcaagggcc tggagtgggt gtccgccatc accggcagcg gctattccac atactatgcc | 240 |
| gactctgtga agggccggtt caccatctct ggcgataaca gcaagaatac actgtacctg | 300 |
| cagatgaact ccctgagggc agaggacacc gccctgtact attgcgccaa agtgggcgag | 360 |
| tactatgact tctggtctgg ctatagccct tttgatagct ggggccaggg caccctggtg | 420 |
| acagtgagct ccgccagcac caagggccca tccgtgtttc cactggcccc ctctagcaag | 480 |
| tctaccagcg gcggcacagc cgccctggga tgtctggtga aggattactt cccagagccc | 540 |
| gtgacagtgt cctggaactc tggcgccctg acctccggag tgcacacatt ccagccgtg | 600 |
| ctgcagtcct ctggcctgta cagcctgagc tccgtggtga ccgtgccctc tagctccctg | 660 |
| ggcacccaga catatatctg caacgtgaat cacaagccat ccatacaaa ggtggacaag | 720 |
| aaggtggagc ccaagtcttg tgataagacc cacacatgcc ctccctgtcc tgcaccagag | 780 |
| ctgctgggcg gcccaagcgt gttcctgttt ccacccaagc ctaaggacac cctgatgatc | 840 |
| agcaggaccc ccgaggtgac atgcgtggtg gtggacgtgt cccacgagga ccccgaggtg | 900 |
| aagtttaact ggtacgtgga tggcgtggag gtgcacaatg ccaagacaaa gccaagggag | 960 |
| gagcagtaca attctaccta tagagtggtg agcgtgctga cagtgctgca ccaggactgg | 1020 |
| ctgaacggca aggagtacaa gtgcaaggtg tctaataagg ccctgcccgc ccctatcgag | 1080 |
| aagaccatca gcaaggcaaa gggacagcct cgggagccac aggtgtatac actgcctcca | 1140 |
| tctcgcgacg agctgaccaa gaaccaggtg agcctgacat gtctggtgaa gggcttctac | 1200 |
| cctagcgata tcgccgtgga gtgggagtcc aatggccagc cagagaacaa ttacaagacc | 1260 |
| acaccccctg tgctggacag cgatggctcc ttctttctgt attccaagct gaccgtggat | 1320 |
| aagtctaggt ggcagcaggg caacgtgttt cctgttctg tgatgcacga ggccctgcac | 1380 |
| aatcactaca cacagaagag cctgtccctg tctcctggca ag | 1422 |

```
<210> SEQ ID NO 157
<211> LENGTH: 108
<212> TYPE: PRT
<213> ORGANISM: Artificial Sequence
<220> FEATURE:
<223> OTHER INFORMATION: DMAb

<400> SEQUENCE: 157
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Phe Thr Phe Gly Pro Gly Thr Lys Val Asp Ile Lys
            100                 105

```
<210> SEQ ID NO 158
<211> LENGTH: 702
<212> TYPE: DNA
<213> ORGANISM: Artificial Sequence
<220> FEATURE:
<223> OTHER INFORMATION: DMAb

<400> SEQUENCE: 158
```

| | | | | | |
|---|---|---|---|---|---|
| atggtgctgc | agacccaggt | gttcatcagc | ctgctgctgt | ggatctccgg | agcatacgga | 60 |
| gagatcgtgc | tgacccagtc | cccaggcaca | ctgtctctga | gccctggaga | gagggccacc | 120 |
| ctgtcttgca | gagcctccca | gtctgtgagc | tcctcttacc | tggcctggta | tcagcagaag | 180 |
| ccaggacagg | cccccaggct | gctgatctac | ggagccttca | acagggcaac | cggcatccca | 240 |
| gaccgcttca | gcggctccgg | ctctggcaca | gacttcaccc | tgacaatcag | caggctggag | 300 |
| cccgaggact | tgccgtgta | ctattgccag | cagtatggca | gatcccttt | cacctttggc | 360 |
| ccaggcacaa | aggtggacat | caagaccgtg | gccgccccta | gcgtgttcat | ctttcccct | 420 |
| agcgatgagc | agctgaagtc | cggcacagcc | tctgtggtgt | gcctgctgaa | caatttctac | 480 |
| ccacgggagg | ccaaggtgca | gtggaaggtg | gacaacgccc | tgcagtctgg | caatagccag | 540 |
| gagtccgtga | ccgagcagga | ctctaaggat | agcacatata | gcctgtccaa | caccctgaca | 600 |
| ctgtctaagg | ccgattacga | gaagcacaag | gtgtatgcat | gcgaggtgac | ccaccagggc | 660 |
| ctgagctccc | cagtgacaaa | gagctttaat | cgcggcgagt | gt | | 702 |

```
<210> SEQ ID NO 159
<211> LENGTH: 129
<212> TYPE: PRT
<213> ORGANISM: Artificial Sequence
<220> FEATURE:
<223> OTHER INFORMATION: DMAb

<400> SEQUENCE: 159
```

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Ile Phe Ser Ser Tyr
            20                  25                  30

Tyr Ile His Trp Val Arg Gln Ala Pro Gly Gln Gly Leu Glu Trp Met
        35                  40                  45

Gly Ile Ile Asn Pro Asp Gly Gly Ser Thr Arg Tyr Ala Gln Lys Phe
    50                  55                  60

Gln Gly Arg Val Thr Met Thr Arg Asp Thr Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Pro Arg Leu Asp Phe Trp Gly Asn Ser Pro Thr Phe
            100                 105                 110

Gly Tyr Gly Met Asp Val Trp Gly Gln Gly Thr Thr Val Thr Val Ser
        115                 120                 125

Ser
```

<210> SEQ ID NO 160
<211> LENGTH: 1434
<212> TYPE: DNA
<213> ORGANISM: Artificial Sequence
<220> FEATURE:
<223> OTHER INFORMATION: DMAb

<400> SEQUENCE: 160

```
atggactgga cctggcgcat cctgttcctg gtggcagcag caaccggaac acacgcagag      60
gtgcagctgg tgcagtccgg agcagaggtg aagaagccag agcctctgt gaaggtgagc      120
tgcaaggcct ccggctacat cttcagctcc tactatatcc actgggtgag acaggcacca     180
ggacagggcc tggagtggat gggcatcatc aaccctgatg gcggcagcac cagatacgca     240
cagaagtttc agggccgggt gaccatgaca cgcgacacct acaaggac cgcctatatg       300
gagctgtcta gcctgaggag cgaggataca gccgtgtact attgcgccag gaccctccc     360
aggctggatt tctgggcaa ttccccaacc tttggctacg gaatggacgt gtggggacag     420
ggaaccacag tgacagtgtc ctctgcctct accaagggcc ccagcgtgtt cctctggcc    480
ccaagctcca gagcacatc cggcggcacc gccgcctgg gatgtctggt gaaggattat    540
ttccctgagc cagtgaccgt gtcctggaac tctggcgccc tgacatctgg cgtgcacacc    600
tttcccgccg tgctgcagtc tagcggcctg tacagcctgt cctctgtggt gacagtgcct    660
agctcctctc tgggcacaca gacctatatc tgcaacgtga atcacaagcc tagcaatacc    720
aaggtggaca gaaggtgga gccaaagtcc tgtgataaga cacacacctg cccaccctgt    780
ccagcacctg agctgctggg cggcccaagc gtgttcctgt tcctccaaa gcccaaggac    840
acactgatga tctccagaac acctgaggtg acctgcgtgg tggtggacgt gtctcacgag    900
gaccccgagg tgaagttcaa ctggtacgtg gatggcgtgg aggtgcacaa tgccaagacc    960
aagcctagag aggagcagta caactccaca tatcgggtgg tgtctgtgct gaccgtgctg   1020
caccaggact ggctgaacgg caaggagtat aagtgcaagg tgagcaataa ggccctgcca   1080
gcccccatcg agaagacaat ctccaaggca aagggacagc cccgcgagcc tcaggtgtac   1140
accctgcccc cttccaggga cgagctgaca aagaaccagg tgtctctgac ctgtctggtg   1200
aagggcttct atccatctga tatcgccgtg gagtgggaga gcaatggcca gcccgagaac   1260
aattacaaga ccacaccacc cgtgctggac agcgatggct ccttctttct gtatagcaag   1320
ctgacagtgg ataagtccag gtggcagcag ggcaacgtgt ttcttgtag cgtgatgcac   1380
```

```
gaggccctgc acaatcacta cacccagaag tccctgtctc tgagcccagg caag        1434
```

<210> SEQ ID NO 161
<211> LENGTH: 111
<212> TYPE: PRT
<213> ORGANISM: Artificial Sequence
<220> FEATURE:
<223> OTHER INFORMATION: DMAb

<400> SEQUENCE: 161

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Pro Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Ser Thr
                85                  90                  95

Ser Thr Val Leu Phe Gly Gly Gly Thr Lys Leu Thr Val Leu Ser
            100                 105                 110
```

<210> SEQ ID NO 162
<211> LENGTH: 696
<212> TYPE: DNA
<213> ORGANISM: Artificial Sequence
<220> FEATURE:
<223> OTHER INFORMATION: DMAb

<400> SEQUENCE: 162

```
atggcctgga cccctctgct gctgccactg ctgacattct gcaccgtgag cgaggcatct    60
cagagcgccc tgacccagcc agcatccgtg tctggcagcc ccggccagag catcacaatc   120
tcctgtacag gcaccagctc cgacgtgggc tcctacaacc tggtgtcttg gtatcagcag   180
caccccggca aggcccctaa gctgatgatc tacgaggtga gcaagaggcc ccctggcgtg   240
tccgatagat tttccggctc taagagcggc aatacagcct ctctgaccat cagcggcctg   300
caggcagagg acgaggcaga ttactattgc tgtagctatg cctccacatc taccgtgctg   360
ttcggcggcg gaacaaagct gaccgtgctg tctgccccaa gcgtgaccct gtttccaccc   420
tctagcgagg agctgcaggc caacaaggcc accctggtgt gcctgatctc cgacttctac   480
ccaggagcag tgacagtggc atggaaggcc gattcctctc ctgtgaaggc cggcgtggag   540
acaacaaccc catccaagca gtctaacaat aagtacgccg ccagctccta tctgtctctg   600 accccgagc agtggaagag ccacaggagc tattcctgcc aggtgacaca cgagggctcc   660
acagtggaga agaccgtggc ccctacagag tgttct                              696
```

<210> SEQ ID NO 163
<211> LENGTH: 120
<212> TYPE: PRT
<213> ORGANISM: Artificial Sequence
<220> FEATURE:
<223> OTHER INFORMATION: DMAb

<400> SEQUENCE: 163

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
         20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Arg His Asp Ser Ser Gly Tyr Asp Ala Phe Asp Ile Trp Gly Gln
             100                 105                 110

Gly Thr Met Val Thr Val Ser Ser
         115                 120
```

<210> SEQ ID NO 164
<211> LENGTH: 1407
<212> TYPE: DNA
<213> ORGANISM: Artificial Sequence
<220> FEATURE:
<223> OTHER INFORMATION: DMAb

<400> SEQUENCE: 164

```
atggactgga cctggagaat cctgttcctg gtggcagcag caaccggaac acacgcagag     60
gtgcagctgg tgcagtccgg agcagaggtg aagaagccag agccagcgt gaaggtgtcc    120
tgcaaggcct ctggctacac cttcacatcc tactatatgc actgggtgag acaggcacct    180
ggacagggcc tggagtggat gggcatcatc aacccaagcg gcggcagcac ctcctacgca    240
cagaagtttc agggcagggt gaccatgaca agagacacct ctacaagcac cgtgtatatg    300
gagctgagct ccctgaggag cgaggacaca gccgtgtact attgcgccag acacgattct    360
agcggctacg acgccttcga tatctggggc cagggcacaa tggtgaccgt gtcctctgcc    420
agcaccaagg gcccttccgt gtttccactg gcccccagct ccaagtccac atctggcggc    480
accgccgccc tgggatgtct ggtgaaggat tatttcccag agcccgtgac cgtgtcttgg    540
aacagcggcg ccctgacatc cggagtgcac acctttcctg ccgtgctgca gtctagcggc    600
ctgtactctc tgtcctctgt ggtgacagtg ccaagctcct ctctgggcac acagacctat    660
atctgcaacg tgaatcacaa gccatccaat accaaggtgg acaagaaggt ggagcccaag    720
tcttgtgata agacacacac ctgccctccc tgtcctgcac cagagctgct gggcggccca    780
agcgtgttcc tgtttccacc caagcctaag gacacactga tgatcagccg gacaccagag    840
gtgacctgcg tggtggtgga cgtgtcccac gaggacccccg aggtgaagtt taactgtgtac    900
gtggatggcg tggaggtgca caatgccaag accaagccac gggaggagca gtacaattct    960
acatatcgcg tggtgagcgt gctgaccgtg ctgcaccagg actggctgaa cggcaaggag   1020
tataagtgca aggtgtctaa taaggccctg cccgccccta tcgagaagac aatcagcaag   1080
gcaaagggac agcctcggga gccacaggtg tacaccctgc ctccatctcg cgacgagctg   1140
acaaagaacc aggtgagcct gacctgtctg gtgaagggct tctatcccag cgatatcgcc   1200
gtggagtggg agtccaatgg ccagcctgag aacaattaca agaccacacc ccctgtgctg   1260
gactccgatg gctctttctt tctgtattcc aagctgacag tggataagtc tcgctggcag   1320
cagggcaacg tgtttagctg ttccgtgatg cacgaggccc tgcacaatca ctacacccag   1380
aagtctctga gcctgtcccc tggcaag                                       1407
```

<210> SEQ ID NO 165
<211> LENGTH: 109
<212> TYPE: PRT
<213> ORGANISM: Artificial Sequence
<220> FEATURE:
<223> OTHER INFORMATION: DMAb

<400> SEQUENCE: 165

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Pro Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ser Asp Ser Ser Gly Thr Tyr
                85                  90                  95

Val Val Phe Gly Gly Gly Thr Lys Leu Thr Val Leu Ser
            100                 105
```

<210> SEQ ID NO 166
<211> LENGTH: 690
<212> TYPE: DNA
<213> ORGANISM: Artificial Sequence
<220> FEATURE:
<223> OTHER INFORMATION: DMAb

<400> SEQUENCE: 166

```
atggcctgga cccctctgct gctgcctctg ctgacattct gcaccgtgtc tgaggccagc      60
tcctatgagc tgacccagcc ccctagcgtg tccgtgtctc aggacagac agcaaggatc     120 acctgttccg gcgacgcact gccaaagcag tacgcatatt ggtaccagca gaagcctgga    180
caggcacctg tgccagtgat ctacaaggat agcgagaggc catccggcat ccccgagagg    240
ttcagcggct ctagctccgg caccacagtg acactgacca tctccggagt gcaggcagag    300
gacgaggcag attactattg ccagtctagc gactcctctg gcacctatgt ggtgttcggc    360
ggcggaacaa agctgaccgt gctgtctgcc cctagcgtga cactgtttcc acccagctcc    420
gaggagctgc aggccaacaa ggccaccctg gtgtgcctga tcagcgactt ctacccagga    480
gcagtgacag tggcatggaa ggccgattct agccctgtga aggccggcgt ggagacaaca    540 acccatcca agcagtctaa caataagtat gccgcctcct cttacctgtc tctgaccccca    600 gagcagtgga agagccaccg cagctattcc tgccaggtga cacgaggg ctccacagtg     660 gagaagaccg tggcccccac agagtgttct                                      690
```

<210> SEQ ID NO 167
<211> LENGTH: 118
<212> TYPE: PRT
<213> ORGANISM: Artificial Sequence
<220> FEATURE:
<223> OTHER INFORMATION: DMAb

<400> SEQUENCE: 167

```
Glu Val Gln Leu Val Gln Ser Gly Gly Gly Leu Val Gln Pro Gly Gly
1               5                   10                  15
```

```
Ser Met Arg Leu Ser Cys Glu Ala Ser Gly Leu Ser Leu Ser Asp Tyr
        20                  25                  30
Phe Met His Trp Val Arg Gln Ala Gln Gly Lys Gly Leu Glu Trp Ile
        35                  40                  45
Gly Leu Ile Gln Thr Lys Ala Phe Thr Tyr Lys Thr Glu Tyr Pro Ala
        50                  55                  60
Ala Val Lys Gly Arg Phe Thr Ile Ser Arg Asp Asp Ser Lys Asn Thr
65                  70                  75                  80
Leu Tyr Leu Gln Met Ser Ser Leu Lys Pro Glu Asp Thr Ala Leu Tyr
                85                  90                  95
Tyr Cys Ile Ala Val Thr Pro Asp Phe Tyr Tyr Trp Gly Gln Gly Val
            100                 105                 110
Leu Val Thr Val Ser Ser
        115
```

<210> SEQ ID NO 168
<211> LENGTH: 1401
<212> TYPE: DNA
<213> ORGANISM: Artificial Sequence
<220> FEATURE:
<223> OTHER INFORMATION: DMAb

<400> SEQUENCE: 168

```
atggactgga cctggagaat cctgttcctg gtggcagcag caaccggaac acacgcagag      60
gtgcagctgg tgcagagcgg cggcggcctg gtgcagcccg gcggctctat gaggctgagc     120
tgcgaggcat ccggactgtc cctgtctgat tactttatgc actgggtgcg ccaggcacag     180
ggcaagggac tggagtggat cggcctgatc agaccaaggc cttcaccta aagacagag      240
tatcctgccg ccgtgaaggg caggtttacc atctctagag acgatagcaa gaacacactg     300
tatctgcaga tgagctccct gaagcctgag gacaccgccc tgtactattg catcgccgtg     360
acaccagatt tctactattg gggccagggc gtgctggtga ccgtgtctag cgcctccaca     420
aagggaccaa gcgtgttccc actggcaccc tcctctaaga gcacctccgg cggcacagcc     480
gccctgggct gtctggtgaa ggactacttc ccagagcccg tgaccgtgtc ctggaactct     540
ggcgccctga cctccggagt gcacacattt cctgccgtgc tgcagagctc cggcctgtac     600
agcctgtcta gcgtggtgac cgtgccatct tctagcctgg gcacccagac atatatctgc     660
aacgtgaatc acaagccatc taatacaaag gtggacaaga aggtggagcc caagagctgt     720
gataagaccc acacatgccc tccctgtcct gcaccagagc tgctgggcgg cccaagcgtg     780
ttcctgtttc cacccaagcc taaggacacc ctgatgatct ccaggacccc agaggtgaca     840
tgcgtggtgg tggacgtgtc tcacgaggac cccgaggtga agttcaactg gtacgtggat     900
ggcgtggagg tgcacaatgc caagacaaag ccacgggagg agcagtacaa tagcacctat     960
cgcgtggtgt ccgtgctgac agtgctgcac caggactggc tgaacggcaa ggagtataag    1020
tgcaaggtgt ccaataaggc cctgcccgcc cctatcgaga agaccatcag caaggccaag    1080
ggccagccta gggagccaca ggtgtacaca ctgcctccaa gcagagacga gctgaccaag    1140
aaccaggtgt ccctgacatg tctggtgaag ggcttctatc cctccgatat cgccgtggag    1200
tgggagtcta atggccagcc tgagaacaat tacaagacca cccccctgt gctggacagc    1260
gatggctcct tctttctgta ttctaagctg accgtggata gagcaggtg gcagcagggc    1320
aacgtgtttt cttgtagcgt gatgcacgag gccctgcaca atcactacac acagaagtcc    1380
ctgtctctga gccctggcaa g                                             1401
```

<210> SEQ ID NO 169
<211> LENGTH: 108
<212> TYPE: PRT
<213> ORGANISM: Artificial Sequence
<220> FEATURE:
<223> OTHER INFORMATION: DMAb

<400> SEQUENCE: 169

```
Asp Val Val Met Thr Gln Ser Pro Ser Phe Leu Ser Ala Ser Val Gly
1               5                   10                  15

Asp Arg Val Thr Ile Thr Cys Arg Ala Ser Gln Asp Ile Thr Ile Asn
            20                  25                  30

Leu Asn Trp Phe Gln His Lys Pro Gly Lys Ala Pro Lys Arg Leu Ile
        35                  40                  45

Tyr Val Ala Ser Arg Leu Glu Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Pro Gly Thr Lys Leu Asp Ile Lys Arg
            100                 105
```

<210> SEQ ID NO 170
<211> LENGTH: 702
<212> TYPE: DNA
<213> ORGANISM: Artificial Sequence
<220> FEATURE:
<223> OTHER INFORMATION: DMAb

<400> SEQUENCE: 170

```
atggtgctgc agacccaggt gttcatcagc ctgctgctgt ggatctccgg cgcctacggc      60
gacgtggtca tgacacagag cccttccttt ctgtctgcca gcgtgggcga cagggtgacc     120
atcacatgca gggcctccca ggatatcacc atcaacctga attggttcca gcacaagcca     180
ggcaaggccc ccaagaggct gatctatgtg gcctccaggc tggagagagg cgtgccctct     240
agattctccg gctctggcag cggcaccgag tttaccctga caatcagctc cctgcagcct     300
gaggatttcg ccacatacta ttgccagcag tacaacaatt atcctctgac ctttggccca     360
ggcacaaagc tggacatcaa ggaccgtgca gcaccaa gcgtgttcat ctttccccct        420
agcgatgagc agctgaagtc cggcacagcc tctgtggtgt gcctgctgaa caatttctac     480
ccccgcgagg ccaaggtgca gtggaaggtg gacaacgccc tgcagtccgg caattctcag     540
gagagcgtga ccgagcagga ctccaaggat tctacatata gcctgtctag cacccctgaca    600 ctgtccaagg ccgattacga gaagcacaag gtgtatgcat gcgaggtgac ccaccaggga    660
ctgtcctctc ccgtgacaaa gagctttaac aggggcgagt gt                       702
```